(12) United States Patent
Dean et al.

(10) Patent No.: US 8,501,946 B2
(45) Date of Patent: Aug. 6, 2013

(54) 5,6,7,8-TETRAHYDRO[1,2,4]TRIAZOLO[4,3-A]PYRAZINE DERIVATIVES AS P2X7 MODULATORS

(75) Inventors: David Kenneth Dean, Harlow (GB); Jorge Munoz-Muriedas, Stevanage (GB); Mairi Sime, Harlow (GB); Jon Graham Anthony Steadman, Harlow (GB); Rachel Elizabeth Anne Thewlis, Harlow (GB); Giancarlo Trani, Harlow (GB); Daryl Simon Walter, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 13/266,592

(22) PCT Filed: Apr. 28, 2010

(86) PCT No.: PCT/EP2010/055715
§ 371 (c)(1),
(2), (4) Date: Mar. 9, 2012

(87) PCT Pub. No.: WO2010/125102
PCT Pub. Date: Nov. 4, 2010

(65) Prior Publication Data
US 2012/0157436 A1    Jun. 21, 2012

Related U.S. Application Data

(60) Provisional application No. 61/173,701, filed on Apr. 29, 2009.

(51) Int. Cl.
*C07D 495/00* (2006.01)

(52) U.S. Cl.
USPC ............ 544/350; 544/118; 544/238; 544/333; 544/405; 546/152; 546/199; 546/268.1; 548/127; 548/128; 548/134; 548/202; 548/206; 548/247; 548/335.1; 548/373.1; 548/469; 548/517; 548/560; 549/505

(58) Field of Classification Search
USPC .......... 544/118, 238, 333, 350, 405; 546/152, 546/199, 268.1; 548/127, 128, 134, 202, 548/206, 247, 335.1, 373.1, 469, 517, 560; 549/505
See application file for complete search history.

(56) References Cited

FOREIGN PATENT DOCUMENTS

| WO | WO 2008/124153 A1 | 10/2008 |
| WO | WO 2009/027730 A1 | 3/2009 |
| WO | WO 2010/125102 | * 4/2010 |

OTHER PUBLICATIONS

Jordan, V. C. Nature Reviews: Drug Discovery, 2, 2003, 205.*
Hackam, et al. JAMA, 296(14), 2006, 1731-1732.*

* cited by examiner

*Primary Examiner* — Douglas M Willis
(74) *Attorney, Agent, or Firm* — Nora L. Stein; Theodore R. Furman

(57) ABSTRACT

The present invention provides a compound of formula (I) or a pharmaceutically acceptable salt thereof:

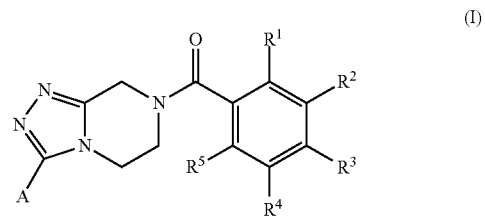

(I)

wherein A is hydrogen, $C_{1-4}$alkyl, $C_{3-6}$cycloalkyl, $C_{1-3}$alkoxy, $C_{1-3}$alkoxy $C_{1-4}$alkyl, $C_{1-2}$fluoroalkyl, halogen, $NR^6R^7$, optionally substituted heteroaryl (Het), or optionally substituted phenyl, and $R^1$, $R^2$, $R^3$, $R^4$, $R^5$, $R^6$ and $R^7$ are as defined in the description.

The compounds or salts are thought to modulate P2X7 receptor function and to be capable of antagonizing the effects of ATP at the P2X7 receptor. The invention also provides the use of the compound or salt in the treatment or prophylaxis of, for example, inflammatory pain, neuropathic pain, visceral pain, rheumatoid arthritis, osteoarthritis or neurodegenerative disorders.

2 Claims, No Drawings

5,6,7,8-TETRAHYDRO[1,2,4]TRIAZOLO [4,3-A]PYRAZINE DERIVATIVES AS P2X7 MODULATORS

This application is a §371 of International Application No. PCT/EP2010/055715, filed 28 Apr. 2010, which claims the benefit of U.S. Provisional Application No. 61/173,701, filed 29 Apr. 2009, which are incorporated herein in their entireties.

The present invention relates to fused bicyclic derivatives, specifically fused triazole derivatives, which modulate P2X7 receptor function and are capable of antagonizing the effects of ATP at the P2X7 receptor ("P2X7 receptor antagonists"); to processes for their preparation; to pharmaceutical compositions containing them; and to the use of such compounds in therapy.

BACKGROUND OF THE INVENTION

The P2X7 receptor is a ligand-gated ion-channel which is expressed in cells of the hematopoietic lineage, e.g. macrophages, microglia, mast cells, and lymphocytes (T and B) (see, for example, Collo, et al. Neuropharmacology, Vol. 36, pp 1277-1283 (1997)), and is activated by extracellular nucleotides, particularly adenosine triphosphate (ATP). Activation of P2X7 receptors has been implicated in giant cell formation, degranulation, cytolytic cell death, CD62L shedding, regulation of cell proliferation, and release of proinflammatory cytokines such as interleukin 1 beta (IL-1β) (e.g. Ferrari, et al., J. Immunol., Vol. 176, pp 3877-3883 (2006)), interleukin 18 (IL-18), and tumour necrosis factor alpha (TNFα) (e.g. Hide, et al. Journal of Neurochemistry, Vol. 75, pp 965-972 (2000)). P2X7 receptors are also located on antigen presenting cells, keratinocytes, parotid cells, hepatocytes, erythrocytes, erythroleukaemic cells, monocytes, fibroblasts, bone marrow cells, neurones, and renal mesangial cells. Furthermore, the P2X7 receptor is expressed by presynaptic terminals in the central and peripheral nervous systems and has been shown to mediate glutamate release in glial cells (Anderson, C. et al. Drug. Dev. Res., Vol. 50, page 92 (2000)).

The localisation of the P2X7 receptor to key cells of the immune system, coupled with its ability to release important inflammatory mediators from these cells suggests a potential role of P2X7 receptor antagonists in the treatment of a wide range of diseases including pain and neurodegenerative disorders. Recent preclinical in vivo studies have directly implicated the P2X7 receptor in both inflammatory and neuropathic pain (Dell'Antonio et al., Neurosci. Lett., Vol. 327, pp 87-90 (2002). Chessell, IP., et al., Pain, Vol. 114, pp 386-396 (2005), Honore et al., J. Pharmacol. Exp. Ther., Vol. 319, p1376-1385 (2006)) while there is in vitro evidence that P2X7 receptors mediate microglial cell induced death of cortical neurons (Skaper, S. D., et al., Glia, Vol. 54, p234-242 (2006)). In addition, up-regulation of the P2X7 receptor has been observed around β-amyloid plaques in a transgenic mouse model of Alzheimer's disease (Parvathenani, L. et al. J. Biol. Chem., Vol. 278(15), pp 13309-13317 (2003)).

SUMMARY OF THE INVENTION

The present invention provides compounds which modulate P2X7 receptor function and are capable of antagonizing the effects of ATP at the P2X7 receptor ("P2X7 receptor antagonists").

In a first aspect, the invention provides a compound of formula (I) or a pharmaceutically acceptable salt thereof:

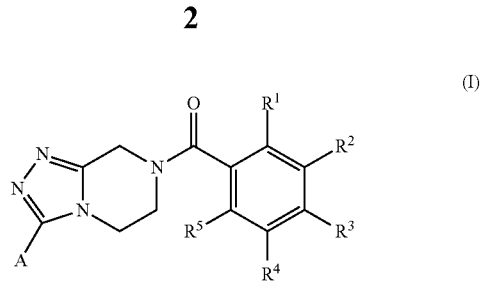

wherein:
A is hydrogen, $C_{1-4}$alkyl (e.g. methyl or ethyl), $C_{3-6}$cycloalkyl (e.g. cyclopropyl, cyclopentyl or cyclohexyl), $C_{1-3}$alkoxy (e.g. methoxy), $C_{1-3}$alkoxy $C_{1-4}$alkyl (e.g. methoxyethyl), $C_{1-2}$fluoroalkyl (e.g. trifluoromethyl), halogen (e.g. bromine, chlorine or iodine), $NR^6R^7$, Het, or phenyl; wherein the phenyl is optionally substituted by one, two or three (e.g. one or two) substituents independently being fluorine, chlorine, $C_{1-3}$alkyl (e.g. methyl), OH, methoxy or deuterium;
wherein Het is:
i) a 6-membered heteroaromatic monocyclic ring containing one, two or three (e.g. one or two) ring-nitrogen atoms, or
ii) a 5-membered heteroaromatic monocyclic ring containing one, two or three (e.g. one or two) ring heteroatoms independently being N, O or S, wherein no more than one of the 5-membered ring heteroatoms is O or S;
iii) a 9 or 10-membered heteroaromatic bicyclic ring containing one, two or three (e.g. one or two) ring nitrogen atoms;
and wherein Het is optionally substituted with one or two substituents independently being $C_{1-3}$alkyl (e.g. methyl), fluorine, chlorine, OH (including a tautomer thereof), methoxy or deuterium;
and wherein:
$R^1$ is hydrogen, chlorine, fluorine, bromine, $C_1$fluoroalkyl (e.g. —$CF_3$), cyano or $C_{1-3}$alkyl (e.g. methyl);
$R^2$ is hydrogen, fluorine, chlorine, bromine, $C_1$fluoroalkyl (e.g. —$CF_3$), cyano or $C_{1-3}$alkyl (e.g. methyl),
$R^3$ is hydrogen, fluorine, chlorine or $C_{1-3}$alkyl (e.g. methyl),
$R^4$ is hydrogen;
$R^5$ is hydrogen, fluorine, chlorine or methyl; and
$R^6$ and $R^7$ independently are hydrogen or $C_{1-3}$alkyl (e.g. hydrogen or methyl); or $R^6$ and $R^7$ are taken together and are —$(CH_2)_2$—O—$(CH_2)_2$—, —$(CH_2)_2$—O—$(CH_2)_3$—, or —$(CH_2)_n$— wherein $n^1$ is 3, 4, 5 or 6 (e.g. 3, 4 or 5);
wherein, when A is hydrogen, $C_{1-4}$alkyl, $C_{3-6}$cycloalkyl, $C_{1-3}$alkoxy, $C_{1-3}$alkoxy $C_{1-2}$fluoroalkyl, halogen or $NR^6R^7$, then $R^1$ is chlorine, fluorine, bromine, $C_1$fluoroalkyl (e.g. —$CF_3$), cyano or $C_{1-3}$alkyl (e.g. methyl), and at least one of $R^2$ and $R^3$ is other than hydrogen;
and when A is Het or optionally substituted phenyl, then $R^1$ is hydrogen, chlorine, fluorine, bromine, $C_1$fluoroalkyl (e.g. —$CF_3$), cyano or $C_{1-3}$alkyl (e.g. methyl), and at least one of $R^1$, $R^2$ and $R^3$ is other than hydrogen;
and wherein, when $R^5$ is fluorine, chlorine or methyl, then $R^1$ is chlorine, fluorine, $C_1$fluoroalkyl (e.g. —$CF_3$) or methyl and $R^2$ is hydrogen.

DETAILED DESCRIPTION OF THE INVENTION

As used herein, the term "alkyl" (when used as a group or as part of a group) refers to a straight or branched hydrocarbon chain containing the specified number of carbon atoms. For example, $C_{1-6}$alkyl means a straight or branched hydrocarbon chain containing at least 1 and at most 6 carbon atoms. Alkyl or $C_{1-6}$alkyl can for example be, but are not limited to:

methyl (Me), ethyl (Et), n-propyl (propyl), isopropyl (1-methylethyl), n-butyl (butyl), isobutyl, sec-butyl, t-butyl, n-pentyl, 3-methylbutyl, 1-ethylpropyl, n-hexyl or isohexyl.

"$C_{1-2}$fluoroalkyl" means $C_{1-2}$alkyl substituted by one, two or three fluorine atoms; for example methyl substituted by one, two or three fluorine atoms (i.e. trifluoromethyl (—$CF_3$), difluoromethyl or monofluoromethyl); in particular trifluoromethyl (—$CF_3$).

"$C_{3-6}$cycloalkyl" can be cyclopropyl, cyclobutyl, cyclopentyl, or cyclohexyl.

The term "halogen" is used herein to mean, unless otherwise stated, a group which is fluorine, chlorine, bromine or iodine. A halogen can for example be fluorine or chlorine.

It is to be understood that the present invention covers and discloses all possible combinations of particular, preferred, suitable, or other embodiments of groups or features (e.g. of A, Het, $R^1$, $R^2$, $R^3$, $R^4$, $R^5$, $R^6$, $R^7$, $R^8$, $R^9$, $R^{10}$, $R^{11}$, $R^{12}$, $R^{13}$, $X^1$, $X^2$, $X^3$, $X^4$, $X^5$, $X^8$, $X^9$, $X^{10}$, and $X^{11}$, and/or $n^1$), e.g. covers and discloses all possible combinations of embodiments of different groups or features, which embodiments are described herein.

In one embodiment of the invention, there is provided a compound of formula (I) or a pharmaceutically acceptable salt thereof:

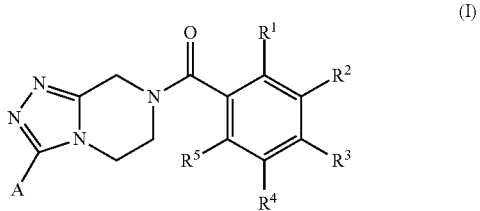

(I)

wherein:
A is hydrogen, $C_{1-4}$alkyl (e.g. methyl or ethyl), $C_{1-3}$alkoxy (e.g. methoxy), $C_{1-2}$fluoroalkyl (e.g. trifluoromethyl), halogen (e.g. bromine, chlorine or iodine), $NR^6R^7$, Het, or phenyl wherein the phenyl is optionally substituted by one, two or three (e.g. one or two) substituents independently being fluorine, chlorine, $C_{1-3}$alkyl (e.g. methyl) or methoxy;
wherein Het is:
i) a 6-membered heteroaromatic monocyclic ring containing one, two or three (e.g. one or two) ring-nitrogen atoms, or
ii) a 5-membered heteroaromatic monocyclic ring containing one, two or three (e.g. one or two) ring heteroatoms independently being N, O or S, wherein no more than one of the 5-membered ring heteroatoms is O or S;
and wherein Het is optionally substituted with one or two substituents independently being $C_{1-3}$alkyl (e.g. methyl), fluorine, chlorine, OH (including a tautomer thereof), or methoxy;
and wherein:
$R^1$ is hydrogen, chlorine, fluorine, bromine, $C_1$fluoroalkyl (e.g. —$CF_3$), cyano or $C_{1-3}$alkyl (e.g. methyl);
$R^2$ is hydrogen, fluorine, chlorine, bromine, $C_1$fluoroalkyl (e.g. —$CF_3$), cyano or $C_{1-3}$alkyl (e.g. methyl),
$R^3$ is hydrogen, fluorine or chlorine,
$R^4$ is hydrogen;
$R^5$ is hydrogen, fluorine, chlorine or methyl; and
$R^6$ and $R^7$ independently are hydrogen or $C_{1-3}$alkyl (e.g. hydrogen or methyl); or $R^6$ and $R^7$ are taken together and are —$(CH_2)_2$—O—$(CH_2)_2$—, —$(CH_2)_2$—O—$(CH_2)_3$—, or —$(CH_2)_{n^1}$— wherein n1 is 3, 4, 5 or 6 (e.g. 3, 4 or 5);

wherein, when A is hydrogen, $C_{1-4}$alkyl, $C_{1-3}$alkoxy, $C_{1-2}$fluoroalkyl, halogen or $NR^6R^7$, then $R^1$ is chlorine, fluorine, bromine, $C_1$fluoroalkyl (e.g. —$CF_3$), cyano or $C_{1-3}$alkyl (e.g. methyl), and at least one of $R^2$ and $R^3$ is other than hydrogen;
and when A is Het or optionally substituted phenyl, then $R^1$ is hydrogen, chlorine, fluorine, bromine, $C_1$fluoroalkyl (e.g. —$CF_3$), cyano or $C_{1-3}$alkyl (e.g. methyl), and at least one of $R^1$, $R^2$ and $R^3$ is other than hydrogen;
and wherein, when $R^5$ is fluorine, chlorine or methyl, then $R^1$ is chlorine, fluorine, $C_1$fluoroalkyl (e.g. —$CF_3$) or methyl and $R^2$ is hydrogen.

In one embodiment, A is hydrogen, $C_{1-4}$alkyl (e.g. methyl or ethyl), $C_{1-3}$alkoxy (e.g. methoxy), $C_{1-2}$fluoroalkyl (e.g. trifluoromethyl), halogen (e.g. bromine, chlorine or iodine), $NR^6R^7$, Het, or optionally substituted phenyl.

In a particular embodiment, A is methyl, ethyl, methoxy, $C_1$fluoroalkyl (e.g. trifluoromethyl), halogen (e.g. bromine, chlorine or iodine, such as bromine or iodine), $NR^6R^7$, Het, or phenyl wherein the phenyl is optionally substituted by one, two or three (e.g. one or two) substituents independently being fluorine, chlorine, $C_{1-3}$alkyl (e.g. methyl) or methoxy.

In a more particular embodiment, A is trifluoromethyl, bromine, iodine, $NR^6R^7$, Het, or phenyl wherein the phenyl is optionally substituted by one or two substituents independently being fluorine, chlorine, methyl or methoxy. In a still more particular embodiment, A is Het or phenyl wherein the phenyl is optionally substituted by one or two substituents independently being fluorine, chlorine, methyl or methoxy.

In one embodiment when A is phenyl, then the A is optionally substituted by one, two or three (e.g. one or two) substituents independently being fluorine, chlorine, $C_{1-3}$alkyl (e.g. methyl), $C_1$fluoroalkyl (e.g. —$CF_3$), OH, or methoxy. In a further embodiment, when A is phenyl, then the phenyl is optionally substituted by one, two or three (e.g. one or two) substituents independently being fluorine, chlorine, $C_{1-3}$alkyl (e.g. methyl) or methoxy.

In one embodiment when A is phenyl, then the phenyl is optionally substituted by one substituent being fluorine, chlorine, $C_{1-3}$alkyl (e.g. methyl), OH, methoxy or deuterium. In a further embodiment when A is phenyl, then the phenyl is optionally substituted by one substituent being fluorine, chlorine, $C_{1-3}$alkyl (e.g. methyl), OH or methoxy.

When A is phenyl optionally substituted by one or two substituents independently being fluorine, chlorine, methyl, OH or methoxy, then: in a particular embodiment A is phenyl optionally substituted by one or two fluorine substituents, one or two chlorine substituents, one OH substiuent, one OH substiuent and one fluorine substiuent or one methoxy substituent; and in a more particular embodiment phenyl optionally substituted by one or two fluorine substituents. In one embodiment, A is 2-methoxyphenyl, 2-hydroxyphenyl (or 2-phenol), 2-hydroxy-4-fluoro-phenyl (or 5-fluoro-2-phenol), 3-methoxyphenyl, 3-chlorophenyl, 2,3-dichlorophenyl, 3-fluorophenyl, 2,3-difluorophenyl, 3,4-difluorophenyl, 4-fluorophenyl or 2,4-difluorophenyl, or in a more particular embodiment A is 4-fluorophenyl or 2,4-difluorophenyl; or preferably A is 4-fluorophenyl.

Preferably, A is Het or phenyl wherein the phenyl is optionally substituted by one or two fluorine substituents. More preferably, A is Het, 4-fluorophenyl or 2,4-difluorophenyl. Still more preferably, A is Het or 4-fluorophenyl.

In a particular embodiment, Het is:
i) a 6-membered heteroaromatic monocyclic ring containing one, two or three (e.g. one or two) ring-nitrogen atoms, or
ii) a 5-membered heteroaromatic monocyclic ring containing one, two or three (e.g. one or two) ring heteroatoms independently being N, O or S, wherein no more than one of the 5-membered ring heteroatoms is O or S;
iii) a 9 or 10-membered heteroaromatic bicyclic ring containing one ring nitrogen atom;
and wherein Het is optionally substituted with one or two substituents (e.g one substiuent) independently being $C_{1-3}$alkyl (e.g. methyl), fluorine, chlorine, OH (including a tautomer thereof), methoxy or deuterium.

In a more particular embodiment, Het is:
i) a 6-membered heteroaromatic monocyclic ring containing one, two or three (e.g. one or two) ring-nitrogen atoms, or
ii) a 5-membered heteroaromatic monocyclic ring containing one, two or three (e.g. one or two) ring heteroatoms independently being N, O or S, wherein no more than one of the 5-membered ring heteroatoms is O or S;
iii) a 9 or 10-membered heteroaromatic bicyclic ring containing one ring nitrogen atom;
and wherein Het is optionally substituted with one or two substituents (e.g. one substiuent) independently being $C_{1-3}$alkyl (e.g. methyl), fluorine, chlorine, OH (including a tautomer thereof), methoxy or deuterium.

In a particular embodiment, Het is:
i) a 6-membered heteroaromatic monocyclic ring containing one, two or three (e.g. one or two) ring-nitrogen atoms, or
ii) a 5-membered heteroaromatic monocyclic ring containing one, two or three (e.g. one or two) ring heteroatoms independently being N, O or S, wherein no more than one of the 5-membered ring heteroatoms is O or S;
and wherein Het is optionally substituted with one or two substituents independently being methyl or fluorine.

Preferably, Het is a carbon-linked heteroaromatic ring system, i.e. the heteroaromatic ring is linked to the 3-position of the tetrahydro[1,2,4]triazolo[4,3-a]pyrazine via a bond to a carbon atom in the heteroaromatic ring system of Het.

In one embodiment Het is substituted with one substiuent being $C_{1-3}$alkyl (e.g. methyl), fluorine, chlorine, OH (including a tautomer thereof), methoxy or deuterium, in particular being methyl, fluorine, chlorine, OH (including a tautomer thereof), methoxy or deuterium, especially being methyl or fluorine.

In a particular embodiment, when Het is the optionally substituted 5-membered heteroaromatic monocyclic ring containing one, two or three ring heteroatoms independently being N, O or S, wherein no more than one of the 5-membered ring heteroatoms is O or S; then at least one of the 5-membered ring heteroatoms is nitrogen.

In a particular embodiment, when Het is an optionally substituted 6-membered heteroaromatic monocyclic ring containing one, two or three (e.g. one or two) ring-nitrogen atoms, then Het is of sub-formula (a):

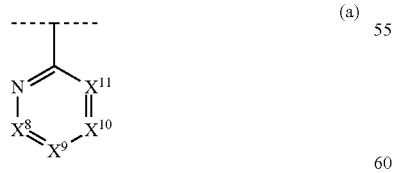

(a)

wherein none, one or two (in particular none or one) of $X^8$, $X^9$, $X^{10}$, and $X^{11}$ are a nitrogen atom, and
the remainder of $X^8$, $X^9$, $X^{10}$, and $X^{11}$ are C—$R^8$, C—$R^9$, C—$R^{10}$, and C—$R^{11}$ respectively in which $R^8$, $R^9$, $R^{10}$, and $R^{11}$ are independently hydrogen, deuterium, $C_{1-3}$alkyl (e.g. methyl), fluorine, chlorine, OH (including a tautomer thereof) or methoxy, especially, hydrogen, $C_{1-3}$alkyl (e.g. methyl), fluorine, chlorine, OH (including a tautomer thereof) or methoxy.

In a particular embodiment, $R^8$, $R^9$, $R^{10}$, and $R^{11}$ are independently hydrogen, deuterium, methyl, fluorine, chlorine, OH or methoxy; for example, hydrogen, methyl, fluorine, chlorine or methoxy; more particularly hydrogen, methyl or fluorine.

In one embodiment, $R^8$ is selected from hydrogen, methyl, fluorine, chlorine, OH or methoxy, for example chlorine or methoxy. In another embodiment, $R^{10}$ is selected from hydrogen, deuterium, $C_{1-3}$alkyl (e.g. methyl), fluorine or OH (including a tautomer thereof), for example hydrogen, methyl or fluorine. In a further particular embodiment $R^9$ is hydrogen or fluorine.

In a particular embodiment, when Het is an optionally substituted 6-membered heteroaromatic monocyclic ring, then Het is of sub-formula (a) as defined in any one of the Examples herein.

In a more particular embodiment, when Het is an optionally substituted 6-membered heteroaromatic monocyclic ring, then Het is of sub-formula (a1) to (a25):

(a1)

(a2)

(a3)

(a4)

(a5)

(a6)

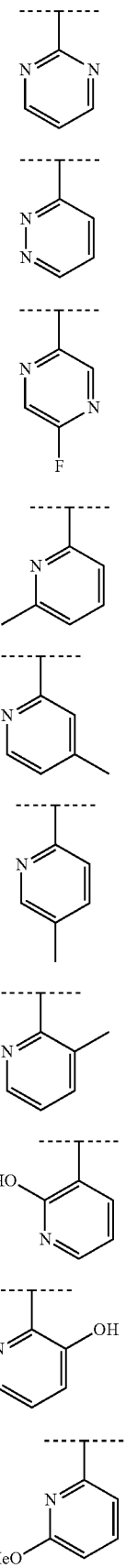
In a further embodiment, when Het is an optionally substituted 6-membered heteroaromatic monocyclic ring, then Het is of sub-formula (a1), (a2), (a3), (a4), (a5), (a6), (a7), (a8), (a9), (a10), (a11), (a12), (a13), (a15), (a16), (a17), (a18), (a19), (a20), (a21) or (a25). In a more particular embodiment, when Het is an optionally substituted 6-membered heteroaromatic monocyclic ring, then Het is of sub-formula (a1), (a2), (a3), (a4), (a5), (a6) or (a7). Preferably, when Het is an optionally substituted 6-membered heteroaromatic monocyclic ring, then Het is of sub-formula (a1), (a2), (a3), (a4), (a5) or (a6).

In a particular embodiment, when Het is an optionally substituted 5-membered heteroaromatic monocyclic ring containing one, two or three (e.g. one or two) ring heteroatoms independently being N, O or S, wherein no more than one of the 5-membered ring heteroatoms is O or S; then Het is of sub-formula (b1), (b2), (b3), (b4) or (b5):

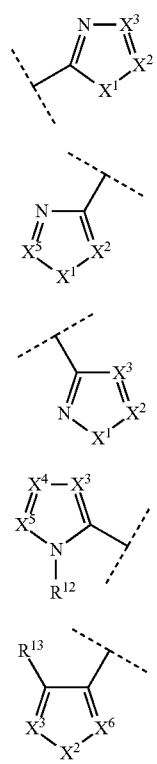

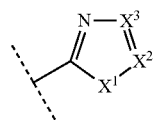
(b1)

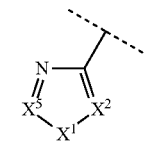
(b2)

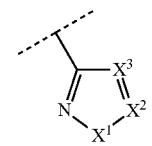
(b3)

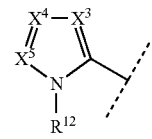
(b4)

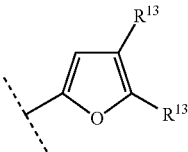
(b5')

wherein:

$X^1$ is O, S or NR$^{12}$;

$X^2$, $X^3$, $X^4$, and $X^5$ independently are N or CR$^{13}$, provided that there are only one, two or three (such as only one or two) ring heteroatoms present in the 5-membered heteroaromatic monocyclic ring of Het; and $X^6$ is O, S; and wherein:

$R^{12}$ is hydrogen or $C_{1-3}$alkyl (particularly hydrogen or methyl); and each $R^{13}$ independently is hydrogen, $C_{1-3}$alkyl (e.g. methyl), fluorine, chlorine, OH (including a tautomer thereof) or methoxy (particularly fluorine or methyl);

provided that $R^{12}$ and each $R^{13}$ are such that the 5-membered heteroaromatic monocyclic ring Het is optionally substituted with one or two substituents.

In a further particular embodiment, when Het is an optionally substituted 5-membered heteroaromatic monocyclic ring containing one, two or three (e.g. one or two) ring heteroatoms independently being N, O or S, wherein no more than one of the 5-membered ring heteroatoms is O or S; then Het is of sub-formula (b1), (b2), (b3), (b4) or (b5'):

wherein:

$X^1$ is O, S or NR$^{12}$; and $X^2$, $X^3$, $X^4$, and $X^5$ independently are N or CR$^{13}$, provided that there are only one, two or three (such as only one or two) ring heteroatoms present in the 5-membered heteroaromatic monocyclic ring of Het; and wherein $R^{12}$ is hydrogen or $C_{1-3}$alkyl (particularly hydrogen or methyl); and each $R^{13}$ independently is hydrogen, $C_{1-3}$alkyl (e.g. methyl), fluorine, chlorine, OH (including a tautomer thereof) or methoxy (particularly fluorine or methyl);

provided that $R^{12}$ and each $R^{13}$ are such that the 5-membered heteroaromatic monocyclic ring Het is optionally substituted with one or two substituents.

In a further particular embodiment, when Het is an optionally substituted 5-membered heteroaromatic monocyclic ring containing one, two or three (e.g. one or two) ring heteroatoms independently being N, O or S, wherein no more than one of the 5-membered ring heteroatoms is O or S; and Het is of sub-formula (b1), (b2), (b3), (b4) or (b5); then Het is one of the following sub-formulae, in which each $R^{12}$ independently is hydrogen or methyl, and each $R^{13}$ independently is hydrogen or methyl:

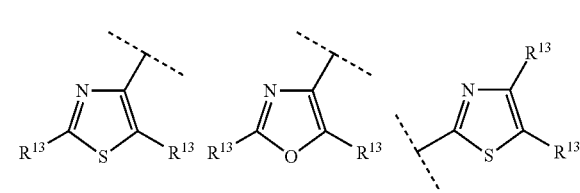

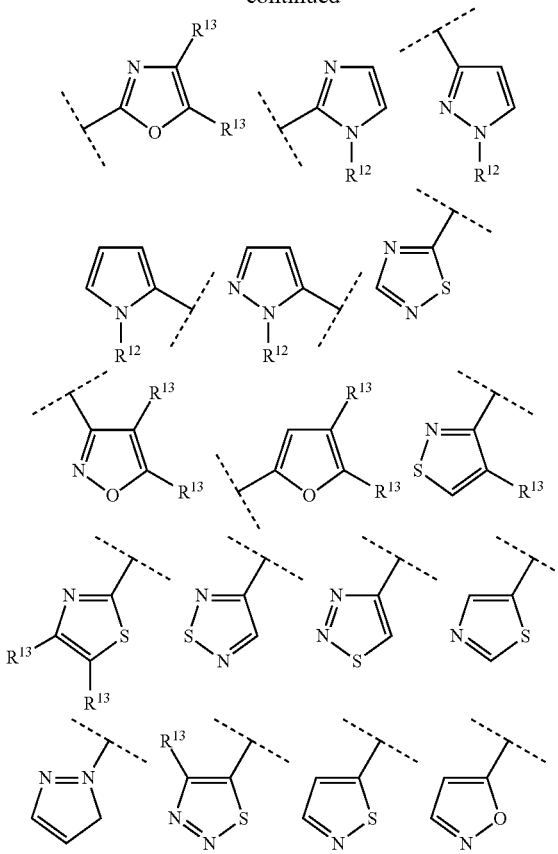

In a more particular embodiment, when Het is an optionally substituted 5-membered heteroaromatic monocyclic ring containing one, two or three (e.g. one or two) ring heteroatoms independently being N, O or S, wherein no more than one of the 5-membered ring heteroatoms is O or S; and Het is of sub-formula (b1), (b2), (b3) or (b4); then Het is one of the following sub-formulae, in which each $R^{12}$ independently is hydrogen or methyl, and each $R^{13}$ independently is hydrogen or methyl:

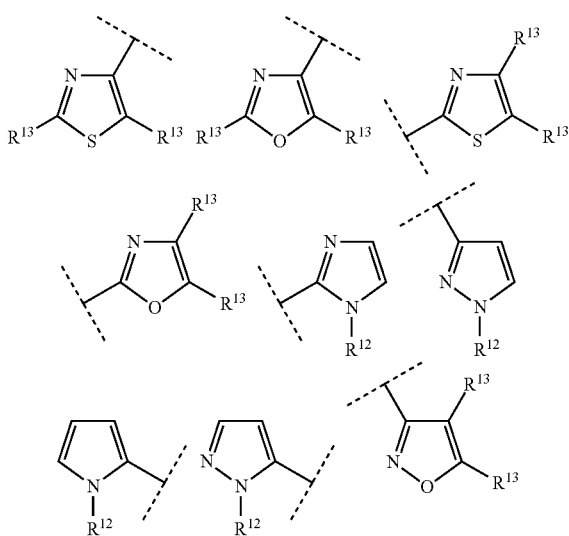

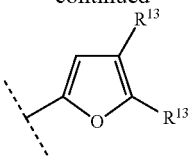

Preferably, when Het is one of the above sub-formulae containing two $R^{13}$ groups, then one of the $R^{13}$ is hydrogen, and the other of the $R^{13}$ is hydrogen or methyl. In one particular embodiment, both $R^{13}$ are hydrogen.

In a particular embodiment, when Het is an optionally substituted 5-membered heteroaromatic monocyclic ring, then Het is as defined in any one of the Examples herein.

Preferably, when Het is an optionally substituted 5-membered heteroaromatic monocyclic ring, then Het is

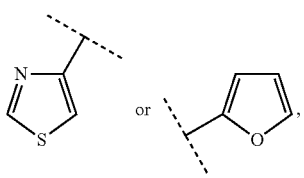

or more preferably

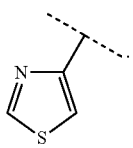

In one embodiment, when Het is an optionally substituted a 9 or 10-membered heteroaromatic bicyclic ring containing one, two or three (e.g. one or two) ring nitrogen atoms, then Het is an optionally substiuted a 9 or 10-membered heteroaromatic bicyclic ring containing one ring nitrogen atom, preferably an unsubstiuted a 9 or 10-membered heteroaromatic bicyclic ring containing one ring nitrogen atom; In a particular embodiment, when Het is an optionally substituted a 9 or 10-membered heteroaromatic bicyclic ring containing one, two or three (e.g. one or two) ring nitrogen atoms; then Het is of sub-formula (c1) or (c2):

(c1)

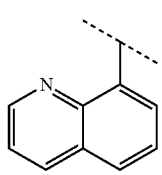

(c2)

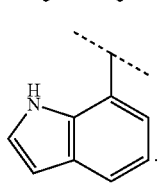

Therefore, preferably, A is 4-fluorophenyl, or A is Het, wherein Het is a 6-membered heteroaromatic monocyclic ring of sub-formula (a1), (a2), (a3), (a4), (a5) or (a6):

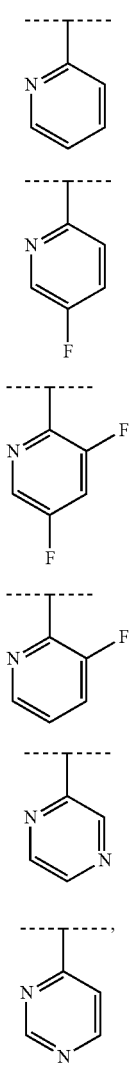

(a1)
(a2)
(a3)
(a4)
(a5)
(a6)

or Het is a 5-membered heteroaromatic monocyclic ring which is

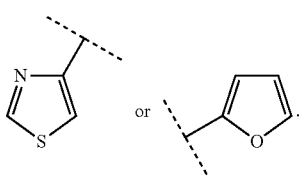

In a particular embodiment, $R^1$ is hydrogen, chlorine, fluorine, $C_1$fluoroalkyl (e.g. —$CF_3$), cyano or methyl. More particularly, $R^1$ is chlorine, fluorine, $C_1$fluoroalkyl (e.g. —$CF_3$), or methyl. Still more particularly, $R^1$ is chlorine, fluorine or methyl. Yet more particularly, $R^1$ is chlorine or fluorine.

Preferably, $R^1$ is chlorine.

In a particular embodiment, $R^2$ is hydrogen, fluorine, chlorine, $C_1$fluoroalkyl (e.g. —$CF_3$), or methyl.

Preferably, $R^2$ is hydrogen, fluorine, chlorine, —$CF_3$ or methyl; in particular hydrogen, fluorine, chlorine or —$CF_3$.

In one embodiment, $R^2$ is chlorine or —$CF_3$.

In one embodiment, $R^3$ is hydrogen, fluorine or chlorine; especially $R^3$ is hydrogen or fluorine.

In a particular embodiment, $R^5$ is hydrogen, fluorine or chlorine. More particularly, $R^5$ is hydrogen or chlorine.

Preferably, $R^5$ is hydrogen.

In one embodiment, when A is Het or optionally substituted phenyl, then $R^1$ is hydrogen, chlorine, fluorine, bromine, $C_1$fluoroalkyl (e.g. —$CF_3$), cyano or $C_{1-3}$alkyl (e.g. methyl), and at least one of $R^1$, $R^2$ and $R^3$ is other than hydrogen.

In a particular embodiment,
$R^1$ is chlorine, fluorine or methyl;
$R^2$ is hydrogen, fluorine, chlorine, —$CF_3$ or methyl;
$R^3$ is hydrogen, fluorine or chlorine; and
$R^5$ is hydrogen, fluorine, chlorine or methyl;
wherein at least one of $R^2$ and $R^3$ is other than hydrogen; and wherein, when $R^5$ is fluorine, chlorine or methyl, then $R^2$ is hydrogen and $R^3$ is fluorine or chlorine.

In a more particular embodiment,
$R^1$ is chlorine, fluorine or methyl;
$R^2$ is hydrogen, fluorine, chlorine, —$CF_3$ or methyl;
$R^3$ is hydrogen, fluorine or chlorine; and
$R^5$ is hydrogen, fluorine or chlorine;
wherein at least one of $R^2$ and $R^3$ is other than hydrogen; and wherein, when $R^5$ is fluorine or chlorine, then $R^2$ is hydrogen and $R^3$ is fluorine or chlorine.

In a still more particular embodiment,
$R^1$ is chlorine;
$R^2$ is hydrogen, fluorine, chlorine, —$CF_3$ or methyl;
$R^3$ is hydrogen, fluorine or chlorine; and
$R^5$ is hydrogen, fluorine, or chlorine (preferably hydrogen);
wherein at least one of $R^2$ and $R^3$ is other than hydrogen; and wherein, when $R^5$ is fluorine or chlorine, then $R^2$ is hydrogen and $R^3$ is fluorine or chlorine.

Preferably,
$R^1$ is chlorine;
$R^2$ is hydrogen, fluorine, chlorine or —$CF_3$;
$R^3$ is hydrogen, fluorine or chlorine; and
$R^5$ is hydrogen;
wherein at least one of $R^2$ and $R^3$ is other than hydrogen, and wherein, when $R^3$ is chlorine then $R^2$ is hydrogen or fluorine.

In a particular embodiment,
$R^1$ is chlorine, $R^2$ is —$CF_3$, and $R^3$, $R^4$ and $R^5$ are hydrogen; or
$R^1$ is chlorine, $R^2$ is chlorine, and $R^3$, $R^4$ and $R^5$ are hydrogen; or
$R^1$ is chlorine, $R^2$, $R^4$ and $R^5$ are hydrogen, and $R^3$ is chlorine; or
$R^1$ is chlorine, $R^2$, $R^4$ and $R^5$ are hydrogen, and $R^3$ is fluorine; or
$R^1$ is chlorine, $R^2$ is methyl, and $R^3$, $R^4$ and $R^5$ are hydrogen; or
$R^1$ is chlorine, $R^2$ and $R^4$ hydrogen, and $R^3$ and $R^5$ are chlorine; or
$R^1$ is chlorine, $R^2$ is chlorine, $R^3$ is fluorine, and $R^4$ and $R^5$ are hydrogen; or
$R^1$ is chlorine, $R^2$ is fluorine, $R^3$ is chlorine, and $R^4$ and $R^5$ are hydrogen; or
$R^1$ is chlorine, $R^2$ and $R^3$ are fluorine, and $R^4$ and $R^5$ are hydrogen; or
$R^1$ is chlorine, $R^2$ is —$CF_3$, $R^3$ is fluorine, and $R^4$ and $R^5$ are hydrogen; or
$R^1$ is fluorine, $R^2$ is —$CF_3$, and $R^3$, $R^4$ and $R^5$ are hydrogen; or
$R^1$ is fluorine, $R^2$ is chlorine, and $R^3$, $R^4$ and $R^5$ are hydrogen; or R¹ is fluorine, R², R⁴ and R⁵ are hydrogen, and R³ is chlorine; or
R¹ is methyl, R², R⁴ and R⁵ are hydrogen, and R³ is fluorine; or
R¹ is methyl, R² is —CF₃, and R³, R⁴ and R⁵ are hydrogen; or
R¹ is chlorine, R², R³, R⁴ and R⁵ are hydrogen, and A is Het or optionally substituted phenyl; or
R¹ is hydrogen, R² is —CF₃, R³ is fluorine, R⁴ and R⁵ are hydrogen, and A is Het or optionally substituted phenyl; or
R¹ is hydrogen, R² is —CF₃, R³ is chlorine, R⁴ and R⁵ are hydrogen, and A is Het or optionally substituted phenyl; or
R¹ is hydrogen, R² is chlorine, R³ is fluorine, R⁴ and R⁵ are hydrogen, and A is Het or optionally substituted phenyl.

Most preferably,
R¹ is chlorine, R² is —CF₃, and R³, R⁴ and R⁵ are hydrogen; or
R¹ is chlorine, R² is chlorine, and R³, R⁴ and R⁵ are hydrogen; or
R¹ is chlorine, R², R⁴ and R⁵ are hydrogen, and R³ is chlorine; or
R¹ is chlorine, R², R⁴ and R⁵ are hydrogen, and R³ is fluorine.

In a particular embodiment, R⁶ and R⁷ independently are hydrogen or methyl; or R⁶ and R⁷ are taken together and are —(CH₂)₂—O—(CH₂)₂— or —(CH₂)ₙ₁—, wherein n1 is 3, 4, 5 or 6 (in particular 3, 4 or 5).

In a particular embodiment, n1 is 3, 4 or 5.

In one particular embodiment of the invention, there is provided a compound of formula (I) or a pharmaceutically acceptable salt thereof, which is:
a compound or salt, named in and/or whose formula is illustrated in any one of the Examples (e.g. any one of Examples 1 to 110), as the compound or a pharmaceutically acceptable salt thereof (for example as the compound or a hydrochloride salt thereof, or in particular as the compound).

Therefore, according to one particular aspect of the invention, there is provided a compound or a pharmaceutically acceptable salt thereof, which is:
3-bromo-7-{[2-chloro-3-(trifluoromethyl)phenyl]carbonyl}-5,6,7,8-tetrahydro[1,2,4]triazolo[4,3-a]pyrazine,
7-{[2-chloro-3-(trifluoromethyl)phenyl]carbonyl}-3-(trifluoromethyl)-5,6,7,8-tetrahydro[1,2,4]triazolo[4,3-a]pyrazine,
7-{[2-chloro-3-(trifluoromethyl)phenyl]carbonyl}-5,6,7,8-tetrahydro[1,2,4]triazolo[4,3-a]pyrazine,
7-{[2-chloro-3-(trifluoromethyl)phenyl]carbonyl}-3-ethyl-5,6,7,8-tetrahydro[1,2,4]triazolo[4,3-a]pyrazine,
7-[(2,3-dichlorophenyl)carbonyl]-3-ethyl-5,6,7,8-tetrahydro[1,2,4]triazolo[4,3-a]pyrazine,
3-bromo-7-[(2,3-dichlorophenyl)carbonyl]-5,6,7,8-tetrahydro[1,2,4]triazolo[4,3-a]pyrazine,
3-bromo-7-[(2,4-dichlorophenyl)carbonyl]-5,6,7,8-tetrahydro[1,2,4]triazolo[4,3-a]pyrazine,
3-bromo-7-[(2,4,6-trichlorophenyl)carbonyl]-5,6,7,8-tetrahydro[1,2,4]triazolo[4,3-a]pyrazine,
3-bromo-7-{[2-fluoro-3-(trifluoromethyl)phenyl]carbonyl}-5,6,7,8-tetrahydro[1,2,4]triazolo[4,3-a]pyrazine,
7-{[2-chloro-3-(trifluoromethyl)phenyl]carbonyl}-3-(4-pyridinyl)-5,6,7,8-tetrahydro[1,2,4]triazolo[4,3-a]pyrazine,
7-{[2-chloro-3-(trifluoromethyl)phenyl]carbonyl}-3-(2-pyridinyl)-5,6,7,8-tetrahydro[1,2,4]triazolo[4,3-a]pyrazine,
7-{[2-chloro-3-(trifluoromethyl)phenyl]carbonyl}-3-(4-pyrimidinyl)-5,6,7,8-tetrahydro[1,2,4]triazolo[4,3-a]pyrazine,
7-{[2-chloro-3-(trifluoromethyl)phenyl]carbonyl}-3-phenyl-5,6,7,8-tetrahydro[1,2,4]triazolo[4,3-a]pyrazine,
7-{[2-chloro-3-(trifluoromethyl)phenyl]carbonyl}-3-(4-fluorophenyl)-5,6,7,8-tetrahydro[1,2,4]triazolo[4,3-a]pyrazine,
7-{[2-chloro-3-(trifluoromethyl)phenyl]carbonyl}-3-methyl-5,6,7,8-tetrahydro[1,2,4]triazolo[4,3-a]pyrazine,
7-{[2-chloro-3-(trifluoromethyl)phenyl]carbonyl}-3-(3-pyridinyl)-5,6,7,8-tetrahydro[1,2,4]triazolo[4,3-a]pyrazine,
7-{[2-chloro-3-(trifluoromethyl)phenyl]carbonyl}-3-(methyloxy)-5,6,7,8-tetrahydro[1,2,4]triazolo[4,3-a]pyrazine,
7-{[2-chloro-3-(trifluoromethyl)phenyl]carbonyl}-3-(4-morpholinyl)-5,6,7,8-tetrahydro[1,2,4]triazolo[4,3-a]pyrazine,
7-{[2-chloro-3-(trifluoromethyl)phenyl]carbonyl}-3-(1-pyrrolidinyl)-5,6,7,8-tetrahydro[1,2,4]triazolo[4,3-a]pyrazine,
7-{[2-chloro-3-(trifluoromethyl)phenyl]carbonyl}-N,N-dimethyl-5,6,7,8-tetrahydro[1,2,4]triazolo[4,3-a]pyrazin-3-amine,
7-{[2-chloro-3-(trifluoromethyl)phenyl]carbonyl}-N-methyl-5,6,7,8-tetrahydro[1,2,4]triazolo[4,3-a]pyrazin-3-amine,
3-(1-azetidinyl)-7-{[2-chloro-3-(trifluoromethyl)phenyl]carbonyl}-5,6,7,8-tetrahydro[1,2,4]triazolo[4,3-a]pyrazine,
7-{[2-chloro-3-(trifluoromethyl)phenyl]carbonyl}-3-(1-piperidinyl)-5,6,7,8-tetrahydro[1,2,4]triazolo[4,3-a]pyrazine,
7-{[2-chloro-3-(trifluoromethyl)phenyl]carbonyl}-3-(2,4-difluorophenyl)-5,6,7,8-tetrahydro[1,2,4]triazolo[4,3-a]pyrazine,
7-{[2-chloro-3-(trifluoromethyl)phenyl]carbonyl}-3-(1,1-dimethylethyl)-5,6,7,8-tetrahydro[1,2,4]triazolo[4,3-a]pyrazine,
7-{[2-chloro-3-(trifluoromethyl)phenyl]carbonyl}-3-(6-methyl-2-pyridinyl)-5,6,7,8-tetrahydro[1,2,4]triazolo[4,3-a]pyrazine,
7-{[2-chloro-3-(trifluoromethyl)phenyl]carbonyl}-3-(1-methyl-1H-pyrazol-3-yl)-5,6,7,8-tetrahydro[1,2,4]triazolo[4,3-a]pyrazine,
7-{[2-chloro-3-(trifluoromethyl)phenyl]carbonyl}-3-(3-methyl-2-pyridinyl)-5,6,7,8-tetrahydro[1,2,4]triazolo[4,3-a]pyrazine,
7-{[2-chloro-3-(trifluoromethyl)phenyl]carbonyl}-3-(1-methyl-1H-pyrrol-2-yl)-5,6,7,8-tetrahydro[1,2,4]triazolo[4,3-a]pyrazine,
7-[(2-chloro-4-fluorophenyl)carbonyl]-3-phenyl-5,6,7,8-tetrahydro[1,2,4]triazolo[4,3-a]pyrazine,
7-[(2-chloro-4-fluorophenyl)carbonyl]-3-(3-fluoro-2-pyridinyl)-5,6,7,8-tetrahydro[1,2,4]triazolo[4,3-a]pyrazine,
7-[(2-chloro-4-fluorophenyl)carbonyl]-3-(3-methyl-2-pyridinyl)-5,6,7,8-tetrahydro[1,2,4]triazolo[4,3-a]pyrazine,
7-[(2-chloro-4-fluorophenyl)carbonyl]-3-(4-pyrimidinyl)-5,6,7,8-tetrahydro[1,2,4]triazolo[4,3-a]pyrazine,
7-[(2,3-dichlorophenyl)carbonyl]-3-(2-pyrazinyl)-5,6,7,8-tetrahydro[1,2,4]triazolo[4,3-a]pyrazine,
7-{[2-chloro-3-(trifluoromethyl)phenyl]carbonyl}-3-(5-methyl-3-isoxazolyl)-5,6,7,8-tetrahydro[1,2,4]triazolo[4,3-a]pyrazine,
7-[(2-chloro-4-fluorophenyl)carbonyl]-3-(2-pyridinyl)-5,6,7,8-tetrahydro[1,2,4]triazolo[4,3-a]pyrazine,
7-{[2-chloro-3-(trifluoromethyl)phenyl]carbonyl}-3-(1H-pyrrol-2-yl)-5,6,7,8-tetrahydro[1,2,4]triazolo[4,3-a]pyrazine,
7-[(2-chloro-4-fluorophenyl)carbonyl]-3-(3-pyridinyl)-5,6,7,8-tetrahydro[1,2,4]triazolo[4,3-a]pyrazine,
7-[(2-chloro-4-fluorophenyl)carbonyl]-3-(5-fluoro-2-pyridinyl)-5,6,7,8-tetrahydro[1,2,4]triazolo[4,3-a]pyrazine, 7-[(2-chloro-4-fluorophenyl)carbonyl]-3-(6-fluoro-2-pyridinyl)-5,6,7,8-tetrahydro[1,2,4]triazolo[4,3-a]pyrazine,
7-{[2-chloro-3-(trifluoromethyl)phenyl]carbonyl}-3-(1,3-thiazol-4-yl)-5,6,7,8-tetrahydro[1,2,4]triazolo[4,3-a]pyrazine,
7-[(2,3-dichlorophenyl)carbonyl]-3-(2-pyridinyl)-5,6,7,8-tetrahydro[1,2,4]triazolo[4,3-a]pyrazine,
7-{[2-chloro-3-(trifluoromethyl)phenyl]carbonyl}-3-(3-pyridazinyl)-5,6,7,8-tetrahydro[1,2,4]triazolo[4,3-a]pyrazine,
7-{[2-chloro-3-(trifluoromethyl)phenyl]carbonyl}-3-(5-fluoro-2-pyridinyl)-5,6,7,8-tetrahydro[1,2,4]triazolo[4,3-a]pyrazine,
7-{[2-chloro-3-(trifluoromethyl)phenyl]carbonyl}-3-(2-pyrazinyl)-5,6,7,8-tetrahydro[1,2,4]triazolo[4,3-a]pyrazine,
7-[(2-chloro-4-fluorophenyl)carbonyl]-3-(2-pyrimidinyl)-5,6,7,8-tetrahydro[1,2,4]triazolo[4,3-a]pyrazine,
7-[(2,3-dichlorophenyl)carbonyl]-3-(1-methyl-1H-pyrrol-2-yl)-5,6,7,8-tetrahydro[1,2,4]triazolo[4,3-a]pyrazine,
7-[(2,3-dichlorophenyl)carbonyl]-3-(5-methyl-3-isoxazolyl)-5,6,7,8-tetrahydro[1,2,4]triazolo[4,3-a]pyrazine,
7-{[2-chloro-3-(trifluoromethyl)phenyl]carbonyl}-3-(2-pyrimidinyl)-5,6,7,8-tetrahydro[1,2,4]triazolo[4,3-a]pyrazine,
7-{[2-chloro-3-(trifluoromethyl)phenyl]carbonyl}-3-(5-methyl-2-pyridinyl)-5,6,7,8-tetrahydro[1,2,4]triazolo[4,3-a]pyrazine,
7-{[2-chloro-3-(trifluoromethyl)phenyl]carbonyl}-3-(3-fluoro-2-pyridinyl)-5,6,7,8-tetrahydro[1,2,4]triazolo[4,3-a]pyrazine,
7-{[2-chloro-3-(trifluoromethyl)phenyl]carbonyl}-3-(6-fluoro-2-pyridinyl)-5,6,7,8-tetrahydro[1,2,4]triazolo[4,3-a]pyrazine,
7-[(2,3-dichlorophenyl)carbonyl]-3-(5-fluoro-2-pyridinyl)-5,6,7,8-tetrahydro[1,2,4]triazolo[4,3-a]pyrazine,
7-[(2,3-dichlorophenyl)carbonyl]-3-(6-fluoro-2-pyridinyl)-5,6,7,8-tetrahydro[1,2,4]triazolo[4,3-a]pyrazine,
7-{[2-chloro-3-(trifluoromethyl)phenyl]carbonyl}-3-(4-methyl-2-pyridinyl)-5,6,7,8-tetrahydro[1,2,4]triazolo[4,3-a]pyrazine,
7-[(2,3-dichlorophenyl)carbonyl]-3-(3-pyridazinyl)-5,6,7,8-tetrahydro[1,2,4]triazolo[4,3-a]pyrazine,
7-[(2,3-dichlorophenyl)carbonyl]-3-(2-pyrimidinyl)-5,6,7,8-tetrahydro[1,2,4]triazolo[4,3-a]pyrazine,
7-[(2-chloro-4-fluorophenyl)carbonyl]-3-(3-pyridazinyl)-5,6,7,8-tetrahydro[1,2,4]triazolo[4,3-a]pyrazine,
7-[(2,3-dichlorophenyl)carbonyl]-3-(5-methyl-2-pyridinyl)-5,6,7,8-tetrahydro[1,2,4]triazolo[4,3-a]pyrazine,
7-[(2,3-dichlorophenyl)carbonyl]-3-(3-pyridinyl)-5,6,7,8-tetrahydro[1,2,4]triazolo[4,3-a]pyrazine,
7-[(2,3-dichlorophenyl)carbonyl]-3-(4-pyrimidinyl)-5,6,7,8-tetrahydro[1,2,4]triazolo[4,3-a]pyrazine,
7-[(2,3-dichlorophenyl)carbonyl]-3-(1-methyl-1H-pyrazol-3-yl)-5,6,7,8-tetrahydro[1,2,4]triazolo[4,3-a]pyrazine,
7-[(2,3-dichlorophenyl)carbonyl]-3-(1H-pyrrol-2-yl)-5,6,7,8-tetrahydro[1,2,4]triazolo[4,3-a]pyrazine,
7-{[2-chloro-3-(trifluoromethyl)phenyl]carbonyl}-3-(2-methyl-3-pyridinyl)-5,6,7,8-tetrahydro[1,2,4]triazolo[4,3-a]pyrazine,
7-[(2,3-dichlorophenyl)carbonyl]-3-(3-methyl-2-pyridinyl)-5,6,7,8-tetrahydro[1,2,4]triazolo[4,3-a]pyrazine,
7-[(2,3-dichlorophenyl)carbonyl]-3-(1,3-thiazol-4-yl)-5,6,7,8-tetrahydro[1,2,4]triazolo[4,3-a]pyrazine,
7-{[2-chloro-3-(trifluoromethyl)phenyl]carbonyl}-3-(1-methyl-1H-pyrazol-5-yl)-5,6,7,8-tetrahydro[1,2,4]triazolo[4,3-a]pyrazine,
7-[(2,3-dichlorophenyl)carbonyl]-3-(6-methyl-2-pyridinyl)-5,6,7,8-tetrahydro[1,2,4]triazolo[4,3-a]pyrazine,
7-[(2,3-dichlorophenyl)carbonyl]-3-phenyl-5,6,7,8-tetrahydro[1,2,4]triazolo[4,3-a]pyrazine,
7-[(2-chloro-4-fluorophenyl)carbonyl]-3-(5-methyl-3-isoxazolyl)-5,6,7,8-tetrahydro[1,2,4]triazolo[4,3-a]pyrazine,
7-[(2-chloro-4-fluorophenyl)carbonyl]-3-(1-methyl-1H-pyrazol-3-yl)-5,6,7,8-tetrahydro[1,2,4]triazolo[4,3-a]pyrazine,
7-[(2,3-dichlorophenyl)carbonyl]-3-(2-methyl-3-pyridinyl)-5,6,7,8-tetrahydro[1,2,4]triazolo[4,3-a]pyrazine,
7-[(2-chloro-4-fluorophenyl)carbonyl]-3-(2-methyl-3-pyridinyl)-5,6,7,8-tetrahydro[1,2,4]triazolo[4,3-a]pyrazine,
7-[(2-chlorophenyl)carbonyl]-3-(2-pyridinyl)-5,6,7,8-tetrahydro[1,2,4]triazolo[4,3-a]pyrazine,
7-[(2,4-dichlorophenyl)carbonyl]-3-(2-pyridinyl)-5,6,7,8-tetrahydro[1,2,4]triazolo[4,3-a]pyrazine,
3-bromo-7-[(2-chloro-4-fluorophenyl)carbonyl]-5,6,7,8-tetrahydro[1,2,4]triazolo[4,3-a]pyrazine,
7-{[2-chloro-3-(trifluoromethyl)phenyl]carbonyl}-3-(2-furanyl)-5,6,7,8-tetrahydro[1,2,4]triazolo[4,3-a]pyrazine,
7-{[2-(methyloxy)phenyl]carbonyl}-3-(2-pyridinyl)-5,6,7,8-tetrahydro[1,2,4]triazolo[4,3-a]pyrazine,
7-[(2,4-difluorophenyl)carbonyl]-3-(2-pyridinyl)-5,6,7,8-tetrahydro[1,2,4]triazolo[4,3-a]pyrazine,
7-[(2-chloro-6-fluorophenyl)carbonyl]-3-(2-pyridinyl)-5,6,7,8-tetrahydro[1,2,4]triazolo[4,3-a]pyrazine,
7-[(3-chlorophenyl)carbonyl]-3-(2-pyridinyl)-5,6,7,8-tetrahydro[1,2,4]triazolo[4,3-a]pyrazine,
7-[(2,3-dichlorophenyl)carbonyl]-3-(1-methyl-1H-pyrazol-5-yl)-5,6,7,8-tetrahydro[1,2,4]triazolo[4,3-a]pyrazine,
7-[(2-chloro-4-fluorophenyl)carbonyl]-3-(1-methyl-1H-pyrrol-2-yl)-5,6,7,8-tetrahydro[1,2,4]triazolo[4,3-a]pyrazine,
7-{[2-chloro-3-(trifluoromethyl)phenyl]carbonyl}-3-(3,5-difluoro-2-pyridinyl)-5,6,7,8-tetrahydro[1,2,4]triazolo[4,3-a]pyrazine,
7-[(2-chloro-4-fluorophenyl)carbonyl]-3-(3,5-difluoro-2-pyridinyl)-5,6,7,8-tetrahydro[1,2,4]triazolo[4,3-a]pyrazine,
7-[(2-chloro-4-fluorophenyl)carbonyl]-3-(2-pyrazinyl)-5,6,7,8-tetrahydro[1,2,4]triazolo[4,3-a]pyrazine,
3-(2-pyridinyl)-7-{[3-(trifluoromethyl)phenyl]carbonyl}-5,6,7,8-tetrahydro[1,2,4]triazolo[4,3-a]pyrazine,
2-{[3-(2-pyridinyl)-5,6-dihydro[1,2,4]triazolo[4,3-a]pyrazin-7(8H)-yl]carbonyl}benzonitrile,
7-[(2,3-difluorophenyl)carbonyl]-3-(2-pyridinyl)-5,6,7,8-tetrahydro[1,2,4]triazolo[4,3-a]pyrazine,
7-[(2,6-dichlorophenyl)carbonyl]-3-(2-pyridinyl)-5,6,7,8-tetrahydro[1,2,4]triazolo[4,3-a]pyrazine,
7-[(2-chloro-4-fluorophenyl)carbonyl]-3-(1,3-thiazol-4-yl)-5,6,7,8-tetrahydro[1,2,4]triazolo[4,3-a]pyrazine,
7-{[2-fluoro-3-(trifluoromethyl)phenyl]carbonyl}-3-(2-pyridinyl)-5,6,7,8-tetrahydro[1,2,4]triazolo[4,3-a]pyrazine,
7-[(2,4-dichlorophenyl)carbonyl]-3-(2-pyrazinyl)-5,6,7,8-tetrahydro[1,2,4]triazolo[4,3-a]pyrazine,
7-[(2,4-dichlorophenyl)carbonyl]-3-(3-fluoro-2-pyridinyl)-5,6,7,8-tetrahydro[1,2,4]triazolo[4,3-a]pyrazine,
7-{[4-fluoro-2-(trifluoromethyl)phenyl]carbonyl}-3-(2-pyridinyl)-5,6,7,8-tetrahydro[1,2,4]triazolo[4,3-a]pyrazine,
7-[(2,4-dichlorophenyl)carbonyl]-3-(5-fluoro-2-pyridinyl)-5,6,7,8-tetrahydro[1,2,4]triazolo[4,3-a]pyrazine,
7-[(4-chloro-2-fluorophenyl)carbonyl]-3-(2-pyridinyl)-5,6,7,8-tetrahydro[1,2,4]triazolo[4,3-a]pyrazine,
7-[(2,4-dichlorophenyl)carbonyl]-3-(1,3-thiazol-4-yl)-5,6,7,8-tetrahydro[1,2,4]triazolo[4,3-a]pyrazine,
7-[(2,3-dichlorophenyl)carbonyl]-3-(2,4-difluorophenyl)-5,6,7,8-tetrahydro[1,2,4]triazolo[4,3-a]pyrazine, 7-[(2,3-dichlorophenyl)carbonyl]-3-(4-fluorophenyl)-5,6,7,8-tetrahydro[1,2,4]triazolo[4,3-a]pyrazine, 7-[(2,4-dichlorophenyl)carbonyl]-3-(4-fluorophenyl)-5,6,7,8-tetrahydro[1,2,4]triazolo[4,3-a]pyrazine, 7-[(2,4-dichlorophenyl)carbonyl]-3-(2,4-difluorophenyl)-5,6,7,8-tetrahydro[1,2,4]triazolo[4,3-a]pyrazine, 7-[(2,4-dichlorophenyl)carbonyl]-3-(4-pyrimidinyl)-5,6,7,8-tetrahydro[1,2,4]triazolo[4,3-a]pyrazine, 7-[(2-chlorophenyl)carbonyl]-3-(1,3-thiazol-4-yl)-5,6,7,8-tetrahydro[1,2,4]triazolo[4,3-a]pyrazine, 7-{[4-chloro-3-(trifluoromethyl)phenyl]carbonyl}-3-(2-pyrazinyl)-5,6,7,8-tetrahydro[1,2,4]triazolo[4,3-a]pyrazine, 7-[(3-chloro-4-fluorophenyl)carbonyl]-3-(2-pyrazinyl)-5,6,7,8-tetrahydro[1,2,4]triazolo[4,3-a]pyrazine, 7-[(4-chloro-2-fluorophenyl)carbonyl]-3-(2-pyrazinyl)-5,6,7,8-tetrahydro[1,2,4]triazolo[4,3-a]pyrazine, 7-[(4-fluoro-2-methylphenyl)carbonyl]-3-(2-pyrazinyl)-5,6,7,8-tetrahydro[1,2,4]triazolo[4,3-a]pyrazine, 7-{[4-fluoro-3-(trifluoromethyl)phenyl]carbonyl}-3-(2-pyrazinyl)-5,6,7,8-tetrahydro[1,2,4]triazolo[4,3-a]pyrazine, 3-bromo-7-[(2-chloro-4-fluorophenyl)carbonyl]-5,6,7,8-tetrahydro[1,2,4]triazolo[4,3-a]pyrazine, 7-[(2,4-dichloro-3-fluorophenyl)carbonyl]-3-(5-fluoro-2-pyridinyl)-5,6,7,8-tetrahydro[1,2,4]triazolo[4,3-a]pyrazine, 7-[(2,4-dichloro-3-fluorophenyl)carbonyl]-3-(2-pyrazinyl)-5,6,7,8-tetrahydro[1,2,4]triazolo[4,3-a]pyrazine, 7-[(2,4-dichloro-3-fluorophenyl)carbonyl]-3-(4-pyrimidinyl)-5,6,7,8-tetrahydro[1,2,4]triazolo[4,3-a]pyrazine, 7-[(2,3-dichloro-4-fluorophenyl)carbonyl]-3-(2-pyrazinyl)-5,6,7,8-tetrahydro[1,2,4]triazolo[4,3-a]pyrazine, or 7-[(2,3-dichloro-4-fluorophenyl)carbonyl]-3-(5-fluoro-2-pyridinyl)-5,6,7,8-tetrahydro[1,2,4]triazolo[4,3-a]pyrazine;

or a pharmaceutically acceptable salt thereof.

According to another particular aspect of the invention, there is provided a compound or a pharmaceutically acceptable salt thereof, which is:

E116 7-[(2-chlorophenyl)carbonyl]-3-(4-pyrimidinyl)-5,6,7,8-tetrahydro[1,2,4]triazolo[4,3-a]pyrazine, E117 7-[(2-chlorophenyl)carbonyl]-3-(2-furanyl)-5,6,7,8-tetrahydro[1,2,4]triazolo[4,3-a]pyrazine, E118 7-[(2-chlorophenyl)carbonyl]-3-(5-fluoro-2-pyridinyl)-5,6,7,8-tetrahydro[1,2,4]triazolo[4,3-a]pyrazine, E119 7-[(2-chlorophenyl)carbonyl]-3-(4-fluorophenyl)-5,6,7,8-tetrahydro[1,2,4]triazolo[4,3-a]pyrazine, E120 7-[(2-chlorophenyl)carbonyl]-3-(2-pyrazinyl)-5,6,7,8-tetrahydro[1,2,4]triazolo[4,3-a]pyrazine, E121 7-[(2-chlorophenyl)carbonyl]-3-(3-fluoro-2-pyridinyl)-5,6,7,8-tetrahydro[1,2,4]triazolo[4,3-a]pyrazine, E122 3-(2-pyridinyl)-7-{[2-(trifluoromethyl)phenyl]carbonyl}-5,6,7,8-tetrahydro[1,2,4]triazolo[4,3-a]pyrazine, E123 7-[(2-chloro-4-fluorophenyl)carbonyl]-3-(3-fluorophenyl)-5,6,7,8-tetrahydro[1,2,4]triazolo[4,3-a]pyrazine, E124 7-[(2-chloro-4-fluorophenyl)carbonyl]-3-(3,4-difluorophenyl)-5,6,7,8-tetrahydro[1,2,4]triazolo[4,3-a]pyrazine, E125 7-[(2-chloro-4-fluorophenyl)carbonyl]-3-[3-(methyloxy)phenyl]-5,6,7,8-tetrahydro[1,2,4]triazolo[4,3-a]pyrazine, E126 7-[(2-chloro-4-fluorophenyl)carbonyl]-3-(3-chlorophenyl)-5,6,7,8-tetrahydro[1,2,4]triazolo[4,3-a]pyrazine, E127 7-[(2-chloro-4-fluorophenyl)carbonyl]-3-[2-(methyloxy)phenyl]-5,6,7,8-tetrahydro[1,2,4]triazolo[4,3-a]pyrazine, E128 2-{7-[(2-chloro-4-fluorophenyl)carbonyl]-5,6,7,8-tetrahydro[1,2,4]triazolo[4,3-a]pyrazin-3-yl}phenol, E129 8-{7-[(2-chloro-4-fluorophenyl)carbonyl]-5,6,7,8-tetrahydro[1,2,4]triazolo[4,3-a]pyrazin-3-yl}quinoline, E130 7-[(2-chloro-4-fluorophenyl)carbonyl]-3-(2,3-dichlorophenyl)-5,6,7,8-tetrahydro[1,2,4]triazolo[4,3-a]pyrazine, E131 7-[(2-chloro-4-fluorophenyl)carbonyl]-3-(2,3-difluorophenyl)-5,6,7,8-tetrahydro[1,2,4]triazolo[4,3-a]pyrazine, E132 7-[(2-chloro-4-fluorophenyl)carbonyl]-3-(1H-indol-7-yl)-5,6,7,8-tetrahydro[1,2,4]triazolo[4,3-a]pyrazine, E133 7-{[2-chloro-3-(trifluoromethyl)phenyl]carbonyl}-3-cyclopropyl-5,6,7,8-tetrahydro[1,2,4]triazolo[4,3-a]pyrazine, E134 7-{[2-chloro-3-(trifluoromethyl)phenyl]carbonyl}-3-propyl-5,6,7,8-tetrahydro[1,2,4]triazolo[4,3-a]pyrazine, E135 7-{[2-chloro-3-(trifluoromethyl)phenyl]carbonyl}-3-cyclohexyl-5,6,7,8-tetrahydro[1,2,4]triazolo[4,3-a]pyrazine, E136 7-[(2-chloro-4-fluorophenyl)carbonyl]-3-(2-methyl-1,3-thiazol-4-yl)-5,6,7,8-tetrahydro[1,2,4]triazolo[4,3-a]pyrazine, E137 7-{[2-chloro-3-(trifluoromethyl)phenyl]carbonyl}-3-[2-(methyloxy)ethyl]-5,6,7,8-tetrahydro[1,2,4]triazolo[4,3-a]pyrazine, E138 2-(7-{[2-chloro-3-(trifluoromethyl)phenyl]carbonyl}-5,6,7,8-tetrahydro[1,2,4]triazolo[4,3-a]pyrazin-3-yl)phenol, E139 7-{[2-chloro-3-(trifluoromethyl)phenyl]carbonyl}-3-cyclopentyl-5,6,7,8-tetrahydro[1,2,4]triazolo[4,3-a]pyrazine, E140 7-[(2-chloro-4-fluorophenyl)carbonyl]-3-(1-methyl-1H-imidazol-2-yl)-5,6,7,8-tetrahydro[1,2,4]triazolo[4,3-a]pyrazine, E141 7-[(2-chloro-4-fluorophenyl)carbonyl]-3-(5-chloro-2-pyrazinyl)-5,6,7,8-tetrahydro[1,2,4]triazolo[4,3-a]pyrazine, E142 7-{[4-chloro-2-(trifluoromethyl)phenyl]carbonyl}-3-(2-pyrazinyl)-5,6,7,8-tetrahydro[1,2,4]triazolo[4,3-a]pyrazine, E143 7-[(2,4-dimethylphenyl)carbonyl]-3-(2-pyrazinyl)-5,6,7,8-tetrahydro[1,2,4]triazolo[4,3-a]pyrazine, E144 7-[(2-chloro-4-fluorophenyl)carbonyl]-3-(1,3-thiazol-2-yl)-5,6,7,8-tetrahydro[1,2,4]triazolo[4,3-a]pyrazine, E145 7-[(4-chloro-2-methylphenyl)carbonyl]-3-(2-pyrazinyl)-5,6,7,8-tetrahydro[1,2,4]triazolo[4,3-a]pyrazine, E146 7-[(3-chloro-4-fluoro-2-methylphenyl)carbonyl]-3-(2-pyrazinyl)-5,6,7,8-tetrahydro[1,2,4]triazolo[4,3-a]pyrazine, E147 7-[(2-bromo-4-fluorophenyl)carbonyl]-3-(2-pyrazinyl)-5,6,7,8-tetrahydro[1,2,4]triazolo[4,3-a]pyrazine, E148 7-{[4-methyl-2-(trifluoromethyl)phenyl]carbonyl}-3-(2-pyrazinyl)-5,6,7,8-tetrahydro[1,2,4]triazolo[4,3-a]pyrazine, E149 7-[(2,4-dichloro-3-fluorophenyl)carbonyl]-3-(1,3-thiazol-4-yl)-5,6,7,8-tetrahydro[1,2,4]triazolo[4,3-a]pyrazine, E150 2-{7-[(2,4-dichloro-3-fluorophenyl)carbonyl]-5,6,7,8-tetrahydro[1,2,4]triazolo[4,3-a]pyrazin-3-yl}-5-fluorophenol, E151 7-[(3,4-difluoro-2-methylphenyl)carbonyl]-3-(2-pyrazinyl)-5,6,7,8-tetrahydro[1,2,4]triazolo[4,3-a]pyrazine, E152 7-[(2,3-dichloro-4-methylphenyl)carbonyl]-3-(2-pyrazinyl)-5,6,7,8-tetrahydro[1,2,4]triazolo[4,3-a]pyrazine, E153 7-[(2-chloro-4-fluoro-3-methylphenyl)carbonyl]-3-(2-pyrazinyl)-5,6,7,8-tetrahydro[1,2,4]triazolo[4,3-a]pyrazine, E154 7-[(2,4-dichloro-3-methylphenyl)carbonyl]-3-(2-pyrazinyl)-5,6,7,8-tetrahydro[1,2,4]triazolo[4,3-a]pyrazine, E155 7-[(3,4-difluoro-2-methylphenyl)carbonyl]-3-(5-fluoro-2-pyridinyl)-5,6,7,8-tetrahydro[1,2,4]triazolo[4,3-a]pyrazine, E156 7-[(3-chloro-4-fluoro-2-methylphenyl)carbonyl]-3-(5-fluoro-2-pyridinyl)-5,6,7,8-tetrahydro[1,2,4]triazolo[4,3-a]pyrazine, E157 7-[(2,4-dichlorophenyl)carbonyl]-3-(5-isoxazolyl)-5,6,7,8-tetrahydro[1,2,4]triazolo[4,3-a]pyrazine, E158 7-[(2,4-dichlorophenyl)carbonyl]-3-(5-isothiazolyl)-5,6,7,8-tetrahydro[1,2,4]triazolo[4,3-a]pyrazine, E159 7-{[2-chloro-3-(trifluoromethyl)phenyl]carbonyl}-3-(5-methyl-2-furanyl)-5,6,7,8-tetrahydro[1,2,4]triazolo[4,3-a]pyrazine, E160 7-[(2,4-dichlorophenyl)carbonyl]-3-(1,2,5-thiadiazol-3-yl)-5,6,7,8-tetrahydro[1,2,4]triazolo[4,3-a]pyrazine, E161 7-[(2,4-dichlorophenyl)carbonyl]-3-(3-isoxazolyl)-5,6,7,8-tetrahydro[1,2,4]triazolo[4,3-a]pyrazine, E163 3-(7-{[2-chloro-3-(trifluoromethyl)phenyl]carbonyl}-5,6,7,8-tetrahydro[1,2,4]triazolo[4,3-a]pyrazin-3-yl)-2-pyridinol, E164 7-{[2-chloro-3-(trifluoromethyl)phenyl]carbonyl}-3-(1,2,4-thiadiazol-5-yl)-5,6,7,8-tetrahydro[1,2,4]triazolo[4,3-a]pyrazine, E165 7-[(2-chloro-4-fluorophenyl)carbonyl]-3-(5-fluoro-2-pyrazinyl)-5,6,7,8-tetrahydro[1,2,4]triazolo[4,3-a]pyrazine, E166 2-(7-{[2-chloro-3-(trifluoromethyl)phenyl]carbonyl}-5,6,7,8-tetrahydro[1,2,4]triazolo[4,3-a]pyrazin-3-yl)-3-pyridinol, E167 7-[(2,3-dichloro-4-fluorophenyl)carbonyl]-3-(5-methyl-2-furanyl)-5,6,7,8-tetrahydro[1,2,4]triazolo[4,3-a]pyrazine, E168 7-[(2,3-dichloro-4-fluorophenyl)carbonyl]-3-(3-pyridazinyl)-5,6,7,8-tetrahydro[1,2,4]triazolo[4,3-a]pyrazine, E169 7-[(2,3-dichloro-4-fluorophenyl)carbonyl]-3-(1,2,4-thiadiazol-5-yl)-5,6,7,8-tetrahydro[1,2,4]triazolo[4,3-a]pyrazine, E170 7-[(2,4-dichloro-3-fluorophenyl)carbonyl]-3-(3-fluoro-2-pyridinyl)-5,6,7,8-tetrahydro[1,2,4]triazolo[4,3-a]pyrazine, E171 3-{7-[(2,4-dichloro-3-fluorophenyl)carbonyl]-5,6,7,8-tetrahydro[1,2,4]triazolo[4,3-a]pyrazin-3-yl}-2-pyridino, E172 7-[(2,4-dichloro-3-fluorophenyl)carbonyl]-3-(4-methyl-2-pyridinyl)-5,6,7,8-tetrahydro[1,2,4]triazolo[4,3-a]pyrazine, E173 7-[(2,4-dichloro-3-fluorophenyl)carbonyl]-3-(2-pyridinyl)-5,6,7,8-tetrahydro[1,2,4]triazolo[4,3-a]pyrazine, E174 7-[(2,4-dichloro-3-fluorophenyl)carbonyl]-3-[4-(methyloxy)-2-pyridinyl]-5,6,7,8-tetrahydro[1,2,4]triazolo[4,3-a]pyrazine, E175 2-{7-[(2,4-dichloro-3-fluorophenyl)carbonyl]-5,6,7,8-tetrahydro[1,2,4]triazolo[4,3-a]pyrazin-3-yl}-3-pyridinol, E176 7-[(2,4-dichloro-3-fluorophenyl)carbonyl]-3-[6-(methyloxy)-2-pyridinyl]-5,6,7,8-tetrahydro[1,2,4]triazolo[4,3-a]pyrazine, E177 7-[(2,4-dichloro-3-fluorophenyl)carbonyl]-3-(4-methyl-2-pyrimidinyl)-5,6,7,8-tetrahydro[1,2,4]triazolo[4,3-a]pyrazine, E178 7-[(2,4-dichloro-3-fluorophenyl)carbonyl]-3-(5-isothiazolyl)-5,6,7,8-tetrahydro[1,2,4]triazolo[4,3-a]pyrazine, E179 7-[(2,4-dichloro-3-fluorophenyl)carbonyl]-3-(4-methyl-1,2,3-thiadiazol-5-yl)-5,6,7,8-tetrahydro[1,2,4]triazolo[4,3-a]pyrazine, E180 7-{[2-chloro-3-(trifluoromethyl)phenyl]carbonyl}-3-(2-pyridinyl)-5,6,7,8-tetrahydro[1,2,4]triazolo[4,3-a]pyrazine-d1, E181 7-{[2-chloro-3-(trifluoromethyl)phenyl]carbonyl}-3-(2-pyridinyl)-5,6,7,8-tetrahydro[1,2,4]triazolo[4,3-a]pyrazine-d1, E182 7-[(2,4-dichloro-3-fluorophenyl)carbonyl]-3-(2-pyridinyl)-5,6,7,8-tetrahydro[1,2,4]triazolo[4,3-a]pyrazine-d1, E183 7-[(2,4-dichloro-3-fluorophenyl)carbonyl]-3-(2-pyridinyl)-5,6,7,8-tetrahydro[1,2,4]triazolo[4,3-a]pyrazine-d1, E184 7-[(2,4-dichloro-3-fluorophenyl)carbonyl]-3-(1H-pyrazol-1-yl)-5,6,7,8-tetrahydro[1,2,4]triazolo[4,3-a]pyrazine, E185 7-[(2,4-dichloro-3-fluorophenyl)carbonyl]-3-(1,3-thiazol-5-yl)-5,6,7,8-tetrahydro[1,2,4]triazolo[4,3-a]pyrazine, E186 7-[(2,4-dichloro-3-fluorophenyl)carbonyl]-3-(1,2,4-thiadiazol-5-yl)-5,6,7,8-tetrahydro[1,2,4]triazolo[4,3-a]pyrazine, E187 7-[(2,4-dichloro-3-fluorophenyl)carbonyl]-3-(1,3-thiazol-2-yl)-5,6,7,8-tetrahydro[1,2,4]triazolo[4,3-a]pyrazine;

E188 7-[(2,4-dichloro-3-fluorophenyl)carbonyl]-3-(5-methyl-1,3-thiazol-2-yl)-5,6,7,8-tetrahydro[1,2,4]triazolo[4,3-a]pyrazine, E189 7-[(2,4-dichloro-3-fluorophenyl)carbonyl]-3-(1,2,3-thiadiazol-4-yl)-5,6,7,8-tetrahydro[1,2,4]triazolo[4,3-a]pyrazine, E190 7-[(2,4-dichloro-3-fluorophenyl)carbonyl]-3-(1,2,5-thiadiazol-3-yl)-5,6,7,8-tetrahydro[1,2,4]triazolo[4,3-a]pyrazine, E191 7-[(2,4-dichloro-3-fluorophenyl)carbonyl]-3-(4-methyl-1,3-thiazol-2-yl)-5,6,7,8-tetrahydro[1,2,4]triazolo[4,3-a]pyrazine, E192 7-[(2,3-dichlorophenyl)carbonyl]-3-(1,2,4-thiadiazol-5-yl)-5,6,7,8-tetrahydro[1,2,4]triazolo[4,3-a]pyrazine, E193 7-[(3-chloro-4-fluoro-2-methylphenyl)carbonyl]-3-(1,2,4-thiadiazol-5-yl)-5,6,7,8-tetrahydro[1,2,4]triazolo[4,3-a]pyrazine, E195 7-[(3-chloro-2-methylphenyl)carbonyl]-3-(1,2,4-thiadiazol-5-yl)-5,6,7,8-tetrahydro[1,2,4]triazolo[4,3-a]pyrazine, E197 7-[(2,4-dichloro-3-fluorophenyl)carbonyl]-3-(5-methyl-1,3-thiazol-4-yl)-5,6,7,8-tetrahydro[1,2,4]triazolo[4,3-a]pyrazine, E198 7-[(2,4-dichloro-3-fluorophenyl)carbonyl]-3-(1,3-thiazol-2-yl)-5,6,7,8-tetrahydro[1,2,4]triazolo[4,3-a]pyrazine;

E199 7-[(2,4-dichlorophenyl)carbonyl]-3-(1,3-thiazol-2-yl)-5,6,7,8-tetrahydro[1,2,4]triazolo[4,3-a]pyrazine, E200 7-[(3-chloro-2-methylphenyl)carbonyl]-3-(1,3-thiazol-2-yl)-5,6,7,8-tetrahydro[1,2,4]triazolo[4,3-a]pyrazine, E201 7-[(3-chloro-4-fluoro-2-methylphenyl)carbonyl]-3-(1,3-thiazol-2-yl)-5,6,7,8-tetrahydro[1,2,4]triazolo[4,3-a]pyrazine, E202 7-[(3,4-difluoro-2-methylphenyl)carbonyl]-3-(1,2,4-thiadiazol-5-yl)-5,6,7,8-tetrahydro[1,2,4]triazolo[4,3-a]pyrazine, E203 7-[(2,4-dichloro-3-fluorophenyl)carbonyl]-3-(4-methyl-3-isothiazolyl)-5,6,7,8-tetrahydro[1,2,4]triazolo[4,3-a]pyrazine, E204 2-chloro-6-{[3-(2-pyridinyl)-5,6-dihydro[1,2,4]triazolo[4,3-a]pyrazin-7(8H)-yl]carbonyl}benzonitrile, E205 7-[(2,4-dichlorophenyl)carbonyl]-3-(1,2,4-thiadiazol-5-yl)-5,6,7,8-tetrahydro[1,2,4]triazolo[4,3-a]pyrazine, E206 7-[(2,4-dichlorophenyl)carbonyl]-3-(5-methyl-1,3-thiazol-4-yl)-5,6,7,8-tetrahydro[1,2,4]triazolo[4,3-a]pyrazine, or E207 7-[(3-chloro-2-methylphenyl)carbonyl]-3-(5-methyl-1,3-thiazol-4-yl)-5,6,7,8-tetrahydro[1,2,4]triazolo[4,3-a]pyrazine;

or a pharmaceutically acceptable salt thereof.

In the above-mentioned particular aspects, the invention can for example be a compound or a hydrochloride salt thereof, or in particular a compound.

According to a preferred aspect of the invention, there is provided a compound or a pharmaceutically acceptable salt thereof, which is:

7-[(2-chloro-4-fluorophenyl)carbonyl]-3-(2-pyrazinyl)-5,6,7,8-tetrahydro[1,2,4]triazolo[4,3-a]pyrazine

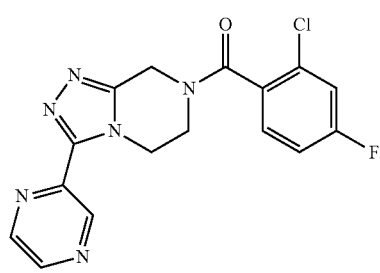

(e.g. see Example 86), or 7-{[2-chloro-3-(trifluoromethyl)phenyl]carbonyl}-3-(5-fluoro-2-pyridinyl)-5,6,7,8-tetrahydro[1,2,4]triazolo[4,3-a]pyrazine

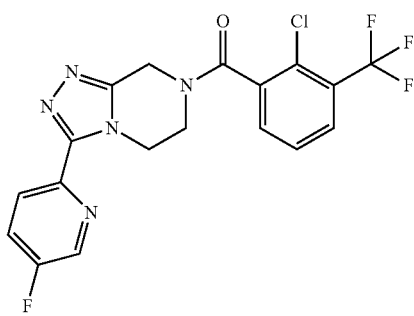 [SMILES: O=C(c1cccc(C(F)(F)F)c1Cl)N1CCn2c(nnc2-c2ccc(F)cn2)C1]

(e.g. see Example 45), or 7-[(2,4-dichlorophenyl)carbonyl]-3-(2-pyrazinyl)-5,6,7,8-tetrahydro[1,2,4]triazolo[4,3-a]pyrazine

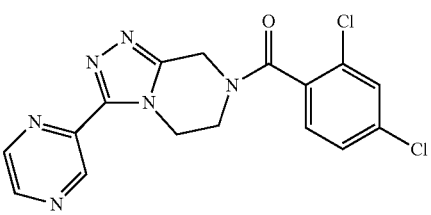 [SMILES: O=C(c1ccc(Cl)cc1Cl)N1CCn2c(nnc2-c2cnccn2)C1]

(e.g. see Example 93), or 7-{[2-chloro-3-(trifluoromethyl)phenyl]carbonyl}-3-(4-pyrimidinyl)-5,6,7,8-tetrahydro[1,2,4]triazolo[4,3-a]pyrazine

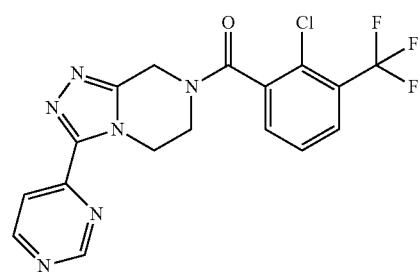 [SMILES: O=C(c1cccc(C(F)(F)F)c1Cl)N1CCn2c(nnc2-c2ccncn2)C1]

(e.g. see Example 12), or 7-[(2,4-dichlorophenyl)carbonyl]-3-(1,3-thiazol-4-yl)-5,6,7,8-tetrahydro[1,2,4]triazolo[4,3-a]pyrazine

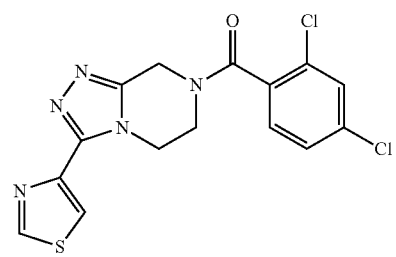 [SMILES: O=C(c1ccc(Cl)cc1Cl)N1CCn2c(nnc2-c2cscn2)C1]

(e.g. see Example 98), or 7-{[2-chloro-3-(trifluoromethyl)phenyl]carbonyl}-3-(2-furanyl)-5,6,7,8-tetrahydro[1,2,4]triazolo[4,3-a]pyrazine

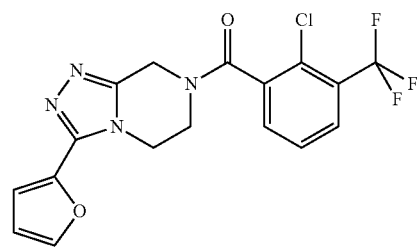 [SMILES: O=C(c1cccc(C(F)(F)F)c1Cl)N1CCn2c(nnc2-c2ccco2)C1]

(e.g. see Example 77), or 7-[(2,3-dichlorophenyl)carbonyl]-3-(1,3-thiazol-4-yl)-5,6,7,8-tetrahydro[1,2,4]triazolo[4,3-a]pyrazine

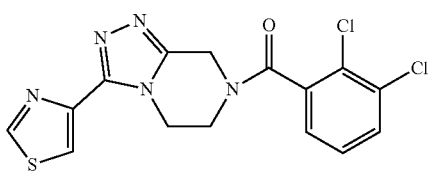 [SMILES: O=C(c1cccc(Cl)c1Cl)N1CCn2c(nnc2-c2cscn2)C1]

(e.g. see Example 67), or 7-[(2,3-dichlorophenyl)carbonyl]-3-(2-pyridinyl)-5,6,7,8-tetrahydro[1,2,4]triazolo[4,3-a]pyrazine

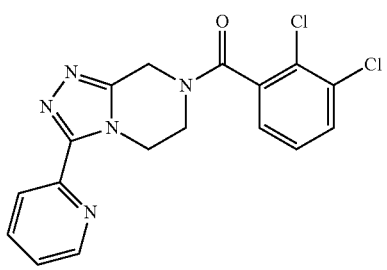 [SMILES: O=C(c1cccc(Cl)c1Cl)N1CCn2c(nnc2-c2ccccn2)C1]

(e.g. see Example 43), or 7-{[2-chloro-3-(trifluoromethyl)phenyl]carbonyl}-3-(1,3-thiazol-4-yl)-5,6,7,8-tetrahydro[1,2,4]triazolo[4,3-a]pyrazine

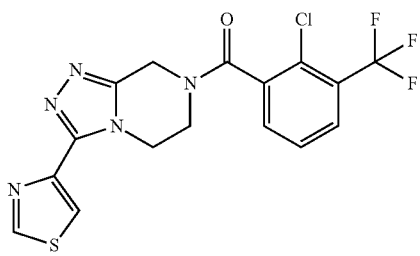 [SMILES: O=C(c1cccc(C(F)(F)F)c1Cl)N1CCn2c(nnc2-c2cscn2)C1]

(e.g. see Example 42), or 7-[(2,3-dichlorophenyl)carbonyl]-3-(2-pyrazinyl)-5,6,7,8-tetrahydro[1,2,4]triazolo[4,3-a]pyrazine

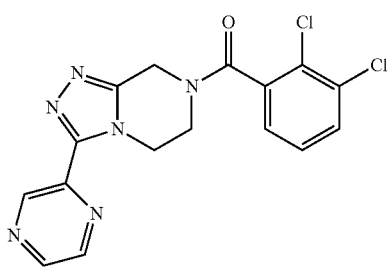 [SMILES: O=C(c1cccc(Cl)c1Cl)N1CCn2c(nnc2-c2cnccn2)C1]

(e.g. see Example 34); or a pharmaceutically acceptable salt of any of these compounds.

According to a more preferred aspect of the invention, there is provided a compound or a pharmaceutically acceptable salt thereof, which is:

7-[(2-chloro-4-fluorophenyl)carbonyl]-3-(2-pyrazinyl)-5,6,7,8-tetrahydro[1,2,4]triazolo[4,3-a]pyrazine

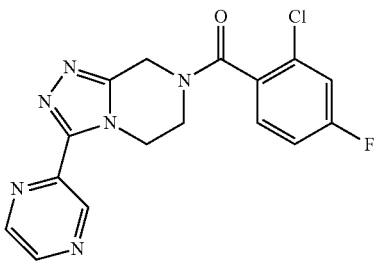

(e.g. see Example 86), or 7-{[2-chloro-3-(trifluoromethyl)phenyl]carbonyl}-3-(5-fluoro-2-pyridinyl)-5,6,7,8-tetrahydro[1,2,4]triazolo[4,3-a]pyrazine

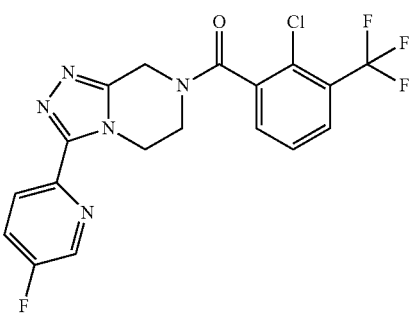 [SMILES: O=C(c1cccc(C(F)(F)F)c1Cl)N1CCn2c(nnc2-c2ccc(F)cn2)C1]

(e.g. see Example 45), or 7-[(2,4-dichlorophenyl)carbonyl]-3-(2-pyrazinyl)-5,6,7,8-tetrahydro[1,2,4]triazolo[4,3-a]pyrazine

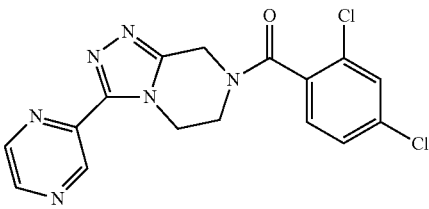 [SMILES: O=C(c1ccc(Cl)cc1Cl)N1CCn2c(nnc2-c2cnccn2)C1]

(e.g. see Example 93), or 7-{[2-chloro-3-(trifluoromethyl)phenyl]carbonyl}-3-(4-pyrimidinyl)-5,6,7,8-tetrahydro[1,2,4]triazolo[4,3-a]pyrazine

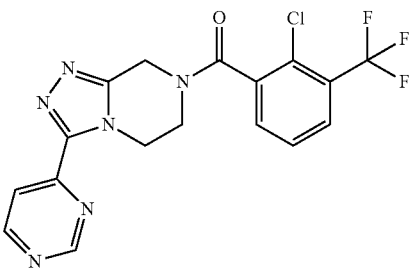 [SMILES: O=C(c1cccc(C(F)(F)F)c1Cl)N1CCn2c(nnc2-c2ccncn2)C1]

(e.g. see Example 12); or a pharmaceutically acceptable salt of any of these compounds.

According to a further preferred aspect of the invention, there is provided a compound or a pharmaceutically acceptable salt thereof, which is:
7-[(3,4-dichlorophenyl)carbonyl]-3-(2-pyrazinyl)-5,6,7,8-tetrahydro[1,2,4]triazolo[4,3-a]pyrazine

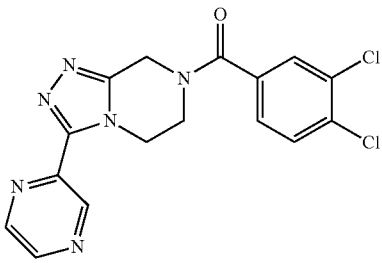 [SMILES: O=C(c1ccc(Cl)c(Cl)c1)N1CCn2c(nnc2-c2cnccn2)C1]

(e.g. see Example 115), or 7-[(2,4-Dichloro-3-fluorophenyl)carbonyl]-3-(4-pyrimidinyl)-5,6,7,8-tetrahydro[1,2,4]triazolo[4,3-a]pyrazine

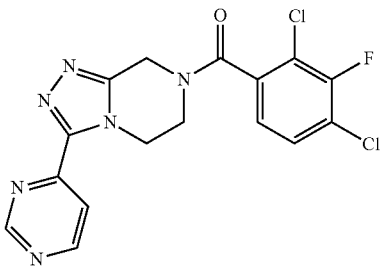 [SMILES: O=C(c1ccc(Cl)c(F)c1Cl)N1CCn2c(nnc2-c2ccncn2)C1]

(e.g. see Example 112); or or a pharmaceutically acceptable salt of any of these compounds.

In the above-mentioned preferred, more preferred or further preferred aspects, the invention can for example be a compound or a hydrochloride salt thereof, or in particular a compound.

Antagonists of P2X7 may be useful in the treatment (e.g. amelioration) or prophylaxis (in particular treatment) of a variety of pain states (e.g. neuropathic pain, chronic inflammatory pain, or visceral pain), inflammation (e.g. rheumatoid arthritis or osteoarthritis), or neurodegenerative diseases, in particular Alzheimer's disease. P2X7 antagonists may constitute useful therapeutic agents in the management of rheumatoid arthritis and inflammatory bowel disease.

Compounds or salts of the present invention which modulate P2X7 receptor function and are capable of antagonizing the effects of ATP at the P2X7 receptor ("P2X7 receptor antagonists") may be competitive antagonists, inverse agonists, or negative allosteric modulators of P2X7 receptor function.

Certain compounds of formula (I) may in some circumstances form acid addition salts thereof. It will be appreciated that for use in medicine compounds of formula (I) may be used as salts, in which case the salts should be pharmaceutically acceptable. Pharmaceutically acceptable salts include those described by Berge, Bighley and Monkhouse, *J. Pharm. Sci.*, 1977, 66, 1-19.

When a compound of formula (I) is basic, in one embodiment a pharmaceutically acceptable salt is formed from a pharmaceutically acceptable acid such as an inorganic or organic acid. Such acids include acetic, p-aminobenzoic, ascorbic, aspartic, benzenesulfonic, benzoic, bismethylene-salicylic, camphorsulfonic, citric, cyclohexylsulfamic, ethanedisulfonic, ethanesulfonic, fumaric, gluconic, glutamic, glycolic, hydrobromic, hydrochloric, isethionic, itaconic, lactic, maleic, malic, mandelic, methanesulfonic, mucic, nitric, palmitic, pamoic, pantothenic, phosphoric, propionic, salicylic, stearic, succinic, sulfuric, tartaric, p-toluenesulfonic acid, and the like.

In one particular embodiment, the pharmaceutically acceptable salt is formed from a pharmaceutically acceptable strong acid. For example, the pharmaceutically acceptable salt can be a benzenesulfonate, camphorsulfonate, ethanesulfonate, hydrobromide, hydrochloride, methanesulfonate, nitrate, phosphate, sulfate, or p-toluenesulfonate.

The compounds of formula (I) or pharmaceutically acceptable salts thereof may be prepared in crystalline or non-crystalline form (e.g. in crystalline or amorphous solid form), and, in particular if crystalline, may optionally be solvated, e.g. as the hydrate. This invention includes within its scope solvates (e.g. hydrates) of compounds of formula (I) or pharmaceutically acceptable salts thereof, for example stoichiometric solvates (e.g. hydrates); as well as compounds or salts thereof containing variable amounts of solvent (e.g. water).

Certain compounds of formula (I) or salts thereof may be capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

Preparation of Compounds

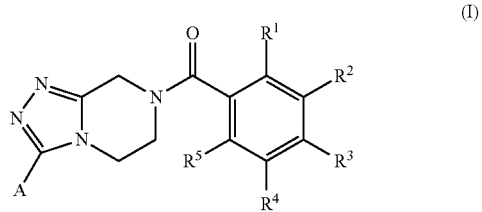

(I)

Compounds of formula (I), wherein the variables are as defined herein, and pharmaceutically acceptable salts thereof may be prepared by the methodology described hereinafter, constituting a further aspect of this invention.

According to a further aspect of the invention, a process for preparing a compound of formula (I) or a pharmaceutically acceptable salt thereof comprises step (a), (b), (c), (d), or (e) as described below;
and optionally preparing a pharmaceutically acceptable salt of the compound.
(a) Preparation of a compound of formula (I) by coupling of a compound of general formula (2) with an acid chloride (Y=Cl) or a carboxylic acid (Y=OH) (or an activated derivative thereof) of general formula (3) (see Scheme 1) wherein A, $R^1$, $R^2$, $R^3$, $R^4$, and $R^5$ are as defined herein. Compounds (2) and (3) are optionally protected.
(b) Preparation of a compound of formula (I) by reacting a compound of general formula (4) with a compound of general formula (5) or (6) (see Schemes 2 and 3) wherein A, $R^1$, $R^2$, $R^3$, $R^4$, and $R^5$ are as defined herein. Compounds (4) and (5) are optionally protected.

(c) Preparation of compound of formula (I) by reacting a compound of general formula (10) with a compound of general formula (11) (see Scheme 4) wherein A, $R^1$, $R^2$, $R^3$, $R^4$, and $R^5$ are as defined herein. Compounds (10) and (11) are optionally protected.

(d) Deprotecting a compound of formula (I) which is protected. Examples of protecting groups and the means for their removal can be found in T. W. Greene and P. G. M. Wuts 'Protective Groups in Organic Synthesis' (Wiley-Interscience, 4$^{th}$ ed., 2006).

(e) Interconversion of compounds of formula (I) to other compounds of formula (I). Examples of conventional interconversion procedures include epimerisation, oxidation, reduction, alkylation, aromatic substitution, nucleophilic substitution, amide coupling and ester hydrolysis.

Representative methods for the preparation of compounds of formula (I) are shown in Schemes 1 to 4 below:

Scheme 1

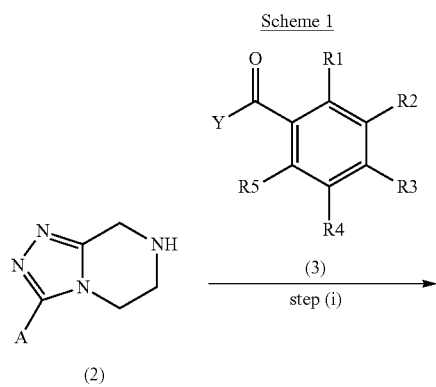

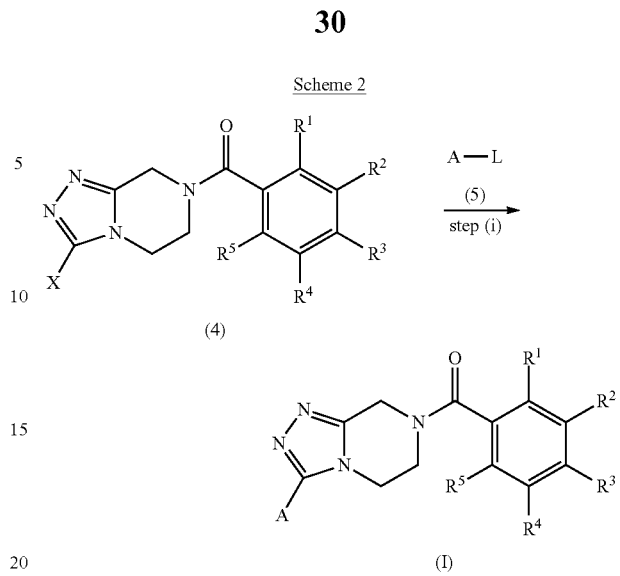

Step (i) typically comprises treatment of a compound of formula (2) (or an acid salt thereof) with an acid chloride of formula (3) (Y=Cl) in the presence of a suitable base such as triethylamine (optionally also with N,N-dimethyl-4-pyridinamine (DMAP)) or diethylaminomethyl polystyrene, in a suitable solvent such as N,N-dimethylformamide or dichloromethane and at a suitable temperature such as between 0° C. and room temperature.

Alternatively, a compound of formula (2) could be treated with a carboxylic acid of formula (3) (where Y=OH) in the presence of an activating agent, such as water soluble carbodiimide or 1-(3-dimethylaminopropyl)-3-ethylcarbodiimide hydrochloride (EDC) or 2-(7-aza-1H-benzotriazole-1-yl)-1,1,3,3-tetramethyluronium hexafluorophosphate (HATU) and a suitable base such as N,N-dimethyl-4-pyridinamine (DMAP) or N,N-diisopropylethylamine (DIPEA), in a suitable solvent such as dichloromethane and at a suitable temperature e.g. between 0° C. and room temperature.

Step (i) typically comprises reacting a compound of formula (4) (where X=H or a halogen e.g. bromine), which can be prepared as described above in Scheme 1, with a compound of formula (5), wherein L represents a suitable leaving group such as a halogen atom (e.g. bromine or iodine) or a boronic acid or ester, in the presence of a suitable catalyst such as palladium(II)acetate or dichlorobis(triphenylphosphine) palladium(II) respectively, and a suitable base such as cesium carbonate or sodium carbonate, in a suitable solvent such as 1,4-dioxane or 1,2-dimethoxyethane and at a suitable temperature e.g. between room temperature and reflux temperature.

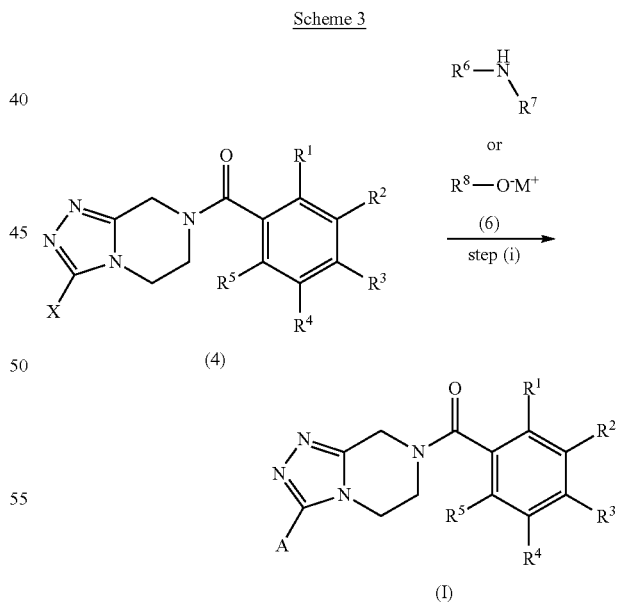

Step (i) typically comprises reacting a compound of formula (4) (where X is a suitable leaving group such as a halogen e.g. bromine or chlorine), with a compound of formula (6), wherein $R^6$, and $R^8$ represent $C_1$-$C_6$ alkyl or $C_1$-$C_8$ cycloalkyl and $R^7$ represents H, $C_1$-$C_6$ alkyl or $C_1$-$C_8$ cycloalkyl ($R^6$ and $R^7$ together may also represent a 3-8 membered heterocycle) and M represents a metal such as sodium, in a suitable solvent such as methanol or ethanol and at a suitable temperature e.g. between 60° C. and 125° C., and in some cases with the addition of microwave radiation.

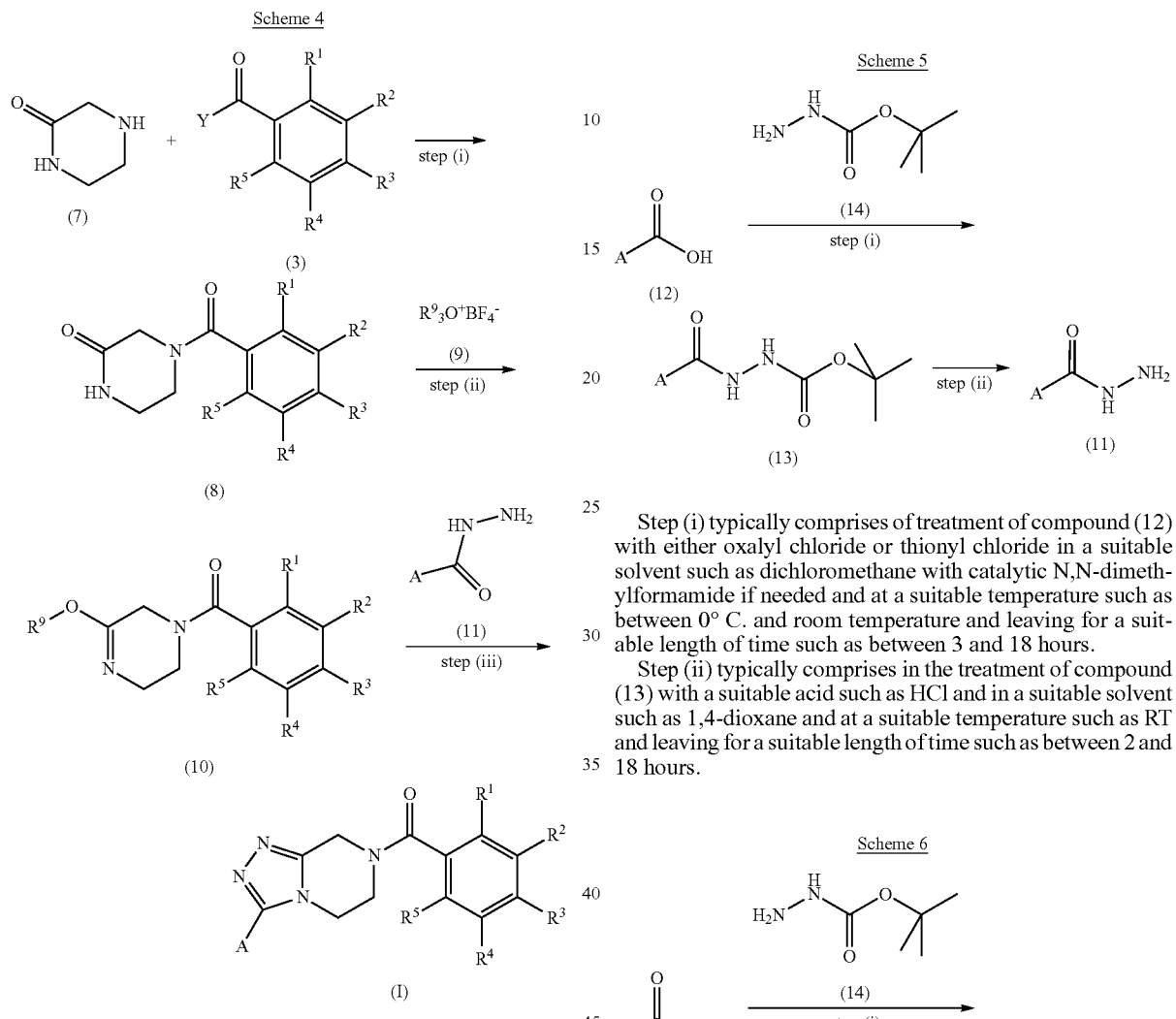

Step (i) typically comprises treatment of compound (7) (where Y is OH or Cl) with compound (3) in a manner analogous to that described in step (i) of Scheme 1.

Step (ii) typically comprises treatment of compound (8) with a trialkyloxonium tetrafluoroborate (e.g. triethyloxonium tetrafluoroborate) reagent, in a suitable solvent such as dichloromethane and e.g. at a suitable temperature such as room temperature.

Step (iii) typically comprises treatment of compound (10) with a suitable hydrazide (11) in a suitable solvent such as 1-butanol e.g. at a suitable temperature such as reflux temperature, for example for 1 to 18 hours e.g. in refluxing 1-butanol.

Steps (ii) and (iii) can also be combined in a single step which results in the conversion of compound (8) to compounds of formula (I) without the intermediate isolation of compounds of formula (10).

Compounds of the general formulae (2), (3), (5), (6), (7), (9) and (11) are typically either available from commercial sources or can be prepared by a person skilled in the art using methods described in the chemical literature (or using analogous methods). See Intermediates 22-31 hereinafter for representative examples of compounds of formula (11) and their preparation method(s).

Representative methods for the preparation of compounds of formula (11) are shown in Schemes 5 to 8 below:

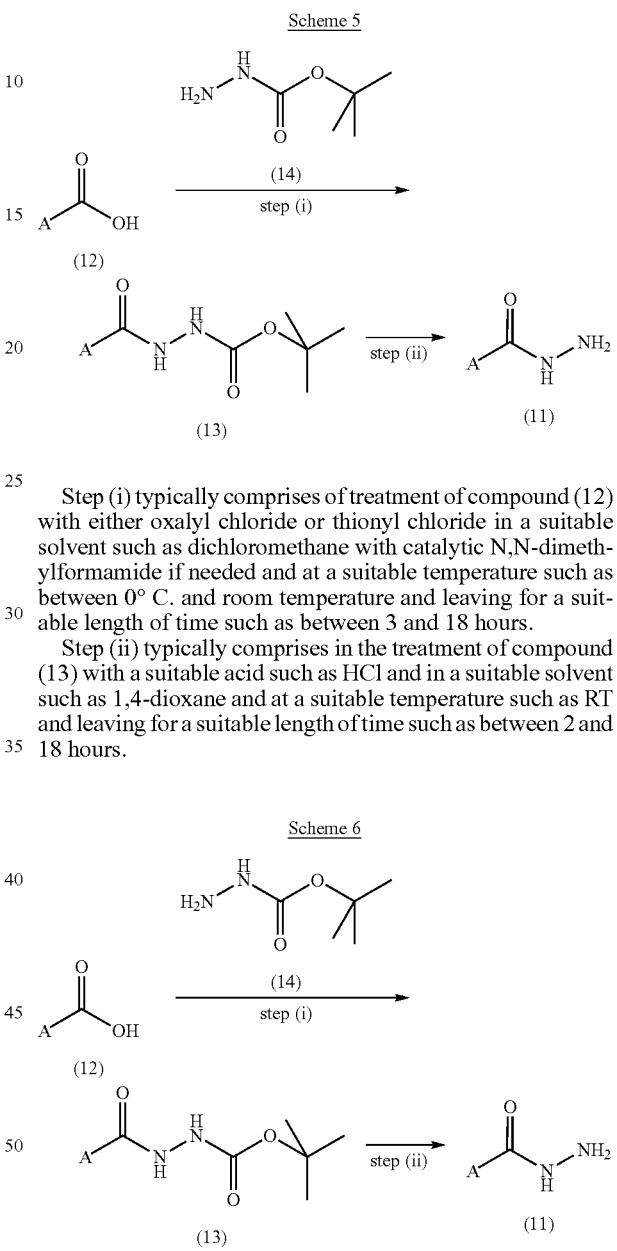

Step (i) typically comprises of treatment of compound (12) with either oxalyl chloride or thionyl chloride in a suitable solvent such as dichloromethane with catalytic N,N-dimethylformamide if needed and at a suitable temperature such as between 0° C. and room temperature and leaving for a suitable length of time such as between 3 and 18 hours.

Step (ii) typically comprises in the treatment of compound (13) with a suitable acid such as HCl and in a suitable solvent such as 1,4-dioxane and at a suitable temperature such as RT and leaving for a suitable length of time such as between 2 and 18 hours.

Step (i) typically comprises the treatment of compound (12) with a suitable activating agent such as 1-(3-dimethylaminopropyl)-3-ethylcarbodiimide hydrochloride (EDC) and suitable base such as 1-hydroxybenzotriazole (HOBt) and in a suitable solvent such as dichloromethane and at a suitable temperature such as RT and for a suitable length of time such as 3 to 18 hours.

Step (ii) typically comprises the treatment of compound (13) with a suitable acid such as HCl and in a suitable solvent such as 1,4-dioxane and at a suitable temperature such as RT and leaving for a suitable length of time such as between 2 and 18 hours.

Scheme 7

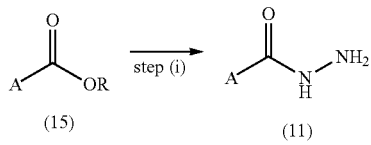

Step (i) typically comprises the treatment of compound (15) with hydrazine monohydrate in a suitable solvent such as methanol or ethanol and at a suitable temperature such as room temperature or reflux and for a suitable length of time such as between 6 and 18 hours.

Scheme 8

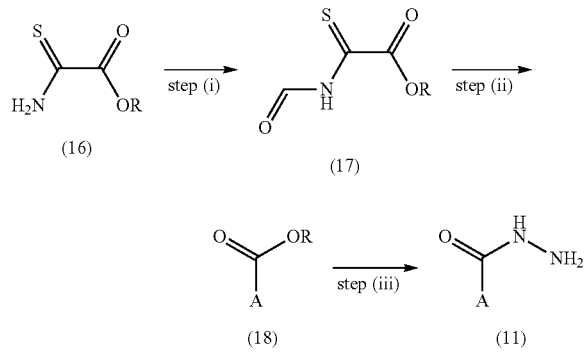

Step (i) typically consists of reacting ethyl thiooxamate in a suitable solvent such as chloroform with a suitable reagent such as N,N-dimethylformamide dimethyl acetal and at a suitable temperature such as room temperature and for a suitable length of time such as 6 hours.

Step (ii) typically consists of reacting ethyl {[(1E)(dimethylamino)methylidene]amino}(thioxo)acetate (17) with (aminooxy)(hydroxy)sulfane dioxide dissolved in a suitable solvent such as ethanol and at a suitable temperature such as room temperature and for a suitable length of time such as 48 hours.

Step (iii) typically consists of reacting 1,2,4-thiadiazole-5-carboxylate ester (18) with hydrazine monohydrate and a suitable solvent and at a suitable temperature such as reflux and for a suitable length of time such as 5 hours.

As an alternative method of preparing compound of the formula (I) to the reaction of compounds of the formula (8) with compounds of the formula (11) as described in Scheme 4 above, compounds of the formula (8) may be reacted with carboximidohydrazide compound in an analogous procedure to that described for steps (ii) and (iii) of Scheme 4 above and/or as exemplified in the preparation of Example 177 described below. The compound of formula (11a) shown in Scheme 9 below is an example of such a carboximidohydrazide compound which includes a pyrimidine ring substituted at the 4-position with Y, wherein Y is selected from $C_{1-3}$ alkyl (e.g. methyl), fluorine, chlorine, OH (including a tautomer thereof), methoxy or deuterium, for example hydrogen, deuterium or methyl. Intermediate 99 is an example of a compound of the formula (11a) in which Y is methyl.

Scheme 9

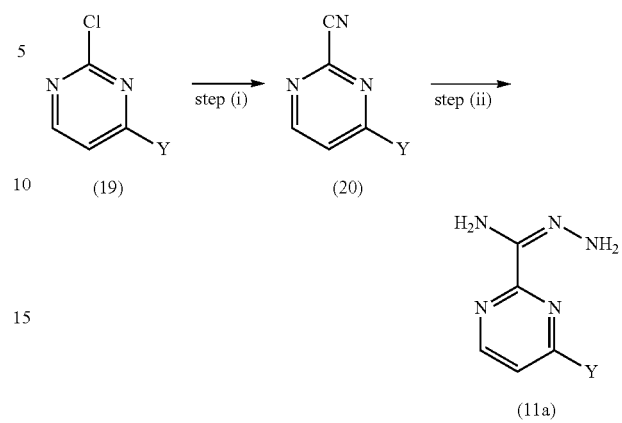

Step (i) typically consists of compound (19) being treated with a suitable reagent such as potassium cyanide and in a suitable solvent such as N,N-dimethylformamide and using suitable base such as triethylamine and using a suitable catalyst such as Bis(triphenylphosphine)palladium(II) chloride and heating at a suitable temperature such as 80° C. for a suitable length of time such as 18 hours.

Step (ii) consists of compound (20) being treated with hydrazine hydrate in a suitable solvent such as ethanol and at a suitable temperature such as reflux and for a suitable length of time such as 2.5 hours.

Compounds of the general formulae (12), (14), (15), (16) and (19) are typically either available from commercial sources or can be prepared by a person skilled in the art using methods described in the chemical literature (or using analogous methods).

Compound (27) is an example of compound (2) in which A is 1,2,4-thiadiazol-5-yl. A representative method for the preparation of compound (27) is shown in Scheme 10 below. Intermediate 115 is an example of compound (27).

Another alternative method of preparing compound of the formula (I) is to react compounds of the formula (3) described above with compound (27) in an in a manner analogous to that described in step (i) of Scheme 1. Compound (27) can be prepared as shown in Scheme 10 below:

Scheme 10

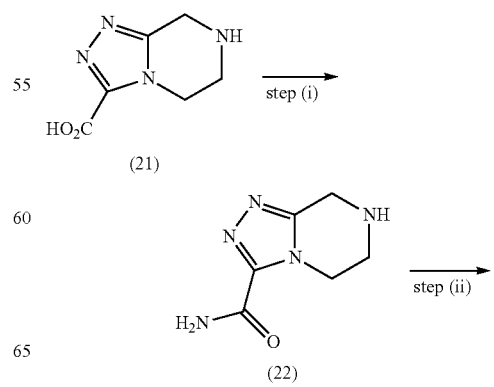

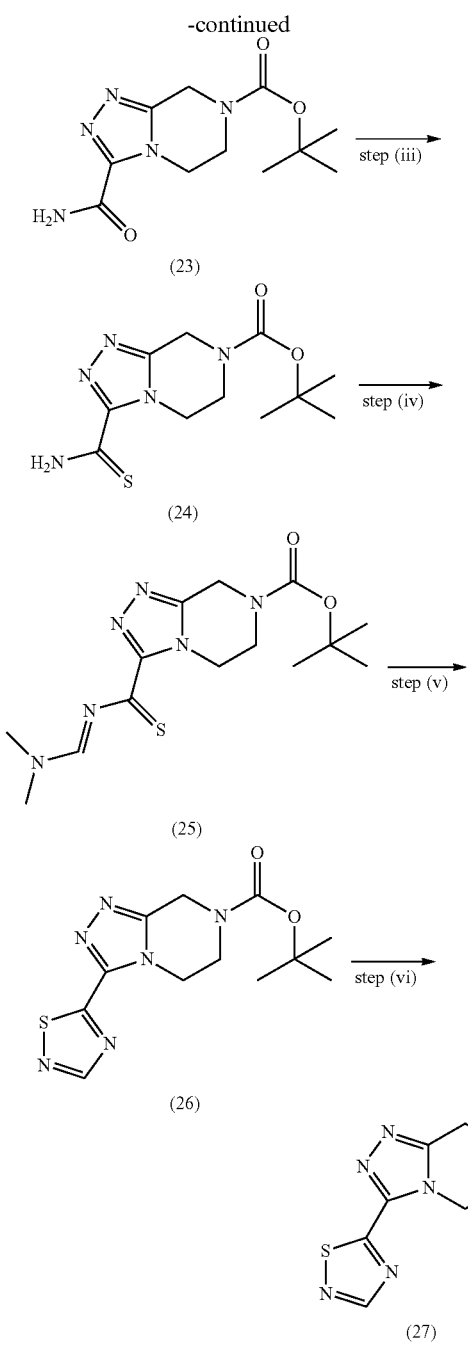

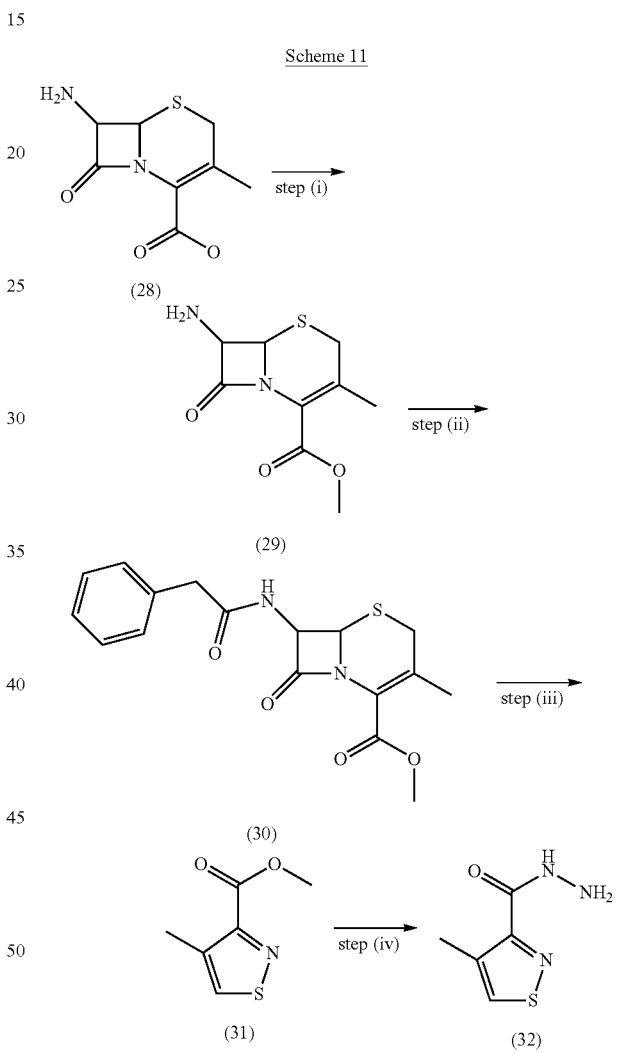

Step (i) typically consists of reacting compound (21) with ammonia for a suitable length of time such as 18 hours and at a suitable temperature such as room temperature.

Step (ii) typically consists of suitable protection of the nitrogen using for example Boc anhydride in a suitable solvent for example dichloromethane or N,N-dimethylformamide and using a suitable base such as diethylaminomethyl polystyrene and stirring for a suitable length of time such as 18 hours.

Step (iii) typically consists of treatment with a suitable reagent such as Lawesson's reagent and in a suitable solvent such as benzene and at a suitable temperature such as 80° C. and for a suitable length of time such as 8 hours.

Step (iv) typically consists of treatment with a suitable reagent such as N,N-dimethylformamide (DMF) dimethyl acetal and at a suitable temperature such as room temperature and for a suitable length of time such as 1 hour.

Step (v) typically consists of reacting compound (25) with hydroxylamine O-sulfonic acid in a suitable solvent such as ethanol with a suitable base such as pyridine and at a suitable temperature such as room temperature and for a suitable length of time such as 1 hour.

Step (vi) typically comprises of the treatment of compound (26) in an analogous manner to step (ii) in Scheme 5.

Compounds of the formula (32) are compounds of the formula (11) in which A is 4-methyl-3-isothiazolyl. Representative methods for the preparation of compounds of formula (32) are shown in Scheme 11 below. Intermediate 129 is an example of a compound of formula (32).

Step (i) typically consists of reaction of compound (28) with a suitable solvent such as methanol in the presence of a suitable acid such as conc sulphuric acid and at a suitable temperature such as reflux for a suitable length of time such as 16 hours.

Step (ii) typically consists of reaction of compound (29) with a suitable acid chloride such as phenyl acetal chloride in the presence of a suitable base such as triethylamine and at a suitable temperature such as 0° C. or room temperature and for a suitable length of time such as 18 hours.

Step (iii) involved reaction of compound (30) with suitable reagent such as N-chlorosuccinimide (NCS) in the presence of a suitable solvent such as Dichloromethane and suitable acid such as trifluoroacetic acid and at a suitable temperature such as room temperature and for an appropriate length of time.

Step (iv) typically comprises of the treatment of compound (32) in an analogous manner to that in step (i) of scheme 7.

Compounds of the formula (I) in which A is a heterocycle substituted with a halogen may be converted to other compounds of the formula (I) in which A is a heterocycle substituted with a fluorine as shown in Scheme 12:

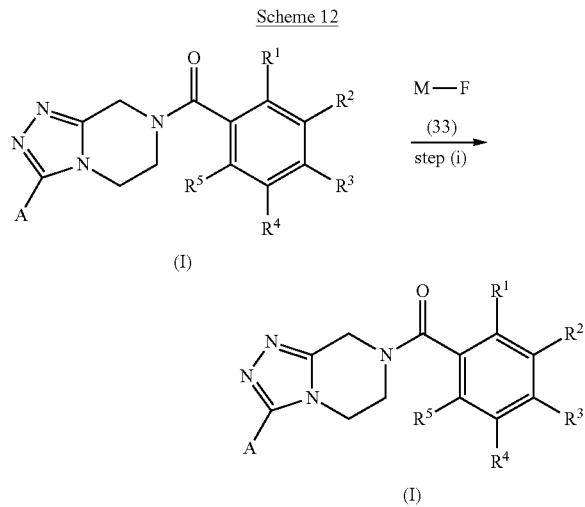

Step (i) typically consists of reaction of compound where the A ring is a heterocycle substituted with a halogen for example chlorine and with reaction of a metal fluoride (33) such as silver fluoride and in a suitable solvent such as acetonitrile at a suitable temperature such as 80° C. and for a suitable length of time such as 24 hours.

Where relevant and possible, pharmaceutically acceptable salts (e.g. HCl salts) may be prepared by reaction with the appropriate acid (e.g. HCl) or acid derivative.

Clinical Indications, Pharmaceutical Compositions, and Dosages

It is believed that, as the compounds or pharmaceutically acceptable salts of the present invention modulate P2X7 receptor function and are capable of antagonizing the effects of ATP at the P2X7 receptor ("P2X7 receptor antagonists"); they may be useful in the treatment or prophylaxis (in particular treatment) of pain; such as acute pain, chronic pain, chronic articular pain, musculoskeletal pain, neuropathic pain, inflammatory pain, visceral pain, pain associated with cancer, pain associated with migraine, tension headache or cluster headaches, pain associated with functional bowel disorders, lower back and/or neck pain, pain associated with sprains and/or strains, sympathetically maintained pain; myositis, pain associated with influenza or other viral infections such as the common cold, pain associated with rheumatic fever, pain associated with myocardial ischemia, post operative pain, cancer chemotherapy, headache, toothache, or dysmenorrhea.

The chronic articular pain condition can be rheumatoid arthritis, osteoarthritis, rheumatoid spondylitis (ankylosing spondylitis), gouty arthritis or juvenile arthritis.

The inflammatory pain condition can be rheumatoid arthritis, osteoarthritis, rheumatoid spondylitis (ankylosing spondylitis) or fibromyalgia.

In particular, the compounds of formula (I) or pharmaceutically acceptable salts thereof may be useful in the treatment or prophylaxis (in particular treatment) of pain (e.g. inflammatory pain) in arthritis, such as pain (e.g. inflammatory pain) in rheumatoid arthritis or osteoarthritis.

Pain associated with functional bowel disorders includes non-ulcer dyspepsia, non-cardiac chest pain and irritable bowel syndrome.

The neuropathic pain condition can be: diabetic neuropathy (e.g. painful diabetic neuropathy), sciatica, non-specific lower back pain, trigeminal neuralgia, multiple sclerosis pain, fibromyalgia, HIV-related neuropathy, post-herpetic neuralgia, trigeminal neuralgia, or lumbar radiculopathy; or pain resulting from physical trauma, amputation, phantom limb syndrome, spinal surgery, cancer, toxins or chronic inflammatory conditions. Alternatively, the neuropathic pain condition can be pain associated with normally non-painful sensations such as "pins and needles" (paraesthesias and/or dysesthesias), increased sensitivity to touch (hyperesthesia), painful sensation following innocuous stimulation (dynamic, static, thermal or cold allodynia), increased sensitivity to noxious stimuli (thermal, cold, or mechanical hyperalgesia), continuing pain sensation after removal of the stimulation (hyperpathia), or an absence of or deficit in selective sensory pathways (hypoalgesia).

The acute pain condition can be post-surgical pain or dysmenorrhea (e.g. primary dysmenorrhea).

The compounds or pharmaceutically acceptable salts of the present invention may potentially be useful in the treatment or prophylaxis (e.g. prophylaxis, e.g. reduction, delay or prevention) of the development of tolerence to the analgesic action of an opioid analgesic (such as morphine, fentanyl, oxycodone, tramadol, hydrocodone, hydromorphone, oxymorphone, methadone or buprenorphine; in particular morphine, fentanyl, oxycodone, or tramadol).

Other conditions which could potentially be subject to treatment or prophylaxis (in particular treatment) using the compounds or salts of the present invention are: fever, inflammation, immunological diseases, abnormal platelet function diseases (e.g. occlusive vascular diseases), impotence or erectile dysfunction; bone disease characterised by abnormal bone metabolism or resorbtion; hemodynamic side effects of non-steroidal anti-inflammatory drugs (NSAID's) such as cyclooxygenase-2 (COX-2) inhibitors, cardiovascular diseases (e.g. atherosclerosis); neurodegenerative diseases and/or neurodegeneration; neurodegeneration following trauma; tinnitus; dependence on (e.g. addiction to) a dependence-inducing agent such as: an opioid analgesic (e.g. morphine), a CNS (central nervous system) depressant (e.g. ethanol), a psychostimulant (e.g. cocaine) or nicotine; diabetes such as Type 1 or Type 2 diabetes, complications of diabetes such as complications of Type I or Type 2 diabetes, kidney dysfunction, liver dysfunction (e.g. hepatitis, cirrhosis), gastrointestinal dysfunction (e.g. diarrhoea), gastric cancer, colon cancer, overactive bladder, or urge incontinence. Depression and alcoholism could potentially also be subject to treatment or prophylaxis by compounds or salts of the present invention.

Inflammation and/or the inflammatory conditions associated with said inflammation can be: arthritis (in particular rheumatoid arthritis or osteoarthritis), skin conditions (e.g. sunburn, burns, eczema, dermatitis, allergic dermatitis, or psoriasis), meningitis, ophthalmic diseases such as glaucoma, retinitis, retinopathies, uveitis or of acute injury to the eye tissue (e.g. conjunctivitis), an inflammatory lung disorder (e.g. asthma, chronic obstructive pulmonary disease (COPD, which includes bronchitis and/or emphysema), allergic rhinitis, respiratory distress syndrome, pigeon fancier's disease, farmer's lung, or airways hyperresponsiveness); a gastrointestinal tract disorder (e.g. aphthous ulcer, Crohn's disease, atopic gastritis, gastritis varialoforme, ulcerative colitis, coeliac disease, regional ileitis, irritable bowel syndrome, inflammatory bowel disease, or gastrointestinal reflux disease); organ transplantation; or other conditions with an inflammatory component such as: vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, gingivitis, myocardial ischemia, pyrexia, systemic lupus erythematosus, polymyositis, tendinitis, bursitis, or Sjogren's syndrome.

The inflammation and/or an inflammatory condition associated with said inflammation can in particular be arthritis (e.g. rheumatoid arthritis or osteoarthritis).

Immunological diseases include autoimmune diseases, immunological deficiency diseases or organ transplantation.

Bone diseases characterised by abnormal bone metabolism or resorbtion can be: osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gouty and/or ankylosing spondylitis, tendinitis or bursitis.

Cardiovascular diseases include hypertension or myocardiac ischemia; atherosclerosis; functional or organic venous insufficiency; varicose therapy; haemorrhoids; and shock states associated with a marked drop in arterial pressure (e.g. septic shock).

Neurodegenerative diseases which could potentially be subject to treatment or prophylaxis (in particular treatment) using the compounds or salts of the present invention are: dementia, particularly degenerative dementia (such as Alzheimer's disease, senile dementia, dementia with Lewy bodies, temporal lobe dementia, Huntingdon's chorea, Parkinson's disease, Pick's disease, Creutzfeldt-Jakob disease, or Amyotrophic Lateral Sclerosis (ALS); in particular Alzheimer's disease); mild cognitive impairment (MCI) e.g. MCI associated with ageing, particularly age associated memory impairment; motor neuron disease; vascular dementia (including multi-infarct dementia and/or dementia associated with cerebral ischaemia); or a neurodegenerative disease (e.g. dementia) associated with: an intracranial space occupying lesion, head trauma, intracranial and/or cerebral infections or related conditions (such as HIV infection, viral or bacterial meningitis, or cerebral herpes virus infections such as shingles or herpes simplex virus), metabolism, toxins, anoxia, hypoxia or vitamin deficiency.

The neurodegenerative disease, e.g. to be subject to treatment or prophylaxis (in particular treatment) by the compound of formula (I) or salt thereof, can in particular be degenerative dementia (in particular Alzheimer's disease), Parkinson's disease (in particular dementia in Parkinson's disease), vascular dementia (in particular multi-infarct dementia), dementia with Lewy bodies, Huntingdon's chorea, or mild cognitive impairment (MCI) e.g. MCI associated with ageing such as age associated memory impairment. The neurodegenerative disease, e.g. to be subject to treatment or prophylaxis (in particular treatment) by the compound of formula (I) or salt thereof, can in particular be degenerative dementia (in particular Alzheimer's disease), vascular dementia (in particular multi-infarct dementia), or mild cognitive impairment (MCI) e.g. MCI associated with ageing such as age associated memory impairment.

In one embodiment, the compound of formula (I) or the salt thereof of the invention is used for treatment or prophylaxis (in particular treatment) of a neurodegenerative disease (such as degenerative dementia e.g. Alzheimer's disease, or vascular dementia, or mild cognitive impairment), by disease modification and/or by neuroprotection. Alternatively or additionally, in one embodiment, the compound of formula (I) or the salt thereof of the invention is used for treatment or prophylaxis (in particular treatment) of a neurodegenerative disease (such as degenerative dementia e.g. Alzheimer's disease, or vascular dementia, or mild cognitive impairment) by symptomatic treatment of cognitive impairment associated with the neurodegenerative disease.

The compounds of formula (I) or pharmaceutically acceptable salts thereof may also be useful for neuroprotection and/or in the treatment or prophylaxis (e.g. treatment) of neurodegeneration following trauma such as stroke, cardiac arrest, pulmonary bypass, traumatic brain injury, spinal cord injury or the like.

The compounds or pharmaceutically acceptable salts of the present invention may also be useful in the treatment or prophylaxis (in particular treatment) of malignant cell growth and/or metastasis, or myoblastic leukaemia.

Complications of Type 1 diabetes can be: diabetic microangiopathy, diabetic retinopathy, diabetic nephropathy, macular degeneration, glaucoma, nephrotic syndrome, aplastic anaemia, uveitis, Kawasaki disease or sarcoidosis.

Kidney dysfunction can be: nephritis, glomerulonephritis, particularly mesangial proliferative glomerulonephritis or nephritic syndrome.

The compounds or pharmaceutically acceptable salts of the present invention may potentially be useful in the treatment or prophylaxis (e.g. treatment) of epilepsy and/or seizures (i.e. as anticonvulsants), for example in a mammal such as a human.

The compounds or pharmaceutically acceptable salts of the present invention may potentially be useful in the treatment or prophylaxis (e.g. treatment) of a human epileptic syndrome, such as: partial and/or generalised seizures (e.g. tonic, tonic-clonic, or absence seizures), temporal lobe epilepsy, absence epilepsies (including childhood, juvenile, myoclonic, photo- or pattern-induced), severe epileptic encephalopathies (including hypoxia-related or Rasmussen's syndrome), febrile convulsions, epilepsy partialis continua, progressive myoclonus epilepsies (including Unverricht-Lundborg disease or Lafora's disease), post-traumatic seizures and/or epilepsy such as those related to head injury, simple reflex epilepsies (including photosensitive, somatosensory, proprioceptive, audiogenic or vestibular), metabolic disorders commonly associated with epilepsy such as pyridoxine-dependent epilepsy, Menkes' kinky hair disease, Krabbe's disease, epilepsy due to alcohol and/or drug abuse (e.g. cocaine abuse), cortical malformations associated with epilepsy (e.g. double cortex syndrome or subcortical band heterotopia), or chromosomal anomolies associated with seizures or epilepsy such as Partial monosomy (15Q/Angelman syndrome); in a human.

According to a further aspect of the invention, we therefore provide a compound of formula (I) or a pharmaceutically acceptable salt thereof for use in human or veterinary medicine and/or for use in therapy.

According to another aspect of the invention, we provide a compound of formula (I) or a pharmaceutically acceptable salt thereof for use in the treatment or prophylaxis (e.g. treatment) of a condition which is mediated by P2X7 receptors, for example a condition or disease disclosed herein (in particular pain, inflammation such as rheumatoid arthritis or osteoarthritis, or a neurodegenerative disease (e.g. Alzheimer's disease or mild cognitive impairment), or epilepsy and/or seizures (e.g. a human epileptic syndrome); more particularly pain such as inflammatory pain, neuropathic pain or visceral pain, or rheumatoid arthritis or osteoarthritis); e.g. in a mammal such as a human or rodent e.g. human or rat e.g. human.

According to a further aspect of the invention, we provide a method of treatment or prophylaxis (e.g. treatment) of a human or animal (e.g. rodent e.g. rat) subject, for example a human subject, suffering from a condition which is mediated by P2X7 receptors, for example a condition or disease disclosed herein (in particular pain, inflammation such as rheumatoid arthritis or osteoarthritis, or a neurodegenerative disease (e.g. Alzheimer's disease or mild cognitive impairment), or epilepsy and/or seizures (e.g. a human epileptic syndrome); more particularly pain such as inflammatory pain, neuropathic pain or visceral pain, or rheumatoid arthritis or osteoarthritis), which comprises administering to said subject an effective amount of a compound of formula (I) or a pharmaceutically acceptable salt thereof.

According to a further aspect of the invention we provide a method of treatment or prophylaxis (e.g. treatment) of a human or animal (e.g. rodent e.g. rat) subject, for example a human subject, suffering from or susceptible to pain, inflammation (e.g. rheumatoid arthritis or osteoarthritis), or a neurodegenerative disease (e.g. Alzheimer's disease or mild cognitive impairment), or epilepsy and/or seizures (e.g. a human epileptic syndrome), (more particularly pain such as inflammatory pain, neuropathic pain or visceral pain, or rheumatoid arthritis or osteoarthritis), which method comprises administering to said subject an effective amount of a compound of formula (I) or a pharmaceutically acceptable salt thereof.

According to a yet further aspect of the invention we provide a method of treatment or prophylaxis (e.g. treatment) of a human or animal (e.g. rodent e.g. rat) subject, for example a human subject, suffering from or susceptible to inflammatory pain, neuropathic pain or visceral pain (e.g. pain, such as inflammatory pain, in arthritis (e.g. rheumatoid arthritis or osteoarthritis)) which method comprises administering to said subject an effective amount of a compound of formula (I) or a pharmaceutically acceptable salt thereof.

According to a further aspect of the invention we provide a method of treatment of a subject, for example a human subject, suffering from Alzheimer's disease or mild cognitive impairment, which method comprises administering to said subject an effective amount of a compound of formula (I) or a pharmaceutically acceptable salt thereof.

In one aspect of the invention we provide a method of treatment or prophylaxis (e.g. prophylaxis, e.g. reduction, delay or prevention) of the development of tolerance to the analgesic action of an opioid analgesic (such as morphine, fentanyl, oxycodone, tramadol, hydrocodone, hydromorphone, oxymorphone, methadone or buprenorphine; in particular morphine, fentanyl, oxycodone, or tramadol), in a subject suffering from or susceptible to the development of such opioid analgesic tolerance, which method comprises administering to said subject an effective amount of a compound of formula (I) or a pharmaceutically acceptable salt thereof.

According to another aspect of the invention, we provide the use of a compound of formula (I) or a pharmaceutically acceptable salt thereof for the manufacture of a medicament for the treatment or prophylaxis (e.g. treatment) of a condition which is mediated by the action of P2X7 receptors, for example a condition or disease disclosed herein (in particular pain, inflammation such as rheumatoid arthritis or osteoarthritis, or a neurodegenerative disease (e.g. Alzheimer's disease or mild cognitive impairment), or epilepsy and/or seizures (e.g. a human epileptic syndrome); more particularly pain such as inflammatory pain, neuropathic pain or visceral pain); e.g. in a mammal such as a human or rodent e.g. human or rat e.g. human.

According to another aspect of the invention we provide the use of a compound of formula (I) or a pharmaceutically acceptable salt thereof for the manufacture of a medicament for the treatment or prophylaxis (e.g. treatment) of pain (e.g. inflammatory pain, neuropathic pain or visceral pain), inflammation (e.g. rheumatoid arthritis or osteoarthritis), or a neurodegenerative disease (e.g. Alzheimer's disease or mild cognitive impairment), or epilepsy and/or seizures (e.g. a human epileptic syndrome), (more particularly: pain such as inflammatory pain, neuropathic pain or visceral pain, or rheumatoid arthritis or osteoarthritis); e.g. in a mammal such as a human or rodent e.g. human or rat e.g. human.

According to another aspect of the invention we provide the use of a compound of formula (I) or a pharmaceutically acceptable salt thereof for the manufacture of a medicament for the treatment or prophylaxis (e.g. treatment) of inflammatory pain, neuropathic pain or visceral pain (in particular inflammatory pain or neuropathic pain; such as inflammatory pain in arthritis such as rheumatoid arthritis or osteoarthritis); e.g. in a mammal such as a human or rodent e.g. human or rat e.g. human.

In one aspect of the invention we provide the use of a compound of formula (I) or a pharmaceutically acceptable salt thereof for the manufacture of a medicament for the treatment or prophylaxis (e.g. treatment) of Alzheimer's disease or mild cognitive impairment; e.g. in a mammal such as a human or rodent e.g. human or rat e.g. human.

In one aspect of the invention we provide the use of a compound of formula (I) or a pharmaceutically acceptable salt thereof for the manufacture of a medicament for the treatment or prophylaxis (e.g. prophylaxis, e.g. reduction, delay or prevention) of the development of tolerance to the analgesic action of an opioid analgesic (such as morphine, fentanyl, oxycodone, tramadol, hydrocodone, hydromorphone, oxymorphone, methadone or buprenorphine; in particular morphine, fentanyl, oxycodone, or tramadol).

For the avoidance of doubt, the term "treatment" as used herein when referring to a particular disease or condition, encompasses the alleviation of the symptoms associated with said disease or condition.

In order to use a compound of formula (I) or a pharmaceutically acceptable salt thereof for the treatment of humans and/or other mammals it can optionally be formulated in accordance with pharmaceutical practice as a pharmaceutical composition. Therefore in another aspect of the invention there is provided a pharmaceutical composition comprising a compound of formula (I), or a pharmaceutically acceptable salt thereof, adapted for use in human or veterinary medicine.

In order to use a compounds of formula (I) or a pharmaceutically acceptable salt thereof in therapy, it will normally be formulated into a pharmaceutical composition in accordance with pharmaceutical practice. The present invention also provides a pharmaceutical composition, which comprises a compound of formula (I), or a pharmaceutically acceptable salt thereof, and a pharmaceutically acceptable carrier or excipient.

The pharmaceutical composition may be for use in a method of treatment or prophylaxis or in a use or in a treatment or prophylaxis, as described herein.

A pharmaceutical composition of the invention, which may be prepared by admixture, for example at ambient temperature and/or atmospheric pressure, is usually adapted for oral, parenteral or rectal administration. As such, the pharmaceutical composition may be in the form of a tablet, a capsule, a oral liquid preparation, a powder, a granule, a lozenge, a reconstitutable powder, an injectable or infusable solution or suspension, or a suppository.

An orally administrable pharmaceutical composition is generally preferred.

Tablets and capsules for oral administration may be in unit dose form, and may contain one or more excipients, such as a binding agent (e.g. hydroxypropylmethylcellulose or povidone), a filler (e.g. lactose and/or microcrystalline cellulose), a lubricant e.g. a tabletting lubricant (e.g. magnesium stearate or calcium stearate), a disintegrant (e.g. a tablet disintegrant such as sodium starch glycolate or croscarmellose sodium), and/or an acceptable wetting agent. The tablets may be coated e.g. according to methods known in pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain additive(s) such as a suspending agent(s), an emulsifying agent(s), a non-aqueous vehicle(s) (such as an edible oil), and/or a preservative(s), and/or, if desired, a flavouring(s) or colourant(s).

For parenteral administration, fluid unit dosage forms are typically prepared utilising a compound of the invention or pharmaceutically acceptable salt thereof and a sterile vehicle. In one embodiment, the compound or salt, depending on the vehicle and concentration used, is either suspended or dissolved in the vehicle. In preparing solutions, the compound or salt can e.g. be dissolved for injection and filter sterilised before filling into a suitable vial or ampoule and sealing. In one embodiment, an adjuvant(s) such as a local anaesthetic, a preservative(s) and/or a buffering agent(s) is or are dissolved in the vehicle. To enhance the stability, the composition can for example be frozen after filling into the vial and the water removed under vacuum. Parenteral suspensions are typically prepared in substantially the same manner, except that the compound or salt is typically suspended in the vehicle instead of being dissolved, and sterilization is not usually accomplished by filtration. The compound or salt can be sterilised, e.g. by exposure to ethylene oxide, before suspension in a sterile vehicle. In one embodiment, a surfactant or wetting agent is included in the composition, e.g. to facilitate uniform distribution of the compound or salt of the invention.

In one embodiment, the composition contains from 0.1% to 99% (by weight of the composition), in particular from 0.1 to 60% or 1 to 60% or 10 to 60% by weight, of the active material (the compound or pharmaceutically acceptable salt of the invention), e.g. depending on the method of administration. The carrier(s) and/or excipient(s) contained in the composition can for example be present in from 1% to 99.9%, e.g. from 10% to 99%, by weight of the composition; and/or in an amount of from 20 mg to 2000 mg such as 50 mg to 1000 mg per unit dose of the composition.

The dose of the compound or pharmaceutically acceptable salt thereof, e.g. for use in the treatment or prophylaxis (e.g. treatment) of the herein mentioned disorders/diseases/conditions, may vary in the usual way with the seriousness of the disorders, the weight of the sufferer, and/or other similar factors. However, as a general guide, in one embodiment a unit dose of 0.05 to 2000 mg or 0.05 to 1000 mg, for example 0.05 to 200 mg, such as 20 to 40 mg, of the compound or pharmaceutically acceptable salt of the invention (measured as the compound), may be used, e.g. in a pharmaceutical composition. In one embodiment, such a unit dose is for administration once a day e.g. to a mammal such as a human; alternatively such a unit dose may be for administration more than once (e.g. twice or three times) a day e.g. to a mammal such as a human. Such therapy may extend for a number of days, weeks, months or years.

Combinations

Compounds of formula (I) or pharmaceutically acceptable salts thereof may be used in combination with other (further) therapeutic agent(s), for example medicaments claimed to be useful in the treatment or prophylaxis (e.g. treatment) of the above mentioned disorders.

Examples of such further therapeutic agent(s) may include a β2-agonist (also known as β2 adrenoceptor agonists; e.g. formoterol) and/or a corticosteroid (e.g. budesonide, fluticasone (e.g. as propionate or furoate esters), mometasone (e.g. as furoate), beclomethasone (e.g. as 17-propionate or 17,21-dipropionate esters), ciclesonide, triamcinolone (e.g. as acetonide), flunisolide, rofleponide or butixocort (e.g. as propionate ester)), e.g. for the treatment of a respiratory disorder (such as asthma or chronic obstructive pulmonary disease (COPD)), e.g. as described in WO 2007/008155 and/or WO 2007/008157.

A further therapeutic agent may include a 3-hydroxy-3-methylglutaryl coenzyme A (HMG CoA) reductase inhibitor (e.g. atorvastatin, fluvastatin, lovastatin, pravastatin, rosuvastatin, or simvastatin) (e.g. for oral administration), e.g. for the treatment of a cardiovascular disorder (such as atherosclerosis), e.g. as described in WO 2006/083214.

A further therapeutic agent may in particular include a non-steroid anti-inflammatory drug (NSAID; e.g. ibuprofen, naproxen, aspirin, celecoxib, diclofenac, etodolac, fenoprofen, indomethacin, ketoprofen, ketoralac, oxaprozin, nabumetone, sulindac, tolmetin, rofecoxib, valdecoxib, lumaricoxib, meloxicam, etoricoxib or parecoxib; or e.g. paracetamol, loxoprofen or aceclofenac; in particular celecoxib, paracetamol, ibuprofen or diclofenac) (e.g. for oral administration), e.g. for the treatment of an inflammatory disease or disorder (such as rheumatoid arthritis or osteoarthritis, and/or inflammatory pain), e.g. as described in WO 2005/025571. Celecoxib (a COX-2 inhibitor) can for example be administered orally at a dosage regimen of 100 mg or 200 mg (measured as the free base) once or twice daily.

A further therapeutic agent may in particular include a tumour necrosis factor α (TNFα) inhibitor (e.g. etanercept or an anti-TNFα antibody such as infliximab or adalimumab) (e.g. for parenteral administration such as subcutaneous or intravenous administration), e.g. for the treatment of an inflammatory disease or disorder (such as rheumatoid arthritis or osteoarthritis), e.g. as described in WO 2004/105798.

A further therapeutic agent may in particular include an anti-CD20 monoclonal antibody (e.g. for parenteral such as intravenous administration), such as ofatumumab (HuMax-CD20™, developed in part by Genmab AS) (e.g. ofatumumab for intravenous administration), rituximab, PRO70769, AME-133 (Applied Molecular Evolution), or hA20 (Immunomedics, Inc.); in particular ofatumumab or rituximab. This further therapeutic agent can e.g. be for the treatment of an inflammatory disease or disorder (such as rheumatoid arthritis or osteoarthritis, and/or inflammatory pain).

A further therapeutic agent may include 2-hydroxy-5-[[4-[(2-pyridinylamino) sulfonyl]phenyl]azo]benzoic acid (sulfasalazine), e.g. for the treatment of an inflammatory disease or disorder (such as rheumatoid arthritis or osteoarthritis; in particular rheumatoid arthritis), e.g. as described in WO 2004/105797.

A further therapeutic agent may in particular include N-[4-[[(2,4-diamino-6-pteridinyl)methyl]methylamino]benzoyl]-L-glutamic acid (methotrexate), e.g. for oral administration and/or e.g. for the treatment of an inflammatory disease or disorder (such as rheumatoid arthritis or osteoarthritis; in particular rheumatoid arthritis), e.g. as described in WO 2004/105796. For the treatment of rheumatoid arthritis, methotrexate can be administered to the human at a dosage regimen of 7.5 mg orally once weekly, or using divided oral doses of 2.5 mg at 12 hour intervals for 3 doses (7.5 mg total) as a course once weekly; the schedule can optionally be adjusted gradually to achieve an optimal response, but typically does not exceed a total weekly oral dose of 20 mg of methotrexate; once a response has been achieved, the methotrexate dose is typically reduced to the lowest possible effective dose.

A further therapeutic agent may include an inhibitor of pro TNFα convertase enzyme (TACE), e.g. for the treatment of an inflammatory disease or disorder (such as rheumatoid arthritis or osteoarthritis; in particular rheumatoid arthritis), e.g. as described in WO 2004/073704.

A further therapeutic agent may include:
a) sulfasalazine;
b) a statin (e.g. for oral administration), such as atorvastatin, lovastatin, pravastatin, simvastatin, fluvastatin, cerivastatin, crilvastatin, dalvastatin, rosuvastatin, tenivastatin, fluindostatin, velostatin, dalvastatin, nisvastatin, bervastatin, pitavastatin, rivastatin, glenvastatin, eptastatin, tenivastatin, flurastatin, rosuvastatin or itavastatin;
c) a glucocorticoid agent (e.g. for oral or skin-topical administration), such as dexamethasone, methylprednisolone, prednisolone, prednisone and hydrocortisone;
d) an inhibitor of p38 kinase (e.g. for oral administration);
e) an anti-IL-6-receptor antibody, e.g. an anti-IL-6-receptor monoclonal antibody (e.g. for parenteral such as intravenous administration);
f) anakinra;
g) an anti-IL-1 (e.g. IL-1β) monoclonal antibody (e.g. for parenteral such as intravenous administration);
h) an inhibitor of JAK3 protein tyrosine kinase;
i) an anti-macrophage colony stimulation factor (M-CSF) monoclonal antibody; or
j) an anti-CD20 monoclonal antibody (e.g. for parenteral such as intravenous administration), such as rituximab, ofatumumab (HuMax-CD20™, developed in part by Genmab AS) (e.g. ofatumumab for intravenous administration), PRO70769, AME-133 (Applied Molecular Evolution), or hA20 (Immunomedics, Inc.); in particular rituximab or ofatumumab;
e.g. for the treatment of an IL-1 (e.g. IL-1R) mediated disease (such as rheumatoid arthritis or osteoarthritis, and/or inflammatory or neuropathic pain; in particular rheumatoid arthritis), e.g. as described in WO 2006/003517.

In particular, the further therapeutic agent or agents can be a therapeutic agent or agents capable of treating inflammatory pain, such as paracetamol and/or an opioid analgesic (such as morphine, fentanyl, oxycodone, tramadol, hydrocodone, hydromorphone, oxymorphone, methadone or buprenorphine; in particular morphine, fentanyl, oxycodone, or tramadol). This/these therapeutic agent(s), and/or the combination comprising this/these therapeutic agent(s), can be for the treatment of inflammatory pain, e.g. in a mammal such as a human. For example, paracetamol can be administered at a human oral dosage regimen of 500 mg to 1000 mg (e.g. 500 mg, 650 mg or 1000 mg, in particular 650 mg) of paracetamol (measured as the free base/free compound), administered two, three or four times daily.

In a particular embodiment of the invention, the further therapeutic agent or agents can be a therapeutic agent or agents capable of treating neuropathic pain, such as:

an opioid analgesic (such as morphine, fentanyl, oxycodone, tramadol, hydrocodone, hydromorphone, oxymorphone, methadone or buprenorphine; in particular morphine, fentanyl, oxycodone, or tramadol, most particularly morphine),
a monoamine reuptake inhibitor (such as duloxetine or amytriptyline),
pregabalin,
gabapentin,
gabapentin enacarbil (XP13512), and/or
carbamazepine.

This/these therapeutic agent(s), and/or the combination comprising this/these therapeutic agent(s), can be for the treatment of neuropathic pain, e.g. in a mammal such as a human.

For example, pregabalin can be administered orally e.g. for neuropathic pain; e.g. at a human oral dosage regimen of 150 mg to 600 mg total pregabalin per day (measured as the free base), split between two to three doses per day. For example, for postherpetic neuralgia (a neuropathic pain condition), pregabalin can be administered at a starting oral dosage regimen of 150 mg total pregabalin per day (split between 2 or 3 doses per day), escalating (e.g. in about one week) to an oral dosage regimen of 300 mg pregabalin total per day, and optionally escalating up to a maximum oral dosage regimen of 600 mg total pregabalin per day. For painful diabetic neuropathy (another neuropathic pain condition), an oral dosage regimen of 150 mg to 300 mg total pregabalin per day can be administered. For fibromyalgia, an oral dosage regimen of 150 mg to 450 mg (e.g. 300 or 450 mg) total pregabalin per day can be administered. Pregabalin can e.g. be administered separately from the compound of formula (I) or the salt thereof.

For example, gabapentin can be administered orally, e.g. for neuropathic pain. Oral dosage units can e.g. contain 100 mg, 300 mg, 400 mg, 600 mg or 800 mg of gabapentin (measured as the free base/acid). The gabapentin dosage regimen for neuropathic pain can e.g. be from 300 mg once, twice or three times per day up to a total dose of 3600 mg/day. Some gradual up-titration of the dosage regimen is usually performed. For example, for peripheral neuropathic pain in adults, gabapentin therapy can be initiated by titrating the dose thus: day 1=300 mg of gabapentin (measured as the free base/acid) once a day, day 2=300 mg two times a day, and day 3=300 mg three times a day; alternatively the starting dose can be 900 mg/day of gabapentin (measured as the free base/acid), administered as three equally divided doses. Thereafter, e.g. based on individual patient response and tolerability, the dose can be further increased, typically in 300 mg/day increments every 2-3 days, up to a maximum total dose of 3600 mg/day of gabapentin (measured as the free base/acid). Slower titration of gabapentin dosage may be appropriate for individual patients. The minimum time to reach a total dose of 1800 mg/day is typically one week, to reach 2400 mg/day is typically a total of 2 weeks, and to reach 3600 mg/day is typically a total of 3 weeks. Gabapentin can e.g. be administered separately from the compound of formula (I) or the salt thereof.

For example, gabapentin enacarbil (XP13512, (±)-1-([(α-isobutanoyloxyethoxy)carbonyl]aminomethyl)-1-cyclohexane acetic acid, which is a prodrug of gabapentin) can be administered orally, e.g. to a human, e.g. separately from the compound of formula (I) or the salt thereof. In one embodiment, gabapentin enacarbil (XP13512) is for example administered orally, e.g. to a human such as a human adult, e.g. at a total daily dose having an equivalent molar quantity of gabapentin enacarbil as the molar quantity present in 900 mg/day to 3600 mg/day of gabapentin (see e.g. page 81 lines 24-32 of WO 02/100347). A 600 mg dose of gabapentin enacarbil (measured as the free acid) contains the molar equivalent of 312 mg of gabapentin. See also K. C. Cundy et al., "Clinical Pharmacokinetics of XP13512, a Novel Transported Prodrug of Gabapentin", *J. Clin. Pharmacol.*, 2008, e-publication 30 Sep. 2008, incorporated herein by reference, and the Materials and Methods—Formulation and Study Designs sections therein, for examples of some oral doses, dosage regimens and formulations of XP13512 used in human pharmacokinetic studies.

In a particular embodiment of the invention, when the further therapeutic agent includes an opioid analgesic (such as morphine, fentanyl, oxycodone, tramadol, hydrocodone, hydromorphone, oxymorphone, methadone or buprenorphine; in particular morphine, fentanyl, oxycodone, or tramadol), then the opioid analgesic and/or the combination comprising the opioid analgesic is for the treatment of pain, in particular inflammatory or neuropathic pain, e.g. in a mammal such as a human. In a more particular embodiment of this embodiment, the compound or salt of the present invention is administered (e.g. to a human), e.g. either sequentially or simultaneously, in combination with the opioid analgesic, wherein the opioid analgesic is administered at a reduced dosage compared to the dosage (e.g. human dosage) typically used for said opioid analgesic (i.e. the compound or salt of the invention might give an opioid-sparing effect); this might give adequate pain control and/or might result in a reduction of opioid-analgesic-induced adverse events.

In a particular embodiment, the further therapeutic agent may be useful in the treatment or prophylaxis (in particular treatment) of a Neurodegenerative disease. For example the further therapeutic agent may be useful in alleviating the symptoms of a Neurodegenerative disase.

When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable salt thereof together with a further therapeutic agent or agents (e.g. as defined herein).

The individual components of the combination of the invention (i.e. the compound of formula (I) or the salt thereof, and the further therapeutic agent or agents) may be present as separate pharmaceutical formulations/compositions, or may be present as a combined pharmaceutical formulation/composition (e.g. may be together in a single combined oral dosage form, e.g. a single combined tablet or capsule). The individual components of this combination can for example be administered either sequentially in separate pharmaceutical formulations/compositions (e.g. oral), or simultaneously in separate or combined pharmaceutical formulation(s)/composition(s) (e.g. oral); in a particular embodiment they are administered sequentially in separate pharmaceutical formulations/compositions (e.g. oral).

The combinations referred to herein may optionally be presented for use in the form of a pharmaceutical formulation and thus pharmaceutical formulations comprising a combination as defined herein together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable salt thereof is used in combination with a second therapeutic agent active against the same disease state the dose of each compound may differ from that when the compound is used alone.

The following Examples and Intermediates illustrate the compounds of the invention, methods for their preparation, and intermediates usable in their preparation, but are not intended to be limiting.

Experimental Section

Abbreviations, some of which may be used herein, include the following:

Boc/BOC tert-butyl oxy carbonyl
br broad
CASS Computational, Analytical and Structural Sciences
cat. catalytic amount (the exact quantity not being measured)
CV column volumes
d doublet
DCM Dichloromethane
DMAP 4-(dimethylamino)pyridine, also named N,N-dimethyl-4-pyridinamine
DME 1,2-dimethoxyethane
DMF N,N-dimethylformamide
DMSO dimethyl sulfoxide
DIPEA N,N-diisopropylethylamine ($^i$Pr$_2$NEt)
EDC 1-(3-dimethylaminopropyl)-3-ethylcarbodiimide hydrochloride
EtOAc ethyl acetate
Et$_2$O diethyl ether
EtOH ethanol
HATU 2-(7-aza-1H-benzotriazole-1-yl)-1,1,3,3-tetramethyluronium hexafluorophosphate
HEPES 4-(2-hydroxyethyl)-1-piperazine-1-ethanesulfonic acid

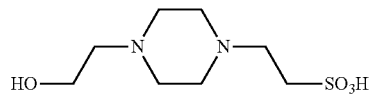

Hex hexane
HOBT 1-hydroxybenzotriazole
IPA isopropanol (isopropyl alcohol)
m multiplet
MeCN acetonitrile
MeOH methanol
q quartet
s singlet
THF tetrahydrofuran
TFA trifluoroacetic acid
TMEDA tetramethylethylenediamine
eq equivalents
HPLC high performance liquid chromatography
h/hr/Hr hours
min minutes
LCMS or LC/MS liquid chromatography/mass spectrometry
MDAP mass directed automated (preparative) HPLC
MS mass spectrometry
NBS N-bromosuccinimide
NCS N-chlorosuccinimide
NMR nuclear magnetic resonance
TLC thin layer chromatography
RT room temperature (ambient temperature); this is usually in the range of about 18 to about 25° C., or a sub-range within this range, unless otherwise disclosed herein.
R.T. retention time
SCX strong cation exchange. A SCX column or cartridge is typically a solid phase extraction (SPE) column with benzene sulfonic acid residues immobilised on the solid phase (eg. IST Isolute™ columns). When eluting with ammonia/methanol, it is thought that compounds isolated by SCX are usually in the free base form (if such a form exists).

INTERMEDIATES AND EXAMPLES

Reagents not detailed in the text below are usually commercially available from chemicals suppliers, e.g. established suppliers such as Sigma-Aldrich. The addresses and/or contact details of the suppliers for some of the starting materials mentioned in the Intermediates and Examples below or elsewhere herein, or some suppliers of miscellaneous chemicals in general, are as follows:

ABCR GmbH KG, Im Schlehert 10, Karlsruhe, D-76187, Germany, telephone: +49 (0)721-95061-0, Fax: +49 (0)721-95061-80, http://www.abcr.de AKos Consulting and Solutions GmbH, Austr. 26, Steinen, D-78585, Germany, telephone: +49 7627 970068, fax: +49 7627 970067, http://www.akosgmbh.eu Alchem Pharmtech, Inc., 160 Liberty Street, Bldg 4A, Metuchen, N.J., 08840, USA, telephone: +1 848-565-5694, fax: +1 732-317-4369, www.alchempharmtech.com Alfa Aesar, 26 Parkridge Road, Ward Hill, Mass., 01835, USA, telephone: 1-978-521-6300, Fax: 1-978-521-6350, http://www.alfa.com Allichem LLC, 8510 Corridor Road Step A, Savage, Md., 20763-9504, USA, telephone: +1 301-317-5072, Fax: +1 301-317-5073, http://www.allichemllc.com American Custom Chemicals Corp., P O Box 262527, San Diego, Calif., 92196-2527, USA, telephone: +1 858-201-6118, Fax: +1 858-451-8607, http://www.acccorporation.com Anichem LLC, 195 Black Horse Lane, North Brunswick, N.J., 08902, USA, telephone: +1 732-821-6500, fax: +1 732-821-6008, http://www.anichemllc.com APAC Pharmaceutical, LLC, 6851 Oak Hall Lane, Suite 101, Columbia, Md., 21045, USA, phone: +1 (410) 469-0727, fax: +1 (410) 309 5955, www.apacpharma.com Apollo Scientific Ltd., Whitefield Rd., Bredbury, Stockport, Cheshire, SK6 2QR, United Kingdom, telephone: +44 (0)161 406 0505, Fax: +44 (0)161 406 0506, http://www.apolloscientific.co.uk Ark Pharm, Inc., 1840 Industrial Drive, Suite 280, Libertyville, Ill., 60048, USA, telephone: +1-847-367-3680, fax: +1-847-367-3681, http://www.arkpharminc.com Atomole Scientific Co., Ltd, 150 Zhongjia Village, Suite 104, Hanyang District, Wuhan, Hubei, 430050, China, telephone: +86-27-82261049, fax: +86-27-82629206, http://www.atomole.com Aurora Fine Chemicals LLC, 7929 Silverton Ave., Suite 609, San Diego, Calif., 92126, USA, tel: +1 858 549 4700, fax: +1 858 549 4701, www.aurorafinechemicals.com Bepharm Ltd., 128 Xiangyin Road, Room C316, Yangpu District, Shanghai, 200433, China, phone: +86-21-51816456, fax: +86-21-51816457, http://www.bepharm.com Beta Pharma, Inc., 91 Shelton Avenue, Suite: 211, New Haven, Conn., 06511, USA, telephone: +1-877-786-1922, Fax: (203)786-5437, http://www.betapharma.com Bosche Scientific, LLC, New Brunswick Technology Center, 100 Jersey Avenue, Box D-12, Building D, 3rd Floor, New Brunswick, N.J., 08901, USA, telephone: +1 (732)-565-9988, fax: +1 (732)-875-0899, http://www.BoscheSci.com Bridge Organics, 311 W. Washington St., Vicksburg, Mich., 49097-1200, USA, telephone: +1 269-649-4200, fax: +1 269-649-0611, http://www.bridgeorganics.com ChemBridge Corporation, 16981 Via Tazon, Suite G, San Diego, Calif., 92127, USA, telephone: +1 (800) 964-6143, fax: +1 (858) 451-7401, http://www.chembridge.com ChemPacific Corp, 6200 Freeport Center, Baltimore, Md., 21224, USA, telephone: +00 1 410-633-5771, Fax: +001 410-633-5808, http://www.chempacific.com China Hallochem Pharma Co., Ltd., 17F, Venus Science Incubate Center, No. 60 Xingguang Road, New North Zone, Chongqing, 401121, China, telephone: +86-23-67030786, Fax: +86-23-67030809, http://www.hallochem.com D-L Chiral Chemicals, LLC, 53 Champlain Road, Monmouth Junction, N.J., 08852, USA, telephone: +1 732-668-8759, fax: +1 732-359-1599, http://www.dlchiral.com Fluorochem Ltd., Wesley Street, Old Glossop, Derbyshire, SK13 7RY, United Kingdom, telephone: +44 (0) 1457 868921, Fax: +44 (0) 1457 869360, http://www.fluorochem.net Haiso PharmChem, Hubei Research Institute of Chemistry, No. 30 Guanshan Road, Wuhan, 430074, China, telephone: +86-27-87422225, fax: +86-27-87496702, http://www.haisopharm.com Indofine Chemical Company, Inc., 121 Stryker Lane, Bldg 30, Suite 1, Hillsborough, N.J., 08844, USA, telephone: +1 (908) 359-6778, fax: +1 (908) 359-1179, http://www.indofinechemical.com International Laboratory Limited, 1067 Sneath Ln, San Bruno, Calif., 94066, USA, telephone: +1 650-278-9963, Fax: +1 650-589-2786, http://www.intlab.org J & W PharmLab LLC, 2000 Hartel Street, Suite B, Levittown, Pa., 19057, USA, telephone: +1-215-945-6595, fax: +1-215-945-6597, http://www.jwpharmlab.com JRD Fluorochemicals Ltd, Unit 11, Mole Business Park, Randalls Road, Leatherhead, Surrey, KT22 7BA, United Kingdom, telephone: +44 (0) 1372 360896, Fax: +44 (0) 1372 360790, http://www.jrdifluoro.co.uk Lanzhou Chon Chemical Co., Ltd., D6, Guchengping Industrial Park, Donggang Town, Lanzhou City, China, telephone: +86-138-93130096, fax: +86-931-4673545, http://www.chonchem.com Matrix Scientific, P O Box 25067, Columbia, S.C., 29224-5067, USA, telephone: 800-733-0244 (from USA and Canada) or (803) 788-9494 (all other calls), Fax: (803) 788-9419, http://www.matrixscientific.com Manchester Organics Ltd., Unit 2, Clifton Lane, Ashville Industrial Estate, Sutton Weaver, Runcorn, Cheshire, Wash.7 3FP, United Kingdom, telephone: +44 (0)1928 710 200, fax: +44 (0)1928 710 225, http://www.manchesterorganics.com Maybridge, Trevillett, Tintagel, Cornwall, PL34 0HW, United Kingdom, telephone: +44 (0)1840 770453, Fax: +44 (0)1840 770111, http://www.maybridge.com Oakwood Products, Inc., 1741 Old Dunbar Rd., West Columbia, S.C., 29172, USA, telephone: +1-800-467-3386, fax: +1 803-739-6957, http://www.oakwoodchemical.com Pfaltz & Bauer, Inc., 172 E. Aurora Street, Waterbury, Conn., 06708, USA, telephone: +1 (203) 574-0075, Fax: +1 (203) 574-3181, http://www.pfaltzandbauer.com Princeton BioMolecular Research, Inc., Princeton Corporate Plaza, 11 Deer Park Drive, Step. 114, Monmouth Junction, N.J., 08852, USA, telephone: +1 732-355-9920 ext. 102, fax: +1 732-355-9921, http://www.princetonbio.com Ryan Scientific, Inc., P O Box 703, Mt. Pleasant, S.C., 29465, USA, telephone: +1 888-884-4911, fax: +1 843-884-5568, http://www.ryansci.com Shanghai AOKChem Group Limited, No. 1768-4-302 Boxing Road, Shanghai, China, telephone: +86-21-68712331, Fax: +86-21-68712362, http://www.aokchem.com Shanghai FWD Chemicals Limited, Room 409, The Technological and Industrial Building, Meilong Road 130, Shanghai, 200237, China, telephone: +86-21-64251348, Fax: +86-21-64251330, http://www.fwdchem.com Shanghai PI Chemicals Ltd, Room 512, Building 1, 88 Cai Lun Road, Zhangjiang Hi-Tech Park, Pudong New Area, Shanghai, 201203, China, telephone: +86-21-58953700, Fax: +86-21-58953701, http://www.pipharma.com Shanghai Sinofluoro Scientific Corporation Ltd., Room113, Building 2, No. 969#

Zhongshan South No. 2 Road, Shanghai, 200030, China, telephone: +86-21-642-793-60, fax: +86-21-642-786-03, http://www.sinofluoro.com Shanghai Specbiochem Co., Ltd., Unit A101-2, No. 326, Edison Rd, Zhangjiang High-tech Park, Shanghai, China, telephone: +86 21-51320052, Fax: +86 21-51320053, http://www.specbiochem.com Sigma-Aldrich, P O Box 14508, St. Louis, Mo., 63178, USA, Tel: 1-800-325-3010, Fax: 1-800-325-5052, http://www.sigma-aldrich.com Spectrum Chemicals and Laboratory Products, Inc., 14422 South San Pedro St., Gardena, Calif., 90248, USA, telephone: 800-395-6723, Fax: 310-5,6-7512, http://www.spectrumchemical.com Strem Chemicals, Inc., Dexter Industrial Park, 7 Mulliken Way, Newburyport, Mass., 01950-4098, USA, telephone: +1 (978) 499-1600, fax: +1 (978) 465-3104, http://www.strem.com Thermo Fisher Scientific, Janssens Pharmaceuticalaan 3A, Geel, 2440, Belgium, telephone: 0032 14 575261, Fax: 0032 14 593434, http://www.acros.com TimTec, Inc., Harmony Business Park 301-A, Newark, Del., 19711, USA, telephone: +1 (302) 292-8500, fax: +1 (302) 292-8520, http://www.timtec.net Tyger Scientific Inc., 324 Stokes Avenue, Ewing, N.J., 08638, USA, telephone: +1 609 434-0144, fax: +1 609 434-0143, http://www.tygersci.com UkrOrgSynthesis, 18 Mechnikova Street, Suite 92, Kiev, 01021, Ukraine, telephone: +38 044 531 94 97, Fax: +38 044 531 94 97, http://www.ukrorgsynth.com Vesino Industrial Co., Ltd., No. 4 Xinglanyuan Building, Changjiang Road, Tianjin, 300193, China, telephone: +86 22 81289555, fax: +86 22 27455635, http://www.vesino.com.cn Wako Pure Chemical Industries, Ltd., 1-2, Doshomachi 3-Chome, Chuo-ku, Osaka, 540-8605, Japan, telephone: +81-6-6203-3741, Fax: +81-6-6201-5964, http://www.wako-chem.co.jp

INTERMEDIATES

Intermediate 1 4-{[2-Chloro-3-(trifluoromethyl)phenyl]carbonyl}-2-piperazinone (I1)

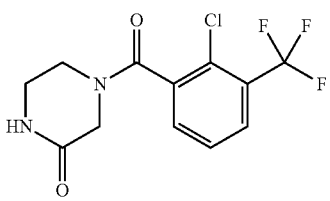 [SMILES: O=C1CN(C(=O)c2cccc(C(F)(F)F)c2Cl)CCN1]

2-piperazinone (1.802 g, 18 mmol, CAS [5625-67-2], commercially available e.g. from Sigma-Aldrich) and triethylamine (3.01 mL, 21.60 mmol) were dissolved in Dichloromethane (DCM) (100 ml) at 0° C. 2-Chloro-3-(trifluoromethyl)benzoyl chloride (4.81 g, 19.80 mmol, commercially available e.g. from Apollo Scientific or Shanghai FWD Chemicals) was added portionwise and the solution was stirred at room temperature for 48 hr. The solution was diluted with Dichloromethane (400 ml), was washed with 1N HCl (100 ml), water (100 ml), saturated sodium bicarbonate solution (100 ml), water (3×100 ml), and brine (100 ml), was dried over anhydrous magnesium sulfate, and was concentrated to a crude solid (5.92 g). The crude product was purified by flash chromatography (Biotage SP4, 40+M, 0% to 25% methanol/Dichloromethane as eluent) to afford crude product (5.01 g), that was recrystallised from toluene to afford pure 4-{[2-chloro-3-(trifluoromethyl)phenyl]carbonyl}-2-piperazinone (4.54 g, 14.80 mmol). LC/MS [M+H]+=307, 309, retention time=1.74 minutes (5 minute method).

Intermediate 2 4-[(2-Chloro-4-fluorophenyl)carbonyl]-2-piperazinone (I2)

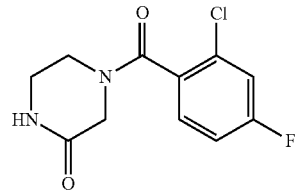 [SMILES: O=C1CN(C(=O)c2ccc(F)cc2Cl)CCN1]

2-piperazinone (4.00 g, 40 mmol, commercially available e.g. from Sigma-Aldrich) was dissolved in Dichloromethane (DCM) (125 mL) and to this was added triethylamine (6.69 mL, 48.0 mmol). This solution was then cooled with ice water. 2-Chloro-4-fluorobenzoyl chloride (8.49 g, 44.0 mmol, commercially available e.g. from Maybridge, Alfa Aesar or ABCR) was then diluted down with Dichloromethane (DCM) (25 mL), before being added via a pressure-equalizing dropping funnel. The solution was allowed to stir at room temperature overnight, and was then washed with sodium bicarbonate (100 ml), the solid was removed, and the remaining solution was washed again with sodium bicarbonate (100 ml) and brine (100 ml), before being dried over magnesium sulphate. The solvent was then removed in vacuo to afford crude product which was triturated with hexane then stirred in ethyl acetate at 80° C., before being filtered and air-dried to give 4-[(2-chloro-4-fluorophenyl)carbonyl]-2-piperazinone (5.179 g).

LC/MS [M+H]+=257.02, retention time=0.61 minutes (2 minute method).

Intermediate 3
4-[(2,3-Dichlorophenyl)carbonyl]-2-piperazinone (I3)

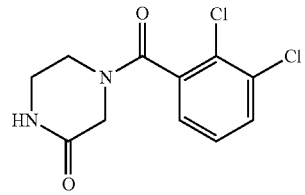 [SMILES: O=C1CN(C(=O)c2cccc(Cl)c2Cl)CCN1]

To a suspension of 2-piperazinone (5.3 g, 52.9 mmol, commercially available e.g. from Sigma-Aldrich) in dry Dichloromethane (DCM) (76 ml) was added triethylamine (16.23 ml, 116 mmol) and finally 2,3-dichlorobenzoyl chloride (12.20 g, 58.2 mmol, commercially available e.g. from ABCR, ChemPacific or UkrOrgSynthesis) dropwise (exothermic). The mixture was stirred at room temperature. After 1 hour the mixture was diluted with Dichloromethane (DCM) (150 mL) and saturated NaHCO$_3$ solution (150 mL), the phases were separated and the aqueous layer was extracted with DCM (2×100 ml). The combined organic fractions were washed with brine and dried over MgSO$_4$. Evaporation gave 4-[(2,3-dichlorophenyl)carbonyl]-2-piperazinone (12 g).

LC/MS [M+H]+=272.93, retention time=0.69 minutes (2 minute method).

Intermediates 4 to 21

Using methods analogous to those described for the synthesis of Intermediates 1 to 3 above, the intermediates tabulated below (Table 1) were prepared by substituting the appropriate substituted benzoyl chlorides for those used in the above procedures. All of the substituted benzoyl chlorides used are available from commercial sources or can be prepared using routes described previously in the chemical literature.

TABLE 1

| Intermediate no. | Chemical structure and name | Benzoyl chloride & possible commercial source(s) | [M + H]+ | Retention time (mins) |
|---|---|---|---|---|
| I4 | 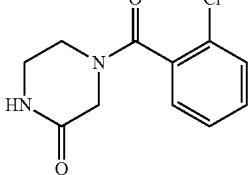 4-[(2-chlorophenyl)carbonyl]-2-piperazinone | 2-chlorobenzoyl chloride; Shanghai AOKChem, Fluorochem, Thermo Fischer Scientific | 239 | 0.57 [b] |
| I5 | 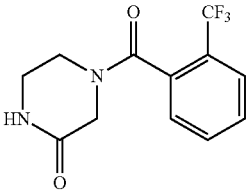 4-{[2-(trifluoromethyl)phenyl]carbonyl}-2-piperazinone | 2-(trifluoromethyl)benzoyl chloride; Matrix Scientific, Sigma-Aldrich | 273 | 0.72 [b] |
| I6 | 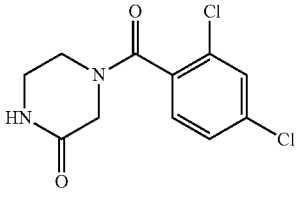 4-[(2,4-dichlorophenyl)carbonyl]-2-piperazinone | 2,4-dichlorobenzoyl chloride; Sigma-Aldrich, Maybridge | 273 | 0.69 [b] |
| I8 | 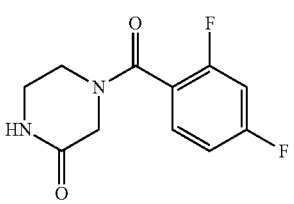 4-[(2,4-difluorophenyl)carbonyl]-2-piperazinone | 2,4-difluorobenzoyl chloride; Matrix Scientific, Sigma-Aldrich | 241 | 0.56 [b] |

TABLE 1-continued

| Intermediate no. | Chemical structure and name | Benzoyl chloride & possible commercial source(s) | [M + H]+ | Retention time (mins) |
|---|---|---|---|---|
| I9 | 4-[(2-chloro-6-fluorophenyl)carbonyl]-2-piperazinone | 2-chloro-6-fluorobenzoyl chloride; Fluorochem, Alfa Aesar, Maybridge | 257 | 0.58 [b] |
| I10 | 4-[(3-chlorophenyl)carbonyl]-2-piperazinone | 3-chlorobenzoyl chloride; Thermo Fischer Scientific, Pfaltz & Bauer | 239 | 0.64 [b] |
| I11 | 4-{[3-(trifluoromethyl)phenyl]carbonyl}-2-piperazinone | 3-(trifluoromethyl)benzoyl chloride; Apollo Scientific | 273 | 0.72 [b] |
| I12 | 2-[(3-oxo-1-piperazinyl)carbonyl]benzonitrile | 2-cyanobenzoyl chloride; Pfaltz & Bauer, American Custom Chemicals, International Laboratory, Beta Pharma | 230 | 0.47 [b] |
| I13 | 4-[(2,3-difluorophenyl)carbonyl]-2-piperazinone | 2,3-difluorobenzoyl chloride; Sigma-Aldrich, Thermo Fischer Scientific | 241 | 0.57 [b] |

TABLE 1-continued

| Intermediate no. | Chemical structure and name | Benzoyl chloride & possible commercial source(s) | [M + H]+ | Retention time (mins) |
|---|---|---|---|---|
| I14 | 4-[(2,6-dichlorophenyl)carbonyl]-2-piperazinone | 2,6-dichlorobenzoyl chloride; Sigma-Aldrich, Spectrum Chemicals | 273 | 0.59 [b] |
| I15 | 4-{[2-fluoro-3-(trifluoromethyl)phenyl]carbonyl}-2-piperazinone | 2-fluoro-3-(trifluoromethyl)-benzoyl chloride; Sigma-Aldrich, Shanghai PI Chemicals | 291 | 0.74 [b] |
| I16 | 4-{[4-fluoro-2-(trifluoromethyl)phenyl]carbonyl}-2-piperazinone | 4-fluoro-2-(trifluoromethyl)-benzoyl chloride; Sigma-Aldrich, Apollo Scientific | 291 | 0.65 [b] |
| I17 | 4-[(4-chloro-2-fluorophenyl)carbonyl]-2-piperazinone | 4-chloro-2-fluorobenzoyl chloride; Matrix Scientific, Apollo Scientific, China Hallochem, ChemPacific | 257 | 0.62 [b] |
| I18 | 4-{[4-chloro-3-(trifluoromethyl)phenyl]carbonyl}-2-piperazinone | 4-chloro-3-(trifluoromethyl)-benzoyl chloride; Shanghai Specbiochem, ABCR, JRD Fluorochemicals | 307 | 0.82 [b] |

TABLE 1-continued

| Intermediate no. | Chemical structure and name | Benzoyl chloride & possible commercial source(s) | [M + H]+ | Retention time (mins) |
|---|---|---|---|---|
| I19 | 4-[(3-chloro-4-fluorophenyl)carbonyl]-2-piperazinone | 3-chloro-4-fluorobenzoyl chloride; Matrix Scientific, Shanghai PI Chemicals, Wako Pure Chemical Industries | 257 | 0.67 [b] |
| I20 | 4-[(4-fluoro-2-methylphenyl)carbonyl]-2-piperazinone | 4-fluoro-2-methylbenzoyl chloride; JRD Fluorochemicals, Apollo Scientific, American Custom Chemicals | 237 | 0.60 [b] |
| I21 | 4-{[4-fluoro-3-(trifluoromethyl)phenyl]carbonyl}-2-piperazinone | 4-fluoro-3-(trifluoromethyl)-benzoyl chloride; Matrix Scientific, Sigma-Aldrich | 291 | 0.76 [b] |

[a] Retention time obtained using 5 minute HPLC method
[b] Retention time obtained using 2 minute HPLC method Intermediate 22 3-Methyl-2-pyridinecarbohydrazide (I22)

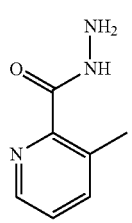

Ethyl 3-methylpyridine-2-carboxylate (2 g, 12.11 mmol, CAS [58997-10-7], commercially available e.g. from Beta Pharma) was dissolved in ethanol (40 mL) and treated with hydrazine monohydrate (0.706 mL, 14.53 mmol). The reaction mixture was stirred at room temperature for 15 mins before heating at reflux for 18 hours. The reaction mixture was cooled to room temperature, more hydrazine monohydrate (0.5 ml) was added, and the reaction mixture was heated at reflux for a further 24 hours. The reaction mixture was cooled to room temperature. The solvent was evaporated to near dryness, and the residue was azeotroped with ethanol (3×35 ml). The mixture was evaporated to dryness after the third time to afford a pale yellow solid. This solid was slurried in diethyl ether, filtered off and dried to afford the title compound as a white solid (0.575 g, 3.80 mmol).

LC/MS [M+H]+=151.86.

Intermediate 23 6-Fluoro-2-pyridinecarbohydrazide (I23)

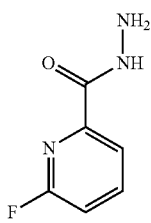 [SMILES: NNC(=O)c1cccc(F)n1]

1,1-Dimethylethyl 2-[(6-fluoro-2-pyridinyl)carbonyl]hydrazinecarboxylate (510 mg, 2 mmol) was dissolved in 1,4-dioxane (5 mL) and treated with 4M HCl in 1,4 dioxane (5.00 mL, 20.00 mmol) at 0° C. The mixture was stirred to room temperature over 24 hr and was concentrated in vacuo, azeotroping with diethyl ether (3×50 ml) to afford a white solid. The solid was dissolved in methanol and loaded on to an SCX cartridge (Varian, 10 g), washing with methanol, and then eluting the product in free base form using 2M ammonia/methanol. The ammoniacal fractions were concentrated in vacuo to afford the product, 6-fluoro-2-pyridinecarbohydrazide (251 mg, 1.618 mmol).

LC/MS [M+H]+=156, retention time=0.38 minutes (2 minute method).

The 1,1-dimethylethyl 2-[(6-fluoro-2-pyridinyl)carbonyl]hydrazinecarboxylate used above can be prepared in the following manner:

6-Fluoro-2-pyridinecarboxylic acid (2.83 g, 20.06 mmol, CAS[402-69-7], commercially available e.g. from Sigma-Aldrich or Apollo Scientific) was dissolved in Dichloromethane (DCM) (100 mL) at 0° C. Oxalyl chloride (2.107 mL, 24.07 mmol) and a drop of N,N-dimethylformamide (DMF) was added and the mixture was stirred for 2 hours. The solvents were removed in vacuo and azeotroped with toluene (3×20 ml). The residue was dissolved in dichloromethane (DCM) (100 ml) whereupon 1,1-dimethylethyl hydrazinecarboxylate (2.92 g, 22.06 mmol) and N,N-diisopropylethylamine (DIPEA) (7.71 mL, 44.1 mmol) were added. The mixture was stirred at room temperature for 3 hours and concentrated in vacuo. The residue was partitioned between ethyl acetate (100 ml) and saturated sodium bicarbonate solution (50 ml). The aqueous phase was extracted with ethyl acetate (3×100 ml), the combined organic extracts were washed with brine (50 ml), were dried over anhydrous sodium sulphate and were concentrated in vacuo. The residue was purified by flash chromatography (Biotage SP4, 40+M, 0-100% ethyl acetate/iso-hexane) to afford 1,1-dimethylethyl 2-[(6-fluoro-2-pyridinyl)carbonyl]hydrazinecarboxylate (5.04 g, 19.75 mmol).

LC/MS=156 (M+H-BOC)+, retention time=0.81 minutes (2 minute method).

Intermediate 24 5-Fluoro-2-pyridinecarbohydrazide (I24)

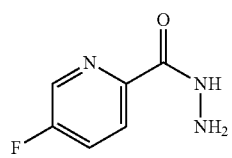 [SMILES: NNC(=O)c1ccc(F)cn1]

5-Fluoro-2-pyridinecarbohydrazide was prepared in a manner analogous to that described above for 6-fluoro-2-pyridinecarbohydrazide (I23) but using 5-fluoro-2-pyridinecarboxylic acid (CAS [107504-08-5], commercially available e.g. from Apollo Scientific or Beta Pharma) in the place of 6-fluoro-2-pyridinecarboxylic acid.

LC/MS=156 (M+H-BOC)+, retention time=0.38 minutes (2 minute method).

Intermediate 25 3-Pyridazinecarbohydrazide (I25)

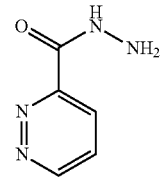

3-Pyridazinecarbohydrazide was prepared in a manner analogous to that described above for 6-fluoro-2-pyridinecarbohydrazide (I23) but using 3-pyridazine carboxylic acid (CAS [2164-61-6], commercially available e.g. from Apollo Scientific, Shanghai AOKChem or Manchester Organics) in the place of 6-fluoro-2-pyridinecarboxylic acid.

Intermediate 26 2-Pyrimidinecarbohydrazide (I26)

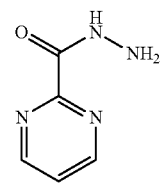

2-Pyrimidinecarbohydrazide was prepared in a manner analogous to that described above for 6-fluoro-2-pyridinecarbohydrazide (I23) but using pyrimidine-2-carboxylic acid (CAS [562101-38-6], commercially available e.g. from TimTec or Manchester Organics) in the place of 6-fluoro-2-pyridinecarboxylic acid.

LC/MS retention time=0.17 minutes (2 minute method).

Intermediate 27 5-Methyl-2-pyridinecarbohydrazide (I27)

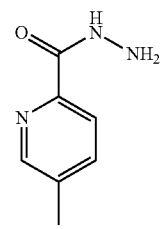

5-Methyl-2-pyridinecarbohydrazide was prepared in a manner analogous to that described above for 6-fluoro-2-pyridinecarbohydrazide (I23) but using 5-methyl-2-pyridinecarboxylic acid (5-methylpicolinic acid, CAS [4434-13-3], commercially available e.g. from Allichem or Ryan Scientific) in the place of 6-fluoro-2-pyridinecarboxylic acid.

LC/MS=152 (M+H)+, retention time=0.42 minutes (2 minute method).

Intermediate 28 4-Methyl-2-pyridinecarbohydrazide (I28)

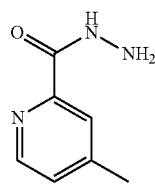

4-Methyl-2-pyridinecarbohydrazide was prepared in a manner analogous to that described above for 6-fluoro-2-pyridinecarbohydrazide (I23) but using 4-methyl-2-pyridinecarboxylic acid (CAS [4021-08-3], commercially available e.g. from Sigma-Aldrich or Fluorochem) in the place of 6-fluoro-2-pyridinecarboxylic acid.

LC/MS retention time=0.36-0.39 minutes (2 minute method).

Intermediate 29 2-Methyl-3-pyridinecarbohydrazide (I29)

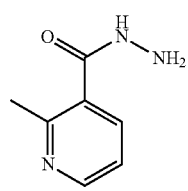

2-Methyl-3-pyridinecarbohydrazide was prepared in a manner analogous to that described above for 3-methyl-2-pyridinecarbohydrazide (I22) but using ethyl 2-methyl-3-pyridinecarboxylate (CAS [1721-26-2], commercially available e.g. from Sigma-Aldirch or Alfa Aesar) in the place of ethyl 6-methyl-2-pyridylcarboxylate.

Intermediate 30
3,5-Difluoro-2-pyridinecarbohydrazide (I30)

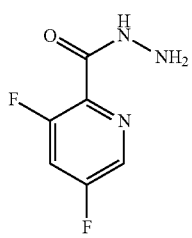 [SMILES: NNC(=O)c1ncc(F)cc1F]

3,5-Difluoro-2-pyridinecarbohydrazide was prepared in a manner analogous to that described above for 6-fluoro-2-pyridinecarbohydrazide (I23) but using 3,5-difluoro-2-pyridinecarboxylic acid (CAS [745784-04-7], commercially available e.g. from Matrix Scientific, Alfa Aesar or Apollo Scientific) in the place of 6-fluoro-2-pyridinecarboxylic acid.

LC/MS retention time=0.31-0.33 minutes (2 minute method).

Intermediate 31 3-Fluoro-2-pyridinecarbohydrazide (I31)

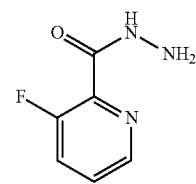 [SMILES: NNC(=O)c1ncccc1F]

3-Fluoro-2-pyridinecarbohydrazide was prepared in a manner analogous to that described above for 3-methyl-2-pyridinecarbohydrazide (I22) but using methyl 3-fluoro-2-pyridinecarboxylate (commercially available, e.g. from Allichem, Atomole Scientific, Bepharm or Vesino Industrial) in the place of ethyl 6-methyl-2-pyridylcarboxylate.

Intermediate 32 2,3-Dichloro-4-fluorobenzoic acid (I32)

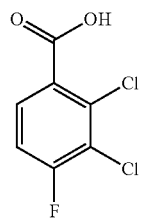

2,3-dichloro-4-fluorobenzoic acid was prepared according to the route described in J. Chem. Soc. Perkin Trans 1 (1995), 1265.

sBuLi (97 mL, 126 mmol) was dissolved in tetrahydrofuran (THF) (200 mL) at −78° C. and TMEDA (19.02 mL, 126 mmol) was added. 3-chloro-4-fluorobenzoic acid (10 g, 57.3 mmol, commercially available from e.g. Sigma-Aldrich, Fluorochem or Apollo) dissolved in tetrahydrofuran (THF) (50 mL) was added dropwise at −78° C. and the solution stirred at this temperature for 30 minutes. Hexachloroethane (54.2 g, 229 mmol) dissolved in tetrahydrofuran (THF) (200 mL) was added dropwise and the solution stirred to room temperature over 4 hours. Water (25 mL) was added and the solution concentrated in vacuo. The residue was partitioned between diethyl ether (300 mL) and saturated sodium bicarbonate solution (50 mL) and extracted with saturated sodium bicarbonate solution (3×50 mL). The aqueous phase was acidified to pH1 with 5N hydrochloric acid, extracted with diethyl ether (3×200 mL), combined extracts dried over anhydrous magnesium sulfate and concentrated in vacuo to afford a crude solid (9.21 g). The crude solid was recrystalised from heptane/diethyl ether to afford the desired product in 4.91 g.

LC/MS=207/209/211(M−H)−, retention time=0.88 minutes (2 minute method).

The mother liquors were concentrated in vacuo, washed with heptane and dried to afford a second batch of desired product in 2.62 g LC/MS=207/209/211 (M−H)−, retention time=0.88 minutes (2 minute method).

Intermediate 33 2,3-Dichloro-4-fluorobenzoyl chloride (I33)

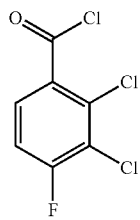 [SMILES: O=C(Cl)c1ccc(F)c(Cl)c1Cl]

2,3-dichloro-4-fluorobenzoic acid (I32) (5.76 g, 27.6 mmol) was suspended in dichloromethane (DCM) (150 mL) at 0° C. and treated with oxalyl chloride (2.89 mL, 33.1 mmol). The mixture was stirred at 0° C. for 10 minutes before 5 drops of DMF were added. The mixture was stirred to room temperature over 4 h. Solvents were removed in vacuo and the residue was azeotroped with toluene (3×100 mL). The residue was used directly in subsequent steps without further purification, assuming 100% yield.

Intermediate 34 4-[(2,3-Dichloro-4-fluorophenyl)carbonyl]-2-piperazinone (I34)

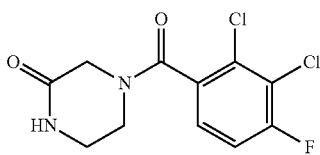 [SMILES: O=C1CN(C(=O)c2ccc(F)c(Cl)c2Cl)CCN1]

Using method analogous to those described for the synthesis of intermediates 1 to 3, the intermediate below was synthesised according to the method described below. 2-piperazinone (2.51 g, 25.07 mmol, commercially available e.g. from Sigma-Aldrich) and triethylamine (4.19 mL, 30.1 mmol) were dissolved in Dichloromethane (DCM) (50 mL). 2,3-dichloro-4-fluorobenzoyl chloride (I33)(6.28 g, 27.6 mmol) dissolved in Dichloromethane (DCM) (50 mL) was added dropwise at 0° C. and the solution allowed to stir to room temperature overnight. The mixture was diluted with Dichloromethane (200 mL) and washed with saturated sodium bicarbonate solution (100 mL). The aqueous phase was extracted with Dichloromethane (3×100 mL) and the combined extracts were washed with water (2×100 mL), brine (100 mL), dried over anhydrous sodium sulfate and concentrated to a crude solid that was triturated with hexane to afford product in 6.94 g. The product was recrystalised from ethanol (Note: slow to come out of solution) to afford the desired product in 5.08 g.

LC/MS=291 (M+H)+, retention time=0.70 minutes (2 minute method).

Intermediate 35 2,4-Dichloro-3-fluorobenzoic acid (I35)

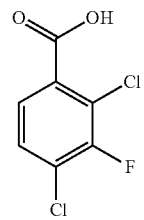 [SMILES: O=C(O)c1ccc(Cl)c(F)c1Cl]

2,4-Dichloro-3-fluorobenzoic acid was prepared according to the route reported in Eur. J. Org. Chem. 2006, 4398-4404 using the methods described below.

a) To 2,2,6,6-tetramethylpiperidine (2.207 mL, 13.00 mmol) dissolved in Tetrahydrofuran (THF) (40 mL) at 0° C. was added nBuLi (8.13 mL, 13.00 mmol) dropwise. The solution was stirred at 0° C. for 10 minutes and cooled to −78° C. 1,3-dichloro-2-fluorobenzene (1.650 g, 10 mmol, commercially available from e.g. Sigma-Aldrich, Apollo or Alfa Aesar) dissolved in Tetrahydrofuran (THF) (10 mL) was added dropwise and the solution stirred at −78° C. for 1 hour. The solution was poured on to dry ice (xs) that had been washed with tetrahydrofuran (3×100 mL) and stirred to room temperature over 3 hours. Solvents were removed in vacuo to afford a white solid. This was combined with a larger scale reaction described below for purification and isolation.

b) To 2,2,6,6-tetramethylpiperidine (20.07 mL, 118 mmol) dissolved in Tetrahydrofuran (THF) (300 mL) at 0° C. was added nBuLi (73.9 mL, 118 mmol) dropwise. The solution was stirred at 0° C. for 10 minutes and cooled to −78° C. 1,3-dichloro-2-fluorobenzene (15 g, 91 mmol, commercially available from e.g. Sigma-Aldrich, Apollo or Alfa Aesar) dissolved in Tetrahydrofuran (THF) (30 mL) was added dropwise and the solution stirred at −78° C. for 1 hour. The solution was poured on to dry ice (xs) that had previously washed with tetrahydrofuran (3×100 mL) and stirred to room temperature over 3 hours. Solvents were removed in vacuo to afford a white solid. The solid was combined with solid isolated from method a) and partitioned between ethyl acetate (200 mL) and 2N Hydrochloric acid. The aqueous solution was extracted with ethyl acetate (3×100 mL); the combined extracts were washed with brine (50 mL) and concentrated to a crude solid. The crude solid was recrystalised from cyclohexane/toluene to afford the product 19.03 g.

LC/MS=207/209 (M−H)−, retention time=0.90 minutes (2 minute method).

The mothor liquors were concentrated to afford a second batch of desired product in 1.7 g. LC/MS=207/209 (M−H)−, retention time=0.90 minutes (2 minute method).

Intermediate 36 2,4-dichloro-3-fluorobenzoyl chloride (I36)

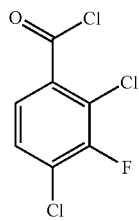 [SMILES: O=C(Cl)c1ccc(Cl)c(F)c1Cl]

A solution of 2,4-dichloro-3-fluorobenzoic acid (1.045 g, 5 mmol) in dichloromethane (DCM) (25 mL) was cooled to 0° C. To this was added oxalyl chloride (0.481 mL, 5.50 mmol) and 4 drops of DMF (catalytic), and the solution was stirred under argon for 4 hours. The solvent was then evaporated in vacuo and the remaining residue was azeotroped with toluene to yield the acid chloride in 1.103 g. Half of this material was used directly in the next step.

$^1$H NMR (400 MHz; CDCl$_3$) δ 7.89 (1H, dd), 7.49 (1H, m)

Intermediate 37 4-[(2,4-Dichloro-3-fluorophenyl)carbonyl]-2-piperazinone (I37)

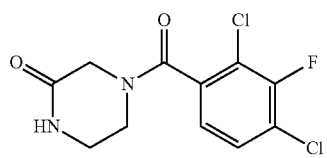 [SMILES: O=C1CN(C(=O)c2ccc(Cl)c(F)c2Cl)CCN1]

This was synthesised in a method analogous to the described for intermediates 1 to 3 and prepared according to the method described below.

2-piperazinone (0.180 g, 1.8 mmol, commercially available e.g. from Sigma-Aldrich) was dissolved in dichloromethane (DCM) (10 mL), and to this was added triethylamine (0.301 mL, 2.160 mmol). The solution was then cooled to 0° C. before 2,4-dichloro-3-fluorobenzoyl chloride (0.450 g, 1.980 mmol) in dichloromethane (DCM) (2 mL) was added dropwise. The solution was stirred, under argon, for 30 minutes before the solvent was evaporated in vacuo. The remaining residue was then dissolved in DCM (20 mL) and the solution was washed with water (10 mL), a saturated solution of sodium bicarbonate (10 mL) and brine (10 mL). The organic phase was then dried over anhydrous sodium sulphate, and the solid sodium sulphate was then filtered off. The solvent was then evaporated in vacuo, and the remaining solid was stirred in hexane, at 55° C., for 30 minutes. The solid was then filtered off to yield the product in 0.369 g.

LCMS [M+H] 290.8 @ 0.71 min (2 min method)

Intermediate 38 4-[(3,4-Dichlorophenyl)carbonyl]-2-piperazinone (I38)

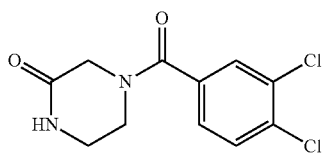 [SMILES: O=C1CN(C(=O)c2ccc(Cl)c(Cl)c2)CCN1]

This compound was synthesised in a method analogous to the method described for intermediates 1 to 3 and prepared according to the method below. To a suspension of 2-piperazinone (2 g, 19.98 mmol, commercially available from e.g. Sigma-Aldrich) in dry dichloromethane (DCM) (28.5 ml) was added triethylamine (6.13 ml, 43.9 mmol), the mixture was cooled to 0° C. and 3,4-dichlorobenzoyl chloride (4.60 g, 21.97 mmol, commercially available from e.g.Sigma-Aldrich, Acros or Alfa Aesar) was added dropwise. The mixture was stirred at 0° C. for 15 minutes then warmed to room temperature overnight. The mixture was diluted with DCM (100 mL) and sat. NaHCO$_3$ (100 ml), the phases separated and the aqueous extracted with DCM (2×100 ml). The combined organics were washed with brine and dried over MgSO$_4$. The crude material (3.37 g) was triturated with isohexane and Et$_2$O to the desired product in 3.02 g as an off-white solid.

LC/MS: (M+H)+=273, retention time=0.76 minutes (2 minutes run).

Intermediate 39 1-[(2-Chlorophenyl)carbonyl]-3-(ethyloxy)piperazine (I39)

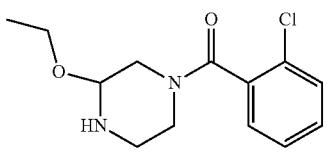 [SMILES: CCOC1CN(C(=O)c2ccccc2Cl)CCN1]

4-[(2-chlorophenyl)carbonyl]-2-piperazinone (I4) (676 mg, 2.83 mmol) was dissolved in dichloromethane (DCM) (10 mL) and was treated with triethyloxonium tetrafluoroborate (628 mg, 3.31 mmol). The solution was stirred at 25° C. for 16 hr and the solution partitioned between ethyl acetate (25 mL) and saturated sodium bicarbonate solution (25 mL). The aqueous phase was extracted with ethyl acetate (3×25 mL), combined extracts were washed with brine (25 mL), dried over anhydrous sodium sulfate and concentrated to a crude oil in 816 mg that was used in the subsequent step without further purification. Compound was not characterised but used directly in the next step.

Intermediate 40 1-[(2-Chlorophenyl)carbonyl]-3-hydrazinopiperazine (I40)

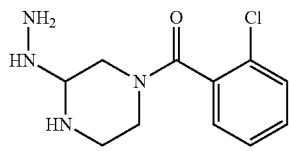 [SMILES: NNC1CN(C(=O)c2ccccc2Cl)CCN1]

1-[(2-chlorophenyl)carbonyl]-5-(ethyloxy)-1,2,3,6-tetrahydropyrazine (I39) (0.755 g, 2.83 mmol) dissolved in Dichloromethane (DCM) (10 mL) was added to hydrazine hydrate (0.220 mL, 7.08 mmol, commercially available from e.g. Alfa Aesar, Acros or Fluka) dissolved in Dichloromethane (DCM) (5 mL) and stirred at 25° C. for 4 hr. The solvents were removed in vacuo and the residue azeotroped with toluene (3×25 mL), to afford product in 715 mg that was used in the subsequent step without further purification.

LCMS [M+H]+ 253.00 @ 0.45 min (2 min run)

Intermediate 41 1,1-Dimethylethyl 2-(8-quinolinylcarbonyl)hydrazinecarboxylate (I41)

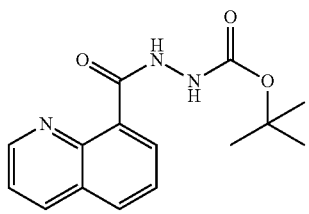 [SMILES: CC(C)(C)OC(=O)NNC(=O)c1cccc2cccnc12]

To a solution of 8-quinolinecarboxylic acid (750 mg, 4.33 mmol, commercially available from e.g. Sigma-Aldrich, Acros or Apollo) and oxalyl chloride (0.417 ml, 4.76 mmol) in dichloromethane (50 ml) stirred under argon at 0° C. was added neat DMF (34 µl, 0.439 mmol). The reaction mixture was stirred at 0° C. for 18 hr, then evaporated in vacuo and azeotroped with toluene (2×5 ml). The residue was dissolved in dichloromethane (50 ml), and to this were added DIPEA (0.908 ml, 5.20 mmol) and t-butyl carbazate (1259 mg, 9.53 mmol). The reaction mixture was stirred at room temp for 6 hr. The reaction mixture was partitioned between dichloromethane (~50 ml) and saturated sodium bicarbonate solution (~25 ml). The aqueous phase was extracted with dichloromethane (2×50 ml) and the combined organic extracts washed with saturated sodium bicarbonate solution (~50 ml), dried over sodium sulphate and evaporated in vacuo to give the crude product as a burgundy gum. This was purified via Biotage (5:1 DCM/MeOH; 40+M Biotage column; flow rate 20 ml/min) to afford impure product as a burgundy foam. This was further purified via Biotage (1:1 Hex/EtOAc; 40+M Biotage column) and dried overnight in a vacuum oven at 40° C. to afford the required product as a fine, pale yellow powder in 947.8 mg.

LCMS: 2 minute run in MeOH. MH+ m/z=288.12; RT=0.84-0.86 min.

Intermediate 42 8-Quinolinecarbohydrazide (I42)

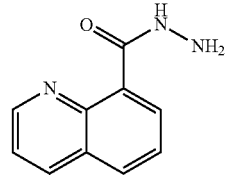 [SMILES: NNC(=O)c1cccc2cccnc12]

To a solution of t-butyl-2-(8-quinolinylcarbonyl)hydrazinecarboxylate (I41) (947.8 mg, 3.07 mmol) in 1,4-dioxane (7.5 ml) stirred under argon at room temp was added a solution of hydrochloric acid (4 M) in dioxane (7.67 ml, 30.7 mmol) dropwise during 1 min. The reaction mixture was stirred at RT for 18 hr, then evaporated in vacuo and azetroped with ether (3×5 ml) to afford the crude dihydrochloride salt as a beige powder. This was purified by SCX and dried for 72 hr in a vacuum oven at 40° C. to afford the free base as a yellow solid in 436.2 mg.

LCMS: 2 minute run in MeOH. MH+ m/z=187.94; RT=0.40-0.43 min.

Intermediate 43 1,1-Dimethylethyl 2-(1H-indol-7-ylcarbonyl)hydrazinecarboxylate (I43)

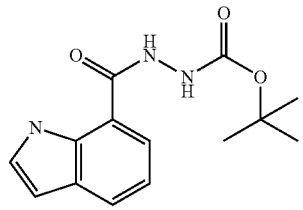 [SMILES: CC(C)(C)OC(=O)NNC(=O)c1cccc2cc[nH]c12]

To a suspension of 1H-indole-7-carboxylic acid (510.9 mg, 2.85 mmol, commercially available from e.g. Maybridge, Apollo or Fluorochem) and N-[3-(dimethylamino)propyl]-N'-ethylcarbodiimide (443 mg, 2.85 mmol) in Dichloromethane (15 ml) stirred under argon at room temp was added solid 1-H-1,2,3-benzotriazol-1-ol (43.7 mg, 0.285 mmol) in dichloromethane (15 ml). The reaction mixture was stirred at RT for 1 hr. Solid t-butyl carbazate (571 mg, 4.28 mmol) was added and the reaction mixture stirred at room temp for 18 hr. The reaction mixture was partitioned between dichloromethane (~50 ml) and saturated sodium bicarbonate solution (~25 ml). The aqueous phase was extracted with dichloromethane (2×25 ml) and the combined organic extracts washed with saturated sodium bicarbonate solution (~25 ml), dried over sodium sulphate and evaporated in vacuo to give the crude product as a yellow gum. The residue was purified via Biotage (1:1 Hex/EtOAc; 25+M Biotage column) to afforded the required product as a white foam in 360.0 mg.

LCMS: 2 minute run in MeCN. [M-Boc+2H]+=175.97, [M-H]−=273.93; RT=0.86-0.88 min.

Intermediate 44 1H-Indole-7-carbohydrazide (I44)

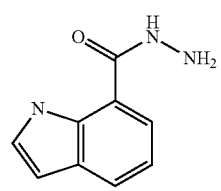 [SMILES: NNC(=O)c1cccc2cc[nH]c12]

To a solution of 1,1-dimethylethyl 2-(1H-indol-7-ylcarbonyl)hydrazinecarboxylate (I43) (0.202 g, 0.734 mmol) in 1,4-Dioxane (8 mL) was added 4M HCl in Dioxane (1.834 mL, 7.34 mmol) dropwise over 1 minutes. The solution was then allowed to stir at room temperature and under argon for 18 hours. Analysis by LCMS and TLC showed starting material to still be present, 4M HCl in Dioxane (5.50 mL, 22.01 mmol) was thus added and the solution was further stirred for 2 hours. TLC confirmed reaction completion and the solvent was evaporated in vacuo. The remaining solid was then azeotroped with ether (2×10 mL). The remaining solid was then loaded onto an SCX cartridge (5 g) and washed with methanol (2×20 mL) before being eluted with 2M NH3/MeOH. The solvent was then evaporated in vacuo and the remaining solid was dried in a vac-oven to yield the product in 0.113 g.

$^1$H NMR (400 MHz; CDCl$_3$) δ 10.18 (1H, s), 7.83 (1H, d), 7.56 (1H, broad s), 7.37-7.33 (2H, m), 7.12 (1H, t), 6.59 (1H, m), 4.12 (2H, broad s)

Intermediate 45 1,1-Dimethylethyl 2-[(1-methyl-1H-imidazol-2-yl)carbonyl]hydrazinecarboxylate (I45)

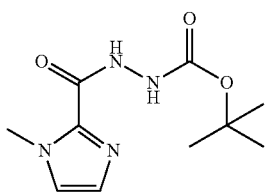 [SMILES: Cn1ccnc1C(=O)NNC(=O)OC(C)(C)C]

To a solution of 1-methyl-1H-imidazole-2-carboxylic acid (500 mg, 3.57 mmol, commercially available from e.g. Sigma-Aldrich), N-[3-(dimethylamino)propyl]-N'-ethylcarbodiimide (554 mg, 3.57 mmol) and 1-H-1,2,3-benzotriazol-1-ol (54.6 mg, 0.357 mmol) in dichloromethane (20 ml) prestirred for 30 mins under argon at room temp was added solid t-butyl carbazate (722 mg, 5.35 mmol). The reaction mixture was stirred at RT for 18 h. The reaction mixture was partitioned between dichloromethane (~50 ml) and saturated sodium bicarbonate solution (~50 ml). The aqueous phase was extracted with dichloromethane (2×25 ml) and the combined organic extracts washed with saturated sodium bicarbonate solution (~25 ml), dried over magnesium sulphate and evaporated in vacuo to give the crude product as a yellow oil.

This was purified via Biotage (1:1 Hex/EtOAc; 40+M Biotage column) to afford the required product as a white solid in 143.8 mg.

LCMS: 2 minute run in MeOH. [M-Boc+H]$^+$=140.93; RT=0.57-0.59 min

Intermediate 46 1-Methyl-1H-imidazole-2-carbohydrazide (I46)

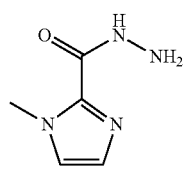

To a solution of t-butyl 2-[(1-methyl-1H-imidazol-2-yl)carbonyl]hydrazinecarboxylate (I45) (143 mg, 0.595 mmol) in 1,4-dioxane (1.5 ml) stirred under argon at room temp was added a solution of hydrochloric acid (4 M) in dioxane (2.232 ml, 8.93 mmol). The reaction mixture was stirred at RT for 48 hr, then evaporated in vacuo and the residue added to an SCX column and eluted with dichloromethane (100 ml) followed by 5% MeOH/DCM (50 ml), 10% MeOH/DCM (30 ml), and 2M NH$_3$/MeOH (50 ml) to afford the required product as a chartreuse solid in 73.1 mg, which was used without further purification in the next step.

LCMS: 2 minute high pH run in MeOH. MH$^+$ m/z=141.13; RT=0.31 min.

Intermediate 47 5-Chloro-2-pyrazinecarbonyl chloride (I47)

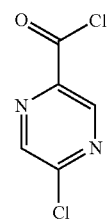

5-Oxo-4,5-dihydro-2-pyrazinecarboxylic acid (2.80 g, 20 mmol, commercially available from e.g. Sigma-Aldrich, Fluorochem or Astatech) and thionyl chloride (14.60 mL, 200 mmol) were heated at reflux in toluene (15 mL) for 2 h. Solvents were decanted from a dark residue and concentrated in vacuo, azeotroping with toluene (3×100 mL) to afford product in 3.15 g that was used in subsequent steps without further purification.

LC/MS=173/175 [methyl ester](M+H)+, retention time=0.58 minutes (2 minute method).

Intermediate 48 1,1-Dimethylethyl 2-[(5-chloro-2-pyrazinyl)carbonyl]hydrazinecarboxylate (I48)

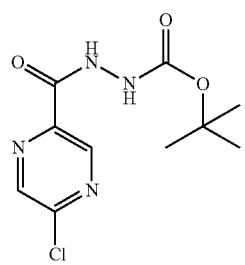 [SMILES: CC(C)(C)OC(=O)NNC(=O)c1cnc(Cl)cn1]

1,1-dimethylethyl hydrazinecarboxylate (2.59 g, 19.58 mmol) and triethylamine (2.98 mL, 21.36 mmol) were dissolved in Dichloromethane (DCM) (50 mL). 5-chloro-2-pyrazinecarbonyl chloride (I47) (3.15 g, 17.80 mmol) dissolved in Dichloromethane (DCM) (50 mL) was added dropwise at 0° C. and the mixture allowed to reach room temperature over 16 hr. Solvents were removed in vacuo and the residue was partitioned between ethyl acetate (100 mL) and saturated sodium bicarbonate solution (50 mL). The aqueous phase was extracted with ethyl acetate (3×100 mL), combined extracts were washed with brine (100 mL) dried over anhydrous sodium sulfate and concentrated to a crude solid (5.05 g). The product was purified by flash chromatography (Isolera, 100 g, 0-100% Methanol:Dichloromethane (1:9)/Dichloromethane) to afford product in 4.63 g.

LC/MS=271/273 (M–H)–, retention time=0.73 minutes (2 minute method).

Intermediate 49 5-Chloro-2-pyrazinecarbohydrazide (I49)

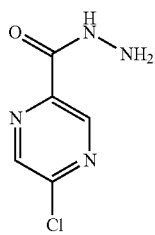 [SMILES: NNC(=O)c1cnc(Cl)cn1]

To a solution of 1,1-dimethylethyl 2-[(5-chloro-2-pyrazinyl)carbonyl]hydrazine carboxylate (I48) (2.182 g, 8 mmol) in 1,4-dioxane (20 mL) was added 4M HCl in 1,4-dioxane (20.00 mL, 80 mmol). The solution was then stirred under argon for 4 hours. Analysis by LCMS showed some sign of starting material still present thus 4M HCl in 1,4-dioxane (8.00 mL, 32.0 mmol) was added. The solvent was then evaporated in vacuo and the remaining solid was loaded onto an SCX cartridge (2×10 g). The solid was then washed with methanol (2×30 mL) before being eluted from the cartridge by 2M NH$_3$/MeOH. TLC confirmed product location and the solvent from the combined fractions was evaporated in vacuo. The solid was triturated with diethyl ether, filtered, and washed with diethyl ether to afford product in 1.02 g.

$^1$H NMR (400 MHz; CDCl$_3$) δ 9.14 (1H, s), 8.68 (1H, broad s), 8.53 (1H, s), 4.11 (2H, s)

Intermediate 50 1,1-Dimethylethyl 2-(1,3-thiazol-2-ylcarbonyl)hydrazinecarboxylate (I50)

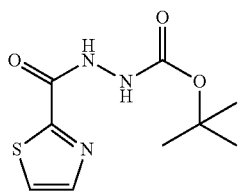 [SMILES: CC(C)(C)OC(=O)NNC(=O)c1nccs1]

Was synthesised according to the methods described below:

1) To a solution of 1,3-thiazole-2-carboxylic acid (646 mg, 5.00 mmol, commercially available from e.g. Apollo), N-[3-(dimethylamino)propyl]-N'-ethylcarbodiimide (959 mg, 5.00 mmol) and 1-H-1,2,3-benzotriazol-1-ol (766 mg, 5.00 mmol) in Dichloromethane (25 ml) pre-stirred under argon for 30 min at room temp was added solid t-butyl carbazate (727 mg, 5.50 mmol). The reaction mixture was stirred at RT for 18 hr. The reaction mixture was partitioned between Dichloromethane (~50 ml) and saturated sodium bicarbonate solution (~50 ml). The aqueous phase was extracted with Dichloromethane (2×25 ml) and the combined organic extracts washed with saturated sodium bicarbonate solution (~25 ml) and brine (~25 ml), dried over sodium sulphate and evaporated in vacuo to give the crude product as a yellow oil. This was purified via Biotage (1:1 Hex/EtOAc; 40+M Biotage column) to afford the required product as a yellow solid in 515.2 mg which was combined with the material obtained below and used in the next step.

LCMS: 2 min high pH run in MeOH. [M–H]$^-$ m/z=242.0; RT=0.54-0.55 min.

2) To a solution of 1,3-thiazole-2-carboxylic acid (129 mg, 0.999 mmol, commercially available from e.g. Apollo) and N[3-(dimethylamino)propyl]-N'-ethylcarbodiimide (191 mg, 0.999 mmol) in Dichloromethane (5 ml) pre-stirred for 5 min under argon at room temp was added solid 1-H-1,2,3-benzotriazol-1-ol (15.30 mg, 0.100 mmol). The reaction mixture was stirred at RT for 20 min. Solid t-butyl carbazate (145 mg, 1.099 mmol) was added and the reaction mixture stirred under argon at RT for 21 hr. The reaction mixture was partitioned between Dichloromethane (~50 ml) and saturated sodium bicarbonate solution (~50 ml). The aqueous phase was extracted with Dichloromethane (2×25 ml) and the combined organic extracts washed with saturated sodium bicarbonate solution (~50 ml) and water (~25 ml), dried over sodium sulphate and evaporated in vacuo to afford the crude product as a yellow oil. This was purified via Biotage (1:1 Hex/EtOAc; 25+M Biotage column) to afford the required product as a colourless oil in 73.4 mg, which was combined with the above material and used in the next step.

LCMS: 2 min run in MeOH. [M+H]$^+$ m/z=244.14; RT=0.68-0.69 min.

3) EDC (742 mg, 3.87 mmol) and HOBt (593 mg, 3.87 mmol) were added to a suspension of 1,3-thiazole-2-carboxylic acid (500 mg, 3.87 mmol) in dry Dichloromethane (DCM) (19 ml)—solution became clear after the addition of EDC. The mixture was stirred at room temperature for 30 mins. 1,1-dimethylethyl hydrazinecarboxylate (512 mg, 3.87 mmol) was added and the resulting mixture was stirred at room temperature 1 day. The reaction mixture was diluted in DCM (150 mL) and washed with sat. NaHCO$_3$ (2×25 mL) and brine (25 mL). The resulting organic layer was dried over MgSO$_4$ and concentrated under reduced pressure. The crude product was purified by flash chromatography (10% MeOH in DCM/DCM–10CV) to afford desired product in 432.9 mg as an orange oil.

LCMS m/z 243.9 [M+H] @ 0.66 min (2 min run)

Intermediate 51 1,3-Thiazole-2-carbohydrazide (I51)

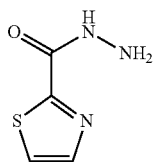

Was prepared according to the procedures described below:

1) To a solution of t-butyl-2-(1,3-thiazol-2-ylcarbonyl)hydrazinecarboxylate (I50) (580 mg, 2.169 mmol) in 1,4-dioxane (5.5 ml) stirred under argon at room temp was added a solution of hydrochloric acid (4 M) in dioxane (7.5 ml, 30.0 mmol). The reaction mixture was stirred at RT for 21 hr, then evaporated in vacuo to afford the crude (di)hydrochloride salt as a yellow solid. This was purified by SCX chromatography and dried (vacuum oven, 40° C., 4 hr) to afford the free base as a tan solid in 303.2 mg.

LCMS: 2 minute high pH run in MeOH. [M+H]$^+$ m/z=144.0; RT=0.28-0.29 min.

2) 4M HCl (2.21 mL, 63.6 mmol) in 1,4-Dioxane was added to 1,1-dimethylethyl 2-(1,3-thiazol-2-ylcarbonyl)hydrazinecarboxylate (432.9 mg, 1.779 mmol). The reaction mixture was stirred at room temperature overnight. The solvent was evaporated. The crude product was purified by SCX cartridge. The column was first washed with methanol. After a wash with 2M $NH_3$ in MeOH and evaporation of the resulting fractions afforded the desired product in 123 mg as an orange powder.

LCMS m/z 143.7 [M+H] @ 0.35 min (2 min run)

Intermediate 52 4-{[4-Chloro-2-(trifluoromethyl)phenyl]carbonyl}-2-piperazinone (I52)

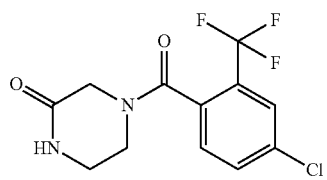 [SMILES: O=C1CN(C(=O)c2ccc(Cl)cc2C(F)(F)F)CCN1]

2-piperazinone (0.5 g, 4.99 mmol, commercially available from e.g. Sigma-Aldrich) was dissolved in dichloromethane (DCM) (30 mL), and to this was added triethylamine (0.835 mL, 5.99 mmol). The solution was then cooled to 0° C. before 4-chloro-2-(trifluoromethyl)benzoyl chloride (1.335 g, 5.49 mmol, commercially available from e.g. 3B Scientific or APAC) in dichloromethane (DCM) (5 mL) was added dropwise. The solution was stirred, under argon, for 30 minutes before the solvent was evaporated in vacuo. The remaining residue was then dissolved in DCM (20 mL) and the solution was washed with water (10 mL), a saturated solution of sodium bicarbonate (10 mL) and brine (10 mL). The organic phase was then dried over anhydrous sodium sulphate, and the solid sodium sulphate was then filtered off. The solvent was then evaporated in vacuo, and the remaining solid was stirred in hexane, at 55° C., for 30 minutes. The solid was then filtered off to yield the desired product in 1.445 g.

LCMS [M+MeCN]+348.1/350.1 @ 0.74 min (2 min run)

Intermediate 53 2,4-Dimethylbenzoyl chloride (I53)

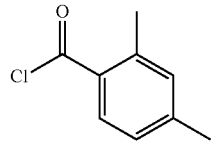

2,4-Dimethylbenzoic acid (1.502 g, 10 mmol, commercially available from e.g. Sigma-Aldrich, Fluka or Alfa Aesar) in dichloromethane (DCM) (40 mL) was cooled to 0° C., before oxalyl chloride (0.963 mL, 11.00 mmol) and a few drops of DMF (cat.) were added. The solution was then stirred under argon for 3 hours. The solvent was then evaporated in vacuo and the remaining residue was azeotroped with toluene (2×20 mL) to yield the product in 1.639 g.

$^1$H NMR (400 MHZ; CDCl3) δ 8.14 (1H, d), 7.15 (1H, d), 7.10 (1H, s), 2.55 (3H, s), 2.39 (3H, s)

Intermediate 54 4-[(2,4-Dimethylphenyl)carbonyl]-2-piperazinone (I54)

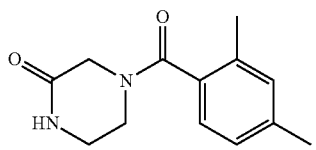 [SMILES: Cc1ccc(C(=O)N2CCNC(=O)C2)c(C)c1]

2-piperazinone (0.851 g, 8.5 mmol, commercially available from e.g. Sigma-Aldrich) was dissolved in dichloromethane (DCM) (30 mL), and to this was added triethylamine (1.422 mL, 10.20 mmol). The solution was then cooled to 0° C. before 2,4-dimethylbenzoyl chloride (I53) (1.577 g, 9.35 mmol) in dichloromethane (DCM) (5 mL) was added dropwise. The solution was stirred, under argon, for 30 minutes before the solvent was evaporated in vacuo. The remaining residue was then dissolved in DCM (40 mL) and the solution was washed with water (20 mL), a saturated solution of sodium bicarbonate (20 mL) and brine (20 mL). The organic phase was then dried over anhydrous sodium sulphate, and the solid sodium sulphate was then filtered off. The solvent was then evaporated in vacuo, and the remaining solid was stirred in hexane, at 55° C., for 30 minutes. The solid was then filtered, and analysis by LCMS showed impurities still to be present. The solid was thus further purified by flash chromatography (Isolera 100 g cartridge) with a gradient of 0-10% MeOH in DCM. TLC confirmed product location and the solvent from the combined fractions was evaporated in vacuo to yield the product in 1.482 g.

LCMS [M+H]+ 233.0 @ 0.61 min (2 min run)

Intermediate 55 4-Chloro-2-metzoyl chloride (I55)

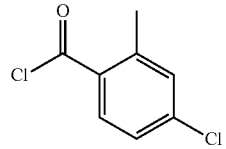

4-Chloro-2-methylbenzoic acid (1.365 g, 8 mmol, commercially available from e.g. Maybridge, Fluorochem or Sigma-Aldrich) in dichloromethane (DCM) (40 mL) was cooled to 0° C., before oxalyl chloride (0.770 mL, 8.80 mmol) and a few drops of DMF (cat.) were added. The solution was then stirred under argon for 3 hours. The solvent was then evaporated in vacuo and the remaining residue was azeotroped with toluene (2×20 mL) to yield the product in 1.464 g.

No characterisation obtained, used directly in next step.

Intermediate 56 4-[(4-Chloro-2-methylphenyl)carbonyl]-2-piperazinone (I56)

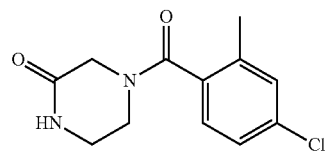 [SMILES: Cc1cc(Cl)ccc1C(=O)N1CCNC(=O)C1]

2-piperazinone (0.701 g, 7 mmol, commercially available from e.g. Sigma-Aldrich) was dissolved in dichloromethane (DCM) (30 mL), and to this was added triethylamine (1.171 mL, 8.40 mmol). The solution was then cooled to 0° C. before 4-chloro-2-methylbenzoyl chloride (I55) (1.456 g, 7.70 mmol) in Dichloromethane (DCM) (5 mL) was added dropwise. The solution was stirred, under argon, for 30 minutes before the solvent was evaporated in vacuo. The remaining residue was then dissolved in DCM (40 mL) and the solution was washed with water (20 mL), a saturated solution of sodium bicarbonate (20 mL) and brine (20 mL). The organic phase was then dried over anhydrous sodium sulphate, and the solid sodium sulphate was then filtered off. The solvent was then evaporated in vacuo, and the remaining solid was stirred in hexane, at 55° C., for 30 minutes. The solid was then filtered off and the remaining solid was further purified by flash chromatography (Biotage SP4, 40S cartridge) with a gradient of 0-10% MeOH in DCM. TLC confirmed product location and the solvent from the combined fractions was evaporated in vacuo to yield the product in 0.798 g.

LCMS [M+H]+ 253.0 @ 0.66 min (2 min run)

Intermediate 57 3-Chloro-4-fluoro-2-methyl benzoic acid (I57)

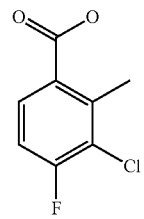

Prepared using a method reported in J. Org. Chem. (2003), 68(5), 2030-2033 and described below:

BuLi (68.8 mL, 110 mmol) was diluted with tetrahydrofuran (THF) (80 mL) and cooled to −20° C. 2,2,6,6-tetramethylpiperidine (18.56 mL, 110 mmol) was added dropwise and the mixture stirred at −20° C. for 15 minutes. The solution was cooled to −50° C. whereupon 3-chloro-4-fluorobenzoic acid (8.73 g, 50 mmol, commercially available from e.g. Sigma-Aldrich, Fluorochem or Apollo) dissolved in tetrahydrofuran (THF) (20 mL) was added dropwise. The mixture was stirred at −50° C. for 4 hours before iodomethane (12.51 mL, 200 mmol) was added dropwise. The mixture was allowed to reach room temperature overnight and quenched with water (100 mL). The mixture was acidified with 5N HCl (200 mL) and extracted with tert-butyl methyl ether (3×300 mL). The combined extracts were washed with water (100 mL), brine (100 mL) dried over anhydrous magnesium sulfate and concentrated to a crude product. The solid was recrystalised from cyclohexane (note: some insolubles not satisfactorarily removed) to afford product in 5.73 g.

LC/MS=187/189 (M−H)−, retention time=0.93 minutes (2 minute method).

Intermediate 58 3-Chloro-4-fluoro-2-methyl benzoyl chloride (I58)

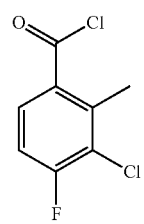

3-chloro-4-fluoro-2-methylbenzoic acid (I57)(0.754 g, 4 mmol) in dichloromethane (DCM) (30 mL) was cooled to 0° C., before oxalyl chloride (0.385 mL, 4.40 mmol) and a few drops of DMF (cat.) were added. The solution was then stirred under argon for 3 hours, before the solvent was evaporated in vacuo. The remaining residue was then azeotroped with toluene to yield the product in 0.819 g.

$^1$H NMR (400 MHz; CDCl$_3$) δ 8.12 (1H, m), 7.15 (1H, m), 2.64 (3H, s).

Intermediate 59 4-[(3-Chloro-4-fluoro-2-methylphenyl)carbonyl]-2-piperazinone (I59)

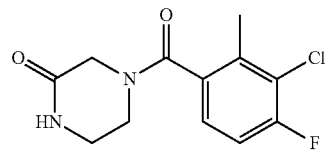 [SMILES: Cc1c(C(=O)N2CCNC(=O)C2)ccc(F)c1Cl]

2-piperazinone (0.350 g, 3.5 mmol, commercially available from e.g. Sigma-Aldrich) was dissolved in dichloromethane (DCM) (15 mL), and to this was added triethylamine (0.585 mL, 4.20 mmol). The solution was then cooled to 0° C. before 3-chloro-4-fluoro-2-methylbenzoyl chloride (I58) (0.797 g, 3.85 mmol) in Dichloromethane (DCM) (5 mL) was added dropwise. The solution was stirred, under argon, for 30 minutes before the solvent was evaporated in vacuo. The remaining residue was then re-dissolved in DCM (50 mL) and washed with water (20 mL), a saturated solution of sodium bicarbonate (20 mL) and brine (20 mL). The organic phase was then dried over anhydrous sodium sulphate, which was then filtered off and the solvent was evaporated in vacuo. The remaining solid was then stirred in hexane (30 mL) at 55° C. for 30 minutes, before being filtered to yield the product in 0.843 g.

LCMS [M+H]+ 271.14 @ 0.69 min (2 min run).

Intermediate 60 2-Bromo-4-fluorobenzoyl chloride (I60)

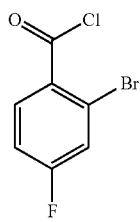

2-Bromo-4-fluorobenzoic acid (1.533 g, 7 mmol, commercially available from e.g. Sigma-Aldrich, Apollo or Fluorochem) in dichloromethane (DCM) (40 mL) was cooled to 0° C., before oxalyl chloride (0.674 mL, 7.70 mmol) and a few drops of DMF (cat.) were added. The solution was then stirred under argon for 3 hours. The solvent was then evaporated in vacuo and the remaining residue was azeotroped with toluene (2×20 mL) to yield the product in 1.645 g.

$^1$H NMR (400 MHz; CDCl$_3$) δ 8.15 (1H, m), 7.47 (1H, dd), 7.18 (1H, m).

Intermediate 61 4-[(2-Bromo-4-fluorophenyl)carbonyl]-2-piperazinone (I61)

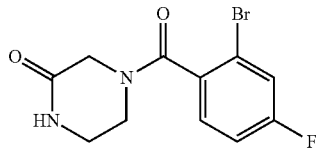 [SMILES: O=C1CN(C(=O)c2ccc(F)cc2Br)CCN1]

2-piperazinone (0.601 g, 6 mmol, commercially available from e.g. Sigma-Aldrich) was dissolved in dichloromethane (DCM) (30 mL), and to this was added triethylamine (1.004 mL, 7.20 mmol). The solution was then cooled to 0° C. before 2-bromo-4-fluorobenzoyl chloride (1.567 g, 6.60 mmol, commercially available from e.g. Sigma-Aldrich, Apollo or Fluorochem) in dichloromethane (DCM) (5 mL) was added dropwise. The solution was stirred, under argon, for 30 minutes before the solvent was evaporated in vacuo. The remaining residue was then re-dissolved in DCM (40 mL) and washed with water (20 mL), a saturated solution of sodium bicarbonate (20 mL) and brine (20 mL), before being dried over anhydrous sodium sulphate. The sodium sulphate was then removed by filtration and the solvent was evaporated in vacuo. The remaining solid was then stirred in hexane (40 mL) at 55° C. for 30 minutes. The solid was then removed by filtration to yield the product in 1.625 g.

LCMS [M+H]+ 301.05/303.05 @ 0.59 min (2 min run).

Intermediate 62 4-Methyl-2-(trifluoromethyl)benzoyl chloride (I62)

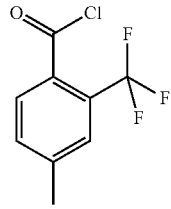

4-Methyl-2-(trifluoromethyl)benzoic acid (1 g, 4.90 mmol, commercially available from e.g. Fluorochem or ABCR) in dichloromethane (DCM) (40 mL) was cooled to 0° C., before oxalyl chloride (0.472 mL, 5.39 mmol) and a few drops of DMF (cat.) were added. The solution was then stirred under argon for 3 hours. The solvent was then evaporated in vacuo and the remaining residue was azeotroped with toluene (2×20 mL) to yield the product in 1.051 g.

$^1$H NMR (400 MHz; CDCl$_3$) δ 8.00 (1H, d), 7.60 (1H, s), 7.50 (1H, dd), 2.50 (3H, s).

Intermediate 63 4-{[4-Methyl-2-(trifluoromethyl)phenyl]carbonyl}-2-piperazinone (I63)

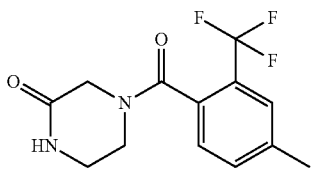 [SMILES: Cc1ccc(C(=O)N2CCNC(=O)C2)c(C(F)(F)F)c1]

2-piperazinone (0.400 g, 4 mmol, commercially available from e.g. Sigma-Aldrich) was dissolved in dichloromethane (DCM) (20 mL), and to this was added triethylamine (0.669 mL, 4.80 mmol). The solution was then cooled to 0° C. before 4-methyl-2-(trifluoromethyl)benzoyl chloride (I62) (0.979 g, 4.40 mmol) in dichloromethane (DCM) (5 mL) was added dropwise. The solution was stirred, under argon, for 30 minutes before the solvent was evaporated in vacuo. The remaining residue was then re-dissolved in DCM (40 mL) and washed with water (20 mL), a saturated solution of sodium bicarbonate (20 mL) and brine (20 mL), before being dried over anhydrous sodium sulphate. The sodium sulphate was then removed by filtration and the solvent was evaporated in vacuo. The remaining solid was then stirred in hexane (40 mL) at 55° C. for 30 minutes. The solid was then removed by filtration to yield the product in 1.110 g.

LCMS [M+H]+ 287.09 @ 0.69 min.

Intermediate 64 1,1-Dimethylethyl 2-(1,3-thiazol-4-ylcarbonyl) hydrazinecarboxylate (I64)

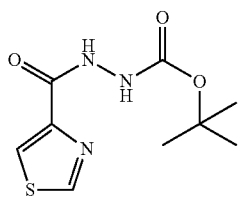 [SMILES: CC(C)(C)OC(=O)NNC(=O)c1cscn1]

1,3-thiazole-4-carboxylic acid (0.775 g, 6 mmol, commercially available from e.g. Sigma-Aldrich, Apollo or Fluorochem) was dissolved in dichloromethane (DCM) (50 mL), and the solution was cooled to 0° C. To this was added oxalyl chloride (0.578 mL, 6.60 mmol) and 5 drops of DMF (cat.) and the solution was stirred, under argon, for 3 hours. The solvent was then removed in vacuo, and the remaining residue was redissolved in dichloromethane (DCM) (50 mL), before 1,1-dimethylethyl hydrazinecarboxylate (0.872 g, 6.60 mmol) and DIPEA (1.258 mL, 7.20 mmol) were added. The solution was stirred under argon for 2 hours, LCMS and TLC confirmed product formation, thus the solvent was evaporated in vacuo. The remaining residue was then partitioned between ethyl acetate (30 mL) and saturated sodium bicarbonate solution (20 ml). The aqueous phase was then further extracted with ethyl acetate (2×30 mL) and the combined extracts were washed with brine (30 mL), and dried over anhydrous sodium sulfate. The solvent was then evaporated in vacuo to yield the product in 1.308 g.

LCMS [M+H-BOC]+143.9 @0.66 min (2 min run).

Intermediate 65 1,3-Thiazole-4-carbohydrazide (I65)

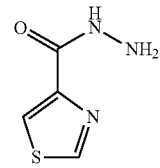

1,1-Dimethylethyl 2-(1,3-thiazol-4-ylcarbonyl)hydrazinecarboxylate (I64) (1.378 g, 5.66 mmol) was dissolved in 1,4-dioxane (15 mL) and to this was added 4M HCl in 1,4-dioxane (14.16 mL, 56.6 mmol). The solution was then stirred at room temperature for 18 hours. The solvent was then evaporated in vacuo and the remaining residue was loaded onto an SCX cartridge and washed with methanol before being eluted with 2M $NH_3$ in DCM. The solution was then evaporated in vacuo to yield the product in 0.784 g.

$^1$H NMR (400 MHz; $CDCl_3$) δ 8.78 (1H, d), 8.47 (1H, broad s), 8.21 (1H, d), 4.10 (2H, broad s).

Intermediate 66 4-Fluoro-2-hydroxybenzohydrazide (I66)

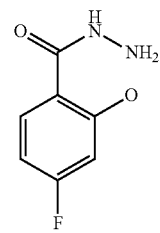 [SMILES: NNC(=O)c1ccc(F)cc1O]

To a solution of methyl 4-fluorosalicylate (500 mg, 2.94 mmol, commercially available from e.g. Apollo, Alfa Aesar or ABCR) in methanol (15 ml) stirred under argon at room temp was added neat hydrazine monohydrate (0.722 ml, 14.69 mmol). The reaction mixture was stirred at 80° C. for 18 hr. The reaction mixture was concentrated in vacuo and partitioned between ethyl acetate (~50 ml) and water (~25 ml). The aqueous phase was extracted with ethyl acetate (2×25 ml) and the combined organic extracts washed with brine (25 ml), dried over sodium sulphate, evaporated in vacuo and dried (vacuum oven, 40° C., 24 hr) to afford the crude product as an off-white solid in 385 mg.

LCMS: 2 minute run in MeOH. [M+H]+ m/z=171.16 Da, retention time=0.50-0.51 min.

Intermediate 67 1-Bromo-3,4-difluoro-2-methylbenzene (I67)

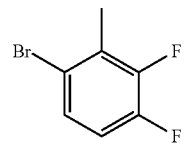

To 1,2-difluoro-3-methylbenzene (5 g, 39.0 mmol, commercially available from e.g. Sigma-Aldrich, Apollo or Fluorochem) containing iron (0.131 g, 2.342 mmol) was added bromine (2.011 ml, 39.0 mmol) dropwise maintaining a temperature of <30° C. with ice cooling. The mixture was stirred at room temperature overnight. The mixture was partitioned between water (50 mL) and diethyl ether (100 mL). The aqueous phase was extracted with diethyl ether (3×50 mL), combined organic extracts were washed with water (50 mL), 5% sodium thiosulfate solution (50 mL), water (50 mL), brine (50 mL), dried over anhydrous magnesium sulfate and concentrated in vacuo to afford product in 8.07 g. (Caution: by of product=68-70° C. @ 57 mBar).

LC/MS=no mass ion, retention time=1.26 minutes (2 minute method).

Intermediate 68 3,4-Difluoro-2-methylbenzoic acid (I68)

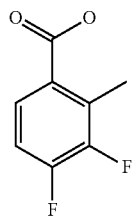

The acid was synthesised as reported in US 2005/0054733A1 and described below 1-bromo-3,4-difluoro-2-methylbenzene (I67) (8.07 g, 39.0 mmol) was cooled to 0° C. in tetrahydrofuran (THF) (40 mL). Isopropylmagnesium chloride (29.2 mL, 58.5 mmol) was added dropwise and the solution stirred at room temperature overnight. The solution was cooled to 0° C. and gassed slowly with Carbon dioxide (excess) for 1 hour. The cooling was removed and gassing continues for 4 hours before allowing the solution to stand at room temperature overnight. Water (10 ml) was added and the solvents removed in vacuo. The residue was partitioned between ethyl acetate (50 mL) and 2N Hydrochloric acid (25 mL). The aqueous phase was extracted with ethyl acetate (5×50 mL). The combined organic extracts were washed with water (50 mL), brine (50 mL), dried over anhydrous magnesium sulfate and concentrated in vacuo to a crude solid that was recrystalised from cyclohexane to afford product in 4.68 g.

LC/MS=171 (M–H)–, retention time=0.86 minutes (2 minute method).

Intermediate 69 4-[(3,4-Difluoro-2-methylphenyl)carbonyl]-2-piperazinone (I69)

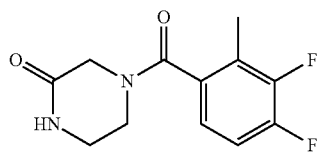 [SMILES: Cc1c(C(=O)N2CCNC(=O)C2)ccc(F)c1F]

3,4-Difluoro-2-methylbenzoic acid (I68) (1.891 g, 10.99 mmol) was suspended in dichloromethane (DCM) (20 mL) at 0° C. Oxalyl chloride (1.749 mL, 19.98 mmol) followed by a few drops of DMF (cat.) was added and the mixture stirred at 0° C. for 15 minutes. The mixture was stirred to room temperature over night. The reaction mixture was concentrated in vacuo and azeotroped with toluene (3×20 mL). The residue was dissolved in dichloromethane (DCM) (20 mL) and added to 2-piperazinone (1 g, 9.99 mmol, commercially available from e.g. Sigma-Aldrich) dissolved in dichloromethane (DCM) (20 mL). The solution was stirred at room temperature overnight. The reaction mixture was concentrated in vacuo and the residue partitioned between ethyl acetate (50 mL) and saturated sodium bicarbonate solution (25 mL). The aqueous phase was extracted with ethyl acetate (3×50 mL), combined extracts were washed with water (3×50 mL), brine (50 mL), dried over ahydrous sodium sulfate and concentrated in vacuo. The residue was triturated with hexane to afford product in 1.64 g.

LC/MS=257 (M+H)+, retention time=0.62 minutes (2 minute method).

Intermediate 70 2,3-Dichloro-4-methylbenzoic acid (I70)

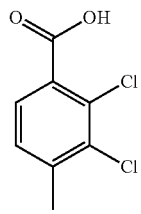

n-Butyllithium (23.04 mL, 57.6 mmol) was dissolved in tetrahydrofuran (THF) (100 mL) at –20° C. 2,2,6,6-tetramethylpiperidine (9.72 mL, 57.6 mmol) was added dropwise and stirred for 15 minutes maintaining a temperature of –20° C. The solution was cooled to –78° C. whereupon 2,3-dichlorobenzoic acid (5 g, 26.2 mmol, commercially available from e.g. Sigma-Aldrich, Alfa Aesar or Fluorochem) dissolved in Tetrahydrofuran (THF) (50 mL) was added dropwise. The solution was stirred at –78° C. for 1 hour whereupon iodomethane (6.55 mL, 105 mmol) was added dropwise and the mixture allowed to reach room temperature overnight. Solvents were removed in vacuo and the residue partitioned between ethyl acetate (100 mL) and 5N HCl (50 mL). The aqueous phase was extracted with ethyl acetate (3×50 mL), combined extracts were washed with water (50 mL), brine (50 mL) dried over anhydrous magnesium sulfate and concentrated in vacuo to afford a crude solid in 5.90 g.

LC/MS=203/205 (M–H)–, retention time=0.97 minutes (2 minute method).

Intermediate 71 2,3-Dichloro-4-methylbenzoyl chloride (I71)

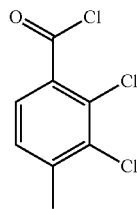

2,3-Dichloro-4-methylbenzoic acid (I70) (5.90 g, 26.2 mmol) and thionyl chloride (30 mL, 411 mmol) were heated at 85° C. for 4 hr in toluene (100 mL). The solvents were removed in vacuo and the residue was azeotroped with toluene (3×100 mL). The residue was used in subsequent steps without further purification assuming 100% yield. Compound not characterised at this step.

Intermediate 72 4-[(2,3-Dichloro-4-methylphenyl)carbonyl]-2-piperazinone (I72)

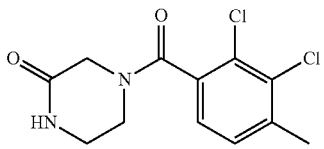 [SMILES: Cc1ccc(C(=O)N2CCNC(=O)C2)c(Cl)c1Cl]

2-piperazinone (1 g, 9.99 mmol, commercially available from e.g. Sigma-Aldrich) and triethylamine (2.78 mL, 19.98 mmol) were dissolved in Dichloromethane (DCM) (25 mL) at 0° C. 2,3-dichloro-4-methylbenzoyl chloride (I71) (2.232 g, 9.99 mmol) dissolved in Dichloromethane (DCM) (25 mL) was added dropwise and the solution stirred to room temperature overnight. Solvents were removed in vacuo and the residue was partitioned between ethyl acetate (50 mL) and saturated sodium bicarbonate solution (25 mL). The aqueous phase was extracted with ethyl acetate (3×50 mL). The combined organic extracts were washed with water (2×50 mL), brine (50 mL), dried over anhydrous sodium sulfate and concentrated to a crude solid. A 100 mg sample was purified by MDAP to afford product in 69 mg.

LC/MS=287/289 (M+H)+, retention time=0.74 minutes (2 minute method).

Product regio chemistry was confirmed by CASS.

The remaining crude product was purified by flash chromatography (Isolera, 100 g, 0-100% Methanol:Dichloromethane (1:9)/Dichloromethane) to afford product in 1.84 g.

This was further purified by MDAP to afford product in 1.04 g.

LC/MS=287/289 (M+H)+, retention time=0.74 minutes (2 minute method).

Intermediate 73
1-(2-Chloro-4-fluoro-3-methylphenyl)ethanone (I73)

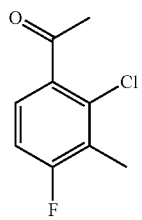

Aluminium chloride (18.67 g, 140 mmol) was suspended in 1-chloro-3-fluoro-2-methylbenzene (8.50 ml, 70 mmol, commercially available from e.g. Sigma-Aldrich, Fluorochem or Apollo). A few drops of acetyl chloride were added and the slurry heated to 40° C. to initiate the reaction (visible by the evolution of HCl). The heat was removed and acetyl chloride (4.98 ml, 70.0 mmol) was added drop wise. The mixture was stirred at room temperature for 2 hours and poured on to ice-water. 5N HCl (50 mL) was added and the aqueous phase extracted with dichloromethane (3×200 mL). Combined extracts were washed with water (3×100 mL), brine (100 mL), dried over anhydrous magnesium sulfate and concentrated in vacuo to afford product, as a purple oil. The product was purified by flash chromatography (Isolera, 340 g, 0-100% [20% ethyl acetate/iso-hexane]/iso-hexane to afford 3 fractions F1 (5.31 g), still crude. F2/F3 which were combined based on NMR and TLC to afford clean product in 4.80 g.

Fraction F1 was further purified by flash chromatography (Isolera, 340 g, 0-50% [20% ethyl acetate/isohexane]/isohexane) to afford product in 3.88 g. The above products were combined to afford the desired product in 8.68 g as an oil.

LC/MS=187 (M+H)+, retention time=1.07 minutes (2 minute method).

Intermediate 74 2-Chloro-4-fluoro-3-methyl benzoic acid (I74)

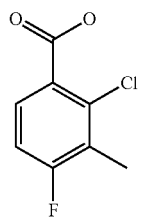

The acid was synthesised according to the method reported in J. Med. Chem., 1996, 39(20, 436-445 and described below:

Bromine (7.61 mL, 148 mmol) was added dropwise to sodium hydroxide (19.70 g, 492 mmol) dissolved in Water (80 mL) maintaining temperature<10° C. 1-(2-chloro-4-fluoro-3-methylphenyl)ethanone (I73) (9.19 g, 49.2 mmol) dissolved in 1,4-dioxane (80 mL) was added dropwise at 0° C. and the mixture was stirred at room temperature for 2 hours. The reaction mixture was washed with chloroform (2×20 mL) and the aqueous phase acidified to pH1 with concentrated hydrochloric acid. The resulting precipitate was filtered, washed with water, a little diethyl ether (Note: product has some ether solubility) and dried to afford product in 8.89 g. This was recrystalised from toluene to afford product in 6.25 g as fine white needles.

LC/MS=187/189 (M−H)−, retention time=0.87 minutes (2 minute method).

Intermediate 75 4-[(2-Chloro-4-fluoro-3-methylphenyl)carbonyl]-2-piperazinone (I75)

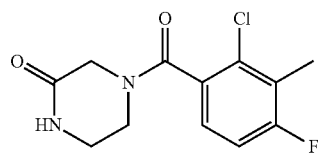 [SMILES: Cc1c(F)ccc(C(=O)N2CCNC(=O)C2)c1Cl]

Step 1

2-Chloro-4-fluoro-3-methylbenzoic acid (I74) (2.072 g, 10.99 mmol) was suspended in Dichloromethane (DCM) (20 mL) at 0° C. Oxalyl chloride (1.749 mL, 19.98 mmol) followed by few drops of DMF (cat) was added and the mixture stirred at 0° C. for 15 minutes. The mixture was stirred to room temperature overnight. The solvent was then evaporated in vacuo and the remaining residue was azeotroped with toluene (2×10 mL) to yield the crude product, which was used directly in the next step.

Step 2

2-piperazinone (1 g, 9.99 mmol, commercially available from e.g. Sigma-Aldrich) was then dissolved in dichloromethane (DCM) (40 mL), and to this was added triethylamine (2.78 mL, 19.98 mmol). The solution was cooled to 0° C. before 2-chloro-4-fluoro-3-methylbenzoyl chloride, (2.072 g, 10.99 mmol), from Step 1, in DCM (10 mL) was added dropwise over 1 minute. The solution was then allowed to stir at room temperature for a further 30 minutes before the solvent was evaporated in vacuo. The remaining solid was then re-dissolved in DCM (80 mL) before being washed with water (30 mL), a saturated solution of sodium bicarbonate (30 mL), and brine (30 mL). The solution was then dried over anhydrous sodium sulphate, which was hen removed by filtration and the solvent was evaporated in vacuo. The remaining solid was then stirred in hexane at 55° C. for 30 minutes, before being filtered off to yield the product in 2.496 g.

LCMS: m/z=271 (M+H)+, retention time=0.67 minutes (2 minutes)

Intermediate 76 2,4-Dichloro-3-methylbenzoic acid (I76)

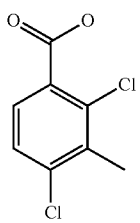

The acid was synthesised by a similar method to that reported in Eur. J. Org. Chem. 2006, p4398-4404 and described below:

n-Butyllithium (80 mL, 200 mmol) was diluted with Tetrahydrofuran (THF) (400 mL) under Argon at −78° C. 2,2,6,6-tetramethylpiperidine (33.8 mL, 200 mmol) dissolved in Tetrahydrofuran (THF) (20 mL) was added dropwise and the solution stirred at −78° C. for 15 minutes. 1,3-dichloro-2-methylbenzene (25.4 mL, 200 mmol, commercially available from e.g. Sigma-Aldrich, Fluka or Acros) dissolved in Tetrahydrofuran (THF) (60 mL) was added dropwise and the solution stirred at −78° C. for 1 hour. The solution was transferred via canula to on to Carbon dioxide (xs) (pre washed with THF) contained in a solution of Tetrahydrofuran (THF) (500 mL) with vigourous stirring. The mixture was allowed to reach room temperature over 4 hours. The solvents were concentrated in vacuo and the residue acidified to pH 1 with 5N HCl (200 mL). The aqueous phase was extracted with ethyl ecetate (3×300 mL), combined extracts were washed with water (100 mL), brine (100 mL), dried over anhydrous magnesium sulfate and concentrated in vacuo to afford product. The solid was triturated with iso-hexane to afford product, as a mixture of 2,4-dichloro-3-methylbenzoic acid and (2,6-dichlorophenyl)acetic acid in 17.87 g.

LC/MS=203/205 (M−H)−, retention time=0.86 minutes (2 minute method) and 203/205 (M−H)−, retention time=0.97 minutes (2 minute method).

Intermediate 77 4-[(2,4-Dichloro-3-methylphenyl) carbonyl]-2-piperazinone (I77)

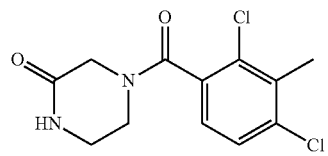 [SMILES: Cc1c(Cl)ccc(C(=O)N2CCNC(=O)C2)c1Cl]

Mixture of (2,6-dichlorophenyl)acetic acid and 2,4-dichloro-3-methylbenzoic acid (I76) (approx 3:1) (7.53 g, 36.7 mmol) was suspended in dichloromethane (DCM) (50 mL) at 0° C. Oxalyl chloride (6.12 mL, 69.9 mmol) followed by a few drops of DMF (cat) and the mixture was stirred at 0° C. for 15 minutes. The reaction mixture was concentrated in vacuo and azeotroped with dichloromethane (3×50 ml). The residue was redissolved in Dichloromethane (50 mL) and added dropwise to a suspension of 2-piperazinone (3.5 g, 35.0 mmol, commercially available from e.g. Sigma-Aldrich) in Dichloromethane (DCM) (50.0 mL) at 0° C. The reaction was stirred to room temperature overnight and concentrated in vacuo. The residue partitioned between ethyl acetate (200 mL) and saturated sodium bicarbonate solution (50 mL). The aqueous phase was extracted with ethyl acetate (5×200 mL), combined extracts were washed with water (3×100 mL), brine (100 mL), dried over ahydrous sodium sulfate and concentrated in vacuo. The residue was triturated with hexane to afford crude product. The solid was purified by MDAP (25 injections of 100 mg) to afford the product in 1.01 g.

LC/MS=287/289 (M+H)+, retention time=0.76 minutes (2 minute method)

Intermediate 78 Ethyl (formylamino)(thioxo)acetate (I78)

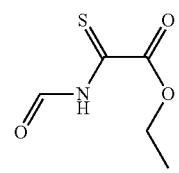

Ethyl thiooxamate (1.25 g, 9.39 mmol, commercially available from e.g. Sigma-Aldrich, Apin or Apollo) was dissolved in chloroform (15 mL) and treated with N,N-dimethylformamide dimethyl acetal (2.67 mL, 18.77 mmol). The solution was stirred at 20° C. for 6 hr. Solvents were removed in vacuo to afford a red oil (2.07 g). The product was purified by flash chromatography (Isolera, 100 g, 0-100% ethyl acetate/iso-hexane, 15 column volumes) to afford the product in 1.42 g, that was used in the next step without further purification. No characterisation was obtained.

Intermediate 79 Ethyl 1,2,4-thiadiazole-5-carboxylate (I79)

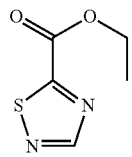

To ethyl {[(1E)-(dimethylamino)methylidene]amino}(thioxo)acetate (I78) (1.42 g, 7.54 mmol) and pyridine (1.220 mL, 15.09 mmol) dissolved in Ethanol (20 mL) was added (aminooxy)(hydroxy)sulfane dioxide (0.938 g, 8.30 mmol) dissolved in Ethanol (18 ml) and the mixture stirred at 25° C. for 48 hr. The solvents were concentrated in vacuo and the residue was dissolved in ethyl acetate (50 mL). The solution was washed with saturated sodium bicarbonate solution (25 mL), aqueous phase back extracted with ethyl acetate (25 mL) and the organic extracts were combined. The solution was washed with brine (25 mL), dried over anhydrous sodium sulfate and concentrated in vacuo to afford a crude oil. The crude oil was purified by flash chromatography (Isolera, 50 g, 0-100% ethyl acetate/iso-hexane, 15 column volumes) to afford product in 246 mg.

$^1$H NMR (400 MHz; CDCl$_3$) δ 8.88 (1H, s), 4.54 (2H, q), 1.48 (3H, t).

Intermediate 80 1,2,4-Thiadiazole-5-carbohydrazide (I80)

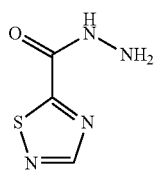

Ethyl 1,2,4-thiadiazole-5-carboxylate (I79) (246 mg, 1.555 mmol) and hydrazine hydrate (0.151 mL, 3.11 mmol) were heated at 80° C. for 5 hr. The solvents were removed in vacuo to afford a yellow solid in 173 mg.

LC/MS=no mass ion, retention time=0.18 minutes (2 minute method (high pH)).

Intermediate 81 1,1-Dimethylethyl 2-(5-isoxazolylcarbonyl) hydrazinecarboxylate (I81)

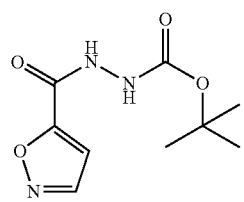

A solution of 5-isoxazolecarboxylic acid (500 mg, 4.42 mmol, commercially available from e.g. Sigma-Aldrich, Maybridge or Apollo) in dry dichloromethane (DCM) (14.700 ml) was stirred at room temperature under an atmosphere of argon. EDC (1017 mg, 5.31 mmol) and HOBt (339 mg, 2.211 mmol) were added to the solution and stirring was continued at room temperature for ½ hour. After this time, 1,1-dimethylethyl hydrazinecarboxylate (701 mg, 5.31 mmol) was added to the reaction mixture and stirring was continued for a further 18 hours at room temperature (overnight). The solution was diluted with DCM (approx 30 ml) and washed with water (2×20 ml). The organics were dried over MgSO$_4$, filtered and concentrated under reduced pressure to give a colourless oil. The oil was chromatographed [SiO$_2$, EtOAc/Hexane 0-100%] to give a colourless, thick oil in 321 mg. The oil was used directly in the next step.

LCMS [M−H] 226.22 and [M+H-BOC]+ 128.07 @ 0.60 min (2 min run).

Intermediate 82 5-Isoxazolecarbohydrazide (I82)

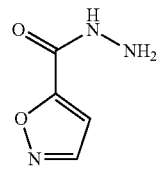

A mixture of 1,1-dimethylethyl 2-(5-isoxazolylcarbonyl)hydrazinecarboxylate (I81) (321 mg, 1.413 mmol) in HCl (2 ml, 8.00 mmol) (4M in 1,4-dioxan) was stirred at room temperature under argon for 18 hours (overnight). After this time, the solvent was removed under reduced pressure to give a pale yellow coloured solid. The material was passed through an SCX cartridge, eluting initially with MeOH and then 2M NH$_3$/MeOH to give the product as a pale yellow solid in 85 mg.

$^1$H NMR (400 MHz; d6-DMSO) δ 12.36 (1H, broad s), 8.86 (1H, d), 7.75 (2H, broad s+H$_2$O), 7.40 (1H, d).

Intermediate 83 1,1-Dimethylethyl 2-(5-isothiazolylcarbonyl) hydrazinecarboxylate (I83)

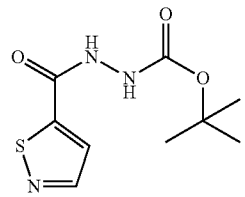 [SMILES: CC(C)(C)OC(=O)NNC(=O)c1ccns1]

A solution of 5-isothiazolecarboxylic acid (500 mg, 3.87 mmol, commercially available from e.g. Fluorochem or Astatech) in dry Dichloromethane (DCM) (12.9 ml) was stirred at room temperature under an atmosphere of argon. EDC (891 mg, 4.65 mmol) and HOBt (296 mg, 1.936 mmol) were added to the stirred solution. The resulting solution was stirred at room temperature under an atmosphere of argon for ½ hour. After this time, 1,1-dimethylethyl hydrazinecarboxylate (614 mg, 4.65 mmol) was added and the solution was stirred for a further 18 hours at room temperature (overnight). The solution was diluted with DCM (approx 30 ml) and washed with water (2×20 ml). The organics were dried over MgSO$_4$, filtered and concentrated under reduced pressure to give a brown coloured oil. The oil was chromatographed

[SiO$_2$, EtOAc/Hexane 0-100%] to give a thick, yellow-coloured oil which solidified on standing to afford the product in 480 mg. The residue was used directly in the next step.

LCMS [M+H]+ 244.14 @ 0.66 min (2 min run).

Intermediate 84 5-Isothiazolecarbohydrazide (I84)

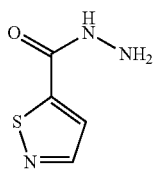

A mixture of 1,1-dimethylethyl 2-(5-isothiazolylcarbonyl)hydrazinecarboxylate (I83) (480 mg, 1.973 mmol) in HCl (2 ml, 8.00 mmol) (4M in 1,4-dioxan) was stirred at room temperature under argon for 18 hours (overnight). After this time, the mixture was concentrated under reduced pressure to give a pale yellow coloured solid. The solid was dissolved in MeOH and passed through and SCX cartridge, eluting initially with MeOH and then with 2M NH$_3$ in MeOH. The NH$_3$/MeOH fractions were concentrated under reduced pressure to give a yellow coloured solid in 217 mg.

$^1$H NMR (400 MHz; d6-DMSO) δ 12.30 (1H, broad s), 8.75 (1H, d), 8.16 (1H, d),

Intermediate 85 5-Methyl-2-furancarbohydrazide (I85)

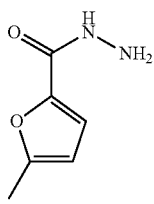

To a solution of methyl 5-methyl-3-furancarboxylate (0.314 mL, 2.5 mmol, commercially available from e.g. Sigma-Aldrich, Fluorochem or Alfa Aesar) in ethanol (20 mL) was added hydrazine monohydrate (0.093 mL, 3.00 mmol) and the solution was stirred under argon and reflux for 18 hours. Analysis by LCMS and TLC showed starting material to still be present, thus more hydrazine monohydrate (0.275 mL, 8.75 mmol) was added and the solution was further stirred under argon and reflux for 18 hours. The solvent was then evaporated in vacuo to yield the product in 0.341 g.

LCMS [M+H]+ 141.0 @ 0.36 min (2 min run).

Intermediate 86 1,1-Dimethylethyl 2-(1,2,5-thiadiazol-3-ylcarbonyl)hydrazinecarboxylate (I86)

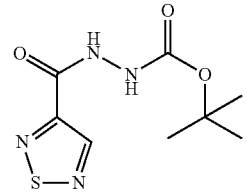 [SMILES: CC(C)(C)OC(=O)NNC(=O)c1cnsn1]

A solution of 1,2,5-thiadiazole-3-carboxylic acid (300 mg, 2.305 mmol, commercially available from Pharmlab, 3B Scientific or Anichem) in dry dichloromethane (DCM) (7.685 ml) was stirred at room temperature under an atmosphere of argon. EDC (530 mg, 2.77 mmol) and HOBt (177 mg, 1.153 mmol) were added to the stirred solution and the resulting solution was stirred at room temperature for a further ¾ hour. After this time, 1,1-dimethylethyl hydrazinecarboxylate (366 mg, 2.77 mmol) was added to the stirred solution and the resulting solution was stirred at room temperature for 18 hours. The reaction mixture was partitioned between DCM (~20 ml) and saturated sodium bicarbonate solution (~20 ml). The aqueous phase was extracted with DCM (2×20 ml) and the combined organic extracts washed with saturated brine (~50 ml), dried over sodium sulphate, evaporated in vacuo and dried (vacuum oven, 40° C., 72 hr) to afford the crude product as a bright yellow gum. This was purified via Biotage SP4 (2-20% MeOH/DCM; 100 g SNAP Biotage column; 12 CV) to afford the required product as a pale yellow oil in 266.2 mg, which was used without further purification in the next step.

LCMS: [M-Boc+H]$^+$ m/z=145; R.T.=0.65-0.66 min.

Intermediate 87 1,2,5-Thiadiazole-3-carbohydrazide (I87)

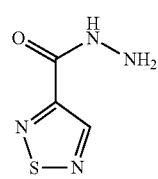

Solid t-butyl-2-(1,2,5-thiadiazol-3-ylcarbonyl)hydrazinecarboxylate (I86) (265 mg, 0.890 mmol) was treated with a solution of hydrochloric acid (4 M) in dioxane (4.45 ml, 17.79 mmol) and stirred under argon at RT for 6 hr. The solvent was evaporated in vacuo and the residue dissolved in methanol (~10 ml), added to a 10 g SCX column and eluted with Dichloromethane (~50 ml), methanol (~50 ml) and a solution of ammonia (2 M) in methanol (~100 ml). The basic fractions were combined and evaporated in vacuo to afford the free base as a white solid in 95.5 mg.

LCMS: [M+H]$^+$ m/z=145.0 Da; R.T.=0.26 min.

Intermediate 88 1,1-Dimethylethyl 2-(3-isoxazolylcarbol) hydrazinecarboxylate (I88)

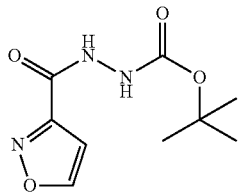 [SMILES: CC(C)(C)OC(=O)NNC(=O)c1ccon1]

A solution of 3-isoxazolecarboxylic acid (500 mg, 4.42 mmol, commercially available from e.g. Manchester Organics, Bio-Farma or APAC) in dry dichloromethane (DCM) (14.700 ml) was stirred at room temperature under an atmosphere of argon. EDC (1017 mg, 5.31 mmol) and HOBt (339 mg, 2.211 mmol) were added to the stirred solution and the resulting solution was stirred for ¾ hour. After this time, 1,1-dimethylethyl hydrazinecarboxylate (701 mg, 5.31 mmol) was added to the stirred solution and stirring continued for a further 18 hours at room temperature (overnight). The reaction mixture was partitioned between DCM (~20 ml) and saturated sodium bicarbonate solution (~20 ml). The aqueous phase was extracted with DCM (2×20 ml) and the combined organic extracts washed with saturated brine (~50 ml), dried over sodium sulphate, evaporated in vacuo and dried (vacuum oven, 40° C., 72 hr) to afford the crude product as a brown oil. This was purified via Biotage SP4 (2-20 MeOH/DCM; 100 g SNAP Biotage column; 12 CV) to afford the required product as an orange oil in 510.6 mg, which was used without further purification in the next step.

LCMS: [M-Boc+H]$^+$ m/z=128.0; R.T.=0.62-0.63 min.

Intermediate 89 3-Isoxazolecarbohydrazide (I89)

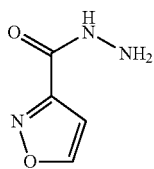

Solid t-butyl-2-(3-isoxazolylcarbonyl)hydrazinecarboxylate (I88) (510 mg, 1.639 mmol) was treated with a solution of hydrochloric acid (4 M) in dioxane (8.19 ml, 32.8 mmol) and stirred under argon at RT for 6 hr. The solvent was evaporated in vacuo and the residue dissolved in methanol (~10 ml), added to a 10 g SCX column and eluted with Dichloromethane (~50 ml), methanol (~50 ml) and a solution of ammonia (2 M) in methanol (~100 ml). The basic fractions were combined and evaporated in vacuo to afford the free base as yellow dendriform crystals in 211.0 mg.

LCMS: No mass ion detected. R.T.=0.20-0.25 min.

Intermediate 90 4-(Trifluoroacetyl)-2-piperazinone (I90)

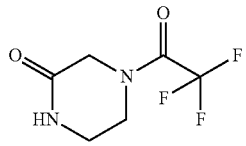 [SMILES: O=C1CN(C(=O)C(F)(F)F)CCN1]

2-piperazinone (1 g, 9.99 mmol, commercially available from e.g. Sigma-Aldrich) and triethylamine (1.671 mL, 11.99 mmol) were dissolved in dichloromethane (DCM) (50 mL) at 0° C. The solution was treated with trifluoroacetic anhydride (1.552 mL, 10.99 mmol) dropwise and the mixture allowed to stir to room temperature over 16 h. The solution was concentrated in vacuo to afford a crude oil that was used in subsequent steps without further purification.

$^1$H NMR (400 MHz; CDCl$_3$) δ 12.25 (1H, broad s), 4.29 (2H, m), 3.92-3.82 (2H, m), 3.53-3.46 (2H, m). Contains Triethylamine hydrochloride

Intermediate 91 2-Chloro-3-(trifluoromethyl)benzohydrazide (I91)

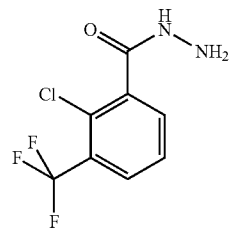 [SMILES: NNC(=O)c1cccc(C(F)(F)F)c1Cl]

To a solution of 2-chloro-3-(trifluoromethyl)benzoyl chloride (15 g, 61.7 mmol, commercially available from e.g. Apollo) and DIPEA (12.94 ml, 74.1 mmol) in anhydrous dichloromethane (DCM) (200 ml) cooled to 0° C. in an ice bath was slowly added 1,1-dimethylethyl hydrazinecarboxylate (8.97 g, 67.9 mmol) under an atmosphere of argon and the mixture was allowed to reach steadily room temperature overnight. It was quenched with water (100 mL), the phases were separated and the aqueous extracted with DCM (2×50 mL). The combined organics were washed with brine (50 mL) and dried over MgSO$_4$. The orange oil isolated (circa 25 g) was the impure BOC-protected hydrazide. It was then dissolved in 1,4-Dioxane (100 ml) and treated with HCl (4M in dioxane) (154 ml, 617 mmol) overnight at room temperature. The slurry was concentrated at the buchi to obtain a yellow solid which was triturated with Et$_2$O to afford a white coloured solid, then applied to 4×10 g SCX cartridges, washed with MeOH and finally eluted with NH$_3$ (2M in MeOH). The basic fractions were concentrated to afford the desired product in 3.5 g as a white solid.

LC/MS: (M+H)$^+$=239, retention time=0.68 minutes (2 minutes run).

Intermediate 92
2-Oxo-1,2-dihydro-3-pyridinecarbohydrazide (I92)

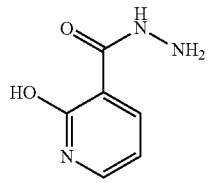 [SMILES: NNC(=O)c1cccnc1O]

Hydrazine hydrate (0.192 mL, 3.92 mmol) was added to a solution of the methyl 2-hydroxy-3-pyridinecarboxylate (400 mg, 2.61 mmol, commercially available from e.g. Apollo or Butt Park) in ethanol (10 mL) and the reaction was heated to reflux for 16 hrs. The reaction was cooled and the solvent was evaporated to afford an off-white solid in 395 mg.

LCMS [M+H]+ 154.1 @ 0.34 min (2 min run).

Intermediate 93
3-Hydroxy-2-pyridinecarbohydrazide (I93)

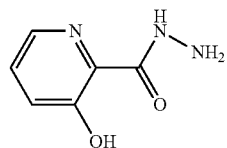 [SMILES: NNC(=O)c1ncccc1O]

Hydrazine (0.248 mL, 7.91 mmol) was added under argon to a solution of methyl 3-hydroxy-2-pyridinecarboxylate (808 mg, 5.28 mmol) in ethanol (25 mL). The reaction mixture was stirred at reflux overnight (yellow solution). After cooling, a solid which has crashed out was filtered to afford the desired product in 826 mg as a yellow solid.

LCMS m/z 154.14 [M+H] @ 0.34 min (2 min run)

Intermediate 94 1,1-Dimethylethyl 2-{[6-(methyloxy)-2-pyridinyl]carbonyl}hydrazinecarboxylate (I94)

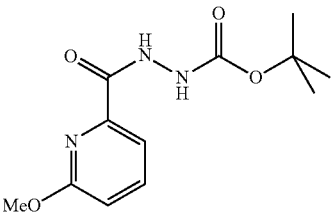 [SMILES: COc1cccc(C(=O)NNC(=O)OC(C)(C)C)n1]

A solution of 6-(methyloxy)-2-pyridinecarboxylic acid (1.00 g, 6.53 mmol) in dichloromethane (DCM) (13.52 ml) was stirred and cooled to 0° C. Oxalyl chloride (0.686 ml, 7.84 mmol) was added dropwise followed by DMF (5.06 µl, 0.065 mmol). The solution immediately turned yellow and the reaction was followed by LCMS. LCMS after circa 1 hour showed the methyl ester of the acid chloride to be present. The solvent was removed under reduced pressure and the residue was azeotroped with toluene. The residue was dissolved in dichloromethane (DCM) (27.0 ml) and cooled to 0° C. DIPEA (1.711 ml, 9.80 mmol) was added dropwise followed by 1,1-dimethylethyl hydrazinecarboxylate (0.949 g, 7.18 mmol) and the solution was left to stir at 20° C., under an argon atmosphere for 18 hours. A dark brown solution formed and LCMS showed the desired compound to be present. The solvent was removed under reduced pressure and the residue was diluted with dichloromethane and washed with saturated sodium bicarbonate, saturated ammonium chloride, water and brine. The organic extracts were dried over magnesium sulfate and the solvent was removed under vacuum to yield the desired product in 1.685 g.

LCMS m/z 268.16 [M+H] @0.83 min (2 min run)

Intermediate 95
6-(Methyloxy)-2-pyridinecarbohydrazide (I95)

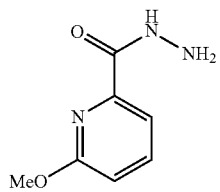

1,1-dimethylethyl 2-{[6-(methyloxy)-2-pyridinyl]carbonyl}hydrazinecarboxylate (194)(1.685 g, 6.30 mmol) was dissolved in 1,4-dioxane (21.01 ml) and HCl (4M in 1,4-dioxane) (15.76 ml, 63.0 mmol) was added. The solution was stirred at room temperature for 5 hours. LCMS showed that no starting material remained and the product had formed. The solvent was removed under reduced pressure to afford 1.76 g of the crude material. The crude material was loaded onto two 10 g SCX columns and these were washed with methanol. The product was eluted off using 2M ammonia in methanol and the solvent was removed under reduced pressure to afford the purified desired product in 0.954 g.

LCMS m/z 168.17 [M+H] @ 0.46 min (2 min run)

Note: This specification does not include an Intermediate 96 or 97.

Intermediate 98 4-Methyl-2-pyrimidinecarbonitrile (I98)

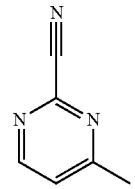

2-Chloro-4-methylpyrimidine (0.5 g, 3.89 mmol) was dissolved in N,N-dimethyl formamide (DMF) (60.8 ml) and triethylamine (0.813 ml, 5.83 mmol) and potassium cyanide (0.507 g, 7.78 mmol) were added. The solution was sonicated till most of the potassium cyanide had gone into solution then bis(triphenylphosphine) palladium(II) chloride (0.273 g, 0.389 mmol) was added. The solution was heated to 80° C. and left to stir over the weekend. LCMS showed that the product had formed. The reaction mixture was diluted in dichloromethane and washed with saturated ammonium chloride, water and brine. The organic extracts were dried over magnesium sulfate and the solvent was removed under

Intermediate 99
4-Methyl-2-pyrimidinecarboximidohydrazide (I99)

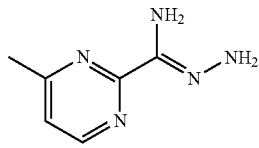

4-methyl-2-pyrimidinecarbonitrile (I98)(0.190 g, 1.595 mmol) was dissolved in ethanol (3.19 ml) and hydrazine hydrate (0.100 ml, 3.19 mmol) was added. The reaction mixture was left at reflux for 2.5 hours. TLC showed that no starting material remained so the solvent was removed under reduced pressure to afford the crude desired product in 247 mg.

$^1$H NMR (400 MHz; d6-DMSO): δ 8.60 (1H, d), 7.26 (1H, d), 5.59 (2H, br s), 5.45 (2H, br s), 2.46 (3H, s).

Intermediate 100 1,1-Dimethylethyl 3-(2-pyridinyl)-5,6-dihydro[1,2,4]triazolo[4,3-a]pyrazine-7(8H)-carboxylate (I100)

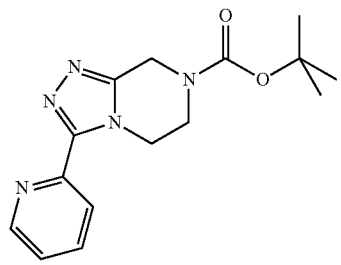 [SMILES: CC(C)(C)OC(=O)N1CCn2c(nnc2-c2ccccn2)C1]

To a solution of 1,1-dimethylethyl 3-bromo-5,6-dihydro[1,2,4]triazolo[4,3-a]pyrazine-7(8H)-carboxylate (200 mg, 0.660 mmol, commercially available) in 1,4-dioxane (2 mL), 2-(tributylstannanyl)pyridine (364 mg, 0.990 mmol) was added and mixture was degassed with a stream of argon for few minutes. Pd(Ph$_3$P)$_4$ (38.1 mg, 0.033 mmol) was then added followed by copper(I) iodide (39.2 mg, 0.206 mmol) and the mixture was submitted to microwave irradiation heating at 130° C. for 25 minutes until the reaction was complete by LCMS. Volatiles were removed under reduced pressure and the residue was purified by chromatography on silica gel (Snap 11 g NH column) eluting with a gradient from 0 to 100% ethyl acetate in iso-hexane (10CV) and then with 100% ethyl acetate (7CV). A colourless oil was obtained. The product was still impure and so was further purified by chromatography on silica gel (Si 5 g) eluting with a 80% ethyl acetate in iso hexane (5CV) and then with 10% MeOH in DCM (5 CV) then by chromatography on silica gel (Si column 5 g) eluting first with ethyl acetate (4CV) and then with 10% MeOH in DCM (6CV). Colourless oil was obtained of the desired product in 115 mg.

LCMS m/z 301.9 [M+H] @ 0.84 min (2 min run)

Intermediate 101 3-(2-Pyridinyl)-5,6,7,8-tetrahydro[1,2,4]triazolo[4,3-a]pyrazine (I101)

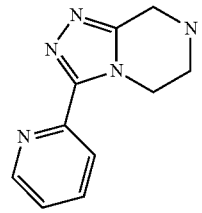 [SMILES: c1ccc(-c2nnc3n2CCNC3)nc1]

To a solution of 1,1-dimethylethyl 3-(2-pyridinyl)-5,6-dihydro[1,2,4]triazolo[4,3-a]pyrazine-7(8H)-carboxylate (I100)(115 mg, 0.382 mmol) in dichloromethane (DCM) (1 mL), TFA (0.588 mL, 7.63 mmol) was added and mixture was stirred at RT for 3 h. Volatiles removed under reduced pressure and residue purified by SCX cartridge eluting first with MeOH and then with 2.0N NH$_3$ in MeOH. Ammonia fractions were concentrated under reduced pressure yielding desired product as a pale yellow solid.60 mg.

LCMS m/z 201.9 [M+H] @ 0.47 min (2 min run)

Intermediate 102 Methyl 2-pyridinecarboxylate-d$_4$(I102)

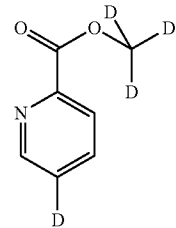

A solution of methyl 5-bromo-2-pyridinecarboxylate (1 g, 4.63 mmol, commercially available from e.g. combi-blocks) in methanol-d$_4$ (9.26 ml) was flushed with argon and then treated with deuterium (balloon filled with D$_2$) in the presence of palladium on charcoal 10% (0.246 g, 0.231 mmol) overnight. LCMS showed complete conversion of the starting material to desired product. It was filtered through a pad of celite, washed with methanol-d$_4$ and concentrated under vacuum to afford circa 1 g of crude material as a yellowish solid. NMR showed broad signals, indicating that the product is probably chelated to Pd. It was applied to a 10 g SCX column, washed with MeOH and eluted with 2M NH$_3$ in MeOH. After concentration of the basic fractions, a yellow oil of desired material was isolated in 700 mg.

$^1$H NMR (400 MHz; CDCl$_3$): δ 8.76 (1H, d), 8.15 (1H, d), 7.85 (1H, dd), 4.02 (3H, s).

Intermediate 103 2-Pyridinecarbohydrazide-d₁
(I103)

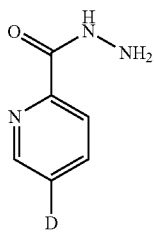 [SMILES: [2H]c1ccc(C(=O)NN)nc1]

Methyl 2-pyridinecarboxylate-d₄ (I102)(0.7 g, 4.96 mmol) containing 5% of the ¹H isotope instead of deuterium in ethanol (9.92 ml) was treated with hydrazine monohydrate (0.486 ml, 9.92 mmol) at 85° C. for 3 hours. LCMS showed complete conversion to the desired product. It was concentrated under vacuum and the residue applied to a 10 g SCX, washed with MeOH and eluted with 2M NH₃ in MeOH. The basic fractions were concentrated to afford the desired product in 400 mg (containing 5% of the H isotope) as an off-white solid.

¹H NMR (400 MHz; CDCl₃) δ 8.97 (1H, br s), 8.55 (1H, d), 8.16 (1H, dd), 7.85 (1H, dd), 4.06 (2H, br s).

Intermediate 104 Methyl 2-pyridinecarboxylate-d₁
(I104)

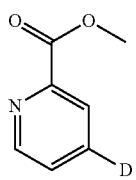

A solution of methyl 4-bromo-2-pyridinecarboxylate (1 g, 4.63 mmol, commercially available from e.g. Apollo) in methanol-d₄ (9.26 ml) was flushed with argon and then treated with deuterium (balloon filled with D₂) in the presence of palladium on charcoal 10% (0.246 g, 0.231 mmol) overnight. LCMS showed complete conversion of the starting material to desired product. It was filtered through a pad of celite, washed with methanol-d4 and concentrated under vacuum to afford circa 1 g of crude materials a yellowish solid. NMR showed broad signals, indicating that the product is probably chelated to Pd. It was applied to a 10 g SCX column, washed with MeOH and eluted with 2M NH₃ in MeOH. After concentration of the basic fractions, a yellow oil of desired material was isolated in 570 mg.

¹H NMR (400 MHz; CDCl₃): δ 8.76 (1H, d), 8.15 (1H, d), 7.49 (1H, d0, 4.02 (3H, s).

Intermediate 105 2-Pyridinecarbohydrazide-d₁
(I105)

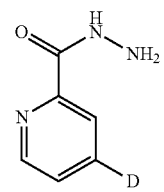 [SMILES: [2H]c1ccnc(C(=O)NN)c1]

Methyl 2-pyridinecarboxylate-d₁ (I104)(0.57 g, 4.13 mmol) in ethanol (8.25 ml) was treated with hydrazine monohydrate (0.405 ml, 8.25 mmol) at 85° C. for 3 hours. LCMS showed complete conversion to the desired product. It was concentrated under vacuum and the residue applied to a 10 g SCX, washed with MeOH and eluted with 2M NH₃ in MeOH. The basic fractions were concentrated to afford the desired product in 390 mg as an off-white solid.

¹H NMR (400 MHz; CDCl₃): δ 8.98 (1H, br s), 8.55 (1H, dd), 8.16 (1H, d), 7.44 (1H, dd), 4.08 (2H, br s).

Intermediate 106 1,1-Dimethylethyl 3-(1H-pyrazol-1-yl)-5,6-dihydro[1,2,4]triazolo[4,3-a]pyrazine-7(8H)-carboxylate (I106)

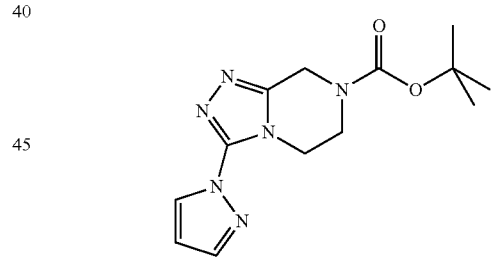

A mixture of pyrazole (33.7 mg, 0.495 mmol) and sodium hydride (19.79 mg, 0.495 mmol) in N,N-dimethylformamide (DMF) (1 ml) was cooled to 0° C. and 1,1-dimethylethyl 3-bromo-5,6-dihydro[1,2,4]triazolo[4,3-a]pyrazine-7(8H)-carboxylate (50 mg, 0.165 mmol, commercially available from e.g. Allichem, Ark Pharm or Bepharm) was added. After completion of the addition, the mixture was stirred at room temp for 30 mins and then at 110° C. After 3 h, the DMF was evaporated and a few drops of NH₄Cl solution were added followed by ethyl acetate (50 ml). The solution was dried (Na₂SO₄), filtered and concentrated. The product was purified by MDAP to give desired product in 24.1 mg.

LCMS MH⁺=291 @ 0.79 min (2 min run)

Intermediate 107 3-(1H-Pyrazol-1-yl)-5,6,7,8-tetrahydro[1,2,4]triazolo[4,3-a]pyrazine (I107)

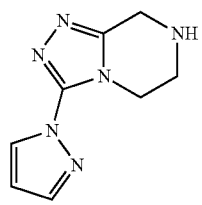 [SMILES: c1cnn(-c2nnc3n2CCNC3)c1]

A mixture of 1,1-dimethylethyl 3-(1H-pyrazol-1-yl)-5,6-dihydro[1,2,4]triazolo[4,3-a]pyrazine-7(8H)-carboxylate (I106) (24 mg, 0.083 mmol) and HCl (2 ml, 8.00 mmol) was stirred at room temp for 40 mins. The solvent was evaporated and the product was passed through SCX (elution with 2 M NH$_3$ in methanol) to give the desired product as a white solid.

$^1$H NMR (400 MHz; CDCl$_3$) δ 8.28 (1H, d), 7.76 (1H, d), 6.49 (1H, m), 4.33 (2H, t), 4.25 (2H, s), 3.36 (2H, t).

Intermediate 108 1,1-Dimethylethyl 2-(1,3-thiazol-5-ylcarbonyl) hydrazinecarboxylate (I108)

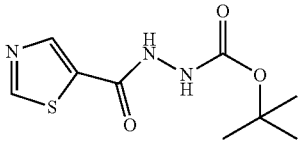 [SMILES: CC(C)(C)OC(=O)NNC(=O)c1cncs1]

1,3-thiazole-5-carboxylic acid (0.5 g, 3.87 mmol, commercially available from e.g. Apollo) was suspended in dry dichloromethane (DCM) (10 mL) under an atmosphere of argon before adding EDC (0.891 g, 4.65 mmol), followed by HOBt (0.296 g, 1.936 mmol) and stirring for 45 mins before adding 1,1-dimethylethyl hydrazinecarboxylate (0.614 g, 4.65 mmol) and stirring overnight at RT. The reaction was worked up by diluting with DCM (25 ml), washing with saturated sodium bicarbonate solution (25 ml). The aqueous layer was then extracted with DCM (2×25 ml) and the combined organic extracts were then washed with saturated brine solution (20 ml), dried over MgSO$_4$, filtered and evaporated to afford a yellow gum of crude product which was purified on a 100 g SNAP cartridge eluting with DCM (3CV) to 100% 20% MeOH/DCM over 12 CV. The desired fractions was isolated and solvent evaporated to afford a colourless gum, which solidified overnight of desired product in 666 mg.

LCMS m/z 243.98 @ 0.61 min (2 min run).

Intermediate 109 1,3-Thiazole-5-carbohydrazide (I109)

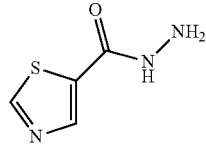

1,1-dimethylethyl 2-(1,3-thiazol-5-ylcarbonyl)hydrazinecarboxylate (I108) (666 mg, 2.74 mmol) was suspended in 1,4-dioxane (10 mL) before adding HCl (4M in 1,4-dioxane) (9 mL, 36.0 mmol). The resulting reaction mixture was stirred at RT for 3 hours. The solution went cloudy immediately. The solvent was removed under reduced pressure to afford an off-white solid of the di-hydrochloride salt. The residue was dissolved in MeOH (20 ml), placed on a 10 g prewetted SCX column and washed with MeOH (2×30 ml). The desired product was eluted off with 2M NH$_3$ in MeOH (3×30 ml). Desired fractions were isolated and the solvent evaporated to afford a pale yellow solid of desired product in 347 mg.

$^1$H NMR (400 MHz; d6-DMSO) δ 9.96 (1H, br s), 9.21 (1H, s), 8.41 (1H, s), 4.55 (2H, br s).

Intermediate 110 5,6,7,8-Tetrahydro[1,2,4]triazolo[4,3-a]pyrazine-3-carboxamide hydrochloride (I110)

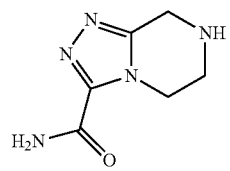

A mixture of ethyl 5,6,7,8-tetrahydro[1,2,4]triazolo[4,3-a]pyrazine-3-carboxylate (930 mg, 4.00 mmol, commercially available from e.g. Activate Scientific) in ammonia (30 ml, 1386 mmol) was stirred at room temp for 1 h and then allowed to stand at rt overnight. The solvent was evaporated and the product triturated with ether and dried to give desired product as a white solid—probably as the HCl salt in 814 mg.

LCMS no chromophore but can see MH+=168 in ELSD

Intermediate 111 1,1-Dimethylethyl 3-(aminocarbonyl)-5,6-dihydro[1,2,4]triazolo[4,3-a]pyrazine-7(8H)-carboxylate (I111)

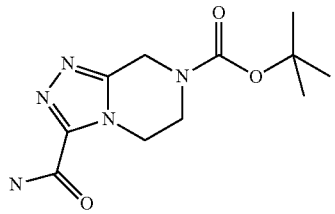 [SMILES: CC(C)(C)OC(=O)N1CCn2c(nnc2C(N)=O)C1]

A mixture of 5,6,7,8-tetrahydro[1,2,4]triazolo[4,3-a]pyrazine-3-carboxamide hydrochloride (I110)(815 mg, 4 mmol) in dichloromethane (DCM) (40 mL) was treated with Boc-anhydride (1.022 mL, 4.40 mmol) and diethylaminomethyl polystyrene (1875 mg, 6.00 mmol). After 1 h N,N-dimethylformamide (DMF) (5 mL) was added and the mixture was reacted at room temperature overnight. Tris amine resin (2 g) was added to scavenge excess Boc anhydride and the mixture was stirred for 2 h. The resins were removed by filtration and the filtrate was concentrated followed by trituration with diethyl ether to give a white solid.

LCMS see MH$^+$=268 @ 0.63 min (min run).

Intermediate 112 1,1-Dimethylethyl 3-(aminocarbonothioyl)-5,6-dihydro[1,2,4]triazolo[4,3-a]pyrazine-7(8H)-carboxylate (I112)

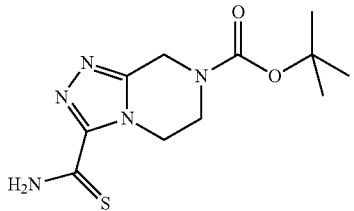 [SMILES: CC(C)(C)OC(=O)N1CCn2c(nnc2C(N)=S)C1]

A mixture of 1,1-dimethylethyl 3-(aminocarbonyl)-5,6-dihydro[1,2,4]triazolo[4,3-a]pyrazine-7(8H)-carboxylate (I111) (0.2 g, 0.748 mmol) and Lawesson's reagent (0.151 g, 0.374 mmol) in benzene (7.48 ml) was heated at 80° C. for 2 h, left to stand over the weekend at RT and then heated for a further 6 h at 80° C. The mixture was cooled, concentrated and then chromatographed (0-5% MeOH in DCM) to give the desired product as a yellow solid in 99 mg.

$^1$H NMR (400 MHz; CDCl$_3$) δ 8.80 (1H, br s), 7.46 (1H, br s), 4.88 (2H, s), 4.65 (2H, t), 3.83 (2H, t), 1.50 (9H, s).

Intermediate 113 1,1-Dimethylethyl 3-({[(1E)-(dimethylamino)methylidene]amino}carbonothioyl)-5,6-dihydro[1,2,4]triazolo[4,3-a]pyrazine-7(8H)-carboxylate (I113)

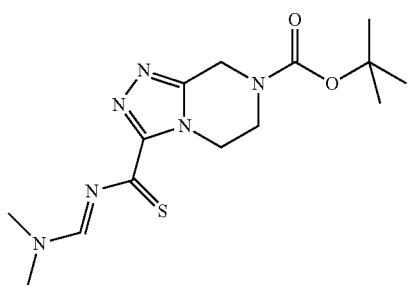 [SMILES: CN(C)/C=N/C(=S)c1nnc2n1CCN(C(=O)OC(C)(C)C)C2]

A mixture of 1,1-dimethylethyl 3-(aminocarbonothioyl)-5,6-dihydro[1,2,4]triazolo[4,3-a]pyrazine-7(8H)-carboxylate (I112) (99 mg, 0.349 mmol) in N,N-dimethylformamide (DMF) dimethyl acetal (3 ml, 22.41 mmol) was stirred at room temperature for 1 h. The mixture became red/orange and never went to a clear solution. The DMF dimethyl acetal was evaporated and the product triturated with ether to give an orange solid of desired product in 118 mg.

$^1$H NMR (400 MHz; CDCl$_3$) δ 8.67 (1H, s), 4.90 (2H, s), 4.50 (2H, t), 3.80 (2H, t), 3.32 (3H, s), 3.27 (3H, s), 1.49 (9H, s).

Intermediate 114 1,1-Dimethylethyl 3-(1,2,4-thiadiazol-5-yl)-5,6-dihydro[1,2,4]triazolo[4,3-a]pyrazine-7(8H)-carboxylate (I114)

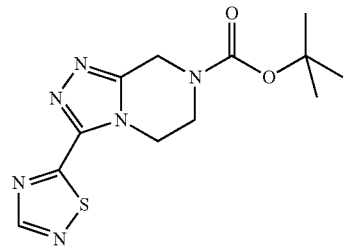 [SMILES: CC(C)(C)OC(=O)N1CCn2c(nnc2-c2ncns2)C1]

A mixture of 1,1-dimethylethyl 3-({[(1E)-(dimethylamino)methylidene]amino}carbonothioyl)-5,6-dihydro[1,2,4]triazolo[4,3-a]pyrazine-7(8H)-carboxylate (I113)(0.118 g, 0.349 mmol) and pyridine (0.056 ml, 0.698 mmol) in ethanol (2 ml) was stirred at 25° C. and hydroxylamine O-sulfonic acid (0.043 g, 0.384 mmol) in methanol (1.2 ml) was added in one batch. The mixture was stirred at RT and after a few minutes the solution became clear. After 1 h, the mixture had changed from orange to pale yellow in colour. The solvents were evaporated and the concentrated mixture was diluted with DCM (50 ml) and washed with water (5 ml), 0.2M NaOH (5 ml) and water (5 ml) and the organic layer was dried and concentrated. Chromatography (SP4, 0-100% ethyl acetate in isohexane) gave a white foam (58 mg). NMR showed some high field impurities therefore the foam was triturated with isohexane to give a white solid in 51.2 mg of desired product.

LC-MS OK trace impurities see MH$^+$=309 @ 0.81 min (2 min run).

Intermediate 115 3-(1,2,4-Thiadiazol-5-yl)-5,6,7,8-tetrahydro[1,2,4]triazolo[4,3-a]pyrazine (I115)

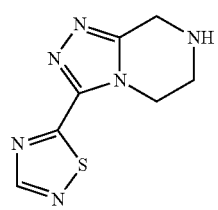 [SMILES: c1nsc(-c2nnc3n2CCNC3)n1]

A mixture of 1,1-dimethylethyl 3-(1,2,4-thiadiazol-5-yl)-5,6-dihydro[1,2,4]triazolo[4,3-a]pyrazine-7(8H)-carboxylate (I114) (51.2 mg, 0.166 mmol) in HCl (3 ml, 99 mmol) was stirred at room temp for 45 mins (a solid came out of solution). The solvents were removed and the product was passed trough an SCX cartridge (elution with 2M NH$_3$ in MeOH) to give desired product as a white solid in 34.6 mg.

LCMS see MH$^+$=209 @ 0.43 min (2 min run).

Intermediate 116 1,1-Dimethylethyl 2-[(5-methyl-1,3-thiazol-2-yl)carbonyl]hydrazinecarboxylate (I116)

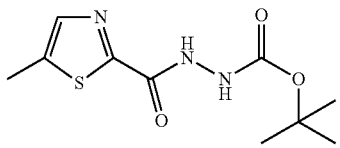 [SMILES: Cc1cnc(C(=O)NNC(=O)OC(C)(C)C)s1]

A solution of 5-methyl-1,3-thiazole-2-carboxylic acid (500 mg, 3.49 mmol) in dry dichloromethane (DCM) (17.500 ml) was stirred at room temperature under an atmosphere of argon. EDC (803 mg, 4.19 mmol) and HOBT (267 mg, 1.746 mmol) were added to the stirred solution. After 15 minutes, 1,1-dimethylethyl hydrazinecarboxylate (554 mg, 4.19 mmol) was added to the stirred solution. The resulting solution was stirred for 18 hours. After this time, the solution was diluted with DCM (approx. 50 ml) and washed with water (2× approx. 20 ml). The organic extracts were dried over MgSO$_4$, filtered and concentrated under reduced pressure to give a yellow coloured oil of desired product in 451 mg.

LCMS m/z 257.93 [M+H] @ 0.79 min (2 min run).

Intermediate 117
5-Methyl-1,3-thiazole-2-carbohydrazide (I117)

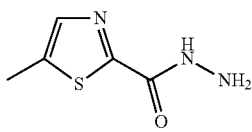

A mixture of 1,1-dimethylethyl 2-[(5-methyl-1,3-thiazol-2-yl)carbonyl]hydrazinecarboxylate (I116)(451 mg, 1.753 mmol) in HCl (2.191 ml, 72.1 mmol) (4M solution in 1,4-dioxan) was stirred at room temperature under an atmosphere of argon for 18 hours. After this time, the solvent was removed under reduced pressure to give an off white coloured solid. The solid was dissovled in MeOH and passed through an SCX cartridge, washing first with MeOH and then with 2M NH$_3$ in MeOH The NH$_3$ containing fractions were combined and concentrated under reduced pressure to give a white coloured solid of desired product in 224 mg.

LCMS m/z 158.01 [M+H] @ 0.40 min (2 min run).

Intermediate 118 1,1-Dimethylethyl 2-(1,2,5-thiadiazol-3-ylcarbonyl) hydrazinecarboxylate (I118)

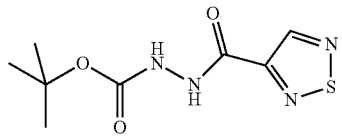 [SMILES: CC(C)(C)OC(=O)NNC(=O)c1cnsn1]

EDC (1.700 g, 8.87 mmol) and HOBt (566 mg, 3.70 mmol) were added at room temperature to a white suspension of 1,2,5-thiadiazole-3-carboxylic acid (961.7 mg, 7.39 mmol) in dry dichloromethane (DCM) (24.5 ml)—after addition of EDC, the mixture became clear and bright yellow. The reaction mixture was stirred at room temperature 1 h 15 mins. 1,1-Dimethylethyl hydrazinecarboxylate (1.172 g, 8.87 mmol) was added and the resulting mixture was stirred at room temperature for 1 day. The mixture was diluted in DCM (200 mL) and washed with sat. NaHCO$_3$ (2×25 mL) and brine (50 mL). The resulting organic layer was dried over MgSO$_4$ and concentrated under reduced pressure. The crude product was purified by flash chromatography (DCM/10% MeOH in DCM, 10CV) to afford the desired product in 1.29 g, as a oil.

LCMS m/z 144.8 [M+H-BOC] @ 0.55 min (2 min run).

Intermediate 119
1,2,5-Thiadiazole-3-carbohydrazide (I119)

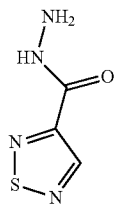

4M HCl (6.60 ml, 26.4 mmol) in 1,4-dioxane was added to 1,1-dimethylethyl 2-(1,2,5-thiadiazol-3-ylcarbonyl)hydrazinecarboxylate (I118) (1.29 g, 5.28 mmol). The reaction mixture was stirred at room temperature for 7 h. The solvent was evaporated under reduced pressure. The crude product was purified by SCX cartridge (2 batches of 500 mg each—MeOH/2M NH$_3$ in MeOH to afford the desired product in 361.4 mg as a white powder.

LCMS m/z 144.2 [M+H] @ 0.32 min (2 min run).

Intermediate 120 Ethyl 4-methyl-1,3-thiazole-2-carboxylate (I120)

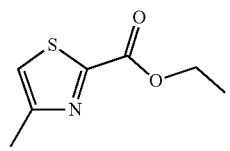

A solution of ethyl amino(thioxo)acetate (500 mg, 3.75 mmol) in ethanol (9.387 ml) was stirred at room temperature under an atmosphere of argon. 1-Chloro-2-propanone (0.299 ml, 3.75 mmol) was added and the solution was heated to reflux for 48 hours. The solution was allowed to cool to room temperature and then it was concentrated under reduced pressure to give a yellow coloured oily solid. The residue was chromatographed [SiO$_2$, 0-100% EtOAc in Hexane] to give a yellow coloured oil identified as product in 208 mg.

LCMS m/z 171.99 [M+H] @ 0.79 min (2 min run).

Intermediate 121
4-Methyl-1,3-thiazole-2-carbohydrazide (I121)

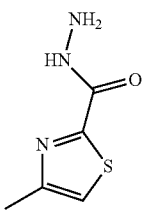

A solution of ethyl 4-methyl-1,3-thiazole-2-carboxylate (I120) (208 mg, 1.215 mmol) in ethanol (6.028 ml) was stirred at room temperature under an atmosphere of argon. Hydrazine (0.046 ml, 1.458 mmol) was added and the solution was heated to reflux for 18 hours. The solution was cooled to room temperature and then the solvent was removed under reduced pressure to give a pale yellow coloured solid of desired product in 115 mg.

LCMS m/z 157.92 [M+H] @ 0.41 min (2 min run).

Intermediate 122 1,1-Dimethylethyl 2-[(5-methyl-1,3-thiazol-4-yl)carbonyl]hydrazinecarboxylate (I122)

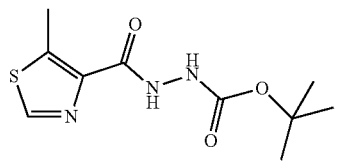 [SMILES: Cc1scnc1C(=O)NNC(=O)OC(C)(C)C]

A solution of 5-methyl-1,3-thiazole-4-carboxylic acid (500 mg, 3.49 mmol) in dry dichloromethane (DCM) (17.500 ml) was stirred at room temperature under an atmosphere of argon. EDC (736 mg, 3.84 mmol) and HOBt (267 mg, 1.746 mmol) were added to the stirred solution and the resulting solution was stirred at room temperature for ½ hour. After this time, 1,1-dimethylethyl hydrazinecarboxylate (554 mg, 4.19 mmol) was added and the solution was stirred for a further 16 hours (overnight) at room temperature. The solution was diluted with DCM (approx. 50 ml) and washed with water (2× approx. 25 ml). The organics were dried over MgSO$_4$, filtered and concentrated under reduced pressure to give a yellow coloured oily solid. The residue was chromatographed [SiO$_2$, MeOH in DCM 0-5%] to give a pale yellow coloured solid of desired material in 544 mg.

Intermediate 123
5-Methyl-1,3-thiazole-4-carbohydrazide (I123)

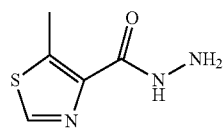

A mixture of 1,1-dimethylethyl 2-[(5-methyl-1,3-thiazol-4-yl)carbonyl]hydrazinecarboxylate (544 mg, 2.114 mmol) in HCl (2643 µl, 10.57 mmol) (4M in 1,4-dioxane) was stirred at room temperature under an atmosphere of argon for 17 hours (overnight). After this time, the reaction mixture was concentrated under reduced pressure to give an off-white coloured solid of desired material in 162 mg.

LCMS: m/z 158.02 [M+H] @ 0.34 min (2 min run).

Intermediate 124 Ethyl 3-chloro-2-cyanobenzoate (I124)

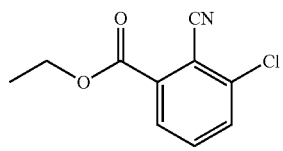

Hydrochloric acid (4.57 mL, 150 mmol) was added to a suspension of the ethyl 2-amino-3-chlorobenzoate (1.5 g, 7.51 mmol) in water (40 mL) and the mixture was cooled to 0° C. [note: compound did not go into solution] To this cooled mixture was added sodium nitrite (0.518 g, 7.51 mmol) portionwise keeping the temperature below 5° C. After addition the reaction was stirred for 40 mins. A small amount of toluene (3 ml) was added to aid dissolution. The mixture was then basified to pH~6 by the addition of Na$_2$CO$_3$. In a separate flask potassium cyanide (2.202 g, 33.8 mmol) was added portionwise to a biphasic solution of copper(II) sulfate (1.439 g, 9.02 mmol) in water (15 mL) and toluene (15 mL) at 0° C. [note: exothermic reaction] After addition the now brown mixture was heated to 60° C. To this was added the diazonium salt dropwise via a dropping funnel (mixture kept at 0° C. during addition). After addition the reaction was stirred at 70° C. for 1 hr. The reaction was cooled and EtOAc was added. The organic layer was collected, dried (Na$_2$SO$_4$) and the solvent evaporated to afford a crude dark brown oil. LCMS: 2 major peaks+1 minor peak present. (One major peak corresponds to the SM—no mass ion observed). The crude material was purified by chromatography, SP4, 100 g SNAP, 0 to 100% EtOAc/i-Hexane (fasted eluting first). The desired product was identified in 398 mg.

LCMS (High pH): 1.05 min peak, clean (no mass ion observed).

Intermediate 125 3-Chloro-2-cyanobenzoic acid (I125)

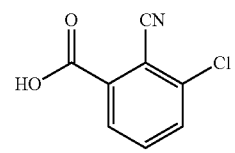 [SMILES: N#Cc1c(Cl)cccc1C(=O)O]

Lithium hydroxide (44.0 mg, 1.049 mmol) was added to a solution of the ethyl 3-chloro-2-cyanobenzoate (200 mg, 0.954 mmol) in 1,4-dioxane (2 mL) and water (2.000 mL) and the reaction was stirred at room temperature for 18 h. LCMS: No SM remains. The solvent was evaporated and the residue was dissolved in water. This was washed with Et$_2$O and then carefully acidified (2M HCl) to pH ~1. The resulting pink solid was collected, washed with water and dried invacuo to afford desired product in 153 mg).

LCMS: 0.47 min (no molecular ion seen) (2 min run).

Intermediate 126 Methyl 7-amino-3-methyl-8-oxo-5-thia-1-azabicyclo[4.2.0]oct-2-ene-2-carboxylate (I126)

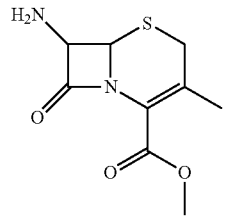

7-Amino-3-methyl-8-oxo-5-thia-1-azabicyclo[4.2.0]oct-2-ene-2-carboxylic acid (1 g, 4.67 mmol) was suspended in methanol (20 mL) before treating with conc. sulphuric acid (0.1 ml, 1.876 mmol) and heated at reflux (75° C.) for 16 hours, under argon. After heating for 15 minutes all the remaining solid had dissolved to form a yellow solution. The solution turned from yellow to brown overnight. LCMS run. Desired product seen. Reaction cooled to RT, amount of solvent reduced in vacuo. Residue partitioned between EtOAc (40 ml) and saturated sodium bicarbonate solution (40 ml). Layers separated and aqueous layer was extracted with EtOAc (2×30 ml). Combined extracts were washed with brine (30 ml), dried over $Na_2SO_4$, filtered and evaporated to afford a brown gum of the desired product in 801 mg.

LCMS: m/z 228-2 peaks seen @ 0.41 and 0.53 min.

Intermediate 127 Methyl 3-methyl-8-oxo-7-[(phenylacetyl)amino]-5-thia-1-azabicyclo[4.2.0]oct-2-ene-2-carboxylate (I127)

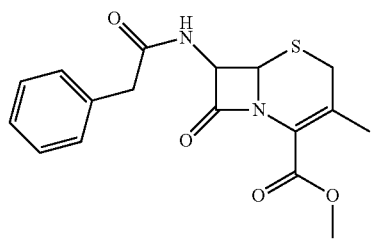 [SMILES: COC(=O)C1=C(C)CSC2C(NC(=O)Cc3ccccc3)C(=O)N12]

Methyl 7-amino-3-methyl-8-oxo-5-thia-1-azabicyclo[4.2.0]oct-2-ene-2-carboxylate (I126) (801 mg, 3.51 mmol) was dissolved in dry dichloromethane (DCM) (20 mL), cooled to ~0° C. in an ice bath before adding triethylamine (0.587 mL, 4.21 mmol) followed by phenylacetyl chloride (0.514 mL, 3.86 mmol) in Dichloromethane (DCM) (5 mL) slowly over 5-10 mins. The reaction was then allowed to warm up to RT and stirred for 4 hours then left to stand overnight. LCMS run, desired material seen. Diluted with DCM (40 ml), washed with saturated sodium bicarbonate solution (45 ml). Aqueous layer extracted with DCM (2×30 ml). Combined extracts were washed with brine (45 ml), dried over $Na_2SO_4$, filtered and evaporated to afford a red gum of crude material. Purified on a SNAP cartridge, eluting with DCM (3CV) to 100% 10% MeOH in DCM (12CV). Compound identified and solvent removed to afford an orange gum of desired product in 972 mg.

LCMS: m/z 368.9 [M+Na] @ 0.87 min (2 min run).

Intermediate 128 Methyl 4-methyl-3-isothiazolecarboxylate (I128)

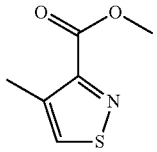

Methyl 3-methyl-8-oxo-7-[(phenylacetyl)amino]-5-thia-1-azabicyclo[4.2.0]oct-2-ene-2-carboxylate (I127) (971 mg, 2.80 mmol) was dissolved in dry dichloromethane (DCM) (37 mL), treated with NCS (749 mg, 5.61 mmol) before adding 2 drops of TFA (0.05 mL, 0.649 mmol) and stirring at RT for 80 mins. LCMS as run and the desired product seen. Reaction left to stand for 16 hours before work up by diluting with DCM (20 ml), washing with saturated sodium bicarbonate solution (50 ml), then water (40 ml), dried over $Na_2SO_4$ before filtering and evaporating to afford an oil. Purified on a 100 g SNAP cartridge eluting with chloroform over 10 CV. 2 spots were isolated, desired product identified and solvent evaporated to afford an orange yellow gum of desired material in 57 mg.

LCMS: 158.01 [M+H] @ 0.67 min (2 min run).

Intermediate 129 4-Methyl-3-isothiazolecarbohydrazide (I129)

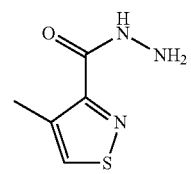

Methyl 4-methyl-3-isothiazolecarboxylate (I128) (57 mg, 0.363 mmol) was dissolved in methanol (3 mL), treated with hydrazine hydrate (0.027 mL, 0.544 mmol) then heated at reflux for 18 hours. Cooled to RT then solvent evaporated, azeotroped with $Et_2O$ (3 ml), and evaporated to afford a pale yellow solid of desired product in 57 mg.

LCMS: m/z 157.95 [M+H] @ 0.38 min (2 min run).

Intermediate 130 3-Chloro-2-methylbenzoyl chloride (I130)

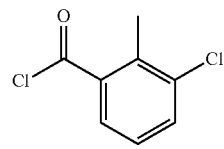

Was prepared according to the following routes described below:

1) A mixture of 3-chloro-2-methylbenzoic acid (300 mg, 1.759 mmol) and in Dichloromethane (DCM) (7 ml) was cooled to 0° C. under argon and treated with oxalyl chloride (0.154 mL, 1.759 mmol) followed by DMF (10 uL) and the mixture was then stirred at room temp for 3 h. The solvent was evaporated and the concentrate azeotroped with toluene to give desired product as a yellow oil in 332 mg.

$^1$H NMR (400 MHz; CDCl$_3$) δ 8.02 (1H, d), 7.62 (1H, d), 7.32-7.25 (1H, m), 2.59 (3H, s).

2) 3-Chloro-2-methylbenzoic acid (2.71 g, 15.87 mmol) was suspended in dry Dichloromethane (DCM) (60 mL), cooled to ~0° C. in an ice bath before adding oxalyl chloride (1.528 ml, 17.46 mmol) dropwise over 5 mins then finally DMF (0.01 ml, 0.129 mmol) was added. Effervescence was immediately seen. The ice bath was removed and stirring was continued at RT for 4 hours. Solvent evaporated and residue azeotroped with toluene (3×27 ml) to afford a colourless oil of desired product in 3 g.

$^1$H NMR (400 MHz; CDCl$_3$) δ 8.01 (1H, d), 7.62 (1H, d), 7.32-7.25 (1H, m), 2.59 (3H, s).

Intermediate 131 4-[(3-Chloro-2-methylphenyl)carbonyl]-2-piperazinone (I131)

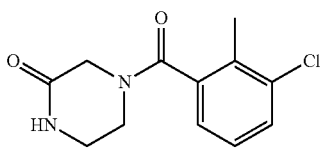 [SMILES: Cc1c(Cl)cccc1C(=O)N1CCNC(=O)C1]

2-Oxopiperazine (1.5 g, 14.98 mmol, commercially available from e.g. Sigma-Aldrich) was suspended in dry dichloromethane (DCM) (40 mL), cooled in an ice bath before adding triethylamine (3.13 mL, 22.47 mmol), followed by 3-chloro-2-methylbenzoyl chloride (I130) (2.97 g, 15.73 mmol) in Dichloromethane (DCM) (15 mL) dropwise over 15 mins. The reaction mixture was then stirred for 16 hours at RT, under argon. Solvent removed under reduced pressure. Residue partitioned between DCM (100 ml) and water (60 ml). Layers separated and aqueous layer extracted with DCM (2×50 ml). Combined extracts were washed with saturated sodium bicarbonate solution (70 ml), brine (70 ml), dried (Na$_2$SO$_4$), filtered and evaporated to afford an off-white solid. Solid was stirred in n-hexane (50 mL) at 55° C. for 30 mins, before filtering and drying in the vacuum oven at 40° C. for 18 hours to afford the desired product in 3.39 g as a pale yellow solid.

LCMS: m/z 252.87 [M+H] @ 0.67 min (2 min run).

Intermediate 132 Methyl 2-pyrazinecarboxylate (I132)

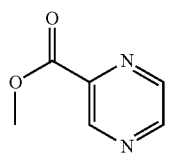

Thionyl chloride (0.146 L, 1998 mmol) was added to methanol (1.5 L) dropwise at −5° to 0° C. over a period of 1 hour and was stirred at this temperature for 30 minutes. The solution was allowed to warm to room temperature whereupon 2-pyrazine carboxylic acid (62 g, 500 mmol) was added. The mixture was cautiously heated at reflux for 6 h and allowed to cool to room temperature overnight. LCMS indicated that the reaction was complete. The solvents were removed in vacuo and the residue was partitioned between ethyl acetate (500 mL) and saturated sodium bicarbonate solution (500 mL). The aqueous phase was extracted with ethyl acetate (3×500 mL), the combined organic extracts were washed with water (250 mL), brine (250 mL), dried over anhydrous sodium sulfate and concentrated in vacuo to afford a crude solid. The solid was recrystalised from ~500 ml of 1:1 pentane:cyclohexane, decanting the hot solution twice off a dark viscous oil. Care was taken to minimise the amount of product oiling out upon cooling affording as cream needles. The mothor liquors were concentrated in vacuo and the residue recrystalised from the same solvent (~200 mL) affording a second crop, as buff needles. Analysis by LCMS and NMR indicates that both materials are consistant with desired product and of comaparable purity. Both batches were combined to afford product in 42.8 g as beige needles.

LC/MS=139 (M+H)$^+$, retention time=0.40 minutes (2 minute method).

Intermediate 133 2-Pyrazinecarbohydrazide (I133)

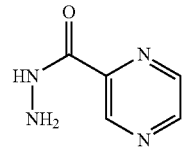

Methyl 2-pyrazinecarboxylate (I132) (42 g, 304 mmol) was dissolved in ethanol (750 mL) and treated with hydrazine hydrate (22.17 mL, 456 mmol). The solution was stirred at room temperature for 5 minutes whereupon a precipitate started to form. The mixture was cautiously heated to 80° C. for 5 h and cooled to room temperature. Approximately 50% of the solvent was then removed in vacuo, the slurry was heated to reflux and the solution cooled to room temperature overnight. The resulting solid was filtered, washed with a little ethanol, diethyl ether and dried in a vacuum oven to afford product in 39.77 g as beige needles.

LC/MS=139 (M+H)$^+$, retention time=0.32 minutes (2 minute method (high pH)).

EXAMPLES

The general methods (a) to (e), along with the synthetic methods outlined in Schemes 1 to 4 above, for the preparation of compounds or salts of the present invention are further illustrated by the following examples.

Example 1

3-Bromo-7-{[2-chloro-3-(trifluoromethyl)phenyl]carbonyl}-5,6,7,8-tetrahydro[1,2,4]triazolo[4,3-a]pyrazine (E1)

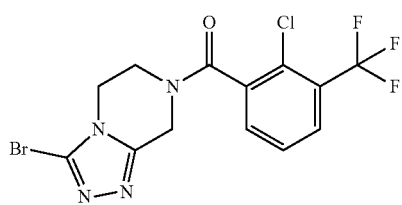 [SMILES: O=C(c1cccc(C(F)(F)F)c1Cl)N1CCn2c(Br)nnc2C1]

3-Bromo-5,6,7,8-tetrahydro[1,2,4]triazolo[4,3-a]pyrazine (prepared by standard BOC deprotection of tert-Butyl 3-bromo-5,6-dihydro-1,2,4-triazolo[4,3-a]pyrazine-7(8H)-carboxylate, CAS [723286-80-4], commercially available e.g. from Allichem, Ark Pharm or Bepharm) (0.6 mmol) and diethylaminomethyl polystyrene (0.6 g, 1.92 mmol) were slurried in Dichloromethane (DCM) (7 mL) under argon. 2-Chloro-3-(trifluoromethyl)benzoyl chloride (0.16 g, 0.66 mmol, commercially available e.g. from Apollo Scientific or Shanghai FWD Chemicals) was added to the reaction. The mixture was stirred for 4 hours. The resin was filtered, washed with Dichloromethane (50 mL) and concentrated in vacuo to afford crude product. The crude product was purified by using mass-directed automated (preparative) HPLC (MDAP). The fractions containing the products were evaporated, diluted with diethyl ether and treated with 1 mL of HCl in diethyl ether; the solutions were stirred for 30 min. and solvent evaporated to give 3-bromo-7-{[2-chloro-3-(trifluoromethyl)phenyl]carbonyl}-5,6,7,8-tetrahydro[1,2,4]triazolo[4,3-a]pyrazine (0.268 g). LC/MS [M+H]+=410.9, retention time=2.07 minutes (5 minute method).

Alternatively, 3-bromo-7-{[2-chloro-3-(trifluoromethyl)phenyl]carbonyl}-5,6,7,8-tetrahydro[1,2,4]triazolo[4,3-a]pyrazine could also be prepared in the following manner:

3-Bromo-5,6,7,8-tetrahydro[1,2,4]triazolo[4,3-a]pyrazine HCl (1.5 g, 6.26 mmol) was treated with N,N-dimethylformamide (DMF) (12 mL) and cooled to 0° C.

Triethylamine (1.790 mL, 12.84 mmol) and N,N-dimethyl-4-pyridinamine (DMAP) (0.077 g, 0.626 mmol) were added under argon and the mixture was stirred for 5 minutes; then 2-chloro-3-(trifluoromethyl)benzoyl chloride (1.674 g, 6.89 mmol, commercially available e.g. from Apollo Scientific or Shanghai FWD Chemicals) was added. The reaction mixture was kept at 0° C. for ½ hour. The reaction was quenched with water, extracted with ethyl acetate (two extractions), and the combined organic phases were washed with a saturated sodium bicarbonate solution, followed by water (four washes). The organic phase was dried, and evaporated to give a yellow oil. The residue was purified by silica gel chromatography using 0-15% of methanol in Dichloromethane as eluent. The resulting material was triturated with diethyl ether/isohexane mixture to give 3-bromo-7-{[2-chloro-3-(trifluoromethyl)phenyl]carbonyl}-5,6,7,8-tetrahydro[1,2,4]triazolo[4,3-a]pyrazine as an off-white solid.

LCMS [M+H]+=410.9, 412.9 Retention time=2.08 (5 min. method)

Examples 2 to 9

In a manner analogous to that described for Example 1 above (the main or alternative embodiment thereof), the compounds tabulated below (Table 2) were prepared, believed to be substantially in the form of the free compounds, by substituting the appropriate 3-substituted (or 3-unsubstituted) 5,6,7,8-tetrahydro[1,2,4]triazolo[4,3-a]pyrazines and/or the appropriate substituted benzoyl chlorides for the 3-bromo-5,6,7,8-tetrahydro[1,2,4]triazolo[4,3-a]pyrazine and/or the 2-chloro-3-(trifluoromethyl)benzoyl chloride used in the above procedure respectively. The purification step(s) and/or the post-purification solvent trituration/workup step used for each of Examples 2 to 9 is or are stated in brief in the following Table 2.

All of the 3-substituted (or 3-unsubstituted) 5,6,7,8-tetrahydro[1,2,4]triazolo[4,3-a]pyrazines and the substituted benzoyl chlorides used are available from commercial sources and/or can be prepared using routes described previously in the chemical literature.

TABLE 2

| Example no. | Chemical structure and name of product (and purification and/or solvent trituration/workup steps used) | Starting material(s) and possible commercial source(s) | [M + H]+ | Retention time (mins) |
|---|---|---|---|---|
| E2 | 7-{[2-chloro-3-(trifluoromethyl)phenyl]carbonyl}-3-(trifluoromethyl)-5,6,7,8-tetrahydro[1,2,4]triazolo[4,3-a]pyrazine (MDAP, then HCl/diethyl ether workup) | 3-(Trifluoromethyl)-1,2,4-triazolo[4,3-a]piperazine e.g. hydrochloride salt available e.g. from Anichem, Princeton BioMolecular Research, or Shanghai Sinofluoro Scientific. | 399, 401 | 2.38[a] |

TABLE 2-continued

| Example no. | Chemical structure and name of product (and purification and/or solvent trituration/workup steps used) | Starting material(s) and possible commercial source(s) | [M + H]⁺ | Retention time (mins) |
|---|---|---|---|---|
| E3 | 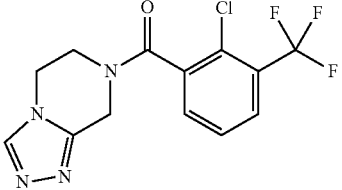 7-{[2-chloro-3-(trifluoromethyl)phenyl]carbonyl}-5,6,7,8-tetrahydro[1,2,4]triazolo[4,3-b]pyrazine (MDAP, then HCl/diethyl ether workup) | 5,6,7,8-Tetrahydro-[1,2,4]triazolo[4,3-a]pyrazine, available e.g. from Alchem Pharmtech, Bosche Scientific or D-L Chiral Chemicals. | 331, 333 | 1.78[a] |
| E4 | 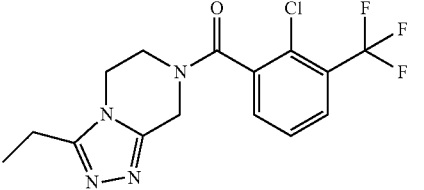 7-{[2-chloro-3-(trifluoromethyl)phenyl]carbonyl}-3-ethyl-5,6,7,8-tetrahydro[1,2,4]triazolo[4,3-a]pyrazine (MDAP, then isohexane/diethyl ether trituration) | 3-Ethyl-5,6,7,8-tetrahydro-[1,2,4]triazolo[4,3-a]pyrazine, available e.g. from Allichem LLC, APAC Pharmaceutical or Lanzhou Chon Chemical. | 359, 361 | 1.79[a] |
| E5 | 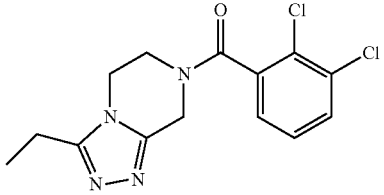 7-[(2,3-dichlorophenyl)carbonyl]-3-ethyl-5,6,7,8-tetrahydro[1,2,4]triazolo[4,3-a]pyrazine (MDAP, then isohexane/diethyl ether trituration) | 3-Ethyl-5,6,7,8-tetrahydro-[1,2,4]triazolo[4,3-a]pyrazine; see E4 for possible sources. 2,3-Dichlorobenzoyl chloride, available e.g. from ABCR, ChemPacific or UkrOrgSynthesis. | 325, 329 | 1.69[a] |
| E6 | 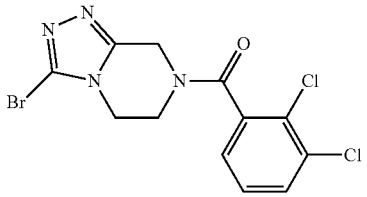 3-bromo-7-[(2,3-dichlorophenyl)carbonyl]-5,6,7,8-tetrahydro[1,2,4]triazolo[4,3-a]pyrazine (MDAP) | 2,3-Dichlorobenzoyl choride, available e.g. from ABCR, ChemPacific or UkrOrgSynthesis. | 377 | 1.89[a] |

TABLE 2-continued

| Example no. | Chemical structure and name of product (and purification and/or solvent trituration/workup steps used) | Starting material(s) and possible commercial source(s) | [M + H]⁺ | Retention time (mins) |
|---|---|---|---|---|
| E7 | 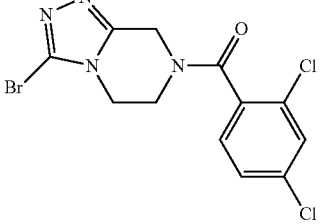<br>3-bromo-7-[(2,4-dichlorophenyl)carbonyl]-5,6,7,8-tetrahydro[1,2,4]triazolo[4,3-a]pyrazine<br>(MDAP, then diethyl ether trituration) | 2,4-Dichlorobenzoyl chloride, available e.g. from Sigma-Aldrich or Maybridge. | 377 | 1.94[a] |
| E8 | 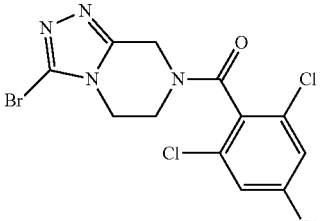<br>3-bromo-7-[(2,4,6-trichlorophenyl)carbonyl]-5,6,7,8-tetrahydro[1,2,4]triazolo[4,3-a]pyrazine<br>(silica gel, then diethyl ether trituration) | 2,4,6-Trichlorobenzoyl chloride, available e.g. from Sigma-Aldrich or Shanghai PI Chemicals. | 411 | 2.08[a] |
| E9 | 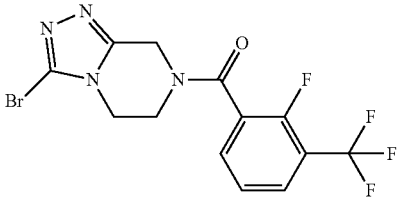<br>3-bromo-7-{[2-fluoro-3-(trifluoromethyl)phenyl]carbonyl}-5,6,7,8-tetrahydro[1,2,4]triazolo[4,3-a]pyrazine<br>(MDAP, then diethyl ether trituration) | 2-Fluoro-3-(trifluoromethyl)-benzoyl chloride, available e.g. from Sigma-Aldrich or Shanghai PI Chemicals. | 393 | 2.01[a] |

[a]Retention time obtained using 5 minute HPLC method
[b]Retention time obtained using 2 minute HPLC method

Example 10

7-{[2-Chloro-3-(trifluoromethyl)phenyl]carbonyl}-3-(4-pyridinyl)-5,6,7,8-tetrahydro[1,2,4]triazolo[4,3-a]pyrazine (E10)

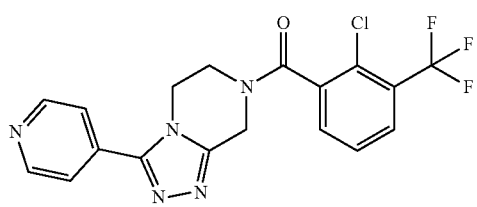 [SMILES: O=C(c1cccc(C(F)(F)F)c1Cl)N1CCn2c(nnc2-c2ccncc2)C1]

3-(4-Pyridinyl)-5,6,7,8-tetrahydro[1,2,4]triazolo[4,3-a]pyrazine (0.150 g, 0.745 mmol, e.g. prepared as described below) was treated with N,N-dimethylformamide (DMF) (3 mL) and cooled to 0° C. Triethylamine (0.109 mL, 0.783 mmol) and N,N-dimethyl-4-pyridinamine (DMAP) (0.009 g, 0.075 mmol) were added at 0° C. under argon and the mixture was stirred for 5 minutes; then 2-chloro-3-(trifluoromethyl) benzoyl chloride (0.199 g, 0.820 mmol, commercially available e.g. from Apollo Scientific or Shanghai FWD Chemicals) was added. The reaction mixture was kept at 0° C. for ½ hour. The reaction was quenched with water, extracted with ethyl acetate (two extractions), and the combined organic phases were washed with a saturated sodium bicarbonate solution, followed by water (four washes). The organic phase was dried, and evaporated to give a yellow oil. The residue was purified by silica gel chromatography using 0-20% of methanol in Dichloromethane as the eluent and then triturated with diethyl ether to give 7-{[2-chloro-3-(trifluoromethyl) phenyl]carbonyl}-3-(4-pyridinyl)-5,6,7,8-tetrahydro[1,2,4] triazolo[4,3-a]pyrazine as a white solid. The solid was dried at 50° C. on the high vacuum for 1 day.

LCMS: [M+H]+=408, 410 retention time=1.74 (5 min. Method)

The 3-(4-pyridinyl)-5,6,7,8-tetrahydro[1,2,4]triazolo[4,3-a]pyrazine used in the above procedure can be prepared as follows:

i) 2-Chloropyrazine (7.79 mL, 87 mmol, commercially available e.g. from Sigma-Aldrich or Haiso PharmChem) was dissolved in ethanol (50 mL), and hydrazine hydrate (6.85 mL, 218 mmol) was added. The solution was refluxed for 6 hours. The mixture was cooled to room temperature and the solvent was partially evaporated.

The residue was diluted with water and extracted with 10% (v/v) of 2-propanol/Dichloromethane solution (5 extractions). The combined organic phases were then dried and evaporated to give a yellow solid which was triturated with diethyl ether to give 2-hydrazinopyrazine as a yellow solid (3.32 g).

ii) To 2-hydrazinopyrazine (2 g, 18.16 mmol) was added isonicotinic acid (pyridine-4-carboxylic acid, 4.47 g, 36.3 mmol, commercially available e.g. from Sigma-Aldrich or Allichem LLC) followed by polyphosphoric acid (50 mL), and the reaction was stirred at 155° C. for 18 hours. The hot solution was added to ice and neutralised by addition of ammonia 0.88. The aqueous solution was then extracted with ethyl acetate (3 extractions), washed with brine, and dried. The yellow solid thus obtained was treated with Dichloromethane, and any remaining solid material was filtered off and put to one side. The filtrate was evaporated and the residue was purified by chromatography using 0-10% of methanol in Dichloromethane as eluent. The fractions containing the product were evaporated to give ~260 mg of yellow solid which was combined with the material set aside earlier to give 0.538 g of 3-(4-pyridinyl)[1,2,4]triazolo[4,3-a]pyrazine.

LCMS: [M+H]+=198 retention time=0.35 minutes (2 minute method)

iii) 3-(4-Pyridinyl)[1,2,4]triazolo[4,3-a]pyrazine (538 mg, 2.73 mmol) was hydrogenated under atmospheric hydrogen with 10% Pd/C as a catalyst in ethanol at ambient temperature for 36 hours. The catalyst was filtered off and the solvent was evaporated. The residue was purified on silica gel chromatography using 0-20% of 2M methanol in ammonia—Dichloromethane as eluent to give 3-(4-pyridinyl)-5,6,7,8-tetrahydro[1,2,4]triazolo[4,3-a]pyrazine (0.288 g).

LCMS [M+H]+=202, 203 retention time=0.18 minutes (2 minute method)

Examples 11 to 12

In a manner analogous to that described for Example 10 above the compounds tabulated below (Table 3) were prepared, believed to be substantially in the form of the free compounds, by substituting the appropriate 3-substituted 5,6,7,8-tetrahydro[1,2,4]triazolo[4,3-a]pyrazines for the 3-bromo-5,6,7,8-tetrahydro[1,2,4]triazolo[4,3-a]pyrazine used in the above procedure. For each of Examples 11 and 12, diethyl ether trituration was used, instead of the silica gel chromatography and diethyl ether trituration used in Example 10 above.

All of the 3-substituted 5,6,7,8-tetrahydro[1,2,4]triazolo[4,3-a]pyrazines could be prepared in a manner analogous to that described in Example 10 steps (i)-(iii) but using the appropriate carboxylic acid in the place of isonicotinic acid. All the requisite starting materials are available from commercial sources and/or can be prepared using routes described previously in the chemical literature.

TABLE 3

| Example no. | Chemical structure and name of product | Starting material and possible commercial source(s) | [M + H]+ | Retention time (mins) |
|---|---|---|---|---|
| E11 | 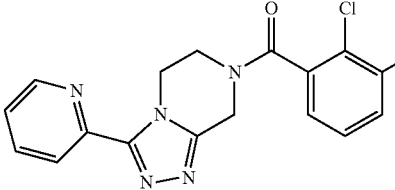<br>7-{[2-chloro-3-(trifluoromethyl)phenyl]carbonyl}-3-(2-pyridinyl)-5,6,7,8-tetrahydro[1,2,4]triazolo[4,3-a]pyrazine | 2-Picolinic acid (pyridine-2-carboxylic acid), available e.g. from Sigma-Aldrich or Maybridge. | 408, 410 | 2.25[a] |
| E12 | 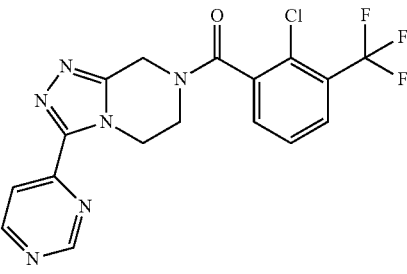<br>7-{[2-chloro-3-(trifluoromethyl)phenyl]carbonyl}-3-(4-pyrimidinyl)-5,6,7,8-tetrahydro[1,2,4]triazolo[4,3-a]pyrazine | Pyrimidine-4-carboxylic acid, available e.g. from Bridge Organics, Indofine Chemical or Ryan Scientific. | 408.9, 410.9 | 0.86[a] |

[a]Retention time obtained using 5 minute HPLC method
[b]Retention time obtained using 2 minute HPLC method

Example 13

7-{[2-Chloro-3-(trifluoromethyl)phenyl]carbonyl}-3-phenyl-5,6,7,8-tetrahydro[1,2,4]triazolo[4,3-a]pyrazine (E13)

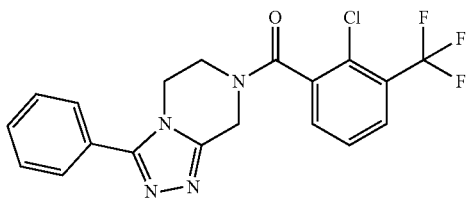 [SMILES: O=C(c1cccc(C(F)(F)F)c1Cl)N1CCn2c(nnc2-c2ccccc2)C1]

To 3-bromo-7-{[2-chloro-3-(trifluoromethyl)phenyl]carbonyl}-5,6,7,8-tetrahydro[1,2,4]triazolo[4,3-a]pyrazine (0.150 g, 0.366 mmol, e.g. see Example 1 for methods of preparation) in 1,2-dimethoxyethane (DME) (3 mL) was added aqueous sodium carbonate solution (1.9 mL, 1 M) followed by phenylboronic acid (0.067 g, 0.549 mmol, commercially available e.g. from Sigma-Aldrich or Strem Chemicals) and dichlorobis(triphenylphosphine)palladium(II) (0.013 g, 0.018 mmol). The reaction mixture was heated at reflux for 7 hours. The mixture was diluted with water (10 mL) and extracted with ethyl acetate (twice). The combined organic fractions were dried, filtered and evaporated. An attempt to purify the crude material on silica gel chromatography using methanol in Dichloromethane (0-20%) as eluent was unsuccessful. The residue was then purified using mass-directed automated (preparative) HPLC (MDAP) to give 7-{[2-chloro-3-(trifluoromethyl)phenyl]carbonyl}-3-phenyl-5,6,7,8-tetrahydro[1,2,4]triazolo[4,3-a]pyrazine (0.076 g) as a white solid.

LCMS: [M+H]+=407, 409 retention time=2.31 minutes. (5 min. method)

Example 14

7-{[2-Chloro-3-(trifluoromethyl)phenyl]carbonyl}-3-(4-fluorophenyl)-5,6,7,8-tetrahydro[1,2,4]triazolo[4,3-a]pyrazine (E14)

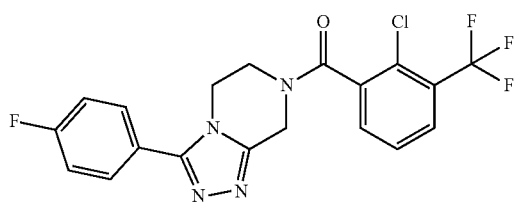 [SMILES: O=C(c1cccc(C(F)(F)F)c1Cl)N1CCn2c(nnc2-c2ccc(F)cc2)C1]

7-{[2-chloro-3-(trifluoromethyl)phenyl]carbonyl}-3-(4-fluorophenyl)-5,6,7,8-tetrahydro[1,2,4]triazolo[4,3-a]pyrazine was prepared in a manner analogous to that described above for 7-{[2-chloro-3-(trifluoromethyl)phenyl]carbonyl}-3-phenyl-5,6,7,8-tetrahydro[1,2,4]triazolo[4,3-a]pyrazine (Example 13), but using (4-fluorophenyl)boronic acid (commercially available e.g. from Alfa Aesar or ABCR) in the place of phenylboronic acid, and using MDAP followed by isohexane trituration rather than MDAP.

LCMS: [M+H]+=425, 426.9 retention time=2.35 minutes. (5 min. method).

Example 15

7-{[2-Chloro-3-(trifluoromethyl)phenyl]carbonyl}-3-methyl-5,6,7,8-tetrahydro[1,2,4]triazolo[4,3-a]pyrazine (E15)

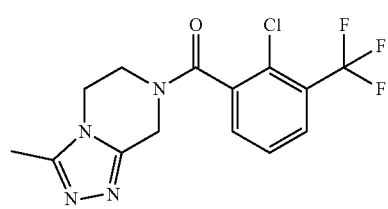 [SMILES: Cc1nnc2n1CCN(C(=O)c1cccc(C(F)(F)F)c1Cl)C2]

3-Bromo-7-{[2-chloro-3-(trifluoromethyl)phenyl]carbonyl}-5,6,7,8-tetrahydro[1,2,4]triazolo[4,3-a]pyrazine (150 mg, 0.366 mmol, e.g. see Example 1 for methods of preparation) was dissolved in 1,4-dioxane (3 mL) and treated with trimethylboroxine (55.2 mg, 0.439 mmol, commercially available e.g. from Sigma-Aldrich or Thermo Fischer Scientific), potassium carbonate (76 mg, 0.549 mmol) and tetrakis(triphenylphosphine)palladium(0) (42.3 mg, 0.037 mmol). The reaction mixture, under argon, was heated at 110° C. for 20 hours. The mixture was then cooled, diluted with water and extracted with ethyl acetate (three times). The organic phase was dried and evaporated. The residue was purified on the mass-directed automated (preparative) HPLC (MDAP) and the residue was triturated with isohexane to give 7-{[2-chloro-3-(trifluoromethyl)phenyl]carbonyl}-3-methyl-5,6,7,8-tetrahydro[1,2,4]triazolo[4,3-a]pyrazine (0.028 g) as a white solid.

LCMS: [M+H]+=345, 347 retention time=1.75 minutes. (5 min. method)

Example 16

7-{[2-Chloro-3-(trifluoromethyl)phenyl]carbonyl}-3-(3-pyridinyl)-5,6,7,8-tetrahydro[1,2,4]triazolo[4,3-a]pyrazine (E16)

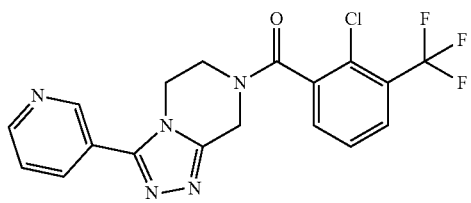 [SMILES: O=C(c1cccc(C(F)(F)F)c1Cl)N1CCn2c(nnc2-c2cccnc2)C1]

7-{[2-Chloro-3-(trifluoromethyl)phenyl]carbonyl}-5,6,7,8-tetrahydro[1,2,4]triazolo[4,3-a]pyrazine (0.160 g, 0.484 mmol, e.g. see Example 3 for method of preparation), 3-bromopyridine (0.084 g, 0.532 mmol, commercially available e.g. from Sigma-Aldrich or Ryan Scientific), palladium(II) acetate (0.011 g, 0.048 mmol) and cesium carbonate (0.159 g, 0.489 mmol) in anhydrous 1,4-dioxane (2.5 mL) were heated, under argon, at 90° C. for 18 hours. The mixture was cooled, water added and extracted with ethyl acetate (three times). The combined organic phases were washed with water (twice), dried and evaporated. The residue was purified on the mass-directed automated (preparative) HPLC (MDAP) to give 7-{[2-chloro-3-(trifluoromethyl)phenyl]carbonyl}-3-(3-pyridinyl)-5,6,7,8-tetrahydro[1,2,4]triazolo[4,3-a]pyrazine (0.015 g).

LCMS: [M+H]+=408, 410 retention time=1.88 minutes. (5 min. method)

Example 17

7-{[2-Chloro-3-(trifluoromethyl)phenyl]carbonyl}-3-(methyloxy)-5,6,7,8-tetrahydro[1,2,4]triazolo[4,3-a]pyrazine (E17)

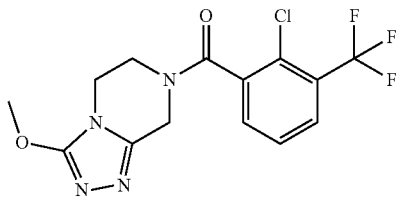 [SMILES: COc1nnc2n1CCN(C(=O)c1cccc(C(F)(F)F)c1Cl)C2]

3-Bromo-7-{[2-chloro-3-(trifluoromethyl)phenyl]carbonyl}-5,6,7,8-tetrahydro[1,2,4]triazolo[4,3-a]pyrazine (0.250 g, 0.610 mmol, see Example 1 for methods of preparation) was added to a solution of sodium (0.042 g, 1.831 mmol) in methanol (8 mL), under argon and refluxed for 1 hour. More sodium (0.040 g) was added and the reaction was refluxed for 22 hours. The reaction was quenched with water and extracted with Dichloromethane (three times), the combined organics were dried and evaporated, and the residue was purified on the mass-directed automated (preparative) HPLC (MDAP) and triturated with diethyl ether to give 7-{[2-chloro-3-(trifluoromethyl)phenyl]carbonyl}-3-(methyloxy)-5,6,7,8-tetrahydro[1,2,4]triazolo[4,3-a]pyrazine (0.082 g) as a white solid.

LCMS: [M+H]+=361, 363 retention time=1.95 minutes. (5 min. method)

Example 18

7-{[2-Chloro-3-(trifluoromethyl)phenyl]carbonyl}-3-(4-morpholinyl)-5,6,7,8-tetrahydro[1,2,4]triazolo[4,3-a]pyrazine (E18)

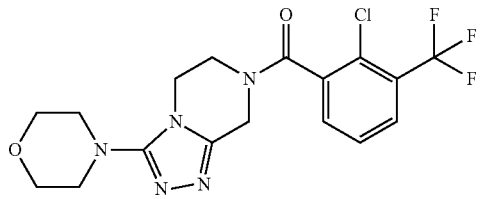 [SMILES: O=C(c1cccc(C(F)(F)F)c1Cl)N1CCn2c(nnc2N2CCOCC2)C1]

3-Bromo-7-{[2-chloro-3-(trifluoromethyl)phenyl]carbonyl}-5,6,7,8-tetrahydro[1,2,4]triazolo[4,3-a]pyrazine (0.075 g, 0.183 mmol, e.g. see Example 1 for methods of preparation) was treated with morpholine (1.5 mL) and heated in a microwave reactor at 110° C. for a total of 7 hours. The solvent was evaporated under reduced vacuum and the residue was purified by mass-directed automated (preparative) HPLC (MDAP) and triturated with isohexane to afford 7-{[2-chloro-3-(trifluoromethyl)phenyl]carbonyl}-3-(4-morpholinyl)-5,6,7,8-tetrahydro[1,2,4]triazolo[4,3-a]pyrazine (0.012 g) as white solid.

LCMS: [M+H]+=416, 418 retention time=1.87 minutes. (5 min. method)

Examples 19 to 23

In a manner analogous to that described for Example 18 above the compounds tabulated below (Table 4) were prepared, either as the free bases and/or as salt(s) thereof, by substituting the appropriate amine (or a solution of the amine in ethanol) for the morpholine used in the above procedure. The purification step(s) and the post-purification solvent trituration step used for each of Examples 19 to 23 (instead of the MDAP then isohexane trituration used in Example 18) are stated in brief in the following table. All of the requisite starting materials are available from commercial sources and/or can be prepared using routes described previously in the chemical literature.

TABLE 4

| Example no. | Chemical structure and name of product (and purification and solvent trituration steps used) | Starting amine; and possible source(s) | [M + H]+ | Retention time (mins) |
|---|---|---|---|---|
| E19 | ![structure] 7-{[2-chloro-3-(trifluoromethyl)phenyl]carbonyl}-3-(1-pyrrolidinyl)-5,6,7,8-tetrahydro[1,2,4]triazolo[4,3-a]pyrazine (silica gel, then MDAP, then isohexane trituration) | pyrrolidine | 400, 402 | 1.4[a] |

TABLE 4-continued

| Example no. | Chemical structure and name of product (and purification and solvent trituration steps used) | Starting amine; and possible source(s) | [M + H]+ | Retention time (mins) |
|---|---|---|---|---|
| E20 | 7-{[2-chloro-3-(trifluoromethyl)phenyl]carbonyl}-N,N-dimethyl-5,6,7,8-tetrahydro[1,2,4]triazolo[4,3-a]pyrazin-3-amine (silica gel, then MDAP, then isohexane trituration) | N,N-dimethylamine | 374, 376 | 1.52[a] |
| E21 | 7-{[2-chloro-3-(trifluoromethyl)phenyl]carbonyl}-N-methyl-5,6,7,8-tetrahydro[1,2,4]triazolo[4,3-a]pyrazin-3-amine (MDAP, then diethyl ether trituration) | N-methylamine | 360, 362 | 1.25[a] |
| E22 | 3-(1-azetidinyl)-7-{[2-chloro-3-(trifluoromethyl)phenyl]carbonyl}-5,6,7,8-tetrahydro[1,2,4]triazolo[4,3-a]pyrazine (MDAP, then diethyl ether trituration) | azetidine; available e.g. from Sigma-Aldrich or Apollo Scientific | 386, 388 | 1.5[a] |
| E23 | 7-{[2-chloro-3-(trifluoromethyl)phenyl]carbonyl}-3-(1-piperidinyl)-5,6,7,8-tetrahydro[1,2,4]triazolo[4,3-a]pyrazine (MDAP, then diethyl ether trituration) | piperidine | 414, 416 | 1.97[a] |

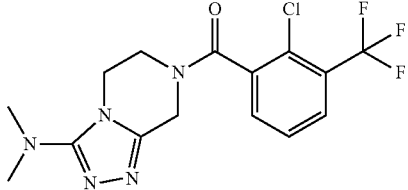

[a]Retention time obtained using 5 minute HPLC method
[b]Retention time obtained using 2 minute HPLC method

Example 24

7-{[2-Chloro-3-(trifluoromethyl)phenyl]carbonyl}-3-(2,4-difluorophenyl)-5,6,7,8-tetrahydro[1,2,4]triazolo[4,3-a]pyrazine (E24)

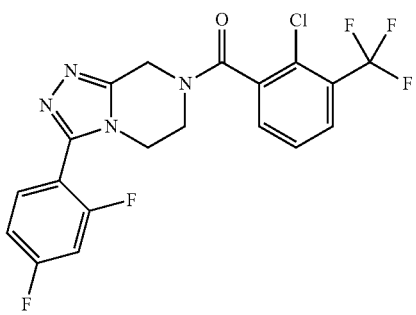 [SMILES: O=C(c1cccc(C(F)(F)F)c1Cl)N1CCn2c(nnc2-c2ccc(F)cc2F)C1]

A mixture of 1-{[2-chloro-3-(trifluoromethyl)phenyl]carbonyl}-5-(ethyloxy)-1,2,3,6-tetrahydropyrazine (0.167 g, 0.5 mmol, e.g. see preparation below) and 2,4-difluorobenzohydrazide (0.086 g, 0.500 mmol, CAS [118737-62-5], commercially available e.g. from Matrix Scientific or ABCR) in 1-butanol (1 ml) was heated at reflux for 1 hour. After cooling to room temperature the solvent was evaporated and the residue was purified by mass-directed automated (preparative) HPLC (MDAP). The residue was triturated with diethyl ether/isohexane and the solid was collected and dried to give 7-{[2-chloro-3-(trifluoromethyl)phenyl]carbonyl}-3-(2,4-difluorophenyl)-5,6,7,8-tetrahydro[1,2,4]triazolo[4,3-a]pyrazine (0.032 g) as a white solid. The solid was dried at 50° C. under high vacuum for 1 day.

LCMS: [M+H]+=443 retention time=2.42 (5 min. Method)

The 1-{[2-chloro-3-(trifluoromethyl)phenyl]carbonyl}-5-(ethyloxy)-1,2,3,6-tetrahydropyrazine used in the above method can be prepared in the following manner:

To a solution of 4-{[2-chloro-3-(trifluoromethyl)phenyl]carbonyl}-2-piperazinone (0.613 g, 2 mmol, e.g. as prepared in Intermediate 1) in Dichloromethane (5 ml) at room temperature was added triethyloxonium tetrafluoroborate (950 mg, 5.00 mmol). The reaction mixture was stirred for 18 hours. Dichloromethane (20 ml) and iced water (10 ml) were added and the pH was adjusted to pH 7 with solid sodium hydrogen carbonate. The organic phase was separated, washed with brine, dried and evaporated to give crude 1-{[2-chloro-3-(trifluoromethyl)phenyl]carbonyl}-5-(ethyloxy)-1,2,3,6-tetrahydropyrazine which was used without further purification.

Examples 25 to 29

In a manner analogous to that described for Example 24 above the compounds tabulated below (Table 5) were prepared, as the free compounds and/or as hydrochloride salts thereof, by substituting the appropriate hydrazide for the 2,4-difluorobenzohydrazide used in the above procedure. Reaction times varied from 1 hr to 18 hr in refluxing 1-butanol. The purification step(s) and the post-purification solvent trituration or workup step used for each of Examples 25 to 29 (instead of the MDAP then diethyl ether/isohexane trituration used in Example 24) are stated in brief in the following Table 5.

In an alternative embodiment, some or all of the products, e.g. the pyridine-containing products, are isolated as acid addition salts (e.g. as hydrochlorides).

All of the requisite hydrazides are available from commercial sources and/or can be prepared using routes described previously in the chemical literature and/or using routes described in the Intermediates section above (e.g. Example 28 can be prepared using Intermediate 22).

TABLE 5

| Example no. | Chemical structure and name of product (and the purification and solvent trituration/workup steps used) | Hydrazide starting material; and possible source(s) | [M + H]+ | Retention time (mins) |
|---|---|---|---|---|
| E25 | ![structure] 7-{[2-chloro-3-(trifluoromethyl)phenyl]carbonyl}-3-(1,1-dimethylethyl)-5,6,7,8-tetrahydro[1,2,4]triazolo[4,3-a]pyrazine (MDAP, then isohexane trituration) | pivaloyl hydrazide $^t$Bu—C(O)—NH—NH$_2$; available e.g. from Thermo Fischer Scientific or ABCR | 387 | 2.15$^a$ |

TABLE 5-continued

| Example no. | Chemical structure and name of product (and the purification and solvent trituration/workup steps used) | Hydrazide starting material; and possible source(s) | [M + H]⁺ | Retention time (mins) |
|---|---|---|---|---|
| E26 | 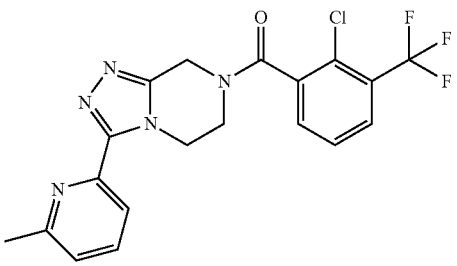<br>7-{[2-chloro-3-(trifluoromethyl)phenyl]carbonyl}-3-(6-methyl-2-pyridinyl)-5,6,7,8-tetrahydro[1,2,4]triazolo[4,3-a]pyrazine<br>(MDAP, then HCl/diethyl ether workup) | 6-methyl-pyridine-2-carbohydrazide, available e.g. from UkrOrg-Synthesis, Aurora Fine Chemicals or AKos Consulting | 421.77 | 1.01[a] |
| E27 | 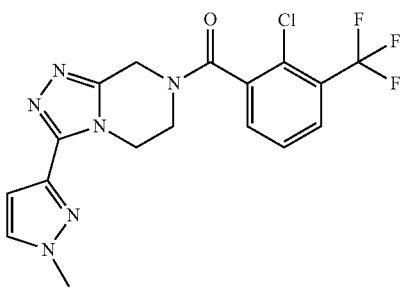<br>7-{[2-chloro-3-(trifluoromethyl)phenyl]carbonyl}-3-(1-methyl-1H-pyrazol-3-yl)-5,6,7,8-tetrahydro[1,2,4]triazolo[4,3-a]pyrazine<br>(silica gel, then MDAP, then isohexane/diethyl ether trituration) | 1-methyl-1H-pyrazole-3-carbohydrazide; available e.g. from Matrix Scientific, Ryan Scientific or TimTec | 410.99 | 0.87[b] |
| E28 | 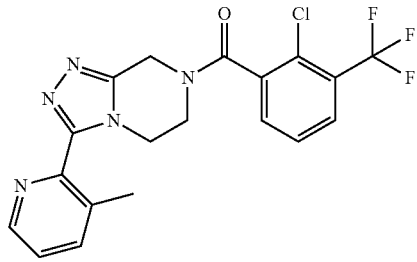<br>7-{[2-chloro-3-(trifluoromethyl)phenyl]carbonyl}-3-(3-methyl-2-pyridinyl)-5,6,7,8-tetrahydro[1,2,4]triazolo[4,3-a]pyrazine<br>(silica gel, then MDAP, then HCl/diethyl ether workup) | 3-methyl-2-pyridine-carbohydrazide; e.g. as prepared in Intermediate 22 | 421.75 | 0.97[b] |

TABLE 5-continued

| Example no. | Chemical structure and name of product (and the purification and solvent trituration/workup steps used) | Hydrazide starting material; and possible source(s) | [M + H]+ | Retention time (mins) |
|---|---|---|---|---|
| E29 | ![structure] 7-{[2-chloro-3-(trifluoromethyl)phenyl]carbonyl}-3-(1-methyl-1H-pyrrol-2-yl)-5,6,7,8-tetrahydro[1,2,4]triazolo[4,3-a]pyrazine (MDAP, then isohexane/diethyl ether trituration) | 1-methyl-1H-pyrrole-2-carbohydrazide; available e.g. from Ryan Scientific, AKos Consulting or Shanghai Specbiochem | 409.99 | 0.95[b] |

[a]Retention time obtained using 5 minute HPLC method
[b]Retention time obtained using 2 minute HPLC method

Example 30

7-[(2-Chloro-4-fluorophenyl)carbonyl]-3-phenyl-5,6,7,8-tetrahydro[1,2,4]triazolo[4,3-a]pyrazine (E30)

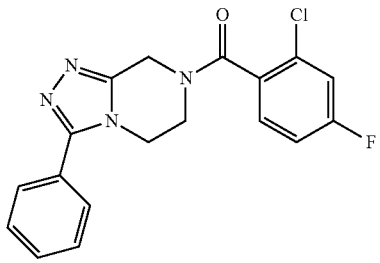 [SMILES: O=C(c1ccc(F)cc1Cl)N1CCn2c(nnc2-c2ccccc2)C1]

A mixture of 1-[(2-chloro-4-fluorophenyl)carbonyl]-5-(ethyloxy)-1,2,3,6-tetrahydropyrazine (0.228 g, 0.8 mmol, e.g. see preparation below) and benzohydrazide (benzoylhydrazine, 0.109 g, 0.800 mmol, CAS [613-94-5], commercially available e.g. from Sigma-Aldrich or ABCR) in 1-butanol (1 ml) was heated at reflux for 18 hours. After cooling to room temperature the solvent was evaporated and the residue was purified by mass-directed automated (preparative) HPLC (MDAP). A trituration with diethyl ether was then carried out to yield 7-[(2-chloro-4-fluorophenyl)carbonyl]-3-phenyl-5,6,7,8-tetrahydro[1,2,4]triazolo[4,3-a]pyrazine (0.053 g).

LC/MS [M+H]+=357, retention time=0.85 mins. (2 min method)

The 1-[(2-chloro-4-fluorophenyl)carbonyl]-5-(ethyloxy)-1,2,3,6-tetrahydropyrazine used in the above method can be prepared in the following manner:

4-[(2-Chloro-4-fluorophenyl)carbonyl]-2-piperazinone (0.770 g, 3 mmol, e.g. as prepared in Intermediate 2) was dissolved in Dichloromethane (8 mL) and to this was added triethyloxonium tetrafluoroborate (1.425 g, 7.50 mmol). The reaction mixture was stirred for 18 hours at room temperature. Dichloromethane (30 ml) and iced water (15 ml) were added and the pH was adjusted to pH 7 with solid sodium hydrogen carbonate. The organic phase was separated, washed with brine, dried and evaporated to give crude 1-[(2-chloro-4-fluorophenyl)carbonyl]-5-(ethyloxy)-1,2,3,6-tetrahydropyrazine (0.556 g) which was used without further purification.

Examples 31 to 33

In a manner analogous to that described for Example 30 above, the compounds tabulated below (Table 6) were prepared, as the free compounds and/or as hydrochloride salts thereof, by substituting the appropriate hydrazide for the benzohydrazide used in the above procedure. Reaction times varied from 1 hr to 18 hr in refluxing 1-butanol. The purification step(s) and the post-purification solvent trituration or workup step used for each of Examples 31 to 33 (instead of the MDAP then diethyl ether trituration used in Example 30) are stated in brief in the following Table 6.

In an alternative embodiment, some or all of the products, e.g. the pyridine-containing products, are isolated as acid addition salts (e.g. as hydrochlorides).

All of the requisite hydrazides are available from commercial sources and/or can be prepared using routes described previously in the chemical literature and/or in the manner described in the Intermediates section above (e.g. Example 31 can be prepared using Intermediate 31; Example 32 can be prepared using Intermediate 22).

TABLE 6

| Example no. | Chemical structure and name of product (and the purification and solvent trituration/workup steps used) | Hydrazide starting material; and possible source(s) | [M + H]+ | Retention time (mins) |
|---|---|---|---|---|
| E31 | 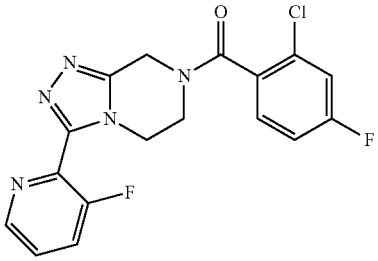<br>7-[(2-chloro-4-fluorophenyl)carbonyl]-3-(3-fluoro-2-pyridinyl)-5,6,7,8-tetrahydro[1,2,4]triazolo[4,3-a]pyrazine<br>(silica gel, then MDAP, then HCl/diethyl ether workup) | 3-Fluoro-2-pyridine-carbohydrazide; e.g. as prepared in Intermediate 31 | 375.95 | 0.79[b] |
| E32 | 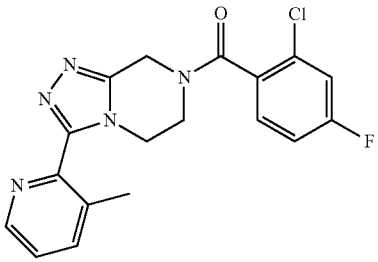<br>7-[(2-chloro-4-fluorophenyl)carbonyl]-3-(3-methyl-2-pyridinyl)-5,6,7,8-tetrahydro[1,2,4]triazolo[4,3-a]pyrazine<br>(silica gel, then MDAP, then HCl/diethyl ether workup) | 3-Methyl-2-pyridine-carbohydrazide; e.g. as prepared in Intermediate 22 | 372.01 | 0.82[b] |
| E33 | 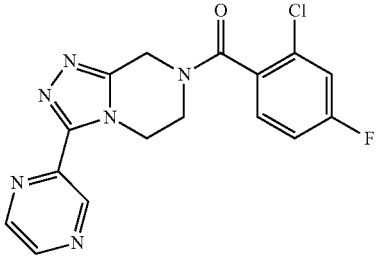<br>7-[(2-chloro-4-fluorophenyl)carbonyl]-3-(4-pyrimidinyl)-5,6,7,8-tetrahydro[1,2,4]triazolo[4,3-a]pyrazine<br>(silica gel, then MDAP, then HCl/diethyl ether workup) | Pyrimidine-4-carboxylic acid hydrazide; available e.g. from Anichem, J & W PharmLab or Bepharm. | 359 | 0.74[b] |

[a]Retention time obtained using 5 minute HPLC method
[b]Retention time obtained using 2 minute HPLC method

Example 32

7-[(2-chloro-4-fluorophenyl)carbonyl]-3-(3-methyl-2-pyridinyl)-5,6,7,8-tetrahydro[1,2,4]triazolo[4,3-a]pyrazine (E32)

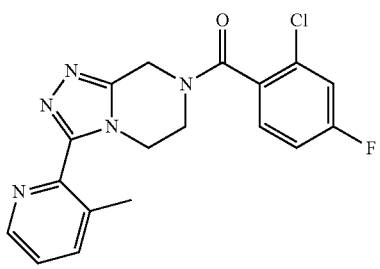

A solution of 4-[(2-chloro-4-fluorophenyl)carbonyl]-2-piperazinone (0.257 g, 1 mmol, e.g. prepared as described in Intermediate 2) in dry Dichloromethane (DCM) (2 ml) was stirred at room temperature under argon. Triethyloxonium tetrafluoroborate (0.190 g, 1.000 mmol) was added and the reaction solution was stirred for 3 hours. 3-Methyl-2-pyridinecarbohydrazide (0.166 g, 1.100 mmol, e.g. prepared as described in Intermediate 22) was added to the solution and stirred for 1 h. The solvent was then evaporated in vacuo and n-butanol (2.000 ml) was added to the residue. The solution was heated at reflux for 18 hours and then allowed to cool to room temperature. The solvent was then evaporated in vacuo and the residue was partitioned between Dichloromethane and brine. The organic layer was dried over sodium sulphate, filtered and the solvent was evaporated in vacuo to give a yellow solid. The solid was then purified by flash chromatography (Biotage SP4, 25+M cartridge) using a gradient of 0 to 10% MeOH/NH$_3$ in Dichloromethane as the eluent. The solvent was then evaporated in vacuo and the remaining residue was purified by mass-directed automated (preparative) HPLC (MDAP) to yield the crude product. The product was then dissolved in methanol (2 mL) and to this was added HCl in diethyl ether (1 mL), the solvent was then evaporated in vacuo and dried in a vacuum-oven yielding 7-[(2-chloro-4-fluorophenyl)carbonyl]-3-(3-methyl-2-pyridinyl)-5,6,7,8-tetrahydro[1,2,4]triazolo[4,3-a]pyrazine (0.108 g).

LC/MS [M+H]$^+$=372, retention time=0.9 mins (2 min method).

Example 34

7-[(2,3-Dichlorophenyl)carbonyl]-3-(2-pyrazinyl)-5,6,7,8-tetrahydro[1,2,4]triazolo[4,3-a]pyrazine (E34)

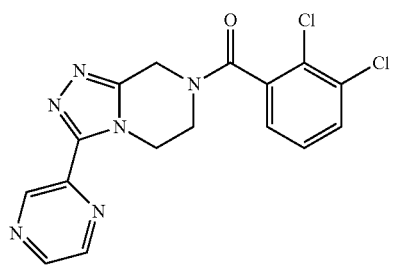 [SMILES: O=C(c1cccc(Cl)c1Cl)N1CCn2c(nnc2-c2cnccn2)C1]

A mixture of 1-[(2,3-dichlorophenyl)carbonyl]-5-(ethyloxy)-1,2,3,6-tetrahydropyrazine (0.48 g, 1.594 mmol, e.g. prepared as described below) and 2-pyrazinecarbohydrazide (0.242 g, 1.753 mmol, CAS [768-05-8], commercially available e.g. from TimTec, J & W PharmLab or AKos Consulting) in anhydrous n-butanol (3.19 ml) was heated to reflux under argon atmosphere. After 2 hours the reaction was cooled to room temperature and concentrated in vacuo. The residue was purified by mass-directed automated (preparative) HPLC (MDAP) to give pure 7-[(2,3-dichlorophenyl)carbonyl]-3-(2-pyrazinyl)-5,6,7,8-tetrahydro[1,2,4]triazolo[4,3-a]pyrazine (0.260 g).

LC/MS [M+H]+=374.95, retention time=0.81 mins. (2 min method)

The 1-[(2,3-dichlorophenyl)carbonyl]-5-(ethyloxy)-1,2,3,6-tetrahydropyrazine used in the above method can be prepared in the following manner:

To a suspension of 4-[(2,3-dichlorophenyl)carbonyl]-2-piperazinone (1 g, 3.66 mmol, e.g. prepared as described in Intermediate 3) in dry Dichloromethane (DCM) (9.15 ml) was added triethyloxonium tetrafluoroborate (1.739 g, 9.15 mmol). The suspension turned shortly to a yellow solution and it was stirred at room temperature under argon. After 5 minutes the mixture was diluted with Dichloromethane (20 mL) and treated with ice (15 mL). The pH was adjusted to circa 7 with saturated bicarbonate solution, the phases were separated and the aqueous extracted with Dichloromethane (50 mL). The combined organics were washed with brine and dried over MgSO$_4$. Evaporation gave 1-[(2,3-dichlorophenyl)carbonyl]-5-(ethyloxy)-1,2,3,6-tetrahydropyrazine (0.98 g) as an orange oil which was used without further purification.

Note: This specification does not include an Example 35.

Examples 36 to 109

In a manner analogous to that described for Example 35 above, the compounds tabulated below (Table 7) were prepared, as the free compounds and/or as hydrochloride salts thereof, by substituting the appropriate hydrazide for the 3-methyl-2-pyridinecarbohydrazide and/or substituting the appropriate acyl piperazinone (e.g. see Intermediates 1-21 for preparations) for the 4-[(2-chloro-4-fluorophenyl)carbonyl]-2-piperazinone used in the above Example 35 procedure. The purification step(s) (if any) and the post-purification solvent trituration or workup step (if any) used for each of Examples 36 to 109 (instead of the flash chromatography, the MDAP, and then the HCl/solvent workup, which was used in Example 35) are stated in brief in the following Table 7.

In an alternative embodiment, some or all of the products, e.g. the pyridine-containing products, are isolated as acid addition salts (e.g. as hydrochlorides) or as the free base.

All of the requisite hydrazides are available from commercial sources and/or can be prepared using routes described previously in the chemical literature and/or in the manner described in the Intermediates section above (e.g. Examples 40 and 45 can be prepared using Intermediate 24; Example 41 can be prepared using Intermediate 23; Example 44 can be prepared using Intermediate 25; Example 47 can be prepared using Intermediate 26).

TABLE 7

| Example no. | Chemical structure and name of product (and purification step(s) and solvent trituration/workup step used) | Hydrazide and/or acyl piperazinone starting material(s); and possible source(s) | [M + H]⁺ | Retention time (mins) |
|---|---|---|---|---|
| E36 | 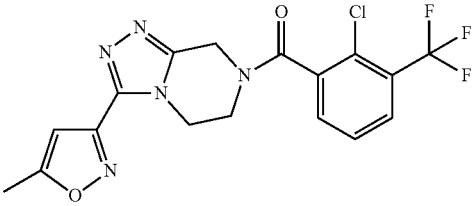<br>7-{[2-chloro-3-(trifluoromethyl)phenyl]carbonyl}-3-(5-methyl-3-isoxazolyl)-5,6,7,8-tetrahydro[1,2,4]triazolo[4,3-a]pyrazine<br>(silica gel, then isohexane/diethyl ether trituration) | 5-Methyl-isoxazole-3-carbo-hydrazide; available e.g. from Matrix Scientific, ChemBridge or Maybridge. See e.g. Intermediate 1 for acyl piperazinone. | 411.99 | 0.96[b] |
| E37 | 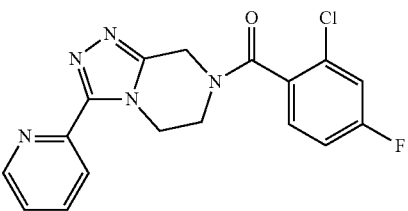<br>7-[(2-chloro-4-fluorophenyl)carbonyl]-3-(2-pyridinyl)-5,6,7,8-tetrahydro[1,2,4]triazolo[4,3-a]pyrazine<br>(silica gel, then MDAP, then HCl/diethyl ether workup) | 2-Pyridine-carboxylic acid hydrazide; available e.g. from TimTec, Ryan Scientific or AKos Consulting. | 357.97 | 0.83[b] |
| E38 | 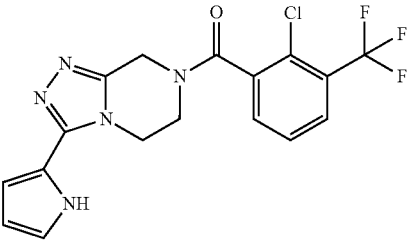<br>7-{[2-chloro-3-(trifluoromethyl)phenyl]carbonyl}-3-(1H-pyrrol-2-yl)-5,6,7,8-tetrahydro[1,2,4]triazolo[4,3-a]pyrazine<br>(isohexane/diethyl ether trituration) | 1H-Pyrrole-2-carbo-hydrazide; available e.g. from Maybridge, AKos or ABCR. See e.g. Intermediate 1 for acyl piperazinone. | 396, 398 | 0.91[b] |
| E39 | 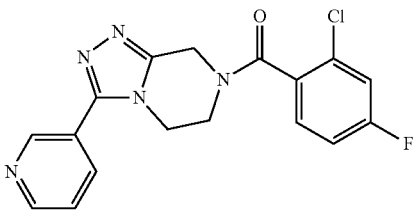<br>7-[(2-chloro-4-fluorophenyl)carbonyl]-3-(3-pyridinyl)-5,6,7,8-tetrahydro[1,2,4]triazolo[4,3-a]pyrazine<br>(silica gel, then HCl/diethyl ether workup) | Nicotinic acid hydrazide; available e.g. from Sigma-Aldrich or Pfaltz & Bauer. | 358 | 0.66[b] |

TABLE 7-continued

| Example no. | Chemical structure and name of product (and purification step(s) and solvent trituration/workup step used) | Hydrazide and/or acyl piperazinone starting material(s); and possible source(s) | [M + H]+ | Retention time (mins) |
|---|---|---|---|---|
| E40 | 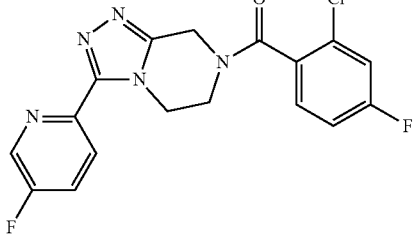<br>7-[(2-chloro-4-fluorophenyl)carbonyl]-3-(5-fluoro-2-pyridinyl)-5,6,7,8-tetrahydro[1,2,4]triazolo[4,3-a]pyrazine<br>(silica gel, then MDAP, then HCl/diethyl ether workup) | 5-Fluoro-2-pyridine-carbo-hydrazide; e.g. see Intermediate 24. | 375.95 | 0.88[b] |
| E41 | 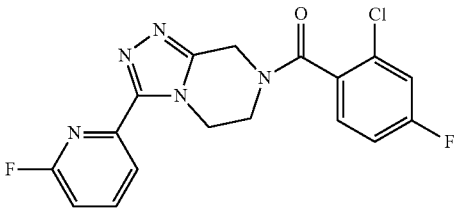<br>7-[(2-chloro-4-fluorophenyl)carbonyl]-3-(6-fluoro-2-pyridinyl)-5,6,7,8-tetrahydro[1,2,4]triazolo[4,3-a]pyrazine<br>(silica gel, then MDAP, then HCl/diethyl ether workup) | 6-Fluoro-2-pyridine-carbo-hydrazide; e.g. see Intermediate 23. | 375.95 | 0.89[b] |
| E42 | 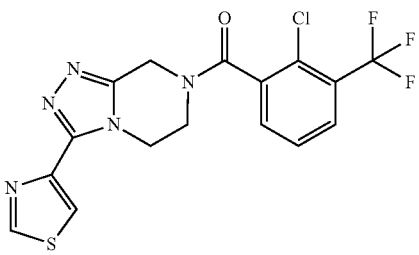<br>7-{[2-chloro-3-(trifluoromethyl)phenyl]carbonyl}-3-(1,3-thiazol-4-yl)-5,6,7,8-tetrahydro[1,2,4]triazolo[4,3-a]pyrazine<br>(silica gel, then isohexane/diethyl ether trituration, then MDAP) | 4-Thiazole-carboxylic acid hydrazide; available e.g. from Princeton BioMocecular, Tyger Scientific or Bepharm. See e.g. Intermediate 1 for acyl piperazinone. | 414, 416 | 0.88[b] |

TABLE 7-continued

| Example no. | Chemical structure and name of product (and purification step(s) and solvent trituration/workup step used) | Hydrazide and/or acyl piperazinone starting material(s); and possible source(s) | [M + H]⁺ | Retention time (mins) |
|---|---|---|---|---|
| E43 | 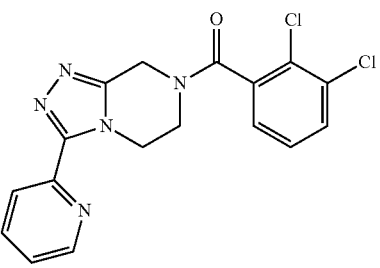<br>7-[(2,3-dichlorophenyl)carbonyl]-3-(2-pyridinyl)-5,6,7,8-tetrahydro[1,2,4]triazolo[4,3-a]pyrazine<br>(silica gel, then MDAP, then HCl/diethyl ether workup) | 2-Pyridine-carboxylic acid hydrazide; available e.g. from TimTec, Ryan Scientific or AKos Consulting. See e.g. Intermediate 3 for acyl piperazinone. | 374, 376, 378 | 0.89[b] |
| E44 | 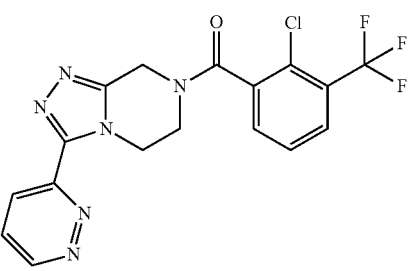<br>7-{[2-chloro-3-(trifluoromethyl)phenyl]carbonyl}-3-(3-pyridazinyl)-5,6,7,8-tetrahydro[1,2,4]triazolo[4,3-a]pyrazine<br>(silica gel, then MDAP, then HCl/diethyl ether workup) | 3-Pyridazine-carbo-hydrazide; e.g. see Intermediate 25. See e.g. Intermediate 1 for acyl piperazinone. | 408 | 0.81[b] |
| E45 | 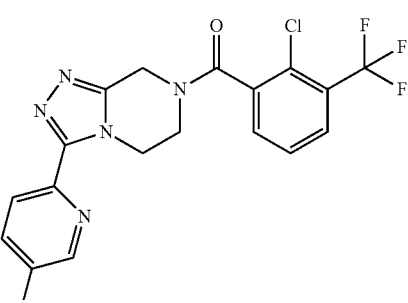<br>7-{[2-chloro-3-(trifluoromethyl)phenyl]carbonyl}-3-(5-fluoro-2-pyridinyl)-5,6,7,8-tetrahydro[1,2,4]triazolo[4,3-a]pyrazine<br>(MDAP, then HCl/diethyl ether workup) | 5-Fluoro-2-pyridine-carbo-hydrazide; e.g. see Intermediate 24. See e.g. Intermediate 1 for acyl piperazinone. | 425 | 0.93[b] |

TABLE 7-continued

| Example no. | Chemical structure and name of product (and purification step(s) and solvent trituration/workup step used) | Hydrazide and/or acyl piperazinone starting material(s); and possible source(s) | [M + H]+ | Retention time (mins) |
|---|---|---|---|---|
| E46 | 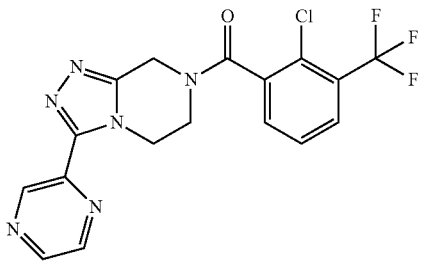<br>7-{[2-chloro-3-(trifluoromethyl)phenyl]carbonyl}-3-(2-pyrazinyl)-5,6,7,8-tetrahydro[1,2,4]triazolo[4,3-a]pyrazine<br>(silic gel, then MDAP, then HCl/diethyl ether workup) | 2-Pyrazine-carbo-hydrazide; available e.g. from TimTec, J & W PharmLab or AKos Consulting. See e.g. Intermediate 1 for acyl piperazinone. | 408 | 0.81[b] |
| E47 | 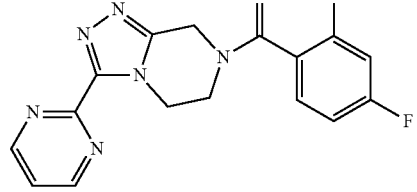<br>7-[(2-chloro-4-fluorophenyl)carbonyl]-3-(2-pyrimidinyl)-5,6,7,8-tetrahydro[1,2,4]triazolo[4,3-a]pyrazine<br>(MDAP, then HCl/diethyl ether workup) | See e.g. Intermediate 26 for hydrazide. | 358.97 | 0.72[b] |
| E48 | 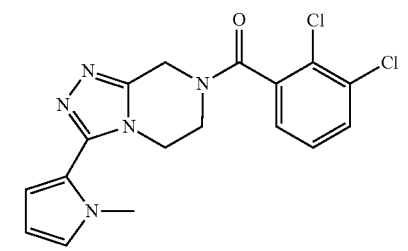<br>7-[(2,3-dichlorophenyl)carbonyl]-3-(1-methyl-1H-pyrrol-2-yl)-5,6,7,8-tetrahydro[1,2,4]triazolo[4,3-a]pyrazine<br>(silica gel, then diethyl ether trituration) | 1-Methyl-1H-pyrrole-2-carbo-hydrazide; e.g. from Ryan, AKos or Shanghai Specbiochem. See e.g. Intermediate 3 for acyl piperazinone. | 376, 379 | 0.90[b] |
| E49 | 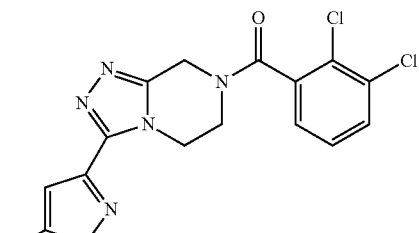<br>7-[(2,3-dichlorophenyl)carbonyl]-3-(5-methyl-3-isoxazolyl)-5,6,7,8-tetrahydro[1,2,4]triazolo[4,3-a]pyrazine<br>(silica gel, then diethyl ether trituration) | 5-Methyl-isoxazole-3-carbo-hydrazide; available e.g. from Matrix, ChemBridge or Maybridge. See e.g. Intermediate 3 for acyl piperazinone. | 378,382 | 0.91[b] |

TABLE 7-continued

| Example no. | Chemical structure and name of product (and purification step(s) and solvent trituration/workup step used) | Hydrazide and/or acyl piperazinone starting material(s); and possible source(s) | [M + H]⁺ | Retention time (mins) |
|---|---|---|---|---|
| E50 | 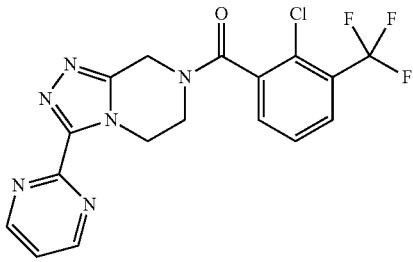<br>7-{[2-chloro-3-(trifluoromethyl)phenyl]carbonyl}-3-(2-pyrimidinyl)-5,6,7,8-tetrahydro[1,2,4]triazolo[4,3-a]pyrazine<br>(silica gel, then HCl/diethyl ether workup) | See e.g. Intermediate 26 for hydrazide. See e.g. Intermediate 1 for acyl piperazinone. | 408.99, 410.99 | 0.85[b] |
| E51 | 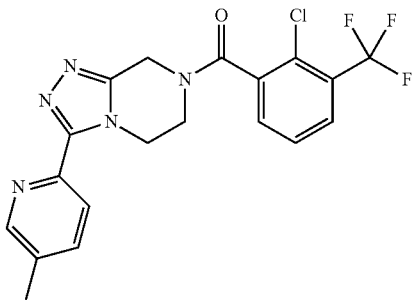<br>7-{[2-chloro-3-(trifluoromethyl)phenyl]carbonyl}-3-(5-methyl-2-pyridinyl)-5,6,7,8-tetrahydro[1,2,4]triazolo[4,3-a]pyrazine<br>(silica gel, then MDAP, then HCl/diethyl ether workup) | See e.g. Intermediate 27 for hydrazide. See e.g. Intermediate 1 for acyl piperazinone. | 421.95, 423.95 | 0.98[b] |
| E52 | 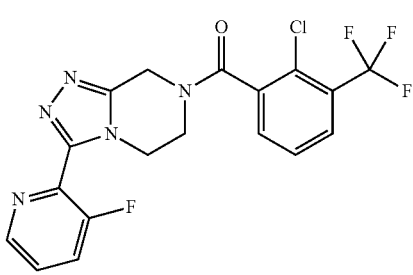<br>7-{[2-chloro-3-(trifluoromethyl)phenyl]carbonyl}-3-(3-fluoro-2-pyridinyl)-5,6,7,8-tetrahydro[1,2,4]triazolo[4,3-a]pyrazine<br>(silica gel, then HCl/diethyl ether workup) | See e.g. Intermediate 31 for hydrazide. See e.g. Intermediate 1 for acyl piperazinone. | 425.95, 427.95 | 0.89[b] |

TABLE 7-continued

| Example no. | Chemical structure and name of product (and purification step(s) and solvent trituration/workup step used) | Hydrazide and/or acyl piperazinone starting material(s); and possible source(s) | [M + H]⁺ | Retention time (mins) |
|---|---|---|---|---|
| E53 | 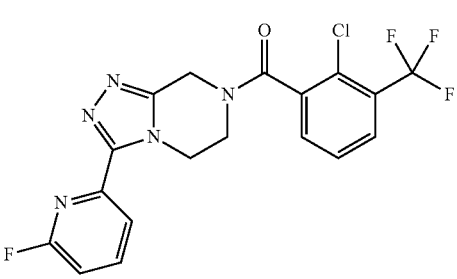<br>7-{[2-chloro-3-(trifluoromethyl)phenyl]carbonyl}-3-(6-fluoro-2-pyridinyl)-5,6,7,8-tetrahydro[1,2,4]triazolo[4,3-a]pyrazine<br>(silica gel, then HCl/diethyl ether workup) | See e.g. Intermediate 23 for hydrazide. See e.g. Intermediate 1 for acyl piperazinone. | 425.91, 427.91 | 0.97-0.99 [b] |
| E54 | 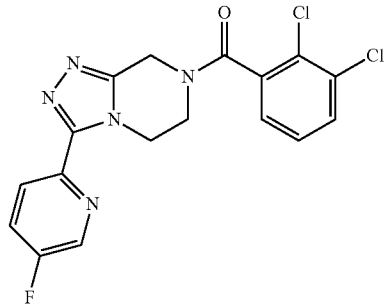<br>7-[(2,3-dichlorophenyl)carbonyl]-3-(5-fluoro-2-pyridinyl)-5,6,7,8-tetrahydro[1,2,4]triazolo[4,3-a]pyrazine<br>(silica gel, then MDAP, then HCl/diethyl ether workup) | See e.g. Intermediate 24 for hydrazide. See e.g. Intermediate 3 for acyl piperazinone. | 393 | 0.93 [b] |
| E55 | 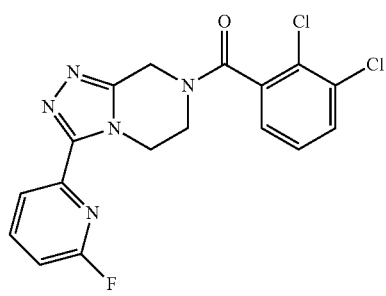<br>7-[(2,3-dichlorophenyl)carbonyl]-3-(6-fluoro-2-pyridinyl)-5,6,7,8-tetrahydro[4,3-a]pyrazine<br>(silica gel, the MDAP, then HCl/diethyl ether workup) | See e.g. Intermediate 23 for hydrazide. See e.g. Intermediate 3 for acyl piperazinone. | 393 | 0.94 [b] |

TABLE 7-continued

| Example no. | Chemical structure and name of product (and purification step(s) and solvent trituration/workup step used) | Hydrazide and/or acyl piperazinone starting material(s); and possible source(s) | [M + H]+ | Retention time (mins) |
|---|---|---|---|---|
| E56 | 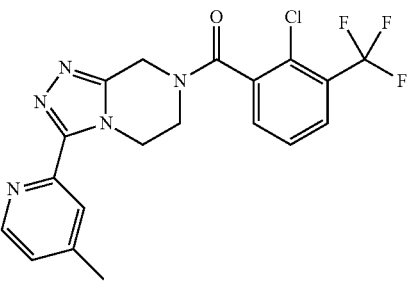<br>7-{[2-chloro-3-(trifluoromethyl)phenyl]carbonyl}-3-(4-methyl-2-pyridinyl)-5,6,7,8-tetrahydro[1,2,4]triazolo[4,3-a]pyrazine<br>(silica gel, then HCl/diethyl ether workup) | See e.g. Intermediate 28 for hydrazide. See e.g. Intermediate 1 for acyl piperazinone. | 421.95, 423.95 | 0.94-0.97[b] |
| E57 | 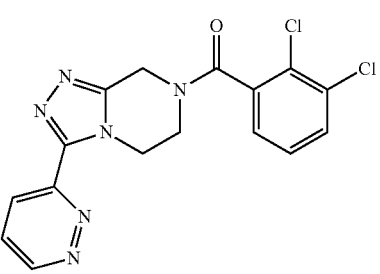<br>7-[(2,3-dichlorophenyl)carbonyl]-3-(3-pyridazinyl)-5,6,7,8-tetrahydro[1,2,4]triazolo[4,3-a]pyrazine<br>(silica gel, then MDAP, then diethyl ether trituration) | See e.g. Intermediate 25 for hydrazide. See e.g. Intermediate 3 for acyl piperazinone. | 374.95 | 1.82[a] |
| E58 | 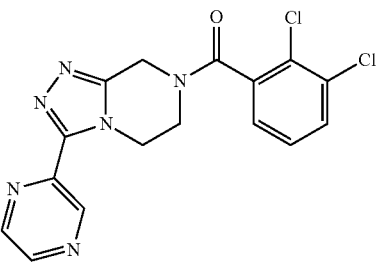<br>7-[(2,3-dichlorophenyl)carbonyl]-3-(2-pyrimidinyl)-5,6,7,8-tetrahydro[1,2,4]triazolo[4,3-a]pyrazine<br>(silica gel, then MDAP, then HCl/diethyl ether workup) | See e.g. Intermediate 26 for hydrazide. See e.g. Intermediate 3 for acyl piperazinone. | 376 | 0.78[b] |

TABLE 7-continued

| Example no. | Chemical structure and name of product (and purification step(s) and solvent trituration/workup step used) | Hydrazide and/or acyl piperazinone starting material(s); and possible source(s) | [M + H]⁺ | Retention time (mins) |
|---|---|---|---|---|
| E59 | 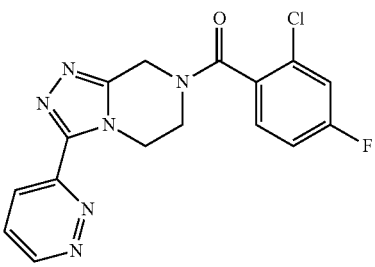<br>7-[(2-chloro-4-fluorophenyl)carbonyl]-3-(3-pyridazinyl)-5,6,7,8-tetrahydro[1,2,4]triazolo[4,3-a]pyrazine<br>(silica gel, then MDAP, then HCl/diethyl ether workup) | See e.g. Intermediate 25 for hydrazide. | 358.97 | 1.65$^a$ |
| E60 | 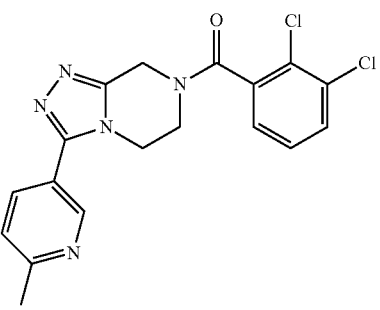<br>7-[(2,3-dichlorophenyl)carbonyl]-3-(5-methyl-2-pyridinyl)-5,6,7,8-tetrahydro[1,2,4]triazolo[4,3-a]pyrazine<br>(silica gel, then MDAP, then HCl/diethyl ether workup) | See e.g. Intermediate 27 for hydrazide. See e.g. Intermediate 3 for acyl piperazinone. | 389 | 0.95$^b$ |
| E61 | 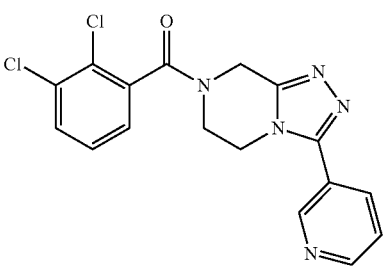<br>7-[(2,3-dichlorophenyl)carbonyl]-3-(3-pyridinyl)-5,6,7,8-tetrahydro[1,2,4]triazolo[4,3-a]pyrazine<br>(silica gel, then MDAP, then HCl/diethyl ether workup) | Nicotinic acid hydrazide; available e.g. from Sigma-Aldrich or Pfaltz & Bauer. See e.g. Intermediate 3 for acyl piperazinone. | 375 | 0.73$^b$ |

TABLE 7-continued

| Example no. | Chemical structure and name of product (and purification step(s) and solvent trituration/workup step used) | Hydrazide and/or acyl piperazinone starting material(s); and possible source(s) | [M + H]⁺ | Retention time (mins) |
|---|---|---|---|---|
| E62 | 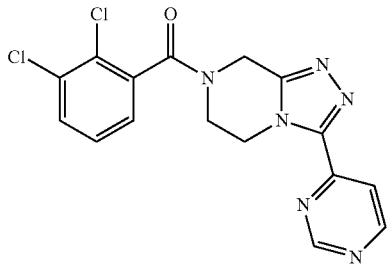<br>7-[(2,3-dichlorophenyl)carbonyl]-3-(4-pyrimidinyl)-5,6,7,8-tetrahydro[1,2,4]triazolo[4,3-a]pyrazine<br>(silica gel, then MDAP, then HCl/diethyl ether workup) | Pyrimidine-4-carboxylic acid hydrazide; available e.g. from Anichem, J & W PharmLab or Bepharm. See e.g. Intermediate 3 for acyl piperazinone. | 376 | 0.80[b] |
| E63 | 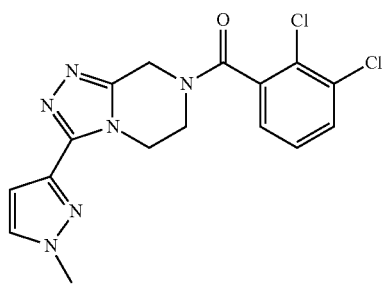<br>7-[(2,3-dichlorophenyl)carbonyl]-3-(1-methyl-1H-pyrazol-3-yl)-5,6,7,8-tetrahydro[1,2,4]triazolo[4,3-a]pyrazine<br>(silica gel, then diethyl ether trituration) | 1-Methyl-1H-pyrazole-3-carbo-hydrazide; available e.g. from Matrix Scientific, Ryan Scientific or TimTec. See e.g. Intermediate 3 for acyl piperazinone. | 377, 381 | 0.82[b] |
| E64 | 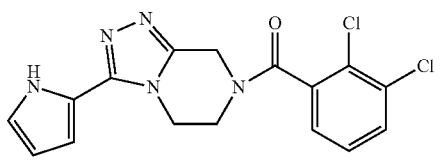<br>7-[(2,3-dichlorophenyl)carbonyl]-3-(1H-pyrrol-2-yl)-5,6,7,8-tetrahydro[1,2,4]triazolo[4,3-a]pyrazine<br>(silica gel, then MDAP, then diethyl ether trituration) | 1H-Pyrrole-2-carbo-hydrazide; from Maybridge, AKos or ABCR. See e.g. Intermediate 3 for acyl piperazinone. | 361.96, 365.03 | 0.86[b] |
| E65 | 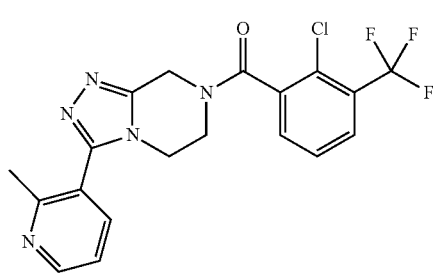<br>7-{[2-chloro-3-(trifluoromethyl)phenyl]carbonyl}-3-(2-methyl-3-pyridinyl)-5,6,7,8-tetrahydro[1,2,4]triazolo[4,3-a]pyrazine<br>(silica gel, then MDAP, then HCl/diethyl ether workup) | See e.g. Intermediate 29 for hydrazide. See e.g. Intermediate 1 for acyl piperazinone. | 421.95, 423.89 | 0.71-0.73[b] |

TABLE 7-continued

| Example no. | Chemical structure and name of product (and purification step(s) and solvent trituration/workup step used) | Hydrazide and/or acyl piperazinone starting material(s); and possible source(s) | [M + H]$^+$ | Retention time (mins) |
|---|---|---|---|---|
| E66 | 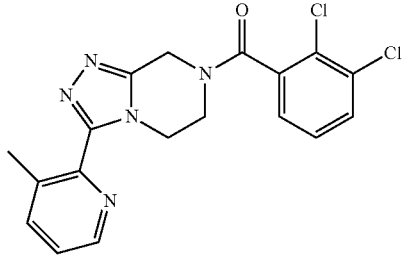<br>7-[(2,3-dichlorophenyl)carbonyl]-3-(3-methyl-2-pyridinyl)-5,6,7,8-tetrahydro[1,2,4]triazolo[4,3-a]pyrazine<br>(silica gel, then MDAP, then HCl/diethyl ether workup) | See e.g. Intermediate 22 for hydrazide. See e.g. Intermediate 3 for acyl piperazinone. | 387.9, 390.9 | 0.83-0.86[b] |
| E67 | 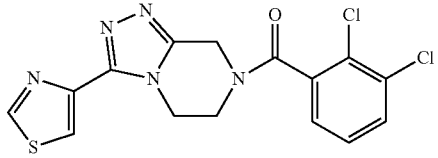<br>7-[(2,3-dichlorophenyl)carbonyl]-3-(1,3-thiazol-4-yl)-5,6,7,8-tetrahydro[1,2,4]triazolo[4,3-a]pyrazine<br>(silica gel, then MDAP, then diethyl ether trituration) | 4-Thiazole-carboxylic acid hydrazide; e.g. from Princeton BioMocecular, Tyger or Bepharm. See e.g. Intermediate 3 for acyl piperazinone. | 380, 384 | 0.83[b] |
| E68 | 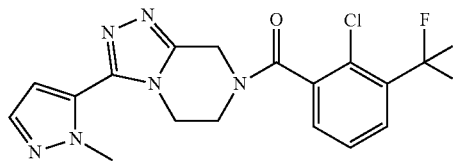<br>7-{[2-chloro-3-(trifluoromethyl)phenyl]carbonyl}-3-(1-methyl-1H-pyrazol-5-yl)-5,6,7,8-tetrahydro[1,2,4]triazolo[4,3-a]pyrazine<br>(silica gel, then MDAP) | 1-Methyl-1H-pyrazole-5-carbo-hydrazide, available e.g. from Matrix, AKos or Oakwood. See e.g. Intermediate 1 for acyl piperazinone. | 411, 413 | 0.85[b] |
| E69 | 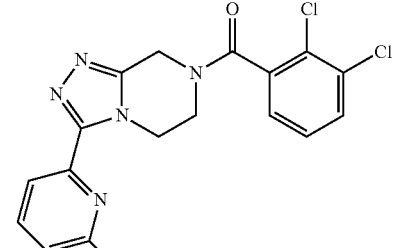<br>7-[(2,3-dichlorophenyl)carbonyl]-3-(6-methyl-2-pyridinyl)-5,6,7,8-tetrahydro[1,2,4]triazolo[4,3-a]pyrazine<br>(silica gel, then MDAP, then HCl/diethyl ether workup) | 6-Methyl-pyridine-2-carbo-hydrazide, e.g. from UkrOrg-Synthesis, Aurora Fine Chemicals or AKos. See e.g. Intermediate 3 for acyl piperazinone. | 389 | 0.94[b] |

TABLE 7-continued

| Example no. | Chemical structure and name of product (and purification step(s) and solvent trituration/workup step used) | Hydrazide and/or acyl piperazinone starting material(s); and possible source(s) | [M + H]⁺ | Retention time (mins) |
|---|---|---|---|---|
| E70 | 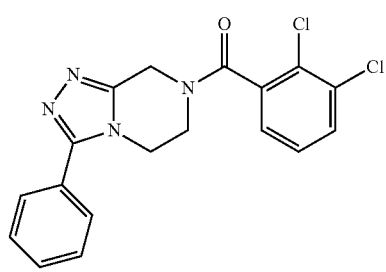<br>7-[(2,3-dichlorophenyl)carbonyl]-3-phenyl-5,6,7,8-tetrahydro[1,2,4]triazolo[4,3-a]pyrazine<br>(silica gel, then MDAP, then HCl/diethyl ether workup) | Benzohydrazide (benzoylhydrazine); available e.g. from Sigma-Aldrich or ABCR. See e.g. Intermediate 3 for acyl piperazinone. | 374 | 0.91[b] |
| E71 | 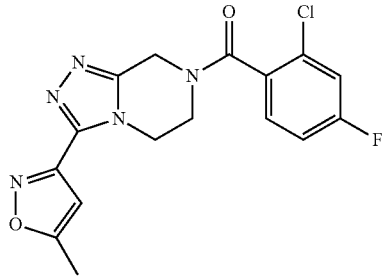<br>7-[(2-chloro-4-fluorophenyl)carbonyl]-3-(5-methyl-3-isoxazolyl)-5,6,7,8-tetrahydro[1,2,4]triazolo[4,3-a]pyrazine<br>(silica gel, then MDAP, then HCl/diethyl ether workup) | 5-Methyl-isoxazole-3-carbohydrazide; available e.g. from Matrix Scientific, ChemBridge or Maybridge. | 361.91, 363.90 | 0.79-0.83[b] |
| E72 | 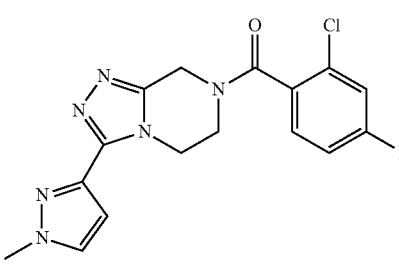<br>7-[(2-chloro-4-fluorophenyl)carbonyl]-3-(1-methyl-1H-pyrazol-3-yl)-5,6,7,8-tetrahydro[1,2,4]triazolo[4,3-a]pyrazine<br>(silica gel, then MDAP, then HCl/diethyl ether workup) | 1-Methyl-1H-pyrazole-3-carbohydrazide; available e.g. from Matrix Scientific, Ryan Scientific or TimTec. | 360.96, 362.96 | 0.76[b] |

TABLE 7-continued

| Example no. | Chemical structure and name of product (and purification step(s) and solvent trituration/workup step used) | Hydrazide and/or acyl piperazinone starting material(s); and possible source(s) | [M + H]+ | Retention time (mins) |
| --- | --- | --- | --- | --- |
| E73 | 7-[(2,3-dichlorophenyl)carbonyl]-3-(2-methyl-3-pyridinyl)-5,6,7,8-tetrahydro[1,2,4]triazolo[4,3-a]pyrazine (silica gel, then MDAP, then HCl/diethyl ether workup) | See e.g. Intermediate 29 for hydrazide. See e.g. Intermediate 3 for acyl piperazinone. | 388 | 0.69[b] |
| E74 | 7-[(2-chloro-4-fluorophenyl)carbonyl]-3-(2-methyl-3-pyridinyl)-5,6,7,8-tetrahydro[1,2,4]triazolo[4,3-a]pyrazine (silica gel, then MDAP, then HCl/diethyl ether workup) | See e.g. Intermediate 29 for hydrazide. | 372 | 0.62[b] |
| E75 | 7-[(2-chlorophenyl)carbonyl]-3-(2-pyridinyl)-5,6,7,8-tetrahydro[1,2,4]triazolo[4,3-a]pyrazine (silica gel, then MDAP, then HCl/diethyl ether workup) | 2-Pyridine-carboxylic acid hydrazide; available e.g. from TimTec, Ryan Scientific or AKos. See e.g. Intermediate 4 for acyl piperazinone. | 340 | 0.76[b] |
| E76 | 7-[(2,4-dichlorophenyl)carbonyl]-3-(2-pyridinyl)-5,6,7,8-tetrahydro[1,2,4]triazolo[4,3-a]pyrazine (silica gel, then MDAP, then HCl/diethyl ether workup) | 2-Pyridine-carboxylic acid hydrazide; available e.g. from TimTec, Ryan Scientific or AKos. See e.g. Intermediate 6 for acyl piperazinone. | 374 | 0.89[b] |

TABLE 7-continued

| Example no. | Chemical structure and name of product (and purification step(s) and solvent trituration/workup step used) | Hydrazide and/or acyl piperazinone starting material(s); and possible source(s) | [M + H]⁺ | Retention time (mins) |
|---|---|---|---|---|
| E77 | 7-{[2-chloro-3-(trifluoromethyl)phenyl]carbonyl}-3-(2-furanyl)-5,6,7,8-tetrahydro[1,2,4]triazolo[4,3-a]pyrazine (MDAP) | 2-Furoic acid hydrazide (2-furoyl-hydrazine); available e.g. from Sigma-Aldrich or Maybridge. See e.g. Intermediate 1 for acyl piperazinone. | 397 | 0.90[b] |
| E78 | 7-[(2,4-difluorophenyl)carbonyl]-3-(2-pyridinyl)-5,6,7,8-tetrahydro[1,2,4]triazolo[4,3-a]pyrazine (silica gel, then MDAP, then HCl/diethyl ether workup) | 2-Pyridine-carboxylic acid hydrazide; available e.g. from TimTec, Ryan Scientific or AKos. See e.g. Intermediate 8 for acyl piperazinone. | 342 | 0.78[b] |
| E79 | 7-[(2-chloro-6-fluorophenyl)carbonyl]-3-(2-pyridinyl)-5,6,7,8-tetrahydro[1,2,4]triazolo[4,3-a]pyrazine (silica gel, then MDAP, then HCl/diethyl ether workup) | 2-Pyridine-carboxylic acid hydrazide; available e.g. from TimTec, Ryan Scientific or AKos. See e.g. Intermediate 9 for acyl piperazinone. | 358 | 0.80[b] |
| E80 | 7-[(3-chlorophenyl)carbonyl]-3-(2-pyridinyl)-5,6,7,8-tetrahydro[1,2,4]triazolo[4,3-a]pyrazine (silica gel, then MDAP, then HCl/diethyl ether workup) | 2-Pyridine-carboxylic acid hydrazide; available e.g. from TimTec, Ryan Scientific or AKos. See e.g. Intermediate 10 for acyl piperazinone. | 340 | 0.84[b] |

TABLE 7-continued

| Example no. | Chemical structure and name of product (and purification step(s) and solvent trituration/workup step used) | Hydrazide and/or acyl piperazinone starting material(s); and possible source(s) | [M + H]⁺ | Retention time (mins) |
|---|---|---|---|---|
| E81 | 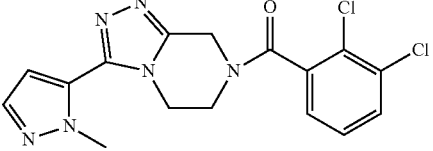<br>7-[(2,3-dichlorophenyl)carbonyl]-3-(1-methyl-1H-pyrazol-5-yl)-5,6,7,8-tetrahydro[1,2,4]triazolo[4,3-a]pyrazine<br>(silica gel, then MDAP, then diethyl ether trituration) | 1-Methyl-1H-pyrazole-5-carbo-hydrazide, e.g. from Matrix, AKos or Oakwood. See e.g. Intermediate 3 for acyl piperazinone. | 377, 380 | 0.80[b] |
| E82 | 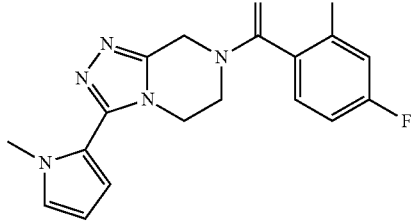<br>7-[(2-chloro-4-fluorophenyl)carbonyl]-3-(1-methyl-1H-pyrrol-2-yl)-5,6,7,8-tetrahydro[1,2,4]triazolo[4,3-a]pyrazine<br>(silica gel, then HCl/diethyl ether workup) | 1-Methyl-1H-pyrrol-2-carbo-hydrazide; e.g. from Ryan Scientific, AKos Consulting or Shanghai Specbiochem. | 359.91, 361.91 | 0.79-0.82[b] |
| E83 | 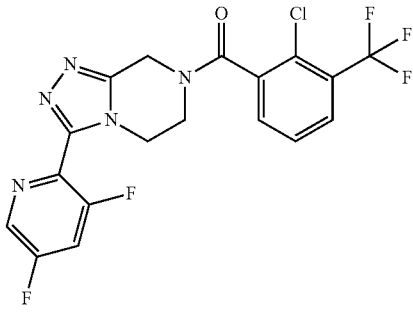<br>7-{[2-chloro-3-(trifluoromethyl)phenyl]carbonyl}-3-(3,5-difluoro-2-pyridinyl)-5,6,7,8-tetrahydro[1,2,4]triazolo[4,3-a]pyrazine<br>(silica gel, then MDAP, then HCl/diethyl ether workup) | See e.g. Intermediate 30 for hydrazide. See e.g. Intermediate 1 for acyl piperazinone. | 443.90, 445.90 | 0.94-0.95[b] |

TABLE 7-continued

| Example no. | Chemical structure and name of product (and purification step(s) and solvent trituration/workup step used) | Hydrazide and/or acyl piperazinone starting material(s); and possible source(s) | [M + H]⁺ | Retention time (mins) |
|---|---|---|---|---|
| E84 | 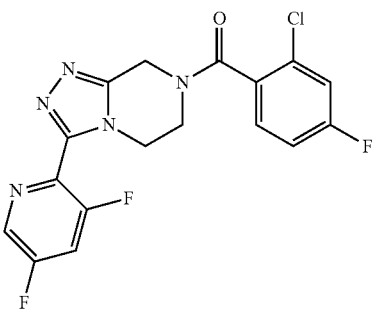 7-[(2-chloro-4-fluorophenyl)carbonyl]-3-(3,5-difluoro-2-pyridinyl)-5,6,7,8-tetrahydro[1,2,4]triazolo[4,3-a]pyrazine (silica gel, then MDAP, then HCl/diethyl ether workup) | See e.g. Intermediate 30 for hydrazide. | 393.87, 395.94 | 0.84-0.86[b] |
| E85 | 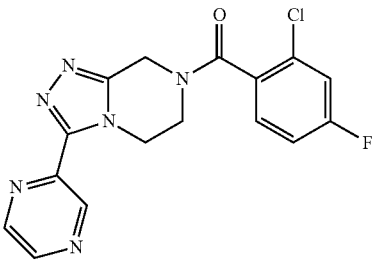 7-[(2-chloro-4-fluorophenyl)carbonyl]-3-(2-pyrazinyl)-5,6,7,8-tetrahydro[1,2,4]triazolo[4,3-a]pyrazine (silica gel, then MDAP) | 2-Pyrazine-carbo-hydrazide; available e.g. form TimTec, J & W PharmLab or AKos Consulting. | 359 | 0.74[b] |
| E86 | 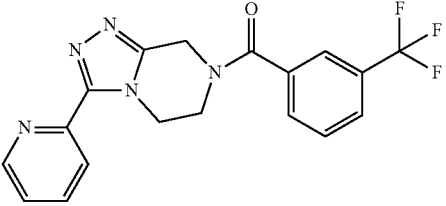 3-(2-pyridinyl)-7-{[3-(trifluoromethyl)phenyl]carbonyl}-5,6,7,8-tetrahydro[1,2,4]triazolo[4,3-a]pyrazine (silica gel, then MDAP, then HCl/diethyl ether workup) | 2-Pyridine-carboxylic acid hydrazide; available e.g. from TimTec, Ryan Scientific or AKos. See e.g. Intermediate 11 for acyl piperazinone. | 374 | 0.89[b] |

TABLE 7-continued

| Example no. | Chemical structure and name of product (and purification step(s) and solvent trituration/workup step used) | Hydrazide and/or acyl piperazinone starting material(s); and possible source(s) | [M + H]+ | Retention time (mins) |
|---|---|---|---|---|
| E87 | 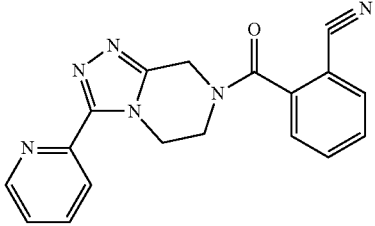<br>2-{[3-(2-pyridinyl)-5,6-dihydro[1,2,4]triazolo[4,3-a]pyrazin-7(8H)-yl]carbonyl}benzonitrile<br>(silica gel, then MDAP, then HCl/diethyl ether workup) | 2-Pyridine-carboxylic acid hydrazide; available e.g. from TimTec, Ryan Scientific or AKos. See e.g. Intermediate 12 for acyl piperazinone. | 331 | 0.70[b] |
| E88 | 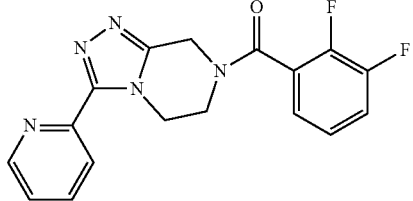<br>7-[(2,3-difluorophenyl)carbonyl]-3-(2-pyridinyl)-5,6,7,8-tetrahydro[1,2,4]triazolo[4,3-a]pyrazine<br>(silica gel, then MDAP, then HCl/diethyl ether workup) | 2-Pyridine-carboxylic acid hydrazide; available e.g. from TimTec, Ryan Scientific or AKos. See e.g. Intermediate 13 for acyl piperazinone. | 342 | 0.79[b] |
| E89 | 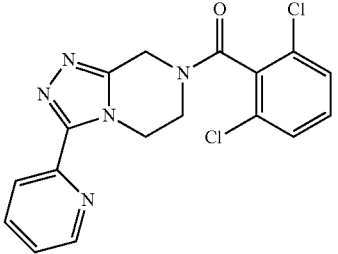<br>7-[(2,6-dichlorophenyl)carbonyl]-3-(2-pyridinyl)-5,6,7,8-tetrahydro[1,2,4]triazolo[4,3-a]pyrazine<br>(silica gel, then HCl/diethyl ether workup) | 2-Pyridine-carboxylic acid hydrazide; available e.g. from TimTec, Ryan Scientific or AKos. See e.g. Intermediate 14 for acyl piperazinone. | 373.95 | 0.81-0.84[b] |
| E90 | 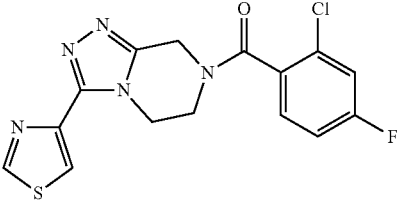<br>7-[(2-chloro-4-fluorophenyl)carbonyl]-3-(1,3-thiazol-4-yl)-5,6,7,8-tetrahydro[1,2,4]triazolo[4,3-a]pyrazine<br>(silica gel, then HCl/diethyl ether workup) | 4-Thiazole-carboxylic acid hydrazide; e.g. from Princeton BioMocecular, Tyger Scientific or Bepharm. | 363.9 | 0.76[b] |

TABLE 7-continued

| Example no. | Chemical structure and name of product (and purification step(s) and solvent trituration/workup step used) | Hydrazide and/or acyl piperazinone starting material(s); and possible source(s) | [M + H]+ | Retention time (mins) |
|---|---|---|---|---|
| E91 | 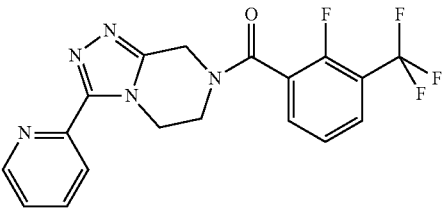<br>7-{[2-fluoro-3-(trifluoromethyl)phenyl]carbonyl}-3-(2-pyridinyl)-5,6,7,8-tetrahydro[1,2,4]triazolo[4,3-a]pyrazine<br>(silica gel, then MDAP) | 2-Pyridine-carboxylic acid hydrazide; available e.g. from TimTec, Ryan Scientific or AKos. See e.g. Intermediate 15 for acyl piperazinone. | 392 | 0.91[b] |
| E92 | 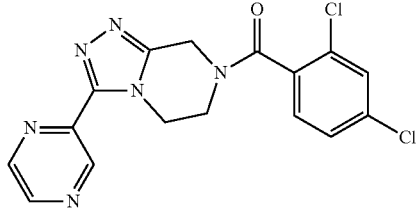<br>7-[(2,4-dichlorophenyl)carbonyl]-3-(2-pyrazinyl)-5,6,7,8-tetrahydro[1,2,4]triazolo[4,3-a]pyrazine<br>(silica gel, then MDAP, then diethyl ether trituration) | 2-Pyrazine-carbo-hydrazide; available e.g. from TimTec, J & W PharmLab or AKos. See e.g. Intermediate 6 for acyl piperazinone. | 375 | 0.83[b] |
| E93 | 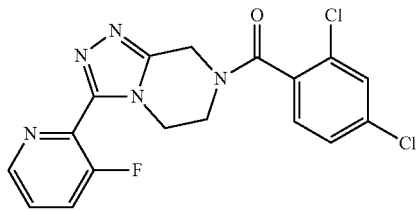<br>7-[(2,4-dichlorophenyl)carbonyl]-3-(3-fluoro-2-pyridinyl)-5,6,7,8-tetrahydro[1,2,4]triazolo[4,3-a]pyrazine<br>(silica gel, then MDAP, then diethyl ether trituration) | See e.g. Intermediate 31 for hydrazide. See e.g. Intermediate 6 for acyl piperazinone. | 392 | 0.97[b] |
| E94 | 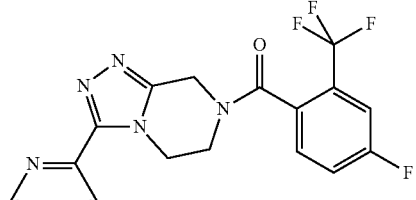<br>7-{[4-fluoro-2-(trifluoromethyl)phenyl]carbonyl}-3-(2-pyridinyl)-5,6,7,8-tetrahydro[1,2,4]triazolo[4,3-a]pyrazine<br>(silica gel, then MDAP, then diethyl ether trituration) | 2-Pyridine-carboxylic acid hydrazide; available e.g. from TimTec, Ryan Scientific or AKos. See e.g. Intermediate 16 for acyl piperazinone. | 392 | 0.88[b] |

TABLE 7-continued

| Example no. | Chemical structure and name of product (and purification step(s) and solvent trituration/workup step used) | Hydrazide and/or acyl piperazinone starting material(s); and possible source(s) | [M + H]+ | Retention time (mins) |
|---|---|---|---|---|
| E95 | 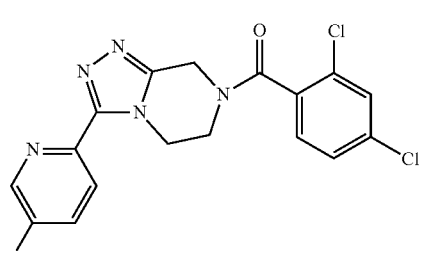<br>7-[(2,4-dichlorophenyl)carbonyl]-3-(5-fluoro-2-pyridinyl)-5,6,7,8-tetrahydro[1,2,4]triazolo[4,3-a]pyrazine<br>(silica gel, then MDAP, then diethyl ether trituration) | See e.g. Intermediate 24 for hydrazide. See e.g. Intermediate 6 for acyl piperazinone. | 392 | 0.96[b] |
| E96 | 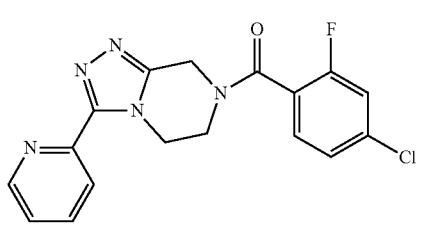<br>7-[(4-chloro-2-fluorophenyl)carbonyl]-3-(2-pyridinyl)-5,6,7,8-tetrahydro[1,2,4]triazolo[4,3-a]pyrazine<br>(silica gel, then MDAP, then HCl/diethyl ether workup) | 2-Pyridine-carboxylic acid hydrazide; available e.g. from TimTec, Ryan Scientific of AKos. See e.g. Intermediate 17 for acyl piperazinone. | 357.85, 359.85 | 0.79-0.83[b] |
| E97 | 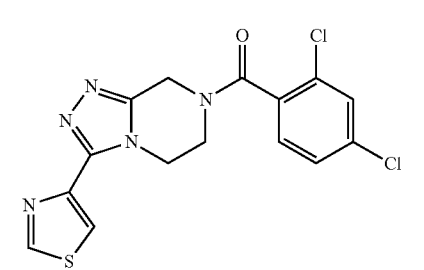<br>7-[(2,4-dichlorophenyl)carbonyl]-3-(1,3-thiazol-4-yl)-5,6,7,8-tetrahydro[1,2,4]triazolo[4,3-a]pyrazine<br>(silica gel, then MDAP, then diethyl ether trituration) | 4-Thiazole-carboxylic acid hydrazide; e.g. from Princeton BioMocecular, Tyger Scientific or Bepharm. See e.g. Intermediate 6 for acyl piperazinone. | 381 | 0.85[b] |

TABLE 7-continued

| Example no. | Chemical structure and name of product (and purification step(s) and solvent trituration/workup step used) | Hydrazide and/or acyl piperazinone starting material(s); and possible source(s) | [M + H]⁺ | Retention time (mins) |
|---|---|---|---|---|
| E98 | 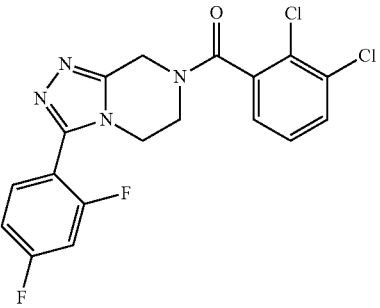<br>7-[(2,3-dichlorophenyl)carbonyl]-3-(2,4-difluorophenyl)-5,6,7,8-tetrahydro[1,2,4]triazolo[4,3-a]pyrazine<br>(silica gel, then MDAP) | 2,4-Difluoro-benzhydrazide; available e.g. from Matrix Scientific or ABCR. See e.g. Intermediate 3 for acyl piperazinone. | 408.89 | 0.93-0.95[b] |
| E99 | 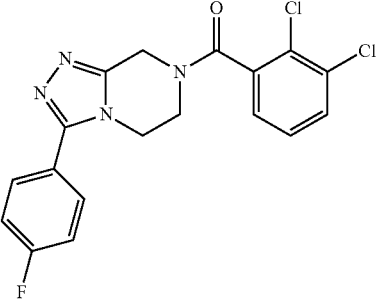<br>7-[(2,3-dichlorophenyl)carbonyl]-3-(4-fluorophenyl)-5,6,7,8-tetrahydro[1,2,4]triazolo[4,3-a]pyrazine<br>(silica gel, then MDAP) | 4-Fluoro-benzhydrazide; e.g. from Oakwood, AKos Consulting or China Hallochem. See e.g. Intermediate 3 for acyl piperazinone. | 390.87 | 0.93-0.94[b] |
| E100 | 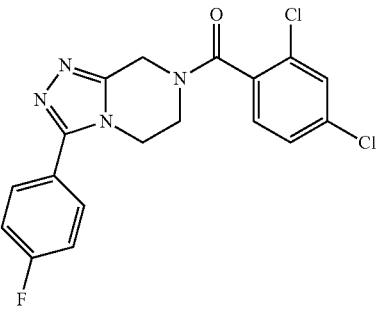<br>7-[(2,4-dichlorophenyl)carbonyl]-3-(4-fluorophenyl)-5,6,7,8-tetrahydro[1,2,4]triazolo[4,3-a]pyrazine<br>(silica gel, then MDAP) | 4-Fluoro-benzhyrazide; e.g. from Oakwood, AKos Consulting or China Hallochem. See e.g. Intermediate 6 for acyl piperazinone. | 390.90 | 0.94-0.97[b] |

TABLE 7-continued

| Example no. | Chemical structure and name of product (and purification step(s) and solvent trituration/workup step used) | Hydrazide and/or acyl piperazinone starting material(s); and possible source(s) | [M + H]+ | Retention time (mins) |
|---|---|---|---|---|
| E101 | 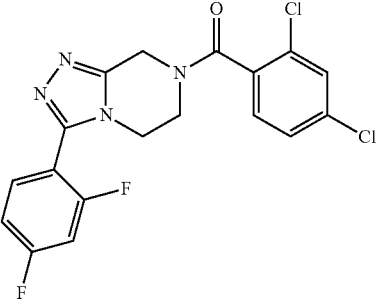<br>7-[(2,4-dichlorophenyl)carbonyl]-3-(2,4-difluorophenyl)-5,6,7,8-tetrahydro[1,2,4]triazolo[4,3-a]pyrazine<br>(silica gel, then MDAP) | 2,4-Difluoro-benzhydrazide; available e.g. from Matrix Scientific or ABCR. See e.g. Intermediate 6 for acyl piperazinone. | 408.86 | 0.96-0.97[b] |
| E102 | 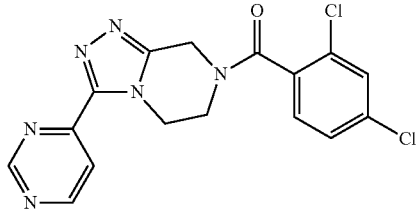<br>7-[(2,4-dichlorophenyl)carbonyl]-3-(4-pyrimidinyl)-5,6,7,8-tetrahydro[1,2,4]triazolo[4,3-a]pyrazine<br>(silica gel, then MDAP, then diethyl ether trituration) | Pyrimidine-4-carboxylic acid hydrazide; e.g. from Anichem, J & W PharmLab or Bepharm. See e.g. Intermediate 6 for acyl piperazinone. | 374 | 0.82[b] |
| E103 | 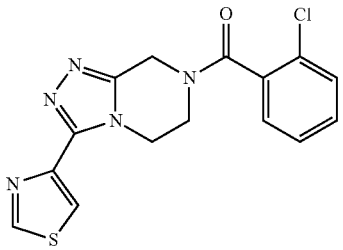<br>7-[(2-chlorophenyl)carbonyl]-3-(1,3-thiazol-4-yl)-5,6,7,8-tetrahydro[1,2,4]triazolol[4,3-a]pyrazine<br>(MDAP) | 4-Thiazole-carboxylic acid hydrazide; e.g. from Princeton BioMocecular, Tyger Scientific or Bepharm. See e.g. Intermediate 4 for acyl piperazinone. | 345.91 | 0.71-0.73[b] |

TABLE 7-continued

| Example no. | Chemical structure and name of product (and purification step(s) and solvent trituration/workup step used) | Hydrazide and/or acyl piperazinone starting material(s); and possible source(s) | [M + H]⁺ | Retention time (mins) |
|---|---|---|---|---|
| E104 | 7-{[4-chloro-3-(trifluoromethyl)phenyl]carbonyl}-3-(2-pyrazinyl)-5,6,7,8-tetrahydro[1,2,4]triazolo[4,3-a]pyrazine (MDAP) | 2-Pyrazine-carbo-hydrazide; available e.g. from TimTec, J & W PharmLab or AKos. See e.g. Intermediate 18 for acyl piperazinone. | 409 | 0.91[b] |
| E105 | 7-[(3-chloro-4-fluorophenyl)carbonyl]-3-(2-pyrazinyl)-5,6,7,8-tetrahydro[1,2,4]triazolo[4,3-a]pyrazine (MDAP) | 2-Pyrazine-carbo-hydrazide; available e.g. from TimTec, J & W PharmLab or AKos. See e.g. Intermediate 19 for acyl piperazinone. | 359 | 0.79[b] |
| E106 | 7-[(4-chloro-2-fluorophenyl)carbonyl]-3-(2-pyrazinyl)-5,6,7,8-tetrahydro[1,2,4]triazolo[4,3-a]pyrazine (MDAP) | 2-Pyrazine-carbo-hydrazide; available e.g. from TimTec, J & W PharmLab or AKos. See e.g. Intermediate 17 for acyl piperazinone. | 359 | 0.79[b] |
| E107 | 7-[(4-fluoro-2-methylphenyl)carbonyl]-3-(2-pyrazinyl)-5,6,7,8-tetrahydro[1,2,4]triazolo[4,3-a]pyrazine (MDAP) | 2-Pyrazine-carbo-hydrazide; available e.g. from TimTec, J & W PharmLab or AKos. See e.g. Intermediate 20 for acyl piperazinone. | 339 | 0.74[b] |

TABLE 7-continued

| Example no. | Chemical structure and name of product (and purification step(s) and solvent trituration/workup step used) | Hydrazide and/or acyl piperazinone starting material(s); and possible source(s) | [M + H]+ | Retention time (mins) |
|---|---|---|---|---|
| E108 | 7-{[4-fluoro-3-(trifluoromethyl)phenyl]carbonyl}-3-(2-pyrazinyl)-5,6,7,8-tetrahydro[1,2,4]triazolo[4,3-a]pyrazine (MDAP) | 2-Pyrazine-carbo-hydrazide; available e.g. from TimTec, J & W PharmLab or AKos. See e.g. Intermediate 21 for acyl piperazinone. | 393 | 0.86[b] |

[a]Retention time obtained using 5 minute HPLC method
[b]Retention time obtained using 2 minute HPLC method

Example 85

7-[(2-chloro-4-fluorophenyl)carbonyl]-3-(2-pyrazinyl)-5,6,7,8-tetrahydro[1,2,4]triazolo[4,3-a]pyrazine (E85)

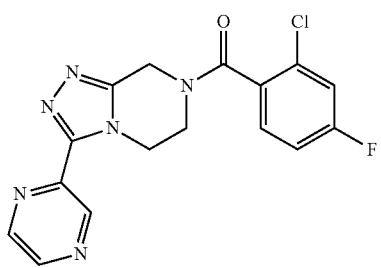 [SMILES: O=C(c1ccc(F)cc1Cl)N1CCn2c(nnc2-c2cnccn2)C1]

To a suspension of 4-[(2-chloro-4-fluorophenyl)carbonyl]-2-piperazinone (I3)(0.78 g, 3.04 mmol) in Dichloromethane (DCM) (7.60 ml) was added triethyloxonium tetrafluoroborate (0.606 g, 3.19 mmol) and the mixture was stirred at room temperature under argon. After 5-10 minutes it turned to a yellow solution. TLC showed the formation of the imidate (some unreacted starting material always present due to instability of imidate on TLC). After 1 hour 2-pyrazinecarbohydrazide (0.504 g, 3.65 mmol, commercially available) was added but it was insoluble. After 15 minutes the solvent was evaporated in vacuo and the residue taken in n-butanol (7.60 ml) and heated at reflux (120° C.). After 2 hours LCMS showed a main peak which is consistent with the desired product. It was concentrated in vacuo and the residue was purified by flash chromatography (Biotage SP4, 40+M cartridge) with a gradient of 2M ammonia in MeOH 0 to 10% in DCM. The crude product was then dissolved in EtOAc (50 mL), the precipitate filtered off (50 mg of impurity by LCMS) and the solution washed with sat. NH₄Cl (30 mL), water (30 mL) and brine (30 mL) and finally dried over MgSO₄ to afford an off-white solid that was fruther purified by MDAP to isolate the desired product in 310 mg as a white solid.

LC/MS: (M+H)+=359, retention time=0.74 minutes (2 minutes run).

¹H NMR (500 MHz; d6-DMSO) δ 9.37 (1H, d), 8.74 (2H, m), 7.65 (1H, m), 7.63 (1H, dd), 7.37 (1H, td), 5.28 (1H, d), 4.94 (1H, d), 4.43 (2H, m), 3.67 (2H, m).

Example 92

7-[(2,4-dichlorophenyl)carbonyl]-3-(2-pyrazinyl)-5,6,7,8-tetrahydro[1,2,4]triazolo[4,3-a]pyrazine (E92)

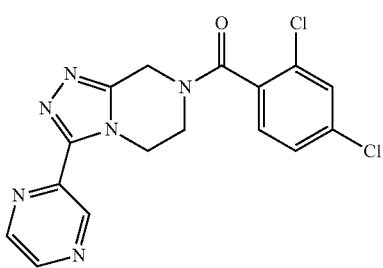 [SMILES: O=C(c1ccc(Cl)cc1Cl)N1CCn2c(nnc2-c2cnccn2)C1]

A solution of 4-[(2,4-dichlorophenyl)carbonyl]-2-piperazinone (I6) (0.273 g, 1 mmol) in dry Dichloromethane (DCM) (3 ml) was stirred at room temperature under argon. Triethyloxonium tetrafluoroborate (0.199 g, 1.050 mmol) was added and the reaction solution was stirred for 10 minutes. 2-pyrazinecarbohydrazide (0.166 g, 1.200 mmol, commercially available) was then added and the solution was stirred for a further 1 hour. The solvent was then concentrated before n-butanol (3.00 ml) was added and the solution was stirred, under reflux and argon, for 4 hours. LCMS confirmed product location, thus the solution was cooled to room temperature before the solvent was evaporated in vacuo. The remaining residue was then purified by flash chromatograpghy (Biotage SP4, 25M cartridge) with a gradient of 0 to 10% 2M NH$_3$/MeOH in DCM. TLC confirmed product location and the solvent from the combined fractions was evaporated in vacuo. The remaining residue was then further purified by mass-directed automated HPLC. The solvent was then evaporated in vacuo, and the remaining solid was triturated with ether, and dried in a vacuum oven to yield the product in 0.137 g.

LCMS: m/z=375 (M+H)+, retention time=0.83 minutes (2 minutes). $^1$H NMR (500 MHz; d6-DMSO) δ 9.37 (1H, d), 8.75 (1H, m), 8.74 (1H, m), 7.79 (1H, d), 7.61 (1H, d), 7.57 (1H, dd), 5.27 (1H, d), 4.94 (1H, d), 4.47 (1H, m), 4.38 (1H, m), 3.69 (2H, m).

Example 109

3-Bromo-7-[(2-chloro-4-fluorophenyl)carbonyl]-5,6,7,8-tetrahydro[1,2,4]triazolo[4,3-a]pyrazine (E109)

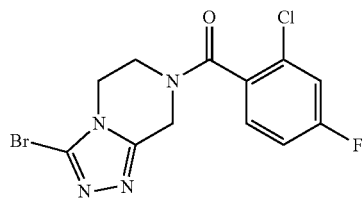 [SMILES: O=C(c1ccc(F)cc1Cl)N1CCn2c(Br)nnc2C1]

3-Bromo-7-[(2-chloro-4-fluorophenyl)carbonyl]-5,6,7,8-tetrahydro[1,2,4]triazolo[4,3-a]pyrazine was prepared in a manner analogous to that described in Example 1 but substituting 2-chloro-4-fluorobenzoyl chloride (commercially available e.g. from Maybridge, Alfa Aesar or ABCR) for the 2-chloro-3-(trifluoromethyl)benzoyl chloride used in Example 1.

LC/MS [M+H]+=359, 361, 363, retention time=0.73 minutes (2 minute method).

Example 110

7-[(2,4-Dichloro-3-fluorophenyl)carbonyl]-3-(5-fluoro-2-pyridinyl)-5,6,7,8-tetrahydro[1,2,4]triazolo[4,3-a]pyrazine (E110)

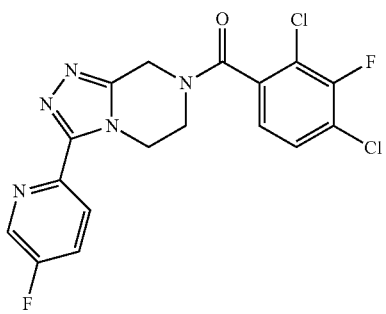

To a solution of 4-[(2,4-dichloro-3-fluorophenyl)carbonyl]-2-piperazinone (I37) (0.146 g, 0.5 mmol) in Dichloromethane (DCM) (3 mL) was added triethyloxonium tetrafluoroborate (0.100 g, 0.525 mmol). The solution was then stirred, under argon, for 10 minutes before 5-fluoro-2-pyridinecarbohydrazide (I24) (0.093 g, 0.600 mmol) was added. The solution was then stirred for a further hour before the solvent was concentrated and n-butanol (3.00 mL) was added. The solution was then stirred, under argon and reflux, for 3 hours before being cooled to room temperature. The solvent was then evaporated in vacuo and the remaining residue was purified by flash chromatography (Biotage SP4, 25M cartridge) with a gradient of 0-10% 2M NH$_3$/MeOH in DCM. TLC confirmed product location and the solvent from the combined fractions was evaporated in vacuo. The remaining residue was then further purified by mass-direct automated HPLC, and the solvent evaporated in vacuo. The remaining solid was then triturated with ether and dried in a vac-oven to yield the product in 0.045 g.

LCMS: m/z=409 (M+H)+, retention time=0.93 minutes (2 minutes)

Example 111

7-[(2,4-Dichloro-3-fluorophenyl)carbonyl]-3-(2-pyrazinyl)-5,6,7,8-tetrahydro[1,2,4]triazolo[4,3-a]pyrazine (E111)

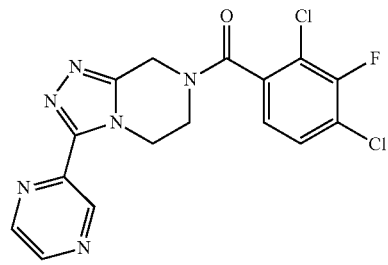 [SMILES: O=C(c1ccc(Cl)c(F)c1Cl)N1CCn2c(nnc2-c2cnccn2)C1]

To a solution of 4-[(2,4-dichloro-3-fluorophenyl)carbonyl]-2-piperazinone (I37) (0.146 g, 0.5 mmol) in Dichloromethane (DCM) (3 mL) was added triethyloxonium tetrafluoroborate (0.100 g, 0.525 mmol). The solution was then stirred, under argon, for 10 minutes before 2-pyrazinecarbohydrazide (commercially available from e.g. TimTec, J& W PharmLab and Akos Consulting, 0.083 g, 0.600 mmol) was added. The solution was then stirred for a further hour before the solvent was concentrated and n-butanol (3.00 mL) was added. The solution was then stirred, under argon and reflux, for 3 hours before being cooled to room temperature. The solvent was then evaporated in vacuo and the remaining residue was purified by flash chromatography (Biotage SP4, 25M cartridge) with a gradient of 0-10% 2M NH$_3$/MeOH in DCM. TLC confirmed product location and the solvent from the combined fractions was evaporated in vacuo. The remaining residue was then further purified by mass-direct automated HPLC, before the solvent was again evaporated in vacuo. The remaining solid was then triturated in ether before being dried in a vac-oven to yield the product in 0.056 g.

LCMS: m/z=392 (M+H)+, retention time=0.80 minutes (2 minutes)

Example 112

7-[(2,4-Dichloro-3-fluorophenyl)carbonyl]-3-(4-pyrimidinyl)-5,6,7,8-tetrahydro[1,2,4]triazolo[4,3-a]pyrazine (E112)

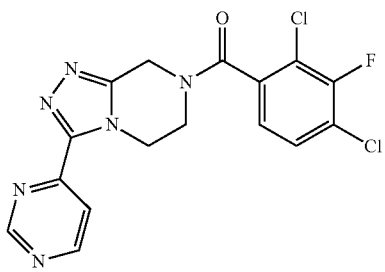 [SMILES: O=C(c1ccc(Cl)c(F)c1Cl)N1CCn2c(nnc2-c2ccncn2)C1]

To a solution of 4-[(2,4-dichloro-3-fluorophenyl)carbonyl]-2-piperazinone (I37) (0.364 g, 1.25 mmol) in Dichloromethane (DCM) (3 mL) was added triethyloxonium tetrafluoroborate (0.249 g, 1.313 mmol). The solution was then stirred, under argon, for 10 minutes before 4-pyrimidinecarbohydrazide (commercially available from e.g. Anichem, J&W PharmLab or Bepharm, 0.207 g, 1.500 mmol) was added. The solution was then stirred for a further hour before the solvent was concentrated and n-butanol (3.00 mL) was added. The solution was then stirred, under argon and reflux, for 3 hours before being cooled to room temperature. The solvent was then evaporated in vacuo and the remaining residue was purified by flash chromatography (Biotage SP4, 25M cartridge) with a gradient of 0-10% 2M $NH_3$/MeOH in DCM. TLC confirmed product location and the solvent from the combined fractions were evaporated in vacuo. The remaining residue was then further purified by mass-direct automated HPLC, before the solvent was again evaporated in vacuo. The remaining solid was then triturated in ether before being dried in a vacuum oven to yield the product in 0.132 g.

LCMS: m/z=392 (M+H)+, retention time=0.79 minutes (2 minutes).

Example 113

7-[(2,3-Dichloro-4-fluorophenyl)carbonyl]-3-(2-pyrazinyl)-5,6,7,8-tetrahydro[1,2,4]triazolo[4,3-a]pyrazine (E113)

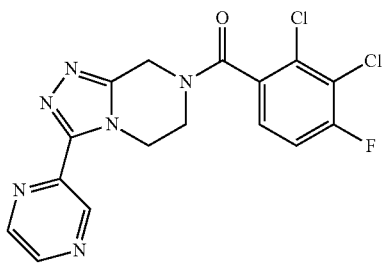

4-[(2,3-dichloro-4-fluorophenyl)carbonyl]-2-piperazinone (I34) (0.210 g, 0.721 mmol) was dissolved in Dichloromethane (DCM) (3 mL), and to this was added triethyloxonium tetrafluoroborate (0.144 g, 0.757 mmol), the solution was stirred for 20 minutes before 2-pyrazinecarbohydrazide (commercially available from e.g. TimTec, J&W PharmLab or AKos Consulting, 0.120 g, 0.866 mmol) was added. The solution was then allowed to stir for an additional 30 minutes before the solvent was concentrated and n-butanol (3 mL) was added. The solution was then stirred, under argon and reflux, for 3 hours before being allowed to cool to room temperature. The solvent was then removed in vacuo and the remaining residue was purified by flash chromatography (Biotage SP4, 25M cartridge) with a gradient of 0-10% 2M $NH_3$/MeOH in DCM. TLC confirmed product location and the solvent from the combined fractions was evaporated in vacuo. The remaining residue was then further purified by mass-directed automated HPLC, and the solvent evaporated in vacuo. The remaining residue was then triturated with ether and dried in a vacuum oven to yield the product in 0.112 g.

LCMS: m/z=392 (M+H)+, retention time=0.78 minutes (2 minutes).

Example 114

7-[(2,3-Dichloro-4-fluorophenyl)carbonyl]-3-(5-fluoro-2-pyridinyl)-5,6,7,8-tetrahydro[1,2,4]triazolo[4,3-a]pyrazine (E114)

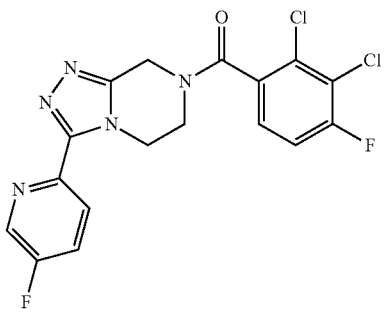

To a solution of 4-[(2,3-dichloro-4-fluorophenyl)carbonyl]-2-piperazinone (I34) (5.08 g, 17.45 mmol) in Dichloromethane (DCM) (80 mL) was added triethyloxonium tetrafluoroborate (3.48 g, 18.32 mmol). The solution was then stirred under argon for 20 minutes before 5-fluoro-2-pyridinecarbohydrazide (I24) (3.25 g, 20.94 mmol) was added. The solution was then stirred for a further 3 hours, before the solvent was concentrated and n-butanol (80 mL) was added. The solution was then stirred, under reflux and argon, for 3 hours before being cooled to room temperature. The solvent was then evaporated in vacuo and the remaining residue was partioned between DCM (100 mL) and water (50 mL), before being dried over anhydrous sodium suphate. The sodium sulphate was then removed by filtration, and the solvent was evaporated in vacuo. The remaining residue was then purified by flash chromatography (Isolera 340 g cartridge) with a gradient of 0-10% MeOH in DCM, TLC confirmed product location and the solvent from the combined fractions was evaporated in vacuo. The remaining solid was then recrystallised from ethyl acetate to yield the product in 2.067 g.

LCMS: m/z=410 (M+H)+, retention time=0.93 minutes (2 minutes); $^1$H NMR (400 MHz; $CDCl_3$) δ 8.50 (0.6H, d), 8.43-8.35 (1.4H, m), 7.6-7.54 (1H, m), 7.31-7.19 2H, m), 5.26 (1H, q), 4.82-4.64 (2.4H, m), 4.60-4.53 (0.4H, m), 4.36-4.14 (1.2H, m), 3.77-3.62 (1H, m).

Example 115

7-[(3,4-dichlorophenyl)carbonyl]-3-(2-pyrazinyl)-5,6,7,8-tetrahydro[1,2,4]triazolo[4,3-a]pyrazine (E115)

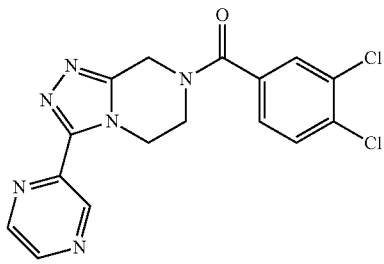

The title compound was synthesised according to a method similar to the method described for Example 111.

To a suspension of 4-[(3,4-dichlorophenyl)carbonyl]-2-piperazinone (I38) (0.165 g, 1.3 mmol) in Dichloromethane (DCM) (3.5 mL) was added triethyloxonium tetrafluoroborate (0.259 g, 1.365 mmol) and the mixture was stirred at room temperature under argon. After 30 minutes 2-pyrazinecarbohydrazide (0.215 g, 1.560 mmol, commercially available from e.g. TimTec, J&W PharmLab or AKos Consulting) was added and the mixture was kept stirring at RT for 15 minutes. The solvent was evaporated and the residue taken in n-butanol (3.50 mL) and heated at reflux (120° C.) for 3 hours after which the solvent was evaporated to dryness at the buchi. The crude mixture was treated with methanol, the insoluble impurity was filtered off and the solution was concentrated and purified by Mass Directed Auto Preparation.

LC/MS: (M+H)$^+$=375, retention time=0.86 minutes (2 minutes run).

Example 116

7-[(2-chlorophenyl)carbonyl]-3-(4-pyrimidinyl)-5,6,7,8-tetrahydro[1,2,4]triazolo[4,3-a]pyrazine (E116)

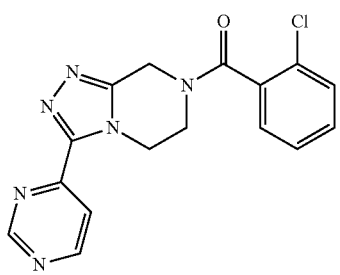 [SMILES: O=C(c1ccccc1Cl)N1CCn2c(nnc2-c2ccncn2)C1]

The title compound was prepared in a method analogous to the example E111. To a solution of 4-[(2-chlorophenyl)carbonyl]-2-piperazinone (I4) (269 mg, 1.127 mmol,) in Dichloromethane (5 ml) stirred under argon at room temp was added solid triethyloxonium tetrafluoroborate (214 mg, 1.127 mmol). The reaction mixture was stirred at RT for 1 hr. Solid 4-pyrimidinecarbohydrazide (171 mg, 1.240 mmol, commerically available from e.g. Anichem, J&W PharmLab or Bepharm) was added and the reaction mixture stirred at RT for 18 hr. The solvent was evaporated in vacuo, and the residue dissolved in n-butanol (5 ml) and stirred at 120° C. for 3 hr. The reaction mixture was cooled to room temperature and partitioned between Dichloromethane (~50 ml) and saturated brine (~25 ml). The aqueous phase was extracted with Dichloromethane (2×25 ml) and the combined organic extracts washed with saturated brine (2×25 ml), dried over sodium sulphate and evaporated in vacuo to afford the crude product (~Z1) as a dark orange oil. This was dissolved in 1:1 MeOH:DMSO and purified by Open Access Mass Directed AutoPrep on Sunfire C18 column using Acetonitrile Water with a Formic acid modifier. The solvent was evaporated in vacuo, and the residue washed with ether (~10 ml) and dried overnight in a vacuum oven at 40° C. to afford the required product as a yellow solid in 74.1 mg.

LCMS: MH$^+$ m/z=340.86; RT=0.63-0.67 min. 2 minute run in MeCN.

Example 117

7-[(2-chlorophenyl)carbonyl]-3-(2-furanyl)-5,6,7,8-tetrahydro[1,2,4]triazolo[4,3-a]pyrazine (E117)

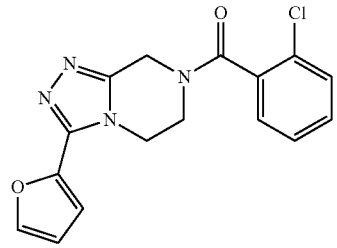 [SMILES: O=C(c1ccccc1Cl)N1CCn2c(nnc2-c2ccco2)C1]

4-[(2-chlorophenyl)carbonyl]-2-piperazinone hydrazone (140) (715 mg, 2.83 mmol) and triethylamine (0.986 mL, 7.08 mmol) were dissolved in Dichloromethane (DCM) (10 mL). 2-furancarbonyl chloride (0.306 mL, 3.11 mmol, commercially available from e.g. Sigma-Aldrich, Apollo or Acros) was added and the solution stirred at 25° C. for 4 hr. Solvents were removed in vacuo and the residue was dissolved in n-butanol (10.00 mL). The solution was heated at reflux for 4 hours and the solvents were removed in vacuo. The residue was partitioned between ethyl acetate (50 mL) and saturated sodium bicarbonate solution (25 mL). The aqueous phase was extracted with ethyl acetate (3×25 mL), the combined extracts were washed with water (3×50 mL), brine (50 mL), dried over anhydrous sodium sulfate and concentrated to a crude solid in 925 mg. The product was purified by flash chromatography (Isolera, 100 g, 0-100% Methanol: Dichloromethane (1:9)/Dichloromethane) to afford product in 260 mg. This was further purified by MDAP to afford product in 85 mg.

LC/MS=329/331 (M+H)+, retention time=0.70 minutes (2 minute method).

Example 118

7-[(2-chlorophenyl)carbonyl]-3-(5-fluoro-2-pyridinyl)-5,6,7,8-tetrahydro[1,2,4]triazolo[4,3-a]pyrazine (E118)

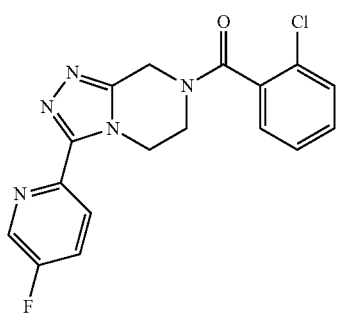

The title compound was prepared in an analogous method to that described in E111. To a solution of 4-[(2-chlorophenyl)carbonyl]-2-piperazinone (I4) (225 mg, 0.943 mmol) in Dichloromethane (5 ml) stirred under argon at room temp was added solid triethyloxonium tetrafluoroborate (179 mg, 0.943 mmol). The reaction mixture was stirred at RT for 2 hr. Solid 5-fluoro-2-pyridinecarbohydrazide (I24) (161 mg, 1.037 mmol) was added and the reaction mixture stirred at RT for 18 hr. The solvent was evaporated in vacuo, and the residue dissolved in n-butanol (5 ml) and stirred at 120° C. for 4 hr. The reaction mixture was cooled to room temperature and partitioned between Dichloromethane (~25 ml) and saturated brine (~25 ml). The aqueous phase was extracted with Dichloromethane (2×25 ml) and the combined organic extracts washed with saturated brine (~25 ml), dried over sodium sulphate, and evaporated in vacuo to afford the crude product as a yellow oil. This was dissolved in 1:1 MeOH:DMSO and purified by Open Access Mass Directed AutoPrep on Sunfire C18 column using Acetonitrile Water with a Formic acid modifier. The solvent was evaporated in vacuo and the residue dried overnight in a vacuum oven at 40° C. to give the required product as a white powder in 126.4 mg.

LCMS: 2 minute run in MeCN. MH$^+$ m/z=358.03; RT=0.80-0.82 min.

Examples 119 to 163

In a manner analogous to that described for Example 118 above, the compounds tabulated below (Table 8) were prepared, as the free compounds and/or as hydrochloride salts thereof, by substituting the appropriate hydrazide for the benzohydrazide used in the above procedure. Reaction times varied from 1 hr to 18 hr in refluxing 1-butanol. The purification step(s) and the post-purification solvent trituration or workup step used for each of Examples 119 to 163 (instead of the MDAP used in Example 118) are stated in brief in the following Table 8.

In an alternative embodiment, some or all of the products, e.g. the pyridine-containing products, are isolated as acid addition salts (e.g. as hydrochlorides).

All of the requisite hydrazides are available from commercial sources and/or can be prepared using routes described previously in the chemical literature and/or in the manner described in the Intermediates section above (e.g. Example 120 can be prepared using Intermediate 4; Example 123 can be prepared using Intermediate 2).

TABLE 8

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E119 | 7-[(2-chlorophenyl)carbonyl]-3-(4-fluorophenyl)-5,6,7,8-tetrahydro[1,2,4]triazolo[4,3-a]pyrazine (MDAP) | 4-fluorobenzoyl hydrazine available from e.g. Simga-Aldrich or Apollo; See e.g. Intermediate 4 for acyl piperazinone | 357.03 | 0.79-0.82 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E120 | 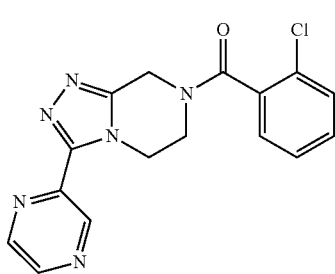<br>7-[(2-chlorophenyl)carbonyl]-3-(2-pyrazinyl)-5,6,7,8-tetrahydro[1,2,4]triazolo[4,3-a]pyrazine<br>(MDAP) | 2-pyrazinecarbohydrazide available from e.g. TimTec, J&W PharmLab or AKos Consulting; See e.g. Intermediate 4 for acyl piperazinone | 340.98 | 0.66-0.68 |
| E121 | 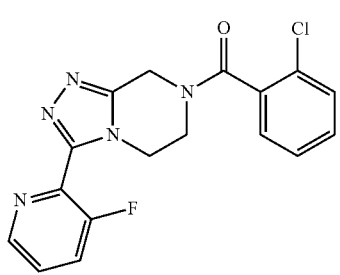<br>7-[(2-chlorophenyl)carbonyl]-3-(3-fluoro-2-pyridinyl)-5,6,7,8-tetrahydro[1,2,4]triazolo[4,3-a]pyrazine<br>(MDAP) | See e.g. Intermediate 31 for hydrazide; See e.g. Intermediate 4 for acyl piperazinone | 358.03 | 0.70-0.72 |
| E122 | 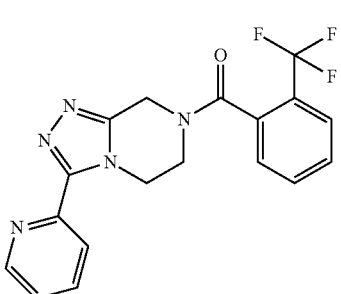<br>3-(2-pyridinyl)-7-{[2-(trifluoromethyl)phenyl]carbonyl}-5,6,7,8-tetrahydro[1,2,4]triazolo[4,3-a]pyrazine<br>(silical gel/MDAP/diethyl ether trituration) | 2-pyridinecarbohydrazide available from e.g. TimTec, Ryan Scientific or AKos Consulting; See e.g. intermediate 5 for acyl piperazinone | 374 | 0.80 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E123 | 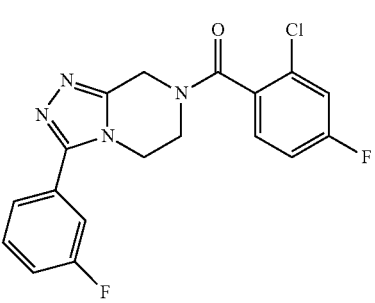<br>7-[(2-chloro-4-fluorophenyl)carbonyl]-3-(3-fluorophenyl)-5,6,7,8-tetrahydro[1,2,4]triazolo[4,3-a]pyrazine<br>(Silica gel/MDAP/MDAP/diethyl ether trituration) | 3-fluorobenzohydrazide available from e.g. Sigma-Aldrich, Apollo; See e.g. Intermediate 2 for acyl piperazinone | 374 | 0.82 |
| E124 | 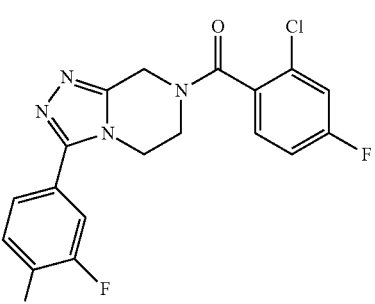<br>7-[(2-chloro-4-fluorophenyl)carbonyl]-3-(3,4-difluorophenyl)-5,6,7,8-tetrahydro[1,2,4]triazolo[4,3-a]pyrazine<br>(Silica gel/MDAP/diethyl ether trituration) | 3,4-difluorobenzohydrazide available from e.g. Apollo, Maybridge; See e.g. Intermediate 2 for acyl piperazinone | 392 | 0.85 |
| E125 | 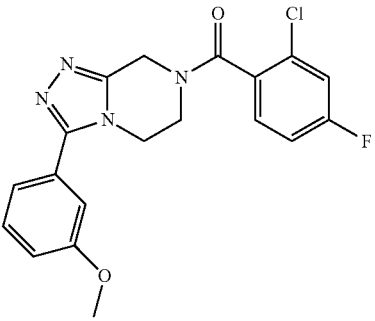<br>7-[(2-chloro-4-fluorophenyl)carbonyl]-3-[3-(methyloxy)phenyl]-5,6,7,8-tetrahydro[1,2,4]triazolo[4,3-a]pyrazine<br>(E128)<br>(Silica gel/MDAP/diethyl ether trituration) | 3-(methyloxy)benzohydrazide available from e.g. Sigma-Aldrich, maybridge; See e.g. Intermediate 2 for acyl piperazinone | 386 | 0.82 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E126 | 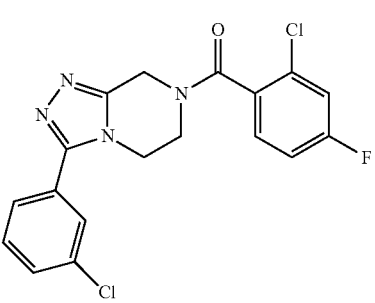<br>7-[(2-chloro-4-fluorophenyl)carbonyl]-3-(3-chlorophenyl)-5,6,7,8-tetrahydro[1,2,4]triazolo[4,3-a]pyrazine (MDAP) | 3-chlorobenzoic acid hydrazide available from e.g. Apollo, ABCR, Acros; See e.g. Intermediate 2 for acyl piperazinone | 390.83 392.84 | 0.88-0.91 |
| E127 | 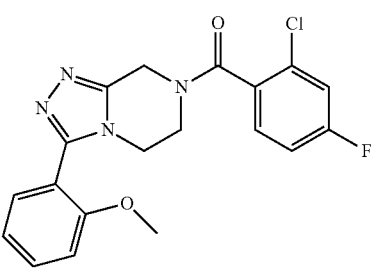<br>7-[(2-chloro-4-fluorophenyl)carbonyl]-3-[2-(methyloxy)phenyl]-5,6,7,8-tetrahydro[1,2,4]triazolo[4,3-a]pyrazine (MDAP) | 2-methoxybenzoic acid hydrazide available from e.g. Alfa Aesar, Apollo, ABCR; See e.g. Intermediate 2 for acyl piperazinone | 386.83 | 0.79-0.81 |
| E128 | 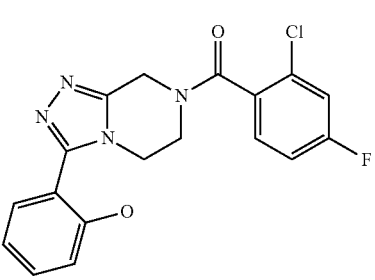<br>2-{7-[(2-chloro-4-fluorophenyl)carbonyl]-5,6,7,8-tetrahydro[1,2,4]triazolo[4,3-a]pyrazin-3-yl}phenol<br>(Silica gel then MDAP then diethyl ether trituration) | 2-hydroxybenzo hydrazide available from e.g. Sigma-Aldrich, Maybridge; See e.g. Intermediate 2 for acyl piperazinone | 372 | 0.75 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E129 | 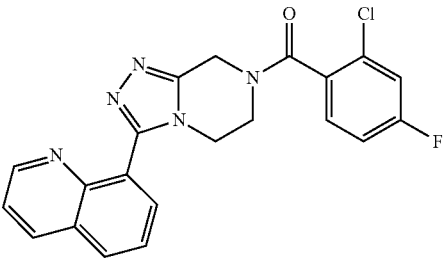<br>8-{7-[(2-chloro-4-fluorophenyl)carbonyl]-5,6,7,8-tetrahydro[1,2,4]triazolo[4,3-a]pyrazin-3-yl}quinoline<br>(MDAP) | See e.g. Intermediate 42 for the hydrazide; See e.g. Intermediate 2 for the acyl piperazinone | 408.15 | 0.77-0.78 |
| E130 | 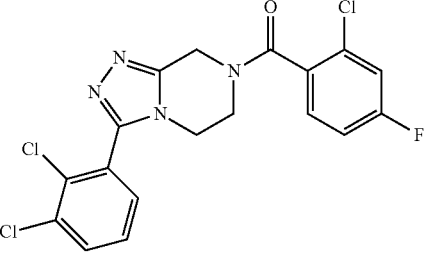<br>7-[(2-chloro-4-fluorophenyl)carbonyl]-3-(2,3-dichlorophenyl)-5,6,7,8-tetrahydro[1,2,4]triazolo[4,3-a]pyrazine<br>(Silica gel/MDAP/diethyl ether trituration) | 2,3-dichlorobenzo hydrazide available from e.g. Matrix, Tim Tec or Chembridge; See e.g. Intermediate 2 for acyl piperazinone | 424.75 426.75 | 0.92 |
| E131 | 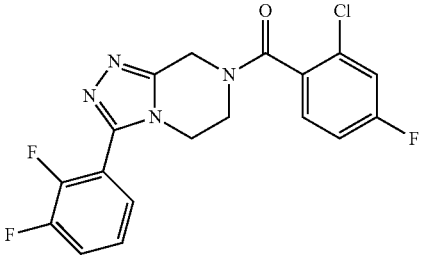<br>7-[(2-chloro-4-fluorophenyl)carbonyl]-3-(2,3-difluorophenyl)-5,6,7,8-tetrahydro[1,2,4]triazolo[4,3-a]pyrazine<br>(Silical gel/MDAP/diethyl ether trituration) | 2,3-difluorobenzo hydrazide available from e.g. Apollo, Butt Park; See e.g. Intermediate 2 for acyl piperazinone | 392.89 394.87 | 0.93 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E132 | 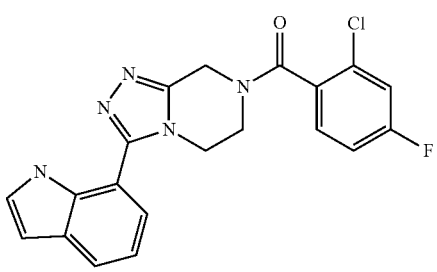<br>7-[(2-chloro-4-fluorophenyl)carbonyl]-3-(1H-indol-7-yl)-5,6,7,8-tetrahydro[1,2,4]triazolo[4,3-a]pyrazine<br>(Silical gel/MDAP/diethyl ether trituration) | See e.g. Intermediate 44 for the hydrazide; See e.g. Intermediate 2 for the acyl piperazinone | 392 | 0.92 |
| E133 | 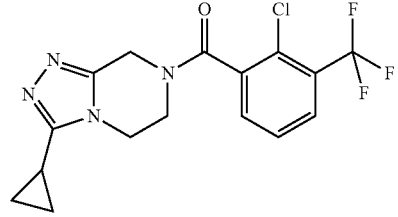<br>7-{[2-chloro-3-(trifluoromethyl)phenyl]carbonyl}-3-cyclopropyl-5,6,7,8-tetrahydro[1,2,4]triazolo[4,3-a]pyrazine<br>(Silical gel/MDAP/Hexane trituration) | cyclopropane carbohydrazide available from Fluorochem, AKos Consulting or ASDI; See e.g. Intermediate 1 for acyl piperazinone | 371, 373 | 0.76 |
| E134 | 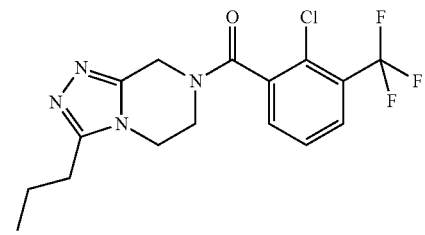<br>7-{[2-chloro-3-(trifluoromethyl)phenyl]carbonyl}-3-propyl-5,6,7,8-tetrahydro[1,2,4]triazolo[4,3-a]pyrazine<br>(Silica gel/MDAP/then Diethyl ether/hexane trituration) | butanohydrazide available from e.g. Alfa Aesar or Pfaltz & Bauer; See e.g. Intermediate 1 for acyl piperazinone | 373 375 | 0.82 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E135 | 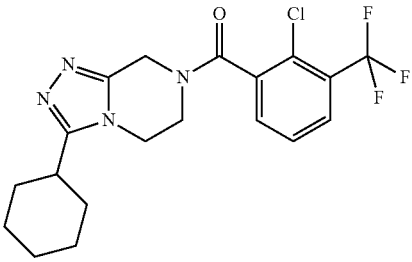<br>7-{[2-chloro-3-(trifluoromethyl)phenyl]carbonyl}-3-cyclohexyl-5,6,7,8-tetrahydro[1,2,4]triazolo[4,3-a]pyrazine<br>(Silica gel/MDAP/then hexane trituration) | cyclohexanecarbohydrazide available from e.g. ABCR or Bepharm; See e.g. Intermediate 1 for acyl piperazinone | 413<br>415 | 0.94 |
| E136 | 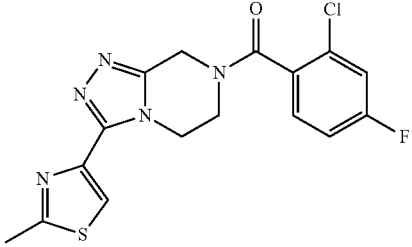<br>7-[(2-chloro-4-fluorophenyl)carbonyl]-3-(2-methyl-1,3-thiazol-4-yl)-5,6,7,8-tetrahydro[1,2,4]triazolo[4,3-a]pyrazine<br>(Silica gel/MDAP) | 2-methyl-1,3-thiazole-4-carbohydrazide available from e.g. Fluorochem, Apollo or Bepharm; See e.g. Intermediate 2 for the acyl piperazinone | 377.84 | 0.77–0.80 |
| E137 | 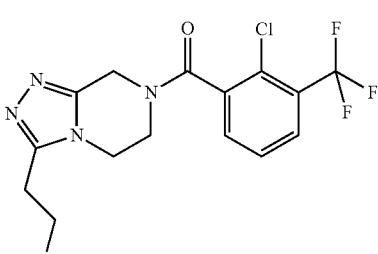<br>7-{[2-chloro-3-(trifluoromethyl)phenyl]carbonyl}-3-[2-(methyloxy)ethyl]-5,6,7,8-tetrahydro[1,2,4]triazolo[4,3-a]pyrazine<br>(Silica gel/MDAP/then hexane trituration) | 3-(methyloxy)propanohydrazide available from Fluorochem or ABCR; See e.g. Intermediate 1 for acyl piperazinone | 389<br>391 | 0.76 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E138 | 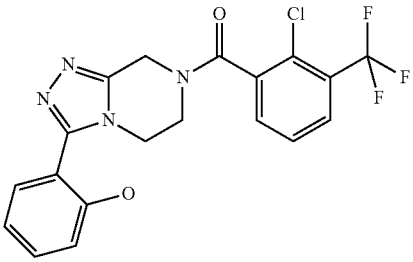<br>2-(7-{[2-chloro-3-(trifluoromethyl)phenyl]carbonyl}-5,6,7,8-tetrahydro[1,2,4]triazolo[4,3-a]pyrazine-3-yl)phenol<br>(MDAP) | 2-hydroxybenzo hydrazide available from e.g. Sigma-Aldrich or Maybridge; See e.g. Intermediate 1 for acyl piperazinone | 422.88 | 0.79-0.90 |
| E139 | 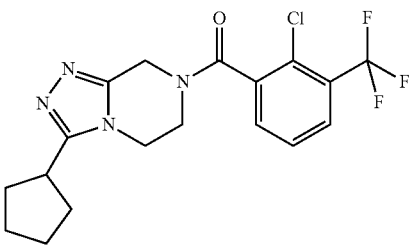<br>7-{[2-chloro-3-(trifluoromethyl)phenyl]carbonyl}-3-cyclopentyl-5,6,7,8-tetrahydro[1,2,4]triazolo[4,3-a]pyrazine<br>(Silical gel/then hexane trituration) | cyclopentane carbohydrazide available from e.g. Matrix or Bepharm; See e.g. Intermedaite 1 for the acyl piperazinone | 399<br>401 | 0.89 |
| E140 | 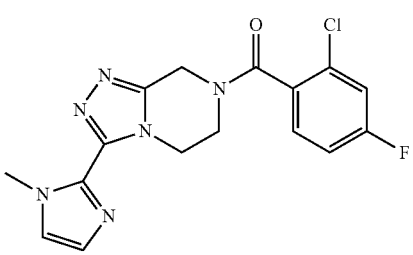<br>7-[(2-chloro-4-fluorophenyl)carbonyl]-3-(1-methyl-1H-imidazol-2-yl)-5,6,7,8-tetrahydro[1,2,4]triazolo[4,3-a]pyrazine<br>(MDAP) | See e.g. Intermediate 46 for the hydrazide; See e.g. Intermediate 2 for the acyl piperazinone | 360.91 | 0.64-0.68 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E141 | 7-[(2-chloro-4-fluorophenyl)carbonyl]-3-(5-chloro-2-pyrazinyl)-5,6,7,8-tetrahydro[1,2,4]triazolo[4,3-a]pyrazine (Silica gel) | See e.g. Intermediate 49 for the hydrazide; See e.g. Intermediate 2 for the acyl piperazinone | 393 395 397 | 0.85 |
| E142 | 7-{[4-chloro-2-(trifluoromethyl)phenyl]carbonyl}-3-(2-pyrazinyl)-5,6,7,8-tetrahydro[1,2,4]triazolo[4,3-a]pyrazine (Silica gel/SCX/then MDAP/then diethyl ether trituration) | 2-pyrazinecarbo hydrazide available from e.g. TimTec, J&W PharmLab or AKos Consulting; See e.g. Intermediate 52 for acyl piperazinone | 409 | 0.84 |
| E143 | 7-[(2,4-dimethylphenyl)carbonyl]-3-(2-pyrazinyl)-5,6,7,8-tetrahydro[1,2,4]triazolo[4,3-a]pyrazine (Silica gel/MDAP then diethyl ether trituration) | 2-pyrazinecarbo hydrazide available from e.g. TimTec, J&W PharmLab or AKos Consulting; See e.g. Intermediate 54 for acyl piperazinone | 335 | 0.75 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E144 | 7-[(2-chloro-4-fluorophenyl)carbonyl]-3-(1,3-thiazol-2-yl)-5,6,7,8-tetrahydro[1,2,4]triazolo[4,3-a]pyrazine (MDAP) | See e.g. Intermediate 51 for the hydrazide; See e.g. Intermediate 2 for the acyl piperazinone | 363.84 | 0.76-0.79 |
| E145 | 7-[(4-chloro-2-methylphenyl)carbonyl]-3-(2-pyrazinyl)-5,6,7,8-tetrahydro[1,2,4]triazolo[4,3-a]pyrazine (Silica gel/then MDAP/then diethyl ether trituration) | 2-pyrazinecarbohydrazide available from e.g. TimTec, J&W PharmLab or AKos Consulting; See e.g. Intermediate 56 for acyl piperazinone | 355 | 0.79 |
| E146 | 7-[(3-chloro-4-fluoro-2-methylphenyl)carbonyl]-3-(2-pyrazinyl)-5,6,7,8-tetrahydro[1,2,4]triazolo[4,3-a]pyrazine (Silica gel/then MDAP/then diethyl ether trituration) | 2-pyrazinecarabohydrazide available from e.g. TimTec, J&W PharmLab or AKos Consulting; See e.g. Intermediate 59 for acyl piperazinone | 373 | 0.80 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E147 | 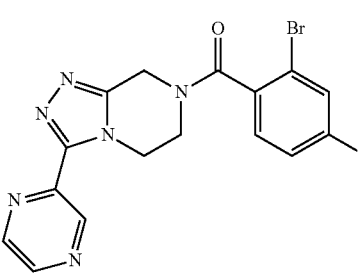<br>7-[(2-bromo-4-fluorophenyl)carbonyl]-3-(2-pyrazinyl)-5,6,7,8-tetrahydro[1,2,4]triazolo[4,3-a]pyrazine<br>(Silica gel/then MDAP/then diethyl ether trituration) | 2-pyrazinecarbohydrazide available from e.g. TimTec, J&W PharmLab or AKos Consulting; See e.g. Intermediate 61 for acyl piperazinone | 403 | 0.72 |
| E148 | 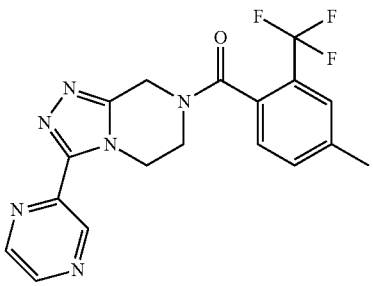<br>7-{[4-methyl-4-(trifluoromethyl)phenyl]carbonyl}-3-(2-pyrazinyl)-5,6,7,8-tetrahydro[1,2,4]triazolo[4,3-a]pyrazine<br>(MDAP) | 2-pyrazinecarbohydrazide available from e.g. TimTec, J&W PharmLab or AKos Consulting; See e.g. Intermediate 63 or acyl piperazinone | 388.96 | 0.78-0.81 |
| E149 | 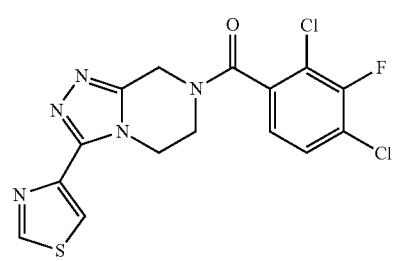<br>7-[(2,4-dichloro-3-fluorophenyl)carbonyl]-3-(1,3-thiazol-4-yl)-5,6,7,8-tetrahydro[1,2,4]triazolo[4,3-a]pyrazine<br>(MDAP) | See e.g. Intermediate 65 for the hydrazide; See e.g. Intermeidate 37 for the acyl piperazinone | 397.82 | 0.82-0.84 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E150 | 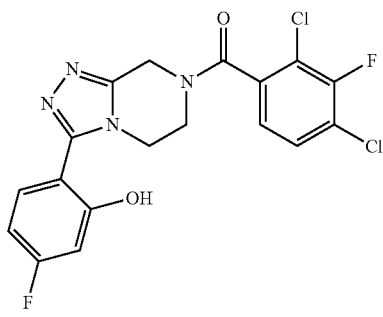<br>2-{7-[(2,4-dichloro-3-fluorophenyl)carbonyl]-5,6,7,8-tetrahydro[1,2,4]triazolo[4,3-a]pyrazin-3-yl}-5-fluorophenol<br>(MDAP) | See e.g. Intermediate 66 for the hydrazide; See e.g. Intermediate 37 for the acyl piperazinone | 424.9 | 0.92-0.93 |
| E151 | 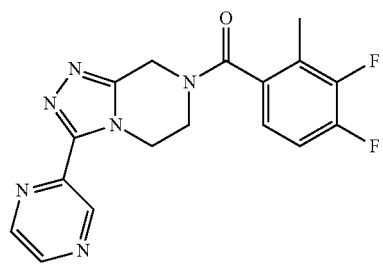<br>7-[(3,4-difluoro-2-methylphenyl)carbonyl]-3-(2-pyrazinyl)-5,6,7,8-tetrahydro[1,2,4]triazolo[4,3-a]pyrazine<br>(Silica gel then MDAP then diethyl ether trituration) | 2-pyrazinecarbo hydrazide available from e.g. TimTec, J&W PharmLab or AKos Consulting; See e.g. Intermediate 69 for the acyl piperazinone | 357 | 0.75 |
| E152 | 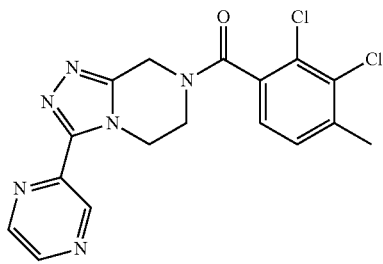<br>7-[(2,3-dichloro-4-methylphenyl)carbonyl]-3-(2-pyrazinyl)-5,6,7,8-tetrahydro[1,2,4]triazolo[4,3-a]pyrazine(E161)<br>(Silica gel then MDAP then diethyl ether trituration) | 2-pyrazinecarbo hydrazide available from e.g. TimTec, J&W PharmLab or AKos Consulting; See e.g. Intermediate 72 for the acyl piperazinone | 389 | 0.85 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E153 | 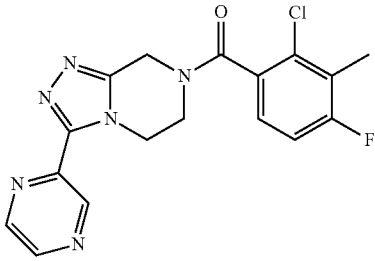<br>7-[(2-chloro-4-fluoro-3-methylphenyl)carbonyl]-3-(2-pyrazinyl)-5,6,7,8-tetrahydro[1,2,4]triazolo[4,3-a]pyrazine<br>(Silica gel then MDAP then diethyl ether trituration) | 2-pyrazinecarbohydrazide available from e.g. TimTec, J&W PharmLab or AKos Consulting; See e.g. Intermediate 75 for the acyl piperazinone | 373 | 0.78 |
| E154 | 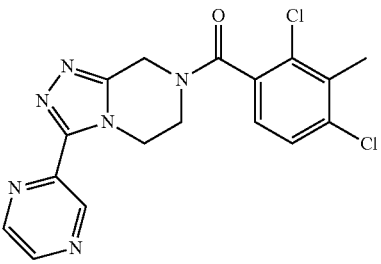<br>7-[(2,4-dichloro-3-methylphenyl)carbonyl]-3-(2-pyrazinyl)-5,6,7,8-tetrahydro[1,2,4]triazolo[4,3-a]pyrazine<br>(Silica gel then MDAP then diethyl ether trituration) | 2-pyrazinecarbohydrazide available from e.g. TimTec, J&W PharmLab or AKos Consulting; See e.g. Intermediate 77 for the acyl piperazinone | 389 | 0.86 |
| E155 | 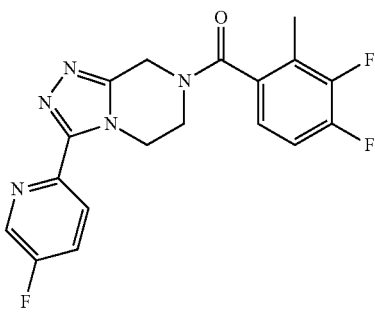<br>7-[(3,4-difluoro-2-methylphenyl)carbonyl]-3-(5-fluoro-2-pyridinyl)-5,6,7,8-tetrahydro[1,2,4]triazolo[4,3-a]pyrazine<br>(Silica gel then MDAP then diethyl ether trituration) | See e.g. Intermediate 24 for hydrazide; See e.g. Intermediate 69 for acyl piperazinone | 374 | 0.88 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E156 | 7-[(3-chloro-4-fluoro-2-methylphenyl)carbonyl]-3-(5-fluoro-2-pyridinyl)-5,6,7,8-tetrahydro[1,2,4]triazolo[4,3-a]pyrazine(E167) (Silica gel then MDAP then diethyl ether trituration) | See e.g. Intermediate 24 for hydrazide; See e.g. intermediate 59 for acyl piperazinone | 389.9 | 0.93 |
| E157 | 7-[(2,4-dichlorophenyl)carbonyl]-3-(5-isoxazolyl)-5,6,7,8-tetrahydro[1,2,4]triazolo[4,3-a]pyrazine (Silica gel/Silica gel reverse phase) | See e.g. Intermediate 82 for hydrazide; See e.g. intermediate 6 for acyl piperazinone | 363.9 | 0.80 |
| E158 | 7-[(2,4-dichlorophenyl)carbonyl]-3-(5-isothiazolyl)-5,6,7,8-tetrahydro[1,2,4]triazolo[4,3-a]pyrazine (Silica gel/Silica gel reverse phase) | See e.g. Intermediate 84 for hydrazide; See e.g. Intermediate 6 for acyl piperazinone | 380.09 | 0.84-0.85 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E159 | 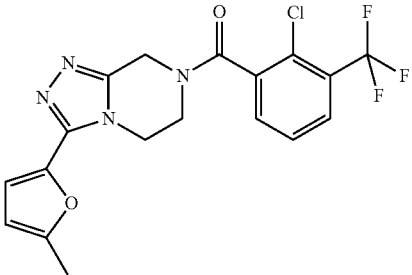<br>7-{[2-chloro-3-(trifluoromethyl)phenyl]carbonyl}-3-(5-methyl-2-furanyl)-5,6,7,8-tetrahydro[1,2,4]triazolo[4,3-a]pyrazine<br>(Silica gel then MDAP then diethyl ether trituration) | See e.g. Intermediate 85 for hydrazide; See e.g. Intermediate 1 for acyl piperazinone | 411 | 0.92 |
| E160 | 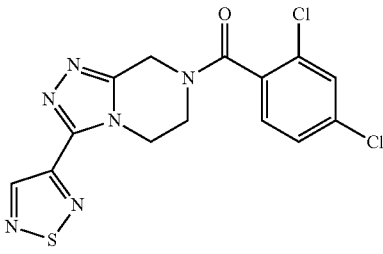<br>7-[(2,4-dichlorophenyl)carbonyl]-3-(1,2,5-thiadiazol-3-yl)-5,6,7,8-tetrahydro[1,2,4]triazolo[4,3-a]pyrazine<br>(MDAP) | See e.g. Intermediate 87 for hydrazide; See e.g. Intermediate 6 for acyl piperazinone | 380.9 | 0.87-0.88 |
| E161 | 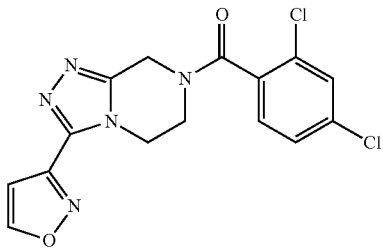<br>7-[(2,4-dichlorophenyl)carbonyl]-3-(3-isoxazolyl)-5,6,7,8-tetrahydro[1,2,4]triazolo[4,3-a]pyrazine<br>(MDAP) | See e.g. Intermediate 89 for hydrazide; See e.g. Intermediate 6 for acyl piperazinone | 363.9 | 0.84-0.88 |

TABLE 8-continued

| Example no. | Chemical structure and name of product (and purification step(s) and solvent trituration/workup step used) | Hydrazide and/or acyl piperazinone starting material(s); and possible source(s) | [M + H] | Retention time (mins) |
|---|---|---|---|---|
| E163 | 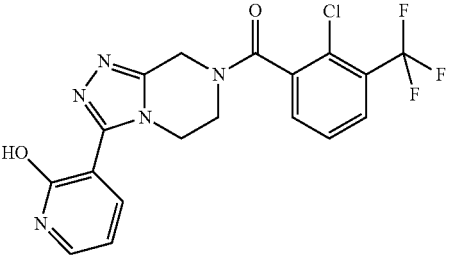<br>3-(7-{[2-chloro-3-(trifluoromethyl)phenyl]carbonyl}-5,6,7,8-tetrahydro[1,2,4]triazolo[4,3-a]pyrazin-3-yl)-2-pyridinol<br>(MDAP then diethyl ether trituration) | See e.g. Intermediate 92 for hydrazide; See e.g. Intermediate 1 for acyl piperazinone | 423.9 | 0.75 |

Note: This specification does not include an Example 162.

Example 164

7-{[2-chloro-3-(trifluoromethyl)phenyl]carbonyl}-3-(1,2,4-thiadiazol-5-yl)-5,6,7,8-tetrahydro[1,2,4]triazolo[4,3-a]pyrazine (E164)

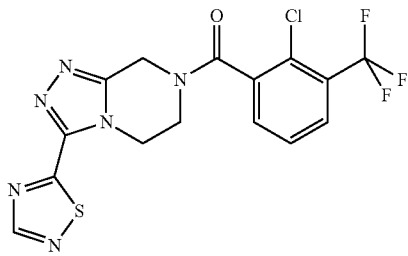 [SMILES: O=C(c1cccc(C(F)(F)F)c1Cl)N1CCn2c(nnc2-c2ncns2)C1]

To a solution of 4-{[2-chloro-3-(trifluoromethyl)phenyl]carbonyl}-2-piperazinone (I1) (0.307 g, 1 mmol) in dry Dichloromethane (DCM) (3 ml) was added triethyloxonium tetrafluoroborate (0.209 g, 1.100 mmol). The solution was then stirred at room temperature and under argon for 30 minutes. 1,2,4-Thiadiazole-5-carbohydrazide (I80) (0.144 g, 1.000 mmol) was then added and the solution was stirred for 1 hour, before the solvent was concentrated and n-BuOH (3.00 ml) was added. The solution was then stirred under argon and reflux for a further 3 hours. The solution was then allowed to cool to room temperature before the solvent was evaporated in vacuo.

The remaining residue was then purified by flash chromatograph (Isolera 50 g snap cartridge) with a gradient of 0-10% MeOH in DCM. TLC confirmed product location and the solvent from the combined fractions was evaporated in vacuo. The remaining residue was then further purified by mass-directed automated HPLC. The solvent was once more evaporated in vacuo and the remaining solid was triturated with ether and dried in a vacuum oven to yield the product in 54 mg.

LCMS: m/z=414 (M+H)+, retention time=0.90 minutes (2 minutes). $^1$H NMR (500 MHz; CDCl$_3$) δ 8.81 (1H, s), 7.84 (1H, m), 7.54 (2H, m), 4.84 (1H, d), 4.79 (1H, m), 4.74 (1H, d), 4.69 (1H, m), 4.54 (1H, dt), 4.24 (2H, ddd).

Example 165

7-[(2-chloro-4-fluorophenyl)carbonyl]-3-(5-fluoro-2-pyrazinyl)-5,6,7,8-tetrahydro[1,2,4]triazolo[4,3-a]pyrazine (E165)

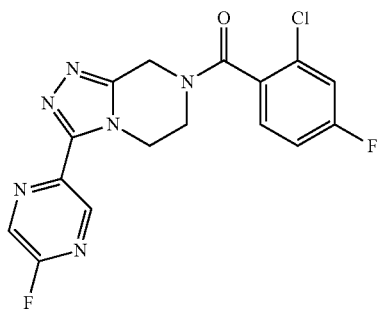

7-[(2-Chloro-4-fluorophenyl)carbonyl]-3-(5-chloro-2-pyrazinyl)-5,6,7,8-tetrahydro[1,2,4]triazolo[4,3-a]pyrazine (E141) (393 mg, 1 mmol) and silver(I)fluoride (381 mg, 3.00 mmol) were heated at 80° C. for 24 h in acetonitrile (5 mL). The solides were filtered, washed with acetonitrile (30 mL) and the filtrate concentrated to a crude solid. The crude solid was purified by MDAP to afford the product in 24 mg.

LC/MS=377 (M+H)+, retention time=0.79 minutes (2 minute method).

Example 166

2-(7-{[2-Chloro-3-(trifluoromethyl)phenyl]carbonyl}-5,6,7,8-tetrahydro[1,2,4]triazolo[4,3-a]pyrazin-3-yl)-3-pyridinol (E166)

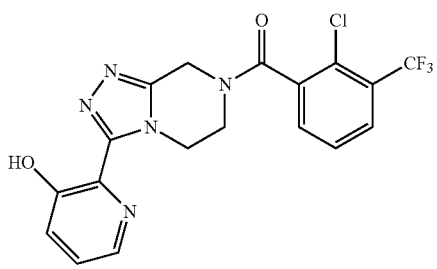

Triethyloxonium tetrafluoroborate (204 mg, 1.076 mmol) was added to a solution of the 4-{[2-chloro-3-(trifluoromethyl)phenyl]carbonyl}-2-piperazinone (I1)(300 mg, 0.978 mmol) in Dichloromethane (DCM) (6 mL) and the reaction was stirred for 1 h. To this was added the 3-hydroxy-2-pyridinecarbohydrazide (I93) (180 mg, 1.174 mmol) and the reaction was stirred for 2 hrs. The solvent was evaporated and 1-butanol (6.00 mL) was added. The mixture was heated at reflux for 3 h. After cooling the solvent was evaporated and the residue was partitioned between water/EtOAc. The organic layer was passed through a phase sep. cartridge and the solvent evaporated to afford an amber oil. This was purified by MDAP to afford a colourless solid of desired material in 90 mg.

LCMS: m/z 423.9 [M+H] @ 0.89 min (2 min run).

Example 167

7-[(2,3-Dichloro-4-fluorophenyl)carbonyl]-3-(5-methyl-2-furanyl)-5,6,7,8-tetrahydro[1,2,4]triazolo[4,3-a]pyrazine (E167)

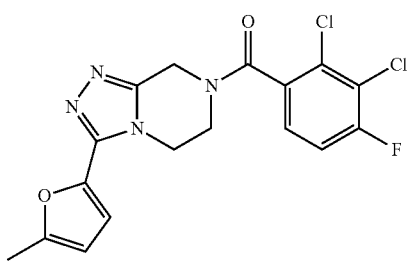 [SMILES: Cc1ccc(-c2nnc3n2CCN(C(=O)c2ccc(F)c(Cl)c2Cl)C3)o1]

Triethyloxonium tetrafluoroborate (197 mg, 1.039 mmol) was added to a solution of the 4-[(2,3-dichloro-4-fluorophenyl)carbonyl]-2-piperazinone (I34) (275 mg, 0.945 mmol) in Dichloromethane (DCM) (6 mL) and the reaction was stirred for 1 h. To this was added the 5-methyl-2-furancarbohydrazide (I85) (159 mg, 1.134 mmol) and the reaction was stirred for 2 h. The solvent was evaporated and 1-butanol (6.00 mL) was added. The mixture was heated at reflux for 3 h. LCMS: Product peak observed. After cooling the solvent was evaporated and the residue was partitioned between water/EtOAc. The organic layer was dried (Na$_2$SO$_4$) and the solvent evaporated to afford a brown oil. This was purified by MDAP to afford a colourless solid of desired material in 38 mg.

LCMS: m/z 394.9 [M+H] @ 0.96 min (2 min run).

Example 168

7-[(2,3-Dichloro-4-fluorophenyl)carbonyl]-3-(3-pyridazinyl)-5,6,7,8-tetrahydro[1,2,4]triazolo[4,3-a]pyrazine (E168)

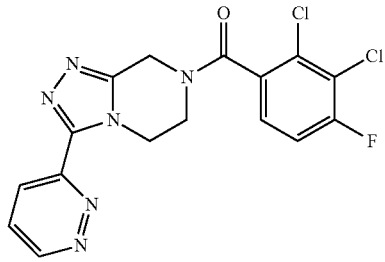 [SMILES: O=C(c1ccc(F)c(Cl)c1Cl)N1CCn2c(nnc2-c2cccnn2)C1]

4-[(2,3-Dichloro-4-fluorophenyl)carbonyl]-2-piperazinone (I34) (0.23 g, 0.790 mmol) was dissolved in Dichloromethane (DCM) (1.975 ml) and triethyloxonium tetrafluoroborate (0.180 g, 0.948 mmol) was added. The solution was left to stir under an argon atmosphere for 40 minutes. A clear solution was formed. 3-pyridazinecarbohydrazide (I23) (0.131 g, 0.948 mmol) was added and the solution was stirred under an argon atmosphere for a further 40 minutes. The solvent was removed under reduced pressure and then 1-butanol (1.975 ml) was added and the solution was left to reflux under an argon atmosphere at 120° C. for 3 hours. The reaction was followed by LCMS. The solvent was removed under reduced pressure. The crude material was purified by flash chromatography (Biotage SP4, 50 g cartridge) with a gradient of MeOH 0-10% in DCM. The solvent was removed under reduced pressure and the isolated material was purified further using MDAP. The columns were combined and the solvent removed under reduced pressure. The material was triturated with ether to afford the desired material in 27 mg.

LCMS: (M+H$^+$)=393, retention time=0.77 (2 minutes run).

Example 169

7-[(2,3-dichloro-4-fluorophenyl)carbonyl]-3-(1,2,4-thiadiazol-5-yl)-5,6,7,8-tetrahydro[1,2,4]triazolo[4,3-a]pyrazine (E169)

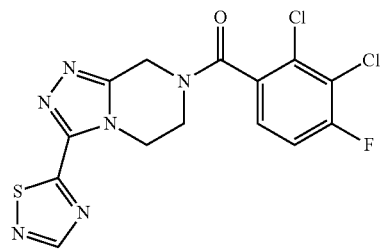 [SMILES: O=C(c1ccc(F)c(Cl)c1Cl)N1CCn2c(nnc2-c2ncns2)C1]

4-[(2,3-Dichloro-4-fluorophenyl)carbonyl]-2-piperazinone (I34) (0.25 g, 0.859 mmol) was dissolved in dichloromethane (DCM) (2.147 ml) and stirred under an argon atmosphere. Triethyloxonium tetrafluoroborate (0.196 g, 1.031 mmol) was added and the solution was left to stir for 40 minutes. A clear solution formed. 1,2,4-Thiadiazole-5-carbohydrazide (I80) (0.149 g, 1.031 mmol) was added and the solution was left to stir under argon for 60 minutes and then the solvent was removed under reduced pressure. 1-Butanol (2.147 ml) was added and the solution was left to reflux at 120° C. under an argon atmosphere for 5 hours. The solvent was removed under reduced pressure to afford a crude light orange solid of 0.56 g. TLC (DCM/MeOH 90:10): showed amide remained but some product had been formed. The crude material was purified by flash chromatography (Biotage SP4, 50 g cartridge) with a gradient of MeOH 0-10% in DCM. The solvent was removed under reduced pressure to afford desired product but still containing some impurities. The isolated material was then purified by MDAP and the solvent was removed under reduced pressure and transferred to a vial. The material was triturated with ether to afford desired product in 5.7 mg.

LCMS: (M+H$^+$)=399, retention time=0.88 (2 minutes run).

Example 170

7-[(2,4-dichloro-3-fluorophenyl)carbonyl]-3-(3-fluoro-2-pyridinyl)-5,6,7,8-tetrahydro[1,2,4]triazolo[4,3-a]pyrazine (E170)

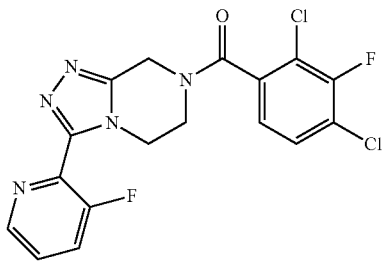 [SMILES: O=C(c1ccc(Cl)c(F)c1Cl)N1CCn2c(nnc2-c2ncccc2F)C1]

4-[(2,4-Dichloro-3-fluorophenyl)carbonyl]-2-piperazinone (I37)(0.3 g, 1.031 mmol) was dissolved in Dichloromethane (DCM) (2.58 ml). triethyloxonium tetrafluoroborate (0.235 g, 1.237 mmol) was added and the solution was left to stir, under an argon atmosphere for 30 minutes. 3-Fluoro-2-pyridinecarbohydrazide (I31) (0.192 g, 1.237 mmol) was added and the solution was left to stir for a further 40 minutes. The solvent was removed under reduced pressure and 1-butanol (2.58 ml) was added. The reaction mixture was left to reflux at 120° C., under an argon atmosphere for 3.5 hours. The solvent was removed under reduced pressure to afford crude product in 0.887 g. The crude material was purified by flash chromatography (Biotage Isolera 4, 50 g cartridge) with a gradient of MeOH 0-10% in DCM. The solvent was removed under reduced pressure to afford 0.254 g of the desired compound. The isolated material was purified using MDAP to afford the purified product in 0.110 g.

LCMS: (M+H$^+$)=410, retention time=0.87 (2 minutes run).

Example 171

3-{7-[(2,4-dichloro-3-fluorophenyl)carbonyl]-5,6,7,8-tetrahydro[1,2,4]triazolo[4,3-a]pyrazin-3-yl}-2-pyridinol (E171)

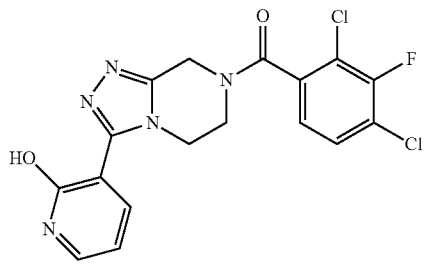 [SMILES: O=C(c1ccc(Cl)c(F)c1Cl)N1CCn2c(nnc2-c2cccnc2O)C1]

Triethyloxonium tetrafluoroborate (215 mg, 1.134 mmol) was added under argon to a solution of 4-[(2,4-dichloro-3-fluorophenyl)carbonyl]-2-piperazinone (I37) (300 mg, 1.031 mmol) in Dichloromethane (DCM) (2.5 mL). The mixture was stirred at room temperature for 1 h 15 min—after 55 min, the mixture became clear. 2-Hydroxy-3-pyridinecarbohydrazide (I92) (189 mg, 1.237 mmol) was added to the solution and the mixture was stirred at room temperature for one day. The solvent was evaporated under reduced pressure and the residue was dissolved in tert-butanol (2.500 mL).

The mixture was stirred at reflux for 3 h and the solvent was evaporated under reduced pressure. The residue was dissolved into ethyl acetate, washed 3 times with water and twice with brine. The organic layer was dried over MgSO$_4$ and concentrated under reduced pressure. The product geliefied in DMSO/MeCN 1:1. The gel was washed with Et$_2$O and the filtrate was evaporated. The crude product was purified by MDAP. The obtained product was dried overnight to afford the desired product in 6.55 mg as a white powder.

LCMS m/z 407.8 [M+H] @ 0.72 min (2 min run).

Example 172

7-[(2,4-dichloro-3-fluorophenyl)carbonyl]-3-(4-methyl-2-pyridinyl)-5,6,7,8-tetrahydro[1,2,4]triazolo[4,3-a]pyrazine (E172)

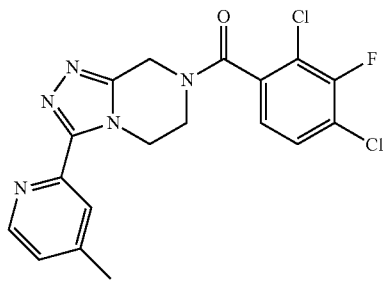 [SMILES: Cc1ccnc(-c2nnc3n2CCN(C(=O)c2ccc(Cl)c(F)c2Cl)C3)c1]

Triethyloxonium tetrafluoroborate (314 mg, 1.654 mmol) was added under argon to a solution of 4-[(2,4-dichloro-3-fluorophenyl)carbonyl]-2-piperazinone (I37)(481 mg, 1.654 mmol) in Dichloromethane (DCM) (4 ml). The reaction was

Example 173

7-[(2,4-dichloro-3-fluorophenyl)carbonyl]-3-(2-pyridinyl)-5,6,7,8-tetrahydro[1,2,4]triazolo[4,3-a]pyrazine (E173)

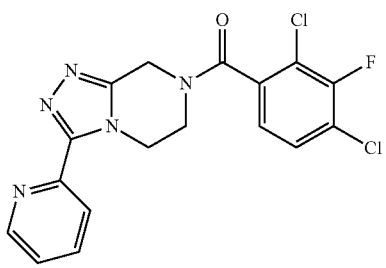

To a suspension of 4-[(2,4-dichloro-3-fluorophenyl)carbonyl]-2-piperazinone (I37) (0.5 g, 1.718 mmol) in anhydrous Dichloromethane (DCM) (4.29 ml) was added triethyloxonium tetrafluoroborate (0.359 g, 1.889 mmol) and the resulting mixture was stirred overnight at room temperature under an atmosphere of argon. The suspension turned to a solution and 2-picolinyl hydrazide (0.259 g, 1.889 mmol, commercially available from e.g. TimTec, Ryan Scientific or AKos Consulting) was added. LCMS after 1 hour showed it was mostly the desired intermediate. The solvent was evaporated at the buchi and the residue was taken up in 1-butanol (4.29 ml) and heated at reflux (130° C.). LCMS after circa 3 hours showed complete conversion to the desired product. It was concentrated at the buchi and the crude material (circa 1 g) was purified by flash chromatography (Biotage SP4, Snap 100 g cartridge) with a gradient of MeOH 0 to 10% in DCM. The isolated material (420 mg) was purified by MDAP to afford the desired product in 294 mg as a white solid.

LC/MS: (M+H)$^+$=392, retention time=0.89 minutes (2 minutes run)

Example 174

7-[(2,4-dichloro-3-fluorophenyl)carbonyl]-3-[4-(methyloxy)-2-pyridinyl]-5,6,7,8-tetrahydro[1,2,4]triazolo[4,3-a]pyrazine (E174)

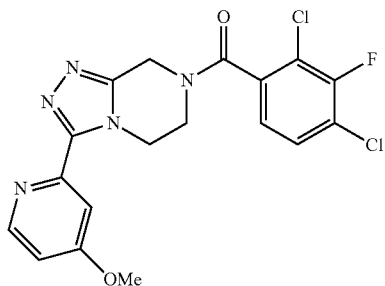

To a suspension of 4-[(2,4-dichloro-3-fluorophenyl)carbonyl]-2-piperazinone (I37) (0.25 g, 0.859 mmol) in anhydrous Dichloromethane (DCM) (2.147 ml) was added triethyloxonium tetrafluoroborate (0.179 g, 0.945 mmol) and the mixture was stirred overnight at room temperature under argon. The white suspension turned to a solution and 4-(methyloxy)-2-pyridinecarbohydrazide (0.158 g, 0.945 mmol, commercially available from e.g. Matrix Scientific, Anichem or 3B Scientific) was added at once. It was a suspension at first but straight after it changed to a yellow solution. After ½ hour a precipitate formed again. LCMS showed that the major product was the intermediate and very little unreacted starting amide was present.

The solvent was removed under vacuum and the residue was taken up in 1-butanol (2.147 ml) and refluxed for 3 hours. LCMS showed complete conversion to the desired compound. It was concentrated in vacuo and the crude (490 mg) was purified by flash chromatography (Biotage SP4, Snap 100 g cartridge) with a gradient of MeOH 0 to 10% in DCM and then by MDAP. The isolated material appeared to contain some formic acid. It was then applied to a 5 g SCX column, washed with MeOH and eluted with NH$_3$ (2M in MeOH) to isolate the desired product in 160 mg as a white solid.

LC/MS: (M+H)$^+$=422, retention time=0.92 minutes (2 minutes run).

Example 175

2-{7-[(2,4-dichloro-3-fluorophenyl)carbonyl]-5,6,7,8-tetrahydro[1,2,4]triazolo[4,3-a]pyrazin-3-yl}-3-pyridinol (E175)

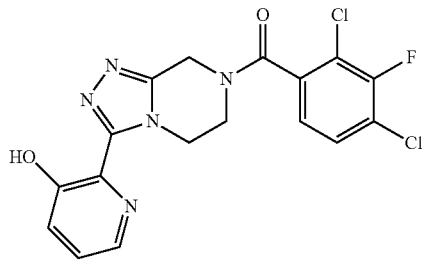 [SMILES: O=C(c1ccc(Cl)c(F)c1Cl)N1CCn2c(nnc2-c2ncccc2O)C1]

Triethyloxonium tetrafluoroborate (341 mg, 1.795 mmol) was added under argon to a solution of 4-[(2,4-dichloro-3-fluorophenyl)carbonyl]-2-piperazinone (I37) (475 mg, 1.632 mmol) in dry Dichloromethane (DCM) (4 mL). The mixture was stirred at room temperature for 1 hour 15 min—the solution was clear. 3-hydroxy-2-pyridinecarbohydrazide (I93) (300 mg, 1.958 mmol) was added under argon. The reaction was stirred at room temperature overnight. The solvent was evaporated under reduced pressure and the remaining residue was dissolved in 1-butanol (4.00 mL). The mixture was stirred at reflux 1 day. The solvent was evaporated under reduced pressure. The remaining residue was dissolved into ethyl acetate (75 mL), extracted with water (3×10 mL) and with brine (2×10 mL). The organic layer was dried over MgSO₄ and concentrated under reduced pressure. The crude product was purified by MDAP. The resulting solid was triturated in diethyl ether (15 mL) and dried under vacuum at 50° C. for 3 days to afford the desired product in 9.0 mg as a pinkish powder.

LCMS m/z 408.18 [M+H] @ 1.03 min (2 min run).

Example 176

7-[(2,4-dichloro-3-fluorophenyl)carbonyl]-3-[6-(methyloxy)-2-pyridinyl]-5,6,7,8-tetrahydro[1,2,4]triazolo[4,3-a]pyrazine (E176)

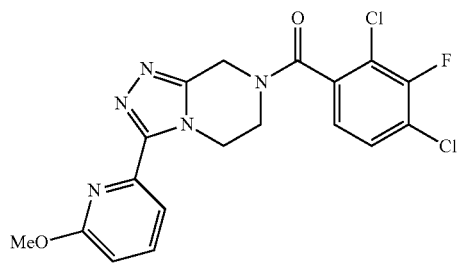 [SMILES: COc1cccc(-c2nnc3n2CCN(C(=O)c2ccc(Cl)c(F)c2Cl)C3)n1]

4-[(2,4-Dichloro-3-fluorophenyl)carbonyl]-2-piperazinone (I37)(0.25 g, 0.859 mmol) was dissolved in Dichloromethane (DCM) (2.147 ml) and triethyloxonium tetrafluoroborate (0.196 g, 1.031 mmol) was added. The solution was left to stir under an argon atmosphere for 18 hours. 6-(Methyloxy)-2-pyridinecarbohydrazide (I95) (0.172 g, 1.031 mmol) was added and the solution was left to stir under argon for a further 60 minutes. The Dichloromethane was removed under reduced pressure and 1-butanol (2.147 ml) was added and the reaction mixture was left at reflux for 3 hours. LCMS showed the product had formed so the solvent was removed under reduced pressure and the crude material was purified by flash chromatography (Biotage Isolera 4, 25 g cartridge) with a gradient of methanol 0-10% in Dichloromethane. The solvent was removed under reduced pressure to afford 0.285 g of material that was further purified using MDAP. The solvent was removed to afford the purified desired product in 0.108 g.

LCMS: (M+H⁺)=421, retention time=0.98 (2 minutes run).

Example 177

7-[(2,4-dichloro-3-fluorophenyl)carbonyl]-3-(4-methyl-2-pyrimidinyl)-5,6,7,8-tetrahydro[1,2,4]triazolo[4,3-a]pyrazine (E177)

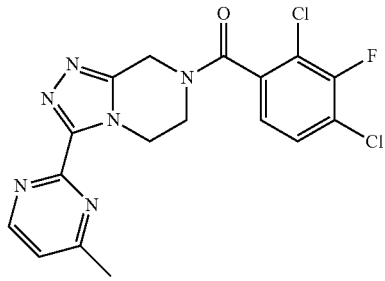 [SMILES: Cc1ccnc(-c2nnc3n2CCN(C(=O)c2ccc(Cl)c(F)c2Cl)C3)n1]

4-[(2,4-Dichloro-3-fluorophenyl)carbonyl]-2-piperazinone (I37)(0.250 g, 0.859 mmol) was dissolved in dichloromethane (DCM) (2.147 ml) and triethyloxonium tetrafluoroborate (0.196 g, 1.031 mmol) was added. The solution was left to stir at room temperature under argon for 18 hours. 4-Methyl-2-pyrimidine carboximidohydrazide (I99) (0.156 g, 1.031 mmol) was dissolved in 1-butanol (2.147 ml) and this was added to the reaction mixture and this was left to stir under argon for a further 60 minutes. The dichloromethane was removed under reduced pressure and the reaction mixture was left at reflux for 4 hours. The solvent was removed under reduced pressure to afford a crude product of 0.690 g. The crude material was purified by flash chromatography (Biotage Isolera 4, 50 g cartridge) with a gradient of methanol 0-10% in Dichloromethane. The solvent was removed under reduced pressure to afford 0.223 g of material which was further purified using MDAP. The solvent was removed under reduced pressure to afford 0.090 g of crude material that was dissolved in methanol and loaded onto a 5 g SCX column. The column was washed with methanol and the desired compound was eluted off using 2M ammonia in methanol. The solvent was removed under reduced pressure to afford the purified product in 0.075 g.

LCMS: (M+H⁺)=406, retention time=0.86 (2 minutes run).

Example 178

7-[(2,4-dichloro-3-fluorophenyl)carbonyl]-3-(5-isothiazolyl)-5,6,7,8-tetrahydro[1,2,4]triazolo[4,3-a]pyrazine (E178)

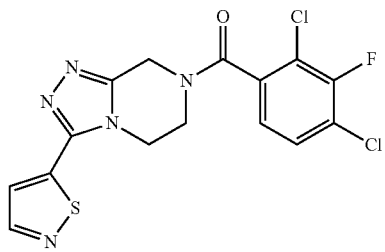 [SMILES: O=C(c1ccc(Cl)c(F)c1Cl)N1CCn2c(nnc2-c2ccns2)C1]

A solution of 4-[(2,4-dichloro-3-fluorophenyl)carbonyl]-2-piperazinone (I37)(244 mg, 0.839 mmol) in dry dichloromethane (DCM) (2098 μl) was stirred at room temperature under an atmosphere of argon. Triethyloxonium tetrafluoroborate (175 mg, 0.923 mmol) was added and the resulting mixture was stirred for ¾ hours. After this time, 5-isothiazolecarbohydrazide (I84) (153 mg, 1.069 mmol) was added and the resulting mixture was stirred at room temperature for 60 hours (over the weekend). 1-Butanol (2098 μl) was added and the reaction mixture was heated to 110° C. for 2 hours. The solution was allowed to cool to room temperature and the solvent was removed under reduced pressure. The residue was partitioned between DCM (approx 40 ml) and NaHCO$_3$ (saturated aqueous solution approx. 20 ml). The organic phases were dried over MgSO$_4$, filtered and concentrated under reduced pressure to give a pale yellow coloured solid. The solid was purified using MDAP to give a white coloured solid.

LCMS m/z 397.93 [M+H] @ 0.83 min (2 min run).

Example 179

7-[(2,4-Dichloro-3-fluorophenyl)carbonyl]-3-(4-methyl-1,2,3-thiadiazol-5-yl)-5,6,7,8-tetrahyro[1,2,4]triazolo[4,3-a]pyrazine (E179)

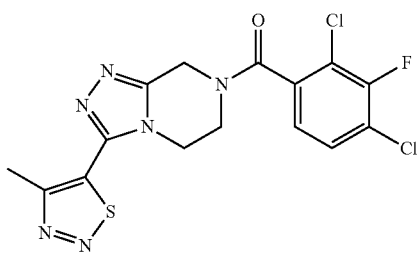 [SMILES: Cc1nnsc1-c1nnc2n1CCN(C(=O)c1ccc(Cl)c(F)c1Cl)C2]

Triethyloxonium tetrafluoroborate (330 mg, 1.738 mmol) was added to a suspension of 4-[(2,4-dichloro-3-fluorophenyl)carbonyl]-2-piperazinone (I37) (460 mg, 1.580 mmol) in dry Dichloromethane (DCM) (3.9 ml). The reaction mixture was stirred at room temperature 45 mins—mixture became clear. 4-Methyl-1,2,3-thiadiazole-5-carbohydrazide (300 mg, 1.896 mmol, commercially available) was added and the resulting reaction mixture was stirred at room temperature 2 h 10 min. The solvent was evaporated under reduced pressure. The residue was dissolved in 1-butanol (3.90 ml) and the reaction mixture was stirred at reflux for 17 h. The reaction mixture was diluted in ethyl acetate (150 mL) and washed with water (2×25 mL), sat. NaHCO$_3$ (25 mL) and brine (2×25 mL). The resulting organic layer was dried over MgSO$_4$ and concentrated under reduced pressure. The crude product was purified by MDAP (basic method). The resulting residue was triturated with ether (5×2 mL) and then dried under vacuum at 50° C. to afford the desired product in 117.4 mg as a cream powder.

LCMS m/z 412.7 [M+H] @ 0.92 min (2 min run).

Example 180

7-{[2-Chloro-3-(trifluoromethyl)phenyl]carbonyl}-3-(2-pyridinyl)-5,6,7,8-tetrahydro[1,2,4]triazolo[4,3-a]pyrazine-d$_1$ (E180)

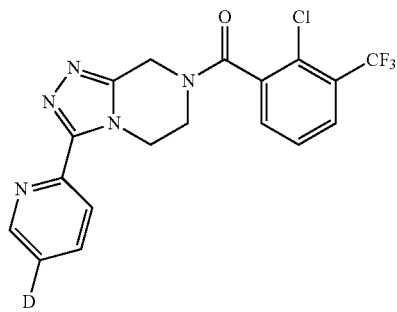 [SMILES: [2H]c1ccc(-c2nnc3n2CCN(C(=O)c2cccc(C(F)(F)F)c2Cl)C3)nc1]

To a suspension of 4-{[2-chloro-3-(trifluoromethyl)phenyl]carbonyl}-2-piperazinone (I1)(0.3 g, 0.978 mmol) in anhydrous Dichloromethane (DCM) (2.446 ml) was added triethyloxonium tetrafluoroborate (0.204 g, 1.076 mmol) and the mixture was stirred at room temperature under argon for 1 hour before 2-pyridinecarbohydrazide-d1 (I103) (0.149 g, 1.076 mmol), containing 4.8% of $^1$H isotope instead of deuterium, was added in one batch. The suspension was stirred for ½ hour and LCMS showed that the major product was the desired intermediate. The solvent was removed under vacuum and the residue was taken up in 1-butanol (2.446 ml) and refluxed for 3 hours. LCMS showed complete conversion to the desired compound. It was concentrated in vacuo and the crude (700 mg) was purified by flash chromatography (Biotage SP4, Snap 50 g cartridge) with a gradient of MeOH 0 to 10% in DCM and then by MDAP. The isolated material was then applied to a 5 g SCX column, washed with MeOH and eluted with NH$_3$ (2M in MeOH) to isolate the free base of the desired product in 165 mg as a white solid.

LCMS m/z 408.7 [M+H] @ 0.91 min (2 min run).

Example 181

7-{[2-Chloro-3-(trifluoromethyl)phenyl]carbonyl}-3-(2-pyridinyl)-5,6,7,8-tetrahydro[1,2,4]triazolo[4,3-a]pyrazine-d$_1$ (E181)

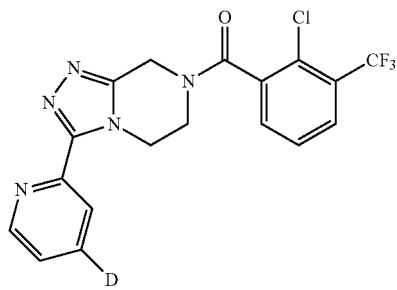 [SMILES: [2H]c1ccnc(-c2nnc3n2CCN(C(=O)c2cccc(C(F)(F)F)c2Cl)C3)c1]

To a suspension of 4-{[2-chloro-3-(trifluoromethyl)phenyl]carbonyl}-2-piperazinone (I1)(0.3 g, 0.978 mmol) in anhydrous Dichloromethane (DCM) (2.446 ml) was added triethyloxonium tetrafluoroborate (0.204 g, 1.076 mmol) and the mixture was stirred at room temperature under argon for 1 hour before 2-pyridinecarbohydrazide-d1 (I105) (0.149 g, 1.076 mmol) was added in one batch. After ½ hour LCMS showed that the major product was the desired intermediate. The solvent was removed under vacuum and the residue was taken up in 1-butanol (2.446 ml) and refluxed for 3 hours. LCMS showed complete conversion to the desired compound. It was concentrated at thand the crude (700 mg) was purified by flash chromatography (Biotage SP4, Snap 50 g cartridge) with a gradient of MeOH 0 to 10% in DCM and then by MDAP. The isolated material was then applied to a 5 g SCX column, washed with MeOH and eluted with $NH_3$ (2M in MeOH) to isolate the free base of the desired product in 150 mg as a white solid.

LC/MS: $(M+H)^+$=409, retention time=0.91 minutes (2 minutes run).

Example 182

7-[(2,4-Dichloro-3-fluorophenyl)carbonyl]-3-(2-pyridinyl)-5,6,7,8-tetrahydro[1,2,4]triazolo[4,3-a]pyrazine-$d_1$ (E182)

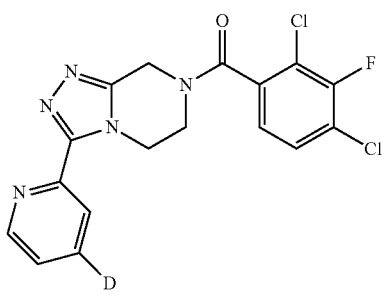 [SMILES: [2H]c1ccnc(-c2nnc3n2CCN(C(=O)c2ccc(Cl)c(F)c2Cl)C3)c1]

To a suspension of 4-[(2,4-dichloro-3-fluorophenyl)carbonyl]-2-piperazinone (I37)(0.25 g, 0.859 mmol) in anhydrous Dichloromethane (DCM) (2.147 ml) was added triethyloxonium tetrafluoroborate (0.179 g, 0.945 mmol) and the mixture was stirred overnight at room temperature under argon. The white suspension turned to a solution and 2-pyridinecarbohydrazide-d1 (I105)(0.131 g, 0.945 mmol) was added in one batch. It was a suspension at first but straight after it changed to a yellow solution. After ½ hour a precipitate formed again. LCMS showed that the major product was the desired intermediate. The solvent was removed under vacuum and the residue was taken up in 1-butanol (2.147 ml) and refluxed for 3 hours. LCMS showed complete conversion to the desired compound. It was concentrated at the buchi and the crude (700 mg) was purified by flash chromatography (Biotage SP4, Snap 50 g cartridge) with a gradient of MeOH 0 to 10% in DCM and then by MDAP. The isolated material was then applied to a 5 g SCX column, washed with MeOH and eluted with $NH_3$ (2M in MeOH) to isolate the free base of the desired product in 139 mg as a white solid.

LC/MS: $(M+H)^+$=393, retention time=0.93 minutes (2 minutes run).

Example 183

7-[(2,4-Dichloro-3-fluorophenyl)carbonyl]-3-(2-pyridinyl)-5,6,7,8-tetrahydro[1,2,4]triazolo[4,3-a]pyrazine-$d_1$ (E183)

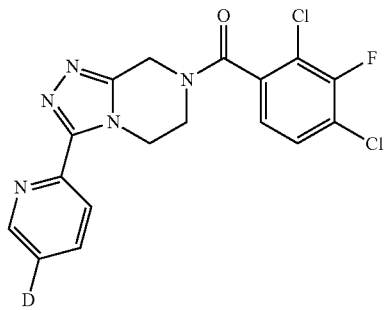

To a suspension of 4-[(2,4-dichloro-3-fluorophenyl)carbonyl]-2-piperazinone (I37)(0.25 g, 0.859 mmol) in anhydrous dichloromethane (DCM) (2.147 ml) was added triethyloxonium tetrafluoroborate (0.179 g, 0.945 mmol) and the mixture was stirred overnight at room temperature under argon. The white suspension turned to a solution and 2-pyridinecarbohydrazide-$d_1$ (I103)(0.131 g, 0.945 mmol) was added in one batch. It was a suspension at first but straight after it changed to a yellow solution. After ½ hour a precipitate formed again. LCMS showed that the major product was the desired intermediate. The solvent was removed under vacuum and the residue was taken up in 1-butanol (2.147 ml) and refluxed for 3 hours. LCMS showed complete conversion to the desired compound. It was concentrated at the buchi and the crude (700 mg) was purified by flash chromatography (Biotage SP4, Snap 50 g cartridge) with a gradient of MeOH 0 to 10% in DCM and then by MDAP. The isolated material was then applied to a 5 g SCX column, washed with MeOH and eluted with $NH_3$ (2M in MeOH) to isolate the free base of the desired compound as a white solid but it was still impure and it was purified by MDAP twice more (standard run and extended method). It was then applied to a 5 g SCX to isolate the free base of the desired product in 100 mg.

LC/MS: $(M+H)^+$=393, retention time=0.89 minutes (2 minutes run).

Example 184

7-[(2,4-Dichloro-3-fluorophenyl)carbonyl]-3-(1H-pyrazol-1-yl)-5,6,7,8-tetrahydro[1,2,4]triazolo[4,3-a]pyrazine (E184)

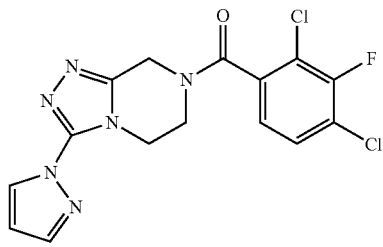 [SMILES: O=C(c1ccc(Cl)c(F)c1Cl)N1CCn2c(nnc2-n2cccn2)C1]

A mixture of 3-(1H-pyrazol-1-yl)-5,6,7,8-tetrahydro[1,2,4]triazolo[4,3-a]pyrazine (I107)(14.3 mg, 0.075 mmol) and triethylamine (0.016 ml, 0.113 mmol) was stirred in Dichloromethane (DCM) (1 ml) at 0° C. and 2,4-dichloro-3-fluorobenzoyl chloride (18.81 mg, 0.083 mmol) in DCM (0.5 ml) was added and the mixture was stirred at 0° C. After 1 h, sat. NaHCO$_3$ (1 ml) and ethyl acetate (30 ml) were added and the product was extracted into ethyl acetate. The organic layer was dried (Na$_2$SO$_4$) and evaporated. Chromatography (SP4 50-100% ethyl acetate in isohexane) gave a crude product which was passed through an SCX column (elution with 2M NH$_3$ in MeOH) to give clean desired product as a gum. This was triturated with ether/hexane to give a white solid in 22.4 mg.

LC-MS MH$^+$=381/383 @ 0.87 min (2 min run).

Example 185

7-[(2,4-Dichloro-3-fluorophenyl)carbonyl]-3-(1,3-thiazol-5-yl)-5,6,7,8-tetrahydro[1,2,4]triazolo[4,3-a]pyrazine (E185)

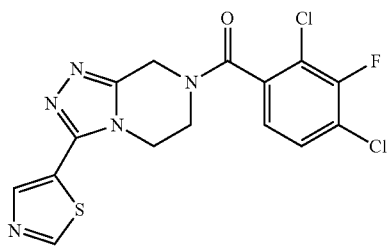 [SMILES: O=C(c1ccc(Cl)c(F)c1Cl)N1CCn2c(nnc2-c2cncs2)C1]

4-[(2,4-Dichloro-3-fluorophenyl)carbonyl]-2-piperazinone (I37) (263 mg, 0.903 mmol) was suspended in dichloromethane (DCM) (2 mL) before treating with triethyloxonium tetrafluoroborate (189 mg, 0.994 mmol) and stirring for 45 mins at RT under argon before adding 1,3-thiazole-5-carbohydrazide (I109)(155 mg, 1.084 mmol) and stirring for 18 hours (overnight). The DCM was removed and the residue was suspended in 1-butanol (2.0 mL) and heated at 110° C. for 3 hours. The reaction was cooled to RT, diluted with DCM (30 ml) and washed with saturated sodium bicarbonate solution (20 ml). The aqueous layers were extracted with DCM (2×20 ml), combined, washed with brine (20 ml), dried (MgSO$_4$), filtered and evaporated to afford a yellow gum of crude product which was purified by MDAP. Desired fractions were isolated and solvent evaporated to afford a colourless gum which solidified when triturated with Et$_2$O to afford a pale yellow solid of desired product in 100 mg.

LCMS m/z 397.99 [M+H] @ 0.79 min (2 min run).

Example 186

7-[(2,4-Dichloro-3-fluorophenyl)carbonyl]-3-(1,2,4-thiadiazol-5-yl)-5,6,7,8-tetrahydro[1,2,4]triazolo[4,3-a]pyrazine (E186)

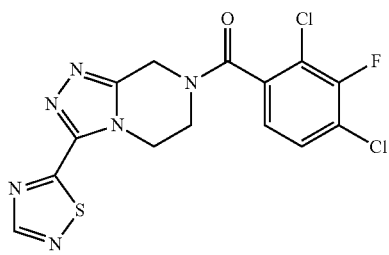

A mixture of 3-(1,2,4-thiadiazol-5-yl)-5,6,7,8-tetrahydro[1,2,4]triazolo[4,3-a]pyrazine (I115) (30 mg, 0.144 mmol) and triethylamine (0.030 mL, 0.216 mmol) in Dichloromethane (DCM) (2 mL) was stirred at room temperature. 2,4-Dichloro-3-fluorobenzoyl chloride (36.0 mg, 0.158 mmol) in DCM (0.5 ml) was added and stirring continued at room temperature. After 30 mins, 2 drops MeOH were added followed by sat. NaHCO$_3$ solution (3 ml) and ethyl acetate (30 ml). The product was extracted into the ethyl acetate which was dried (Na$_2$SO$_4$) and concentrated. The product was purified by high pH MDAP to give desired product as a white solid after evaporation of the fractions.

LCMS: MH$^+$=398/400 @ 0.94 min (2 min run).

Example 187

7-[(2,4-Dichloro-3-fluorophenyl)carbonyl]-3-(1,3-thiazol-2-yl)-5,6,7,8-tetrahydro[1,2,4]triazolo[4,3-a]pyrazine (E187)

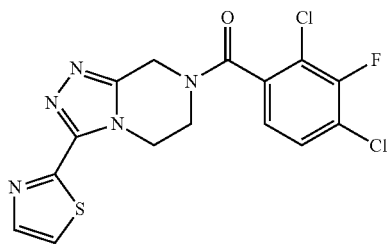

Triethyloxonium tetrafluoroborate (144 mg, 0.756 mmol) was added to a suspension of 4-[(2,4-dichloro-3-fluorophenyl)carbonyl]-2-piperazinone (I37) (200 mg, 0.687 mmol) in dry dichloromethane (DCM) (1.7 ml). The reaction was stirred at room temperature 1 h—everything dissolved. 1,3-thiazole-2-carbohydrazide (I50)(118 mg, 0.824 mmol) was added and the mixture was stirred at room temperature overnight. The solvent was evaporated under reduced pressure and 1-butanol (1.700 ml) was added to the residue. The resulting reaction mixture was stirred at reflux for 9 h. The reaction mixture was diluted with ethyl acetate (I25 mL) and washed with water (2×25 mL), sat. NaHCO$_3$ (25 mL) and brine (2×25 mL). The resulting organic layer was dried over MgSO$_4$ and concentrated under reduced pressure. The crude product was purified by MDAP (acidic method). The resulting residue was triturated with Et₂O and dried 3 days at 50° C. under vacuum to afford desired product in 30.5 mg as a white solid.

LCMS m/z 397.7 [M+H] @ 0.95 min (2 min run).

Example 188

7-[(2,4-Dichloro-3-fluorophenyl)carbonyl]-3-(5-methyl-1,3-thiazol-2-yl)-5,6,7,8-tetrahydro[1,2,4]triazolo[4,3-a]pyrazine (E188)

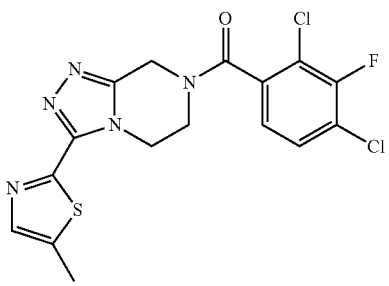 [SMILES: Cc1cnc(-c2nnc3n2CCN(C(=O)c2ccc(Cl)c(F)c2Cl)C3)s1]

A solution of 4-[(2,4-dichloro-3-fluorophenyl)carbonyl]-2-piperazinone (I37) (329 mg, 1.13 mmol) in dry dichloromethane (DCM) (1413 μl) was stirred at room temperature under an atmosphere of argon. Triethyloxonium tetrafluoroborate (236 mg, 1.243 mmol) was added and the mixture was stirred for 1 hour. After this time, 5-methyl-1,3-thiazole-2-carbohydrazide (I117) (224 mg, 1.425 mmol) was added and the mixture was stirred for a further 60 hours (over weekend). The solvent was removed under reduced pressure. The resulting residue was dissolved in 1-butanol (1413 μl) and the solution was heated to 110° C. for 4 hours. The solution was concentrated under reduced pressure and the residue dissolved in DCM (approx. 40 ml). The organics were washed with NaHCO₃ (sat. aqueous solution approx. 20 ml), before being dried over MgSO₄, filtered and concentrated under reduced pressure to give a yellow coloured oil. The oil was chromatographed [SiO₂, 0-10% MeOH in DCM] then further purified using MDAP (formic acid method) to give a white coloured solid of desired product in 74 mg.

LCMS m/z 411.98 [M+H] @ 0.98 min (2 min run).

Example 189

7-[(2,4-Dichloro-3-fluorophenyl)carbonyl]-3-(1,2,3-thiadiazol-4-yl)-5,6,7,8-tetrahydro[1,2,4]triazolo[4,3-a]pyrazine (E189)

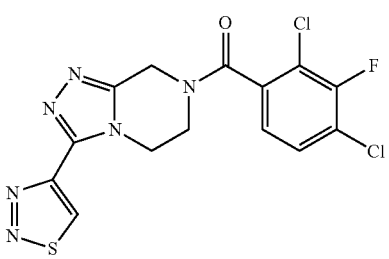 [SMILES: O=C(c1ccc(Cl)c(F)c1Cl)N1CCn2c(nnc2-c2csnn2)C1]

Triethyloxonium tetrafluoroborate (363 mg, 1.908 mmol) was added to a suspension of 4-[(2,4-dichloro-3-fluorophenyl)carbonyl]-2-piperazinone (I37)(505 mg, 1.735 mmol) in dry dichloromethane (DCM) (4.2 ml). The reaction mixture was stirred at room temperature 45 mins—until everything was dissolved. 1,2,3-Thiadiazole-4-carbohydrazide (300 mg, 2.082 mmol, commercially available from e.g. Apollo) was added and the resulting mixture was stirred at room temperature for 3 h. DCM was evaporated and the residue was dissolved into 1-butanol (4.2 ml). The reaction mixture was stirred at reflux for 19 h. The mixture was washed with ethyl acetate and washed with water (2×25 mL) and brine (2×25 mL). The resulting organic layer was dried over MgSO₄ and dried under reduced pressure. The crude product was purified by flash chromatography (DCM–10% MeOH in DCM). The residue was triturated with Et₂O and then dried under vacuum at 50° C. for 2 days. The resulting solid was triturated with n-hexane and dried at 50° C. under vacuum 20 h to afford the desired product in 4.71 mg, as a white solid.

LCMS m/z 398.6 [M+H] @ 0.91 min (2 min run).

Example 190

7-[(2,4-Dichloro-3-fluorophenyl)carbonyl]-3-(1,2,5-thiadiazol-3-yl)-5,6,7,8-tetrahydro[1,2,4]triazolo[4,3-a]pyrazine (E190)

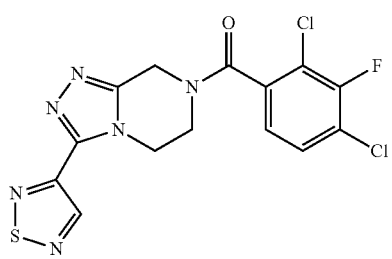

Triethyloxonium tetrafluoroborate (144 mg, 0.756 mmol) was added under argon to a suspension of 4-[(2,4-dichloro-3-fluorophenyl)carbonyl]-2-piperazinone (I37) (200 mg, 0.687 mmol) in dry dichloromethane (DCM) (1.7 ml). The reaction mixture was stirred at room temperature for 1 h—everything dissolved. 1,2,5-thiadiazole-3-carbohydrazide (I119)(119 mg, 0.824 mmol) was added and the mixture was stirred at room temperature overnight. The solvent was evaporated under reduced pressure and 1-butanol (1.700 ml) was added to the residue. The resulting reaction mixture was stirred at reflux for 5 h. The reaction mixture was diluted with ethyl acetate (I25 mL) and washed with water (2×25 mL), sat. NaHCO₃ (25 mL) and brine (2×25 mL). The resulting organic layer was dried over MgSO₄ and concentrated under reduced pressure. The crude product was purified by MDAP (basic method). The resulting residue was triturated with Et₂O and dried 3 days at 50° C. under vacuum. The resulting solid was triturated with n-hexane and dried at 50° C. under vacuum for 20 h. The resulting solid was triturated again with n-hexane and dried at 50° C. under vacuum overnight to afford the desired product in 37.5 mg as a white powder.

LCMS m/z: 398.6 [M+H] @ 0.96 min (2 min run).

Example 191

7-[(2,4-Dichloro-3-fluorophenyl)carbonyl]-3-(4-methyl-1,3-thiazol-2-yl)-5,6,7,8-tetrahydro[1,2,4]triazolo[4,3-a]pyrazine (E191)

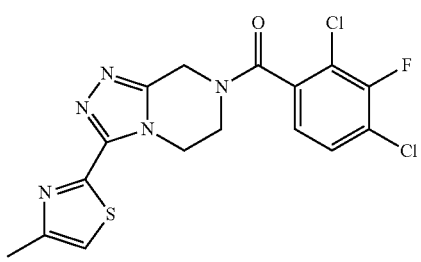 [SMILES: Cc1csc(-c2nnc3n2CCN(C(=O)c2ccc(Cl)c(F)c2Cl)C3)n1]

A mixture of 4-[(2,4-dichloro-3-fluorophenyl)carbonyl]-2-piperazinone (I37) (170 mg, 0.585 mmol) in dry dichloromethane (DCM) (1.463 ml) was stirred at room temperature under an atmosphere of argon. Triethyloxonium tetrafluoroborate (122 mg, 0.644 mmol) was added and the resulting mixture was stirred for 2½ hours. After this time, 4-methyl-1,3-thiazole-2-carbohydrazide (I121)(115 mg, 0.732 mmol) was added and the solution was stirred for a further 18 hours at room temperature. The solution was concentrated under reduced pressure and then redissolved in 1-butanol (1.463 ml) and the resulting solution was heated at reflux for 4 hours. The solution was cooled to room temperature, diluted with DCM (approx. 50 ml) and washed with water (2× approx. 20 ml). The organics were dried over MgSO₄, filtered and concentrated under reduced pressure to give a yellow coloured oil. The residue was purified using MDAP and dried under vacuum for 4 days to give the desired product in 42 mg.

LCMS Rt=0.97 mins (2 minute acidic method), [M+H]⁺ 412, 415.

Example 192

7-[(2,3-Dichlorophenyl)carbonyl]-3-(1,2,4-thiadiazol-5-yl)-5,6,7,8-tetrahydro [1,2,4]triazolo[4,3-a]pyrazine (E192)

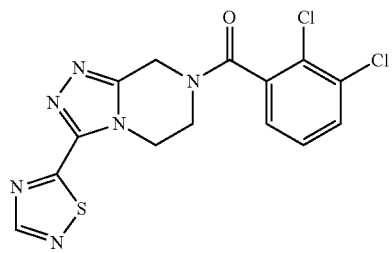 [SMILES: O=C(c1cccc(Cl)c1Cl)N1CCn2c(nnc2-c2ncns2)C1]

A mixture of 3-(1,2,4-thiadiazol-5-yl)-5,6,7,8-tetrahydro [1,2,4]triazolo[4,3-a]pyrazine (I115) (50 mg, 0.240 mmol) and triethylamine (0.050 mL, 0.360 mmol) in Dichloromethane (DCM) (1.5 mL) was treated with 2,3-dichlorobenzoyl chloride (55.3 mg, 0.264 mmol, commercially available) and stirred at room temp for 1 hr. After 1 hr, 2 drops of methanol and then NaHCO₃ solution (5 ml) and ethyl acetate (30 ml) were added and the product was extracted into the ethyl acetate which was dried (Na₂SO₄) and concentrated. Purification by high pH MDAP gave desired material as a white solid in 76 mg.

LCMS m/z: 380.6 [M+H] @ 0.89 min (2 min run).

Example 193

7-[(3-Chloro-4-fluoro-2-methylphenyl)carbonyl]-3-(1,2,4-thiadiazol-5-yl)-5,6,7,8-tetrahydro[1,2,4]triazolo[4,3-a]pyrazine (E193)

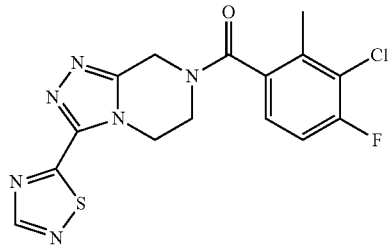 [SMILES: Cc1c(C(=O)N2CCn3c(nnc3-c3ncns3)C2)ccc(F)c1Cl]

A mixture of 3-(1,2,4-thiadiazol-5-yl)-5,6,7,8-tetrahydro [1,2,4]triazolo[4,3-a]pyrazine (I115) (50 mg, 0.240 mmol) and triethylamine (0.050 mL, 0.360 mmol) in DCM (1.5 ml) was treated with 3-chloro-4-fluoro-2-methylbenzoyl chloride (I58) (54.7 mg, 0.264 mmol) in DCM (0.5 ml) and stirred at room temp for 1 h. After 1 h, 2 drops of methanol and then NaHCO₃ solution (5 ml) and ethyl acetate (30 ml) were added. The product was extracted into the ethyl acetate which was dried (Na₂SO₄) and concentrated. Purification by high pH MDAP gave desired product as a white solid in 44 mg.

LC-MS see MH+ =379/381 @ 0.92 min (2 min run).

Note: This specification does not include an Example 194.

Example 195

7-[(3-Chloro-2-methylphenyl)carbonyl]-3-(1,2,4-thiadiazol-5-yl)-5,6,7,8-tetrahydro[1,2,4]triazolo[4,3-a]pyrazine (E195)

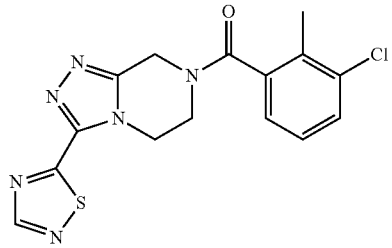 [SMILES: Cc1c(Cl)cccc1C(=O)N1CCn2c(nnc2-c2ncns2)C1]

A mixture of 3-(1,2,4-thiadiazol-5-yl)-5,6,7,8-tetrahydro [1,2,4]triazolo[4,3-a]pyrazine (I115) (50 mg, 0.240 mmol) and triethylamine (0.050 mL, 0.360 mmol) in DCM (1.5 ml) was treated with 3-chloro-2-methylbenzoyl chloride (I130) (49.9 mg, 0.264 mmol) in DCM (0.5 ml) and stirred at room temp for 1 h. After 1 h, 2 drops of methanol and then NaHCO₃ solution (5 ml) and ethyl acetate (30 ml) were added. The product was extracted into the ethyl acetate which was dried (Na₂SO₄) and concentrated. Purification by high pH MDAP gave the desired product as a white solid in 66 mg.

LC-MS see MH+=361/363 @ 0.90 min (2 min run).

Note: This specification does not include an Example 196.

Example 197

7-[(2,4-Dichloro-3-fluorophenyl)carbonyl]-3-(5-methyl-1,3-thiazol-4-yl)-5,6,7,8-tetrahydro[1,2,4]triazolo[4,3-a]pyrazine (E197)

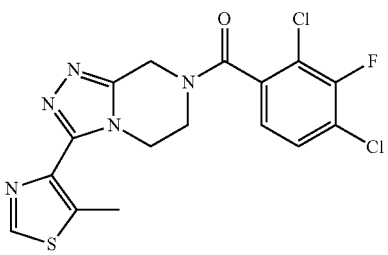 [SMILES: Cc1scnc1-c1nnc2n1CCN(C(=O)c1ccc(Cl)c(F)c1Cl)C2]

A solution of 4-[(2,4-dichloro-3-fluorophenyl)carbonyl]-2-piperazinone (I37)(250 mg, 0.859 mmol) in dry dichloromethane (DCM) (2147 µl) was stirred at room temperature under an atmosphere of argon. Triethyloxonium tetrafluoroborate (179 mg, 0.945 mmol) was added to the stirred solution and the solution was stirred for 2 hours. 5-methyl-1,3-thiazole-4-carbohydrazide (I123) (162 mg, 1.031 mmol) was then added and the resulting solution was stirred for 65 hours (over the weekend), during which time the solvent evaporated. The residue was redissolved in 1-butanol (2147 pl) and the resulting mixture was heated to 110° C. for 3 hours. The solution was allowed to cool to room temperature before being concentrated under reduced pressure to give a yellow coloured oil. The oil was redissolved in DCM (approx. 30 ml) and the organics were subsequently washed with NaHCO₃ (sat. aqueous solution approx. 20 ml) and brine (approx. 20 ml). The organics were dried over MgSO₄, filtered and concentrated under reduced pressure to give a yellow coloured oil. The oil was chromatographed [SiO₂, 0-10% MeOH in DCM] to give a pale yellow coloured oil. The oil was subsequently further purified using MDAP (formic acid method) to give a white coloured solid of desired material in 68 mg.

LCMS Rt=0.91 mins, [M+H]⁺ 412, 416 (2 min run).

Example 198

7-[(2,4-Dichloro-3-fluorophenyl)carbonyl]-3-(1,3-thiazol-2-yl)-5,6,7,8-tetrahydro[1,2,4]triazolo[4,3-a]pyrazine (E198)

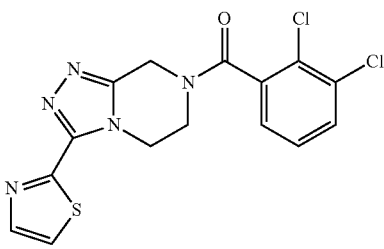

A solution of 4-[(2,3-dichlorophenyl)carbonyl]-2-piperazinone (I3) (200 mg, 0.732 mmol) in dry Dichloromethane (DCM) (3329 µl) was stirred at room temperature under an atmosphere of argon. Trimethyloxonium tetrafluoroborate (137 mg, 0.879 mmol) was added and the resulting mixture was stirred at room temperature for 15 hours (overnight). 1,3-Thiazole-2-carbohydrazide (I51) (157 mg, 1.098 mmol) was added and the resulting mixture was stirred for 90 minutes. After this time, 1-butanol (3329 µl) was added and the mixture was heated to reflux for 2 hour. The DCM was removed under reduced pressure and the resulting solution (containing BuOH) was refluxed for 1 hour. The solution was then allowed to cool to room temperature and stirred for a further 15 hours. The solution was diluted with DCM (approx. 50 ml) and washed sequentially by NaHCO₃ sat. aqueous solution (approx. 20 ml) and water (approx. 20 ml), dried over MgSO₄, filtered and concentrated under reduced pressure to give a pale yellow coloured solid. The solid was triturated with Et₂O and hexane before being chromatographed [SiO₂, MeOH in DCM 0-10%] to give a white coloured solid in 133 mg of desired material.

LCMS Rt=0.84 mins, [M+H]⁺ 380, 384 (2 min run).

Example 199

7-[(2,4-Dichlorophenyl)carbonyl]-3-(1,3-thiazol-2-yl)-5,6,7,8-tetrahydro[1,2,4]triazolo[4,3-a]pyrazine (E199)

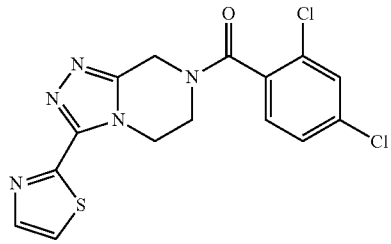

A solution of 4-[(2,4-dichlorophenyl)carbonyl]-2-piperazinone (I6) (0.200 g, 0.732 mmol), Dichloromethane (DCM) (3.21 ml) and trimethyloxonium tetrafluoroborate (0.130 g, 0.879 mmol) was prepared and left to stir overnight. LCMS showed the intermediate imidate had formed so 1,3-thiazole-2-carbohydrazide (I51) (0.157 g, 1.098 mmol) was added and the solution was left to stir for another 2 hours. The Dichloromethane was removed under reduced pressure and 1-butanol (3.21 ml) was added and the reaction mixture was left at reflux overnight. LCMS: (M+H⁺)=379, retention time=0.86 (2 minutes run). The solvent was removed under vacuum to afford a crude product in 0.587 g. The crude material was purified by flash chromatography (Biotage Isolera 4, 25 g cartridge) with a gradient of methanol 0-10% in Dichloromethane, this afforded 0.244 g. The material was further purified using MDAP, to afford the desired product in 0.142 g as a white solid.

LCMS: (M+H⁺)=379, retention time=0.92 (2 minutes run).

Example 200

7-[(3-Chloro-2-methylphenyl)carbonyl]-3-(1,3-thiazol-2-yl)-5,6,7,8-tetrahydro[1,2,4]triazolo[4,3-a]pyrazine (E200)

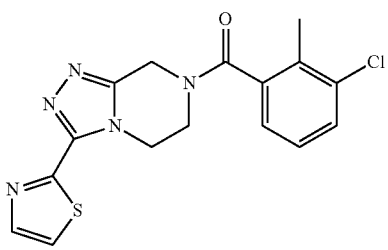

4-[(3-Chloro-2-methylphenyl)carbonyl]-2-piperazinone (I134) (185 mg, 0.732 mmol) was suspended in dry Dichloromethane (DCM) (3 mL) before treating with trimethyloxonium tetrafluoroborate (137 mg, 0.879 mmol) and stirring for 16 hours at RT, under argon before adding 1,3-thiazole-2-carbohydrazide (I51) (157 mg, 1.098 mmol) and stirring for a further 4 hours. 1-Butanol (3.00 mL) was added then DCM was removed by evaporation and the residue was heated at 110° C. for 3 hours. The reaction was cooled to RT overnight and then worked up by diluting with DCM (50 ml), washing with saturated sodium bicarbonate solution (50 ml). The aqueous layer was extracted with DCM (2×30 ml), the combined extracts were washed with brine (30 ml), dried (MgSO$_4$), filtered and evaporated to afford an orange gum, of crude material which was purified by MDAP. The desired fractions were isolated, combined and evaporated to afford a white solid, 125 mg. This was dried over the weekend at 40° C. and then dried overnight in a vacuum oven at 40° C. to afford the white solid of desired product in 115 mg.

LCMS: m/z 359.98/361.94 [M+H] @ 0.86 min (2 min run).

Example 201

7-[(3-Chloro-4-fluoro-2-methylphenyl)carbonyl]-3-(1,3-thiazol-2-yl)-5,6,7,8-tetrahydro[1,2,4]triazolo[4,3-a]pyrazine (E201)

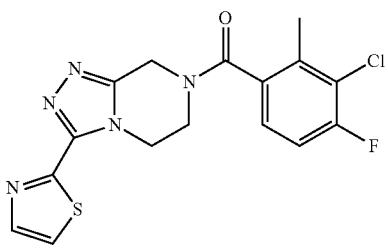 [SMILES: Cc1c(C(=O)N2CCn3c(nnc3-c3nccs3)C2)ccc(F)c1Cl]

Trimethyloxonium tetrafluoroborate (138 mg, 0.887 mmol) was added under argon to a suspension of 4-[(3-chloro-4-fluoro-2-methylphenyl)carbonyl]-2-piperazinone (I59) (200 mg, 0.739 mmol) in dry dichloromethane (DCM) (3.694 ml). The reaction mixture was stirred at room temperature overnight—cloudy mixture. 1,3-thiazole-2-carbohydrazide (I51) (159 mg, 1.108 mmol) was added and the resulting mixture was stirred at room temperature 2 h—reaction mixture was in solution before that a precipitate had appeared. 1-Butanol (3.69 ml) was added—mixture went into solution—and the reaction mixture was stirred at reflux 2 h. The reaction mixture was cooled down to room temperature and DCM was removed in vacuo. The reaction mixture was heated at reflux for 2 h and left at room temperature overnight. The mixture was diluted with DCM (150 mL) and washed with sat. NaHCO$_3$ (2×25 mL), water (25 mL) and brine (25 mL). The resulting organic layer was dried over MgSO$_4$ and concentrated under reduced pressure. NMR: lots of butanol left. The crude product was dissolved in DCM (150 mL) and washed with water (25 mL, 50 mL) and brine (25 mL). The resulting DCM layer was dried over MgSO$_4$ and concentrated under reduced pressure. The foam residue was triturated with Et$_2$O to afford a yellow solid (143.3 mg). The crude product was purified by MDAP (High pH). The obtained solid was dried at 50° C. under vacuum for 1.5 days. The solid was triturated with hexane to get remove the methanol and dried under vacuum at 50° C. to afford the desired product in 75.36 mg as a cream solid.

LCMS m/z 377.8 [M+H] @ 0.93 min (2 min run).

Example 202

7-[(3,4-Difluoro-2-methylphenyl)carbonyl]-3-(1,2,4-thiadiazol-5-yl)-5,6,7,8-tetrahydro[1,2,4]triazolo[4,3-a]pyrazine (E202)

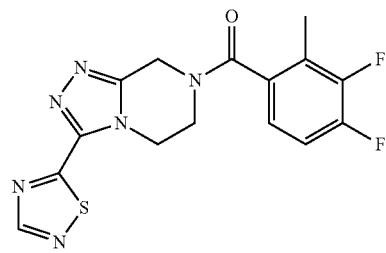 [SMILES: Cc1c(C(=O)N2CCn3c(nnc3-c3ncns3)C2)ccc(F)c1F]

3,4-Difluoro-2-methylbenzoic acid (I68)(124 mg, 0.720 mmol) was dissolved in dry N,N-dimethylformamide (DMF) (4.7 mL) before treating with HATU (274 mg, 0.720 mmol) and DIPEA (0.252 mL, 1.441 mmol) and stirring for 15 mins at RT, under argon before adding 3-(1,2,4-thiadiazol-5-yl)-5,6,7,8-tetrahydro[1,2,4]triazolo[4,3-a]pyrazine (I115)(100 mg, 0.480 mmol) and stirring for a further 18 hours. LCMS confirmed that the desired material was present and that no start material was left. The reaction was worked up by diluting with DCM (50 ml), washing with water (50 ml). The aqueous layer was extracted with DCM (2×30 ml). The combined extracts were washed with brine (30 ml), dried (Na$_2$SO$_4$), filtered and evaporated to afford a pale pink gum. The product was purified on a SNAP 50 g cartridge, eluting with 0-10% MeOH in DCM, the desired fractions were collected and the solvent was evaporated to afford a dark orange gum. Due to presence of residual DMF the crude gum product was diluted with DCM (30 ml), washed with brine (2×20 ml), dried (Na$_2$SO4), filtered and evaporated to afford an orange foam. The foam triturated with n-hexane to afford a pale orange solid. Liquers were removed and the residue was triturated again with n-Hexane. Liquers were removed and the solid was dried overnight in the vac oven at 40° C. to afford desired product in 146 mg as a pale orange solid.

LCMS: m/z 362.94 [M+H] @ 0.82 min (2 min run).

Example 203

7-[(2,4-dichloro-3-fluorophenyl)carbonyl]-3-(4-methyl-3-isothiazolyl)-5,6,7,8-tetrahydro[1,2,4]triazolo[4,3-a]pyrazine (E203)

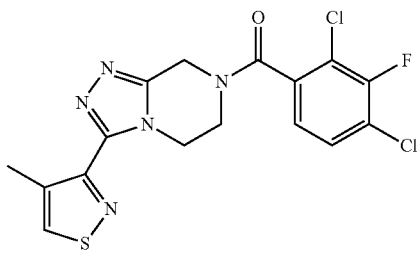 [SMILES: Cc1csnc1-c1nnc2n1CCN(C(=O)c1ccc(Cl)c(F)c1Cl)C2]

4-[(2,4-Dichloro-3-fluorophenyl)carbonyl]-2-piperazinone (I37) (90 mg, 0.309 mmol) was suspended in dichloromethane (DCM) (1.5 mL) before treating with trimethyloxonium tetrafluoroborate (57.8 mg, 0.371 mmol) and stirring for 16 hours at RT under argon before adding 4-methyl-3-isothiazolecarbohydrazide (I129)(58.3 mg, 0.371 mmol) and stirring for 4 hours. Adding 1-butanol (1.500 mL) then removing the DCM by evaporation before heating at 110° C. for 3 hours. As LCMS indicated that some start material remained, the reaction mixture was left heating for a further 17 hours. The reaction was worked up by diluting with DCM (30 ml) and washing with saturated sodium bicarbonate solution (30 ml). The aqueous layer was extracted with DCM (2×20 ml), the combined extracts were washed with brine (20 ml), dried (MgSO$_4$), filtered and evaporated to afford a brown gum, 120 mg. The gum was purified by MDAP, the desired fraction isolated and the solvent evaporated to afford a white solid. The solid dried over the weekend in the vac oven at 40° C. to afford an off white solid of desired product in 22 mg.

LCMS: m/z 411.88/413.83 [M+H] @ 0.98 min. (2 min run).

Example 204

2-Chloro-6-{[3-(2-pyridinyl)-5,6-dihydro[1,2,4]triazolo[4,3-a]pyrazin-7(8H)-yl]carbonyl}benzonitrile (E204)

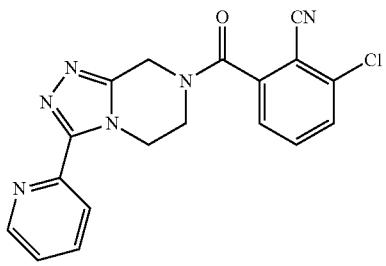 [SMILES: N#Cc1c(Cl)cccc1C(=O)N1CCn2c(nnc2-c2ccccn2)C1]

EDC (174 mg, 0.909 mmol) followed by HOBT (127 mg, 0.826 mmol) was added to a suspension of 3-(2-pyridinyl)-5,6,7,8-tetrahydro[1,2,4]triazolo[4,3-a]pyrazine (I101) (166 mg, 0.826 mmol) and 3-chloro-2-cyanobenzoic acid (I125) (150 mg, 0.826 mmol) in Dichloromethane (DCM) (4 mL) and N,N-dimethylformamide (DMF) (1 mL) and the reaction was stirred at room temperature for 18 h. LCMS indicated that the major peak was the desired product. The solvent was evaporated and the residue partitioned between EtOAc and sat. NaHCO$_3$ and the organic layer was collected. This was dried (Na$_2$SO$_4$) and the solvent evaporated to afford an orange oil. This was purified by MDAP to afford a pale yellow oil which solidified on standing to afford 174 mg of desired product.

LCMS: m/z 364.8 [M+H] @ 0.82 min (2 min run).

Example 205

7-[(2,4-dichlorophenyl)carbonyl]-3-(1,2,4-thiadiazol-5-yl)-5,6,7,8-tetrahydro[1,2,4]triazolo[4,3-a]pyrazine (E205)

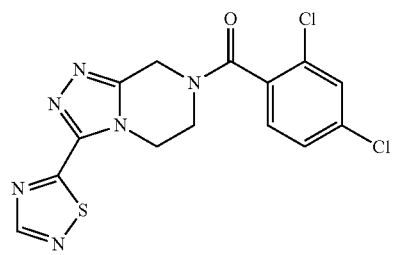 [SMILES: O=C(c1ccc(Cl)cc1Cl)N1CCn2c(nnc2-c2ncns2)C1]

HATU (274 mg, 0.720 mmol) and DIPEA (0.252 ml, 1.441 mmol) were added to a colourless solution of 2,4-dichlorobenzoic acid (I38 mg, 0.720 mmol, commercially available) in N,N-dimethylformamide (DMF) (4.718 ml). The mixture was stirred at RT for 15 minutes. 3-(1,2,4-thiadiazol-5-yl)-5,6,7,8-tetrahydro[1,2,4]triazolo[4,3-a]pyrazine (I115) (100 mg, 0.480 mmol) was added and the reaction mixture was stirred at RT for 18 h. The mixture was diluted in diethyl ether (100 mL) and washed with water (25 mL). The aqueous layer was extracted with diethyl ether (2×50 mL) and DCM (2×50 mL). The combined organic layers were dried over MgSO$_4$ and concentrated under reduced pressure. The crude product (brown liquid, 329.0 mg) was purified by flash chromatography (10 g SNAP, 0-100% ethyl acetate in hexane, 12 CV). The obtained oil residue was triturated with hexane. The product was diluted in DCM (100 mL) and washed with brine (3×25 mL). The resulting organic layer was dried over MgSO$_4$ and concentrated under reduced pressure. The obtained product was dried at 50° C. under vacuum 3 days to afford the desired product in 62.05 mg as a white foam.

4-[(2,4-Dichlorophenyl)carbonyl]-2-piperazinone (I6) (0.250 g, 0.915 mmol) was suspended in dry Dichloromethane (DCM) (3 mL) before treating with trimethyloxonium tetrafluoroborate (0.171 g, 1.098 mmol) and stirring for 16 hours at RT, under argon before adding 5-methyl-1,3-thiazole-4-carbohydrazide (I123)(0.216 g, 1.373 mmol) and stirring for a further 3 hours. DCM was removed by evaporation and the residue was dissolved in 1-butanol (3.00 mL) before heating at 110° C. for 19 hours. 3 Å molecular sieves were added and the reaction mixture was left heating for a further 6 hours before being cooled to RT over the weekend. The reaction was worked up by diluting with DCM (50 ml) and washing with saturated sodium bicarbonate solution (50 ml). The aqueous layer was extracted with DCM (2×30 ml), combined extracts were washed with brine (30 ml), dried (MgSO$_4$), filtered and evaporated to afford a brown gum. The product was purified by MDAP (formic acid method), the desired fraction isolated and the solvent evaporated to afford

Example 207

7-[(3-chloro-2-methylphenyl)carbonyl]-3-(5-methyl-1,3-thiazol-4-yl)-5,6,7,8-tetrahydro[1,2,4]triazolo[4,3-a]pyrazine (E207)

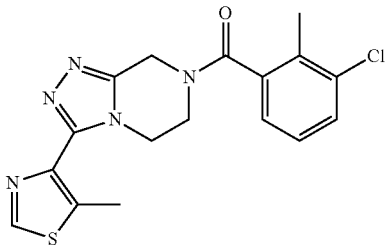 [SMILES: Cc1scnc1-c1nnc2n1CCN(C(=O)c1cccc(Cl)c1C)C2]

4-[(3-Chloro-2-methylphenyl)carbonyl]-2-piperazinone (I131)(250 mg, 0.989 mmol) was suspended in dry Dichloromethane (DCM) (3 mL) before treating with trimethyloxonium tetrafluoroborate (185 mg, 1.187 mmol) and stirring for 16 hours at RT under argon before adding 5-methyl-1,3-thiazole-4-carbohydrazide (I123) (233 mg, 1.484 mmol) and stirring for a further 3 hours. DCM was removed by evaporation and the residue was dissolved in 1-butanol (3.00 mL) before heating at 110° C. for 4 hours then cooled to RT overnight. The reaction was worked up by diluting with DCM (50 ml) and washing with saturated sodium bicarbonate solution (50 ml). The aqueous layer was extracted with DCM (2×30 ml), the combined extracts were washed with brine (30 ml), dried (MgSO$_4$), filtered and evaporated to afford a pale yellow cloudy gum as crude product. The product was purified on 50 g Isolera column, eluting with DCM (3CV) then 0-10% MeOH/DCM over 10CV. The desired fractions were isolated, the solvent evaporated and the residue was further purified by MDAP (formic acid method). The desired fraction was identified and the solvent evaporated to afford a white foam of desired product in 130 mg.

LCMS: m/z 373.97/375.97 [M+H] @ 0.89 min (2 min run).

Mass-Directed Automated HPLC

Where applicable, purification by mass-directed automated HPLC was carried out using the following apparatus and conditions:

Hardware
  Waters 2525 Binary Gradient Module
  Waters 515 Makeup Pump
  Waters Pump Control Module
  Waters 2767 Inject Collect
  Waters Column Fluidics Manager
  Waters 2996 Photodiode Array Detector
  Waters ZQ Mass Spectrometer
  Gilson 202 fraction collector
  Gilson Aspec waste collector
Software
  Waters MassLynx version 4 SP2
Column
  The columns used are Waters Atlantis, the dimensions of which are 19 mm×100 mm (small scale) and 30 mm×100 mm (large scale). The stationary phase particle size is 5 μm.

Solvents
  A: Aqueous solvent=Water+0.1% Formic Acid
  B: Organic solvent=Acetonitrile+0.1% Formic Acid
  Make up solvent=Methanol:Water 80:20
  Needle rinse solvent=Methanol
Methods
  There are five methods used depending on the analytical retention time of the compound of interest. They have a 13.5-minute runtime, which comprises of a 10-minute gradient followed by a 3.5 minute column flush and re-equilibration step.
  Large/Small Scale 1.0-1.5=5-30% B
  Large/Small Scale 1.5-2.2=15-55% B
  Large/Small Scale 2.2-2.9=30-85% B
  Large/Small Scale 2.9-3.6=50-99% B
  Large/Small Scale 3.6-5.0=80-99% B (in 6 minutes followed by 7.5 minutes flush and re-equilibration)
Flow Rate
  All of the above methods have a flow rate of either 20 mls/min (Small Scale) or 40 mls/min (Large Scale).

Liquid Chromatography/Mass Spectrometry

Analysis of the above Examples by Liquid Chromatography/Mass Spectrometry (LC/MS) was carried out using the apparatus and conditions indicated in the methods shown below:

5 Minute Method: Formic Acid Generic Analytical HPLC Open Access LC/MS

The HPLC analysis was conducted on a Sunfire C18 column (30 mm×4.6 mm i.d. 3.5 μm packing diameter) at 30 degrees centigrade.

The solvents employed were:
A=0.1% v/v solution of Formic Acid in Water.
B=0.1% v/v solution of Formic Acid in Acetonitrile.

| Time (min) | Flow Rate (ml/min) | % A | % B |
|---|---|---|---|
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.

2 Minute Method: Formic Acid Generic Analytical UPLC Open Access LC/MS

The UPLC analysis was conducted on an Acquity UPLC BEH C18 column (2.1 mm×50 mm i.d. 1.7 μm packing diameter) at 40 degrees centigrade.

The solvents employed were:
A=0.1% v/v solution of Formic Acid in Water.
B=0.1% v/v solution of Formic Acid in Acetonitrile.

| Time (min) | Flow Rate (ml/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

Pharmacological Data

Compounds or salts of the invention may be tested for in vitro biological activity at the P2X7 receptor in accordance with the following studies:

Eithidium Accumulation Assay 1

Studies were performed using NaCl assay buffer of the following composition: 140 mM NaCl, 10 mM HEPES [4-(2-hydroxyethyl)-1-piperazine-1-ethanesulfonic acid], 5 mM N-methyl-D-glucamine, 5.6 mM KCl, 10 mM D-glucose, 0.5 mM $CaCl_2$ (pH 7.4).

Human Embryonic Kidney (HEK) 293 cells, stably expressing human recombinant P2X7 receptors, were grown in poly-D-lysine pretreated 96 well plates for 18-24 hours. (The cloning of the human P2X7 receptor is described in U.S. Pat. No. 6,133,434, e.g. see Example 3 therein).

The cells were washed twice with 350 µl of the assay buffer, before addition of 50 µl of the assay buffer containing the putative P2X7 receptor antagonist compound. (A small amount of dimethyl sulfoxide, for initially dissolving the compound, is optionally used and present in this 50 µl test compound sample.) The cells were then incubated at room temperature (19-21° C.) for 30 min before addition of ATP and ethidium (100 µM final assay concentration). The ATP concentration was chosen to be close to the $EC_{80}$ for the receptor type and was 1 mM for studies on the human P2X7 receptor. Incubations were continued for 8 or 16 min and were terminated by addition of 25 µl of 1.3M sucrose containing 4 mM of the P2X7 receptor antagonist Reactive Black 5 (Aldrich). Cellular accumulation of ethidium was determined by measuring fluorescence (excitation wavelength of 530 nm and emission wavelength of 620 nm) from below the plate with a Can berra Packard Fluorocount (14 Station Road, Pangbourne, Reading, Berkshire RG8 7AN, United Kingdom) or a FlexStation II 384 from Molecular Molecular Devices (660-665 Eskdale Road, Wokingham, Berkshire RG41 5TS, United Kingdom). Antagonist $pIC_{50}$ values for blocking ATP responses were determined using iterative curve fitting techniques.

Eithidium Accumulation Assay 2

Studies were performed using NaCl assay buffer of the following composition: 140 mM NaCl (8.182 g/liter), 10 mM Hepes Acid (2.383 g/liter), 5 mM KCl (0.4175 g/liter), 10 mM glucose (1.8 g/liter), 1 mM $CaCl_2$ (0.5 ml of 1M solution/liter) and 5 mM N-methyl-D-glucamine (approximately 4.5 ml of 1M solution to adjust pH to 7.4); an Ethidium Bromide solution of the following composition: 395 ul of 10 mg/ml purchased stock into 49.61 mL of NaCl buffer; and an ATP solution of the following composition: 1.56 mL of a 32 mM ATP solution (Na salt prepared in water) to 23.44 ml of the Ethidium Bromide solution.

Human Embryonic Kidney (HEK) 293 cells, stably expressing human recombinant P2X7 receptors, were grown in poly-D-lysine pretreated 96 well plates for 24 hours at 37° C. (The cloning of the human P2X7 receptor is described in U.S. Pat. No. 6,133,434, e.g. see Example 3 therein).

The cells were washed with assay buffer (100 µL), before addition of 25 µL of assay buffer and then 25 ul of assay buffer containing the putative P2X7 receptor antagonist compound. The cells were then incubated at room temperature (19-21° C.) for 30 min before addition of ATP solution (50 µM). Incubations were continued for 16 min and were terminated by addition of 25 0 of 1.28M sucrose containing 4 mM of the P2X7 receptor antagonist Reactive Black 5 (Aldrich). Cellular accumulation of ethidium was determined by measuring fluorescence (excitation wavelength of 535 nm and emission wavelength of 620 nm) from below the plate with an EnVision plate reader from Wallac (PerkinElmer, Life and Analytical Sciences, Via Tiepolo, 24, -20052 Monza, Italy). Antagonist $pIC_{50}$ values for blocking ATP responses were determined using iterative curve fitting techniques.

Fluorescent Imaging Plate Reader (FLIPR) Ca Assay

Studies were performed using NaCl assay buffer of the following composition for human P2X7: 137 mM NaCl; 20 mM HEPES [4-(2-hydroxyethyl)-1-piperazine-1-ethanesulfonic acid]; 5.37 mM KCl; 4.17 mM $NaHCO_3$; 1 mM $CaCl_2$; 0.5 mM $MgSO_4$; and 1 g/L of D-glucose (pH 7.4).

Human Embryonic Kidney (HEK) 293 cells, stably expressing human recombinant P2X7 receptors, were grown in poly-D-lysine pretreated 384 well plates for 24 hours at room temperature (for a time sufficient for growth of a homogeneous layer of cells at the bottom of the wells). Alternatively, human osteosarcoma (U-20S) cells (commercially available), transduced with modified Baculovirus (BacMam) vector to deliver the gene coding for human P2X7 receptor (i.e. transiently expressing human recombinant P2X7 receptors), were grown in substantially the same conditions as for the HEK293 cells except that the well plates were not pretreated with poly-D-lysine. (The cloning of the human P2X7 receptor is described in U.S. Pat. No. 6,133,434, e.g. see Example 3 therein). The cells were washed three times with 800 of assay buffer, loaded for 1 h at 37° C. with 2 µM Fluo-4-AM [4-(6-acetoxymethoxy-2,7-difluoro-3-oxo-9-xanthenyl)-4'-methyl-2,2'-(ethylenedioxy)dianiline-N,N,N', N'-tetraacetic acid tetrakis(acetoxymethyl) ester], a $Ca^{2+}$-sensitive, cell-permeable, fluorescent dye (Tef Labs. Inc., 9415 Capitol View Drive, Austin, Tex. 78747, USA), washed three times again (3×80 µl), and left with 30 µl buffer before the addition of 10 µl of the assay buffer containing the putative P2X7 receptor antagonist compound, the compound being added at 4× the final assay concentration chosen. The solution of the putative P2X7 receptor antagonist compound was created by (i) dissolving the compound in dimethyl sulfoxide (DMSO) to create a stock solution in DMSO at 200× the final assay concentration, and (ii) mixing 10 of the stock solution of the compound in DMSO with 50 µl of the assay buffer to create a solution at about 4× the final assay concentration. The cells were then incubated at room temperature for 30 mins before addition (online, by FLIPR384 or FLIPR3 instrument (Molecular Devices, 1311 Orleans Drive, Sunnyvale, Calif. 94089-1136, USA)) of 100 of the assay buffer containing benzoylbenzoyl-ATP (BzATP) such as to create a 60 µM final assay concentration of BzATP (BzATP was added at 5× this final concentration). The BzATP concentration was chosen to be close to the $EC_{80}$ for the receptor type. Incubations and reading were continued for 90 sec, and intracellular calcium increase was determined by measuring fluorescence (excitation wavelength of 488 nm and emission wavelength of 516 nm) from below the plate, with FLIPR charged-coupled device (CCD) camera. Antagonist $pIC_{50}$ values for blocking BzATP responses were determined using iterative curve fitting techniques.

In the above FLIPR Ca Assay (or a slightly modified version thereof) for human P2X7 receptor antagonist activity, the compounds of Examples 1, 2, 4, 5, 6, 8 to 17, 19 to 26, 30, 38 to 70, 72 to 77, 79 to 98, 100 and 103 were found to have pIC50 values of about 5 or above in the FLIPR Ca Assay or a slightly modified version thereof.

The compounds of Examples 1 to 207 were tested in the Ethidium Accumulation Assays 1 and/or 2 (or a slightly modified version thereof) for human P2X7 receptor antagonist activity, and were found to have pIC50 values of from about 6.3 to about 8.9 (sometimes as a mean of more than one measurement) in the Ethidium Accumulation Assays or a slightly modified version thereof. The results obtained are shown in the table below wherein an entry of * indicates a pIC50 value of 6.3 or higher, an entry of  indicates a pIC50 value of 7.0 or higher and an entry of * indicates a pIC50 value of 8.0 or higher.

| Ex | Name | Structure | Assay 1 | Assay 2 |
|---|---|---|---|---|
| 1 | 3-Bromo-7-{[2-chloro-3-(trifluoromethyl)phenyl]carbonyl}-5,6,7,8-tetrahydro[1,2,4]triazolo[4,3-a]pyrazine | 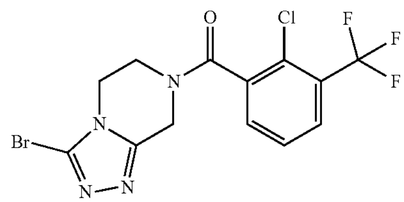 [SMILES: O=C(c1cccc(C(F)(F)F)c1Cl)N1CCn2c(Br)nnc2C1] | *** | |
| 2 | 7-{[2-chloro-3-(trifluoromethyl)phenyl]carbonyl}-3-(trifluoromethyl)-5,6,7,8-tetrahydro[1,2,4]triazolo[4,3-a]pyrazine | 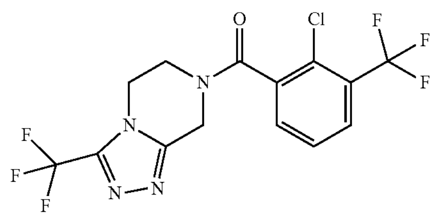 [SMILES: O=C(c1cccc(C(F)(F)F)c1Cl)N1CCn2c(nnc2C(F)(F)F)C1] | ** | |
| 3 | 7-{[2-chloro-3-(trifluoromethyl)phenyl]carbonyl}-5,6,7,8-tetrahydro[1,2,4]triazolo[4,3-a]pyrazine | 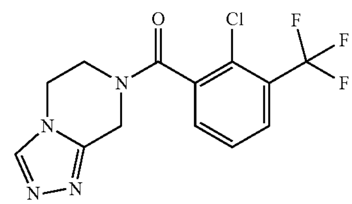 [SMILES: O=C(c1cccc(C(F)(F)F)c1Cl)N1CCn2cnnc2C1] | * | * |
| 4 | 7-{[2-chloro-3-(trifluoromethyl)phenyl]carbonyl}-3-ethyl-5,6,7,8-tetrahydro[1,2,4]triazolo[4,3-a]pyrazine | 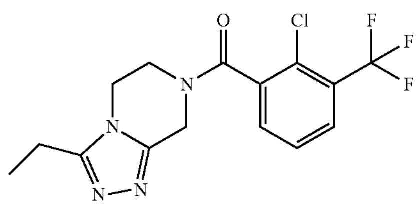 [SMILES: CCc1nnc2n1CCN(C(=O)c1cccc(C(F)(F)F)c1Cl)C2] |  |  |
| 5 | 7-[(2,3-dichlorophenyl)carbonyl]-3-ethyl-5,6,7,8-tetrahydro[1,2,4]triazolo[4,3-a]pyrazine | 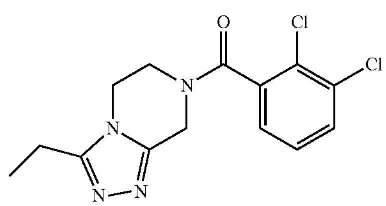 [SMILES: CCc1nnc2n1CCN(C(=O)c1cccc(Cl)c1Cl)C2] | ** | |
| 6 | 3-bromo-7-[(2,3-dichlorophenyl)carbonyl]-5,6,7,8-tetrahydro[1,2,4]triazolo[4,3-a]pyrazine | 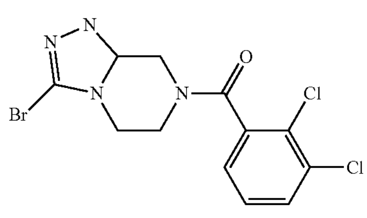 [SMILES: O=C(c1cccc(Cl)c1Cl)N1CCN2C(Br)=NNC2C1] | ** | |
| 7 | 3-bromo-7-[(2,4-dichlorophenyl)carbonyl]-5,6,7,8-tetrahydro[1,2,4]triazolo[4,3-a]pyrazine | 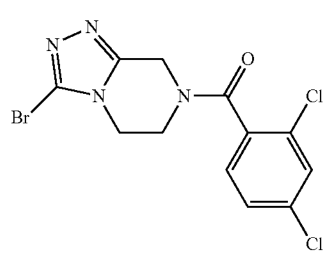 [SMILES: O=C(c1ccc(Cl)cc1Cl)N1CCn2c(Br)nnc2C1] | * | |

-continued

| Ex | Name | Structure | Assay 1 | Assay 2 |
|----|------|-----------|---------|---------|
| 8 | 3-bromo-7-[(2,4,6-trichlorophenyl)carbonyl]-5,6,7,8-tetrahydro[1,2,4]triazolo[4,3-a]pyrazine | 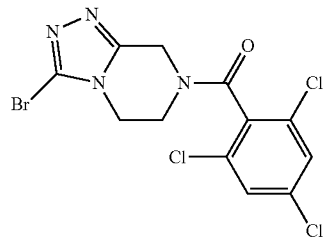 [SMILES: O=C(c1c(Cl)cc(Cl)cc1Cl)N1CCn2c(Br)nnc2C1] | * | |
| 9 | 3-bromo-7-{[2-fluoro-3-(trifluoromethyl)phenyl]carbonyl}-5,6,7,8-tetrahydro[1,2,4]triazolo[4,3-a]pyrazine | 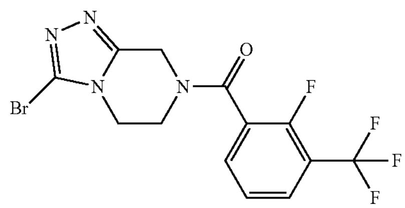 [SMILES: O=C(c1cccc(C(F)(F)F)c1F)N1CCn2c(Br)nnc2C1] | ** | |
| 10 | 7-{[2-Chloro-3-(trifluoromethyl)phenyl]carbonyl}-3-(4-pyridinyl)-5,6,7,8-tetrahydro[1,2,4]triazolo[4,3-a]pyrazine | 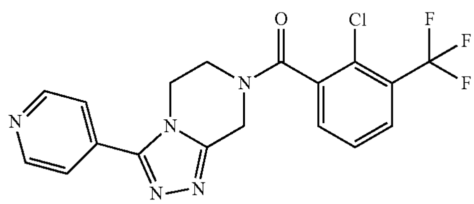 [SMILES: O=C(c1cccc(C(F)(F)F)c1Cl)N1CCn2c(nnc2-c2ccncc2)C1] | ** | |
| 11 | 7-{[2-chloro-3-(trifluoromethyl)phenyl]carbonyl}-3-(2-pyridinyl)-5,6,7,8-tetrahydro[1,2,4]triazolo[4,3-a]pyrazine | 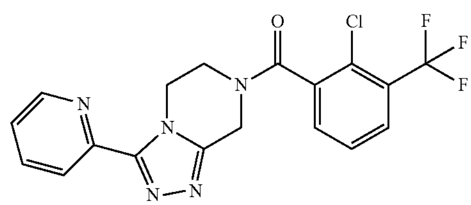 [SMILES: O=C(c1cccc(C(F)(F)F)c1Cl)N1CCn2c(nnc2-c2ccccn2)C1] | *** | |
| 12 | 7-{[2-chloro-3-(trifluoromethyl)phenyl]carbony}-3-(4-pyrimidinyl)-5,6,7,8-tetrahydro[1,2,4]triazolo[4,3-a]pyrazine | 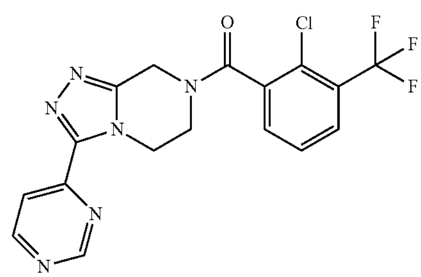 [SMILES: O=C(c1cccc(C(F)(F)F)c1Cl)N1CCn2c(nnc2-c2ccncn2)C1] | ** | |
| 13 | 7-{[2-Chloro-3-(trifluoromethyl)phenyl]carbonyl}-3-phenyl-5,6,7,8-tetrahydro[1,2,4]triazolo[4,3-a]pyrazine | 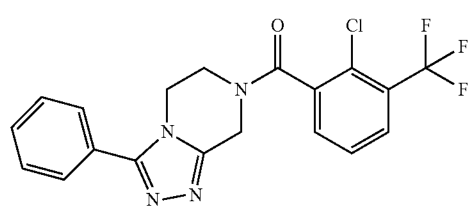 [SMILES: O=C(c1cccc(C(F)(F)F)c1Cl)N1CCn2c(nnc2-c2ccccc2)C1] | *** | |
| 14 | 7-{[2-Chloro-3-(trifluoromethyl)phenyl]carbonyl}-3-(4-fluorophenyl)-5,6,7,8-tetrahydro[1,2,4]triazolo[4,3-a]pyrazine | 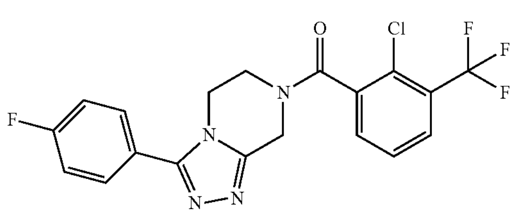 [SMILES: O=C(c1cccc(C(F)(F)F)c1Cl)N1CCn2c(nnc2-c2ccc(F)cc2)C1] | *** | |

-continued

| Ex | Name | Structure | Assay 1 | Assay 2 |
|---|---|---|---|---|
| 15 | 7-{[2-Chloro-3-(trifluoromethyl)phenyl]carbonyl}-3-methyl-5,6,7,8-tetrahydro[1,2,4]triazolo[4,3-a]pyrazine | 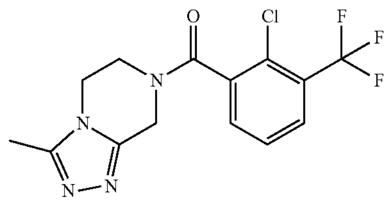 [SMILES: Cc1nnc2n1CCN(C(=O)c1cccc(C(F)(F)F)c1Cl)C2] | ** | * |
| 16 | 7-{[2-Chloro-3-(trifluoromethyl)phenyl]carbonyl}-3-(3-pyridinyl)-5,6,7,8-tetrahydro[1,2,4]triazolo[4,3-a]pyrazine | 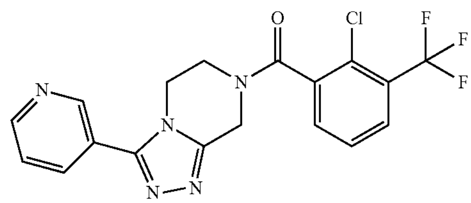 [SMILES: O=C(c1cccc(C(F)(F)F)c1Cl)N1CCn2c(nnc2-c2cccnc2)C1] | *** | |
| 17 | 7-{[2-Chloro-3-(trifluoromethyl)phenyl]carbonyl}-3-(methyloxy)-5,6,7,8-tetrahydro[1,2,4]triazolo[4,3-a]pyrazine | 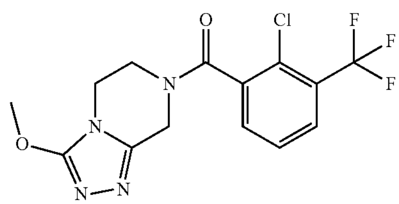 [SMILES: COc1nnc2n1CCN(C(=O)c1cccc(C(F)(F)F)c1Cl)C2] | ** | |
| 18 | 7-{[2-Chloro-3-(trifluoromethyl)phenyl]carbonyl}-3-(4-morpholinyl)-5,6,7,8-tetrahydro[1,2,4]triazolo[4,3-a]pyrazine | 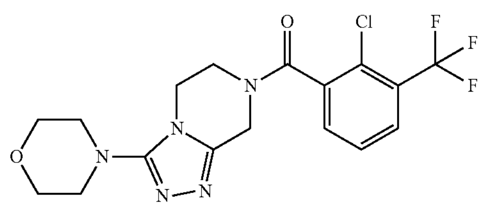 [SMILES: O=C(c1cccc(C(F)(F)F)c1Cl)N1CCn2c(nnc2N2CCOCC2)C1] | * | |
| 19 | 7-{[2-chloro-3-(trifluoromethyl)phenyl]carbonyl}-3-(1-pyrrolidinyl)-5,6,7,8-tetrahydro[1,2,4]triazolo[4,3-a]pyrazine | 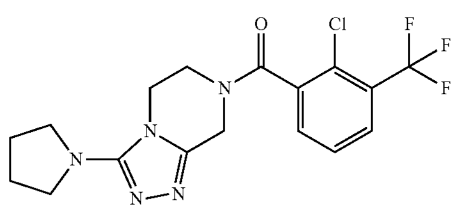 [SMILES: O=C(c1cccc(C(F)(F)F)c1Cl)N1CCn2c(nnc2N2CCCC2)C1] | ** | |
| 20 | 7-{[2-chloro-3-(trifluoromethyl)phenyl]carbonyl}-N,N-dimethyl-5,6,7,8-tetrahydro[1,2,4]triazolo[4,3-a]pyrazine-3-amine | 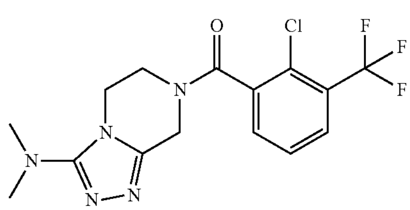 [SMILES: CN(C)c1nnc2n1CCN(C(=O)c1cccc(C(F)(F)F)c1Cl)C2] | ** | |
| 21 | 7-{[2-chloro-3-(trifluoromethyl)phenyl]carbonyl}-N-methyl-5,6,7,8-tetrahydro[1,2,4]triazolo[4,3-a]pyrazine-3-amine | 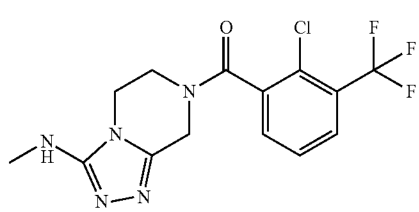 | * | |

| Ex | Name | Structure | Assay 1 | Assay 2 |
|---|---|---|---|---|
| 22 | 3-(1-azetidinyl)-7-{[2-chloro-3-(trifluoromethyl)phenyl]carbonyl}-5,6,7,8-tetrahydro[1,2,4]triazolo[4,3-a]pyrazine | 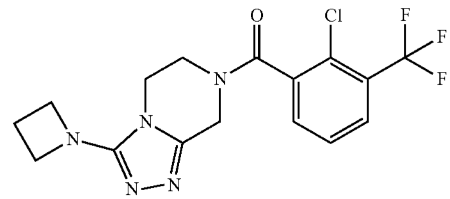 [SMILES: O=C(c1cccc(C(F)(F)F)c1Cl)N1CCn2c(nnc2N2CCC2)C1] | ** | |
| 23 | 7-{[2-chloro-3-(trifluoromethyl)phenyl]carbonyl}-3-(1-piperidinyl)-5,6,7,8-tetrahydro[1,2,4]triazolo[4,3-a]pyrazine | 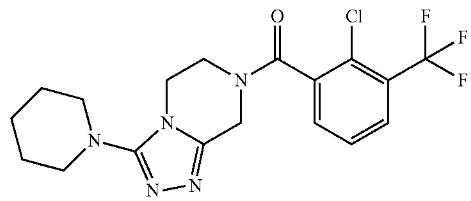 [SMILES: O=C(c1cccc(C(F)(F)F)c1Cl)N1CCn2c(nnc2N2CCCCC2)C1] | ** | |
| 24 | 7-{[2-Chloro-3-(trifluoromethyl)phenyl]carbonyl}-3-(2,4-difluorophenyl)-5,6,7,8-tetrahydro[1,2,4]triazolo[4,3-a]pyrazine | 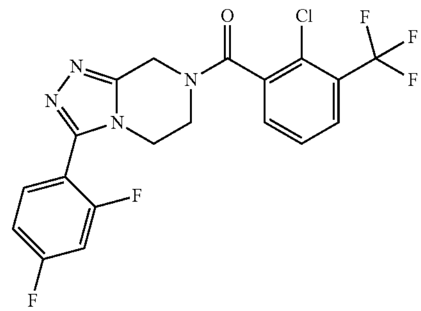 [SMILES: O=C(c1cccc(C(F)(F)F)c1Cl)N1CCn2c(nnc2-c2ccc(F)cc2F)C1] | ** | |
| 25 | 7-{[2-chloro-3-(trifluoromethyl)phenyl]carbonyl}-3-(1,1-dimethylethyl)-5,6,7,8-tetrahydro[1,2,4]triazolo[4,3-a]pyrazine | 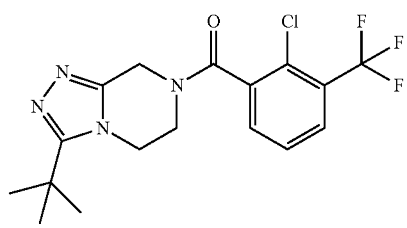 [SMILES: CC(C)(C)c1nnc2n1CCN(C(=O)c1cccc(C(F)(F)F)c1Cl)C2] | * | |
| 26 | 7-{[2-chloro-3-(trifluoromethyl)phenyl]carbonyl}-3-(6-methyl-2-pyridinyl)-5,6,7,8-tetrahydro[1,2,4]triazolo[4,3-a]pyrazine | 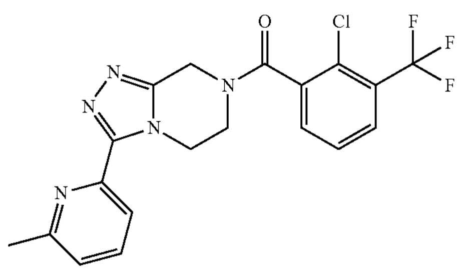 [SMILES: Cc1cccc(-c2nnc3n2CCN(C(=O)c2cccc(C(F)(F)F)c2Cl)C3)n1] | *** | |
| 27 | 7-{[2-chloro-3-(trifluoromethyl)phenyl]carbonyl}-3-(1-methyl-1H-pyrazol-3-yl)-5,6,7,8-tetrahydro[1,2,4]triazolo[4,3-a]pyrazine | 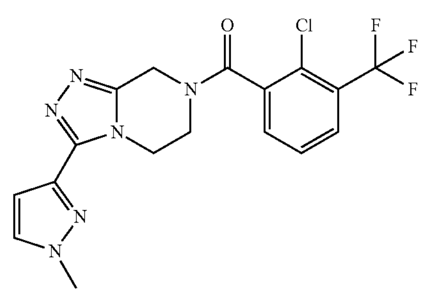 [SMILES: Cn1ccc(-c2nnc3n2CCN(C(=O)c2cccc(C(F)(F)F)c2Cl)C3)n1] | *** | |

-continued

| Ex | Name | Structure | Assay 1 | Assay 2 |
|----|------|-----------|---------|---------|
| 28 | 7-{[2-chloro-3-(trifluoromethyl)phenyl]carbonyl}-3-(3-methyl-2-pyridinyl)-5,6,7,8-tetrahydro[1,2,4]triazolo[4,3-a]pyrazine | 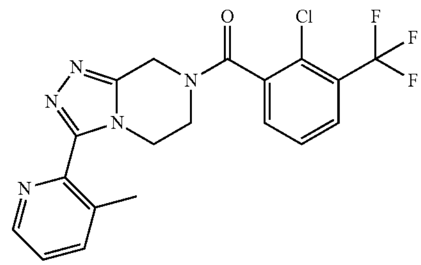 [SMILES: Cc1cccnc1-c1nnc2n1CCN(C(=O)c1cccc(C(F)(F)F)c1Cl)C2] | *** | |
| 29 | 7-{[2-chloro-3-(trifluoromethyl)phenyl]carbonyl}-3-(1-methyl-1H-pyrrol-2-yl)-5,6,7,8-tetrahydro[1,2,4]triazolo[4,3-a]pyrazine | 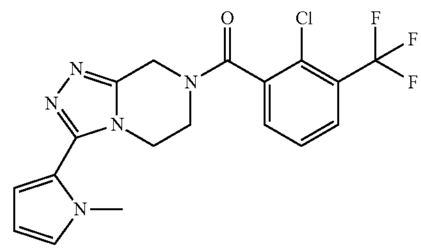 [SMILES: Cn1cccc1-c1nnc2n1CCN(C(=O)c1cccc(C(F)(F)F)c1Cl)C2] | *** | |
| 30 | 7-[(2-Chloro-4-fluorophenyl)carbonyl]-3-phenyl-5,6,7,8-tetrahydro[1,2,4]triazolo[4,3-a]pyrazine | 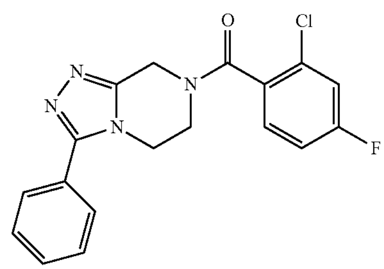 [SMILES: O=C(c1ccc(F)cc1Cl)N1CCn2c(nnc2-c2ccccc2)C1] | ** | |
| 31 | 7-[(2-chloro-4-fluorophenyl)carbonyl]-3-(3-fluoro-2-pyridinyl)-5,6,7,8-tetrahydro[1,2,4]triazolo[4,3-a]pyrazine | 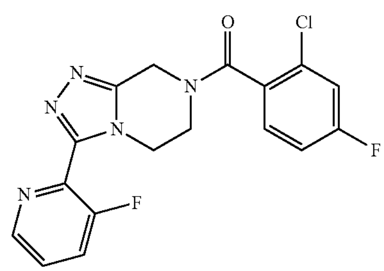 | *** | |
| 32 | 7-[(2-chloro-4-fluorophenyl)carbonyl]-3-(3-methyl-2-pyridinyl)-5,6,7,8-tetrahydro[1,2,4]triazolo[4,3-a]pyrazine | 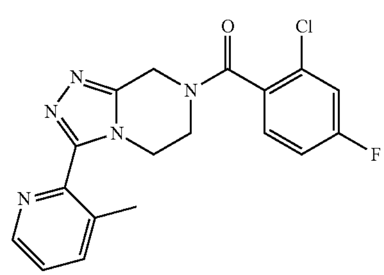 [SMILES: Cc1cccnc1-c1nnc2n1CCN(C(=O)c1ccc(F)cc1Cl)C2] | ** | |
| 33 | 7-[(2-chloro-4-fluorophenyl)carbonyl]-3-(4-pyrimidinyl)-5,6,7,8-tetrahydro[1,2,4]triazolo[4,3-a]pyrazine | 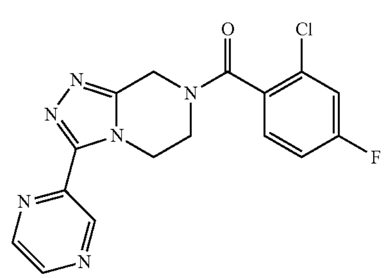 [SMILES: O=C(c1ccc(F)cc1Cl)N1CCn2c(nnc2-c2cnccn2)C1] | *** | |

-continued

| Ex | Name | Structure | Assay 1 | Assay 2 |
|---|---|---|---|---|
| 34 | 7-[(2,3-Dichlorophenyl)carbonyl]-3-(2-pyrazinyl)-5,6,7,8-tetrahydro[1,2,4]triazolo[4,3-a]pyrazine | 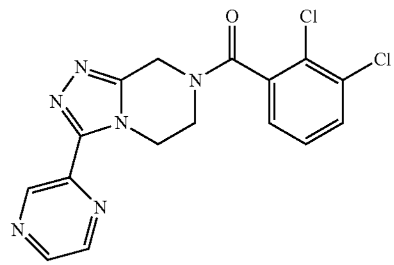 [SMILES: O=C(c1cccc(Cl)c1Cl)N1CCn2c(nnc2-c2cnccn2)C1] | *** | |
| 36 | 7-{[2-chloro-3-(trifluoromethyl)phenyl]carbonyl}-3-(5-methyl-3-isoxazolyl)-5,6,7,8-tetrahydro[1,2,4]triazolo[4,3-a]pyrazine | 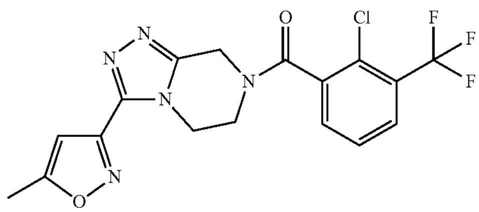 [SMILES: Cc1cc(-c2nnc3n2CCN(C(=O)c2cccc(C(F)(F)F)c2Cl)C3)no1] | ** | |
| 37 | 7-[(2-chloro-4-fluorophenyl)carbonyl]-3-(2-pyridinyl)-5,6,7,8-tetrahydro[1,2,4]triazolo[4,3-a]pyrazine | 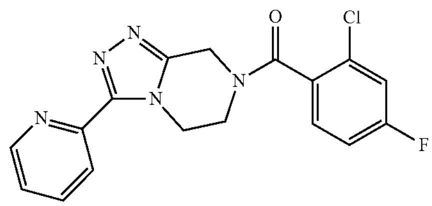 [SMILES: O=C(c1ccc(F)cc1Cl)N1CCn2c(nnc2-c2ccccn2)C1] | *** | |
| 38 | 7-{[2-chloro-3-(trifluoromethyl)phenyl]carbonyl}-3-(1H-pyrrol-2-yl)-5,6,7,8-tetrahydro[1,2,4]triazolo[4,3-a]pyrazine | 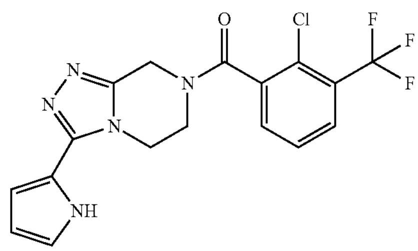 [SMILES: O=C(c1cccc(C(F)(F)F)c1Cl)N1CCn2c(nnc2-c2ccc[nH]2)C1] | *** | |
| 39 | 7-[(2-chloro-4-fluorophenyl)carbonyl]-3-(3-pyridinyl)-5,6,7,8-tetrahydro[1,2,4]triazolo[4,3-a]pyrazine | 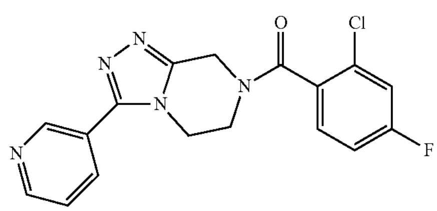 [SMILES: O=C(c1ccc(F)cc1Cl)N1CCn2c(nnc2-c2cccnc2)C1] | ** | |
| 40 | 7-[(2-chloro-4-fluorophenyl)carbonyl]-3-(5-fluoro-2-pyridinyl)-5,6,7,8-tetrahydro[1,2,4]triazolo[4,3-a]pyrazine | 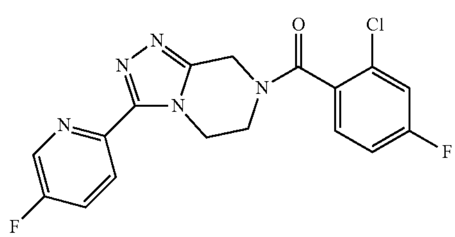 [SMILES: O=C(c1ccc(F)cc1Cl)N1CCn2c(nnc2-c2ccc(F)cn2)C1] | ** | |
| 41 | 7-[(2-chloro-4-fluorophenyl)carbonyl]-3-(6-fluoro-2-pyridinyl)-5,6,7,8-tetrahydro[1,2,4]triazolo[4,3-a]pyrazine | 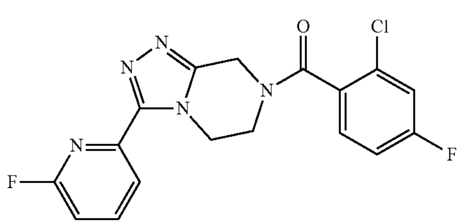 [SMILES: O=C(c1ccc(F)cc1Cl)N1CCn2c(nnc2-c2cccc(F)n2)C1] | * | |

-continued

| Ex | Name | Structure | Assay 1 | Assay 2 |
|---|---|---|---|---|
| 42 | 7-{[2-chloro-3-(trifluoromethyl)phenyl]carbonyl}-3-(1,3-thiazol-4-yl)-5,6,7,8-tetrahydro[1,2,4]triazolo[4,3-a]pyrazine | 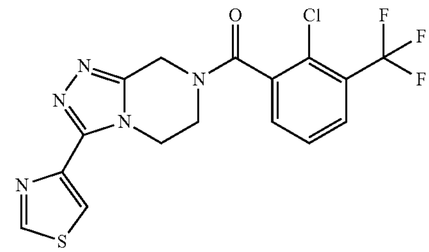 [SMILES: O=C(c1cccc(C(F)(F)F)c1Cl)N1CCn2c(nnc2-c2cscn2)C1] | *** | |
| 43 | 7-[(2,3-dichlorophenyl)carbonyl]-3-(2-pyridinyl)-5,6,7,8-tetrahydro[1,2,4]triazolo[4,3-a]pyrazine | 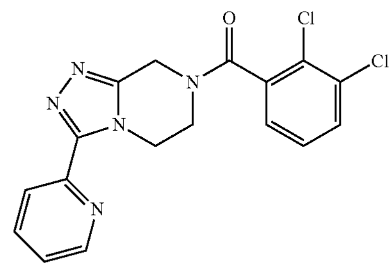 | *** | |
| 44 | 7-{[2-chloro-3-(trifluoromethyl)phenyl]carbonyl}-3-(3-pyridazinyl)-5,6,7,8-tetrahydro[1,2,4]triazolo[4,3-a]pyrazine | 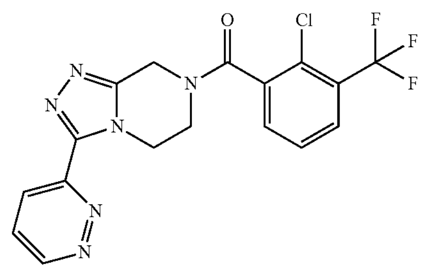 [SMILES: O=C(c1cccc(C(F)(F)F)c1Cl)N1CCn2c(nnc2-c2cccnn2)C1] |  |  |
| 45 | 7-{[2-chloro-3-(trifluoromethyl)phenyl]carbonyl}-3-(5-fluoro-2-pyridinyl)-5,6,7,8-tetrahydro[1,2,4]triazolo[4,3-a]pyrazine | 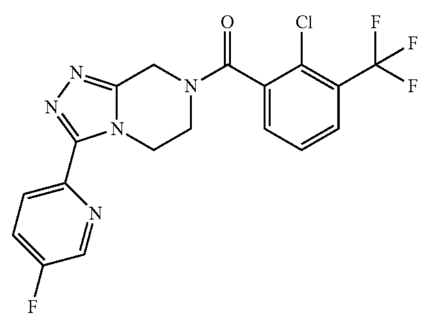 [SMILES: O=C(c1cccc(C(F)(F)F)c1Cl)N1CCn2c(nnc2-c2ccc(F)cn2)C1] | * | * |
| 46 | 7-{[2-chloro-3-(trifluoromethyl)phenyl]carbonyl}-3-(2-pyrazinyl)-5,6,7,8-tetrahydro[1,2,4]triazolo[4,3-a]pyraizne | 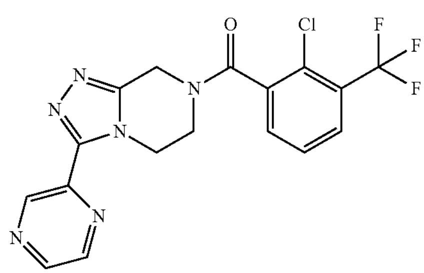 [SMILES: O=C(c1cccc(C(F)(F)F)c1Cl)N1CCn2c(nnc2-c2cnccn2)C1] | *** | |
| 47 | 7-[(2-chloro-4-fluorophenyl)carbonyl]-3-(2-pyrimidinyl)-5,6,7,8-tetrahydro[1,2,4]triazolo[4,3-a]pyrazine | 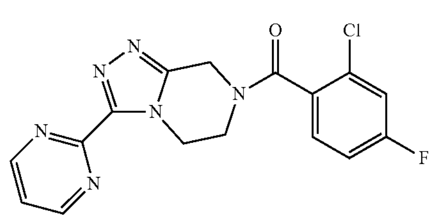 [SMILES: O=C(c1ccc(F)cc1Cl)N1CCn2c(nnc2-c2ncccn2)C1] | *** | |

-continued

| Ex | Name | Structure | Assay 1 | Assay 2 |
|---|---|---|---|---|
| 48 | 7-[(2,3-dichlorophenyl)carbonyl]-3-(1-methyl-1H-pyrrol-2-yl)-5,6,7,8-tetrahydro[1,2,4]triazolo[4,3-a]pyrazine | 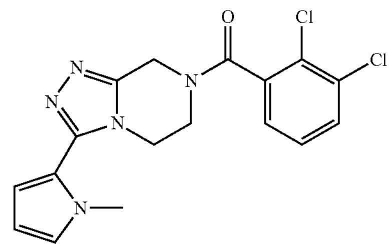 [SMILES: Cn1cccc1-c1nnc2n1CCN(C(=O)c1cccc(Cl)c1Cl)C2] | ** | |
| 49 | 7-[(2,3-dichlorophenyl)carbonyl]-3-(5-methyl-3-isoxazolyl)-5,6,7,8-tetrahydro[1,2,4]triazolo[4,3-a]pyrazine | 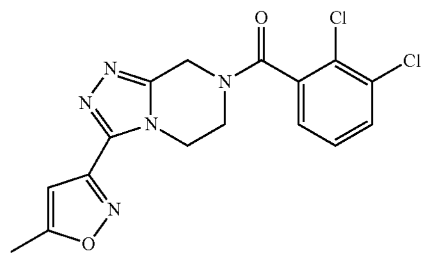 [SMILES: Cc1cc(-c2nnc3n2CCN(C(=O)c2cccc(Cl)c2Cl)C3)no1] | ** | |
| 50 | 7-{[2-chloro-3-(trifluoromethyl)phenyl]carbonyl}-3-(2-pyrimidinyl)-5,6,7,8-tetrahydro[1,2,4]triazolo[4,3-a]pyrazine | 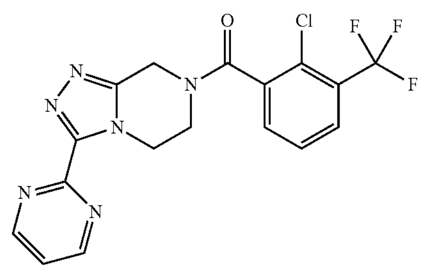 [SMILES: O=C(c1cccc(C(F)(F)F)c1Cl)N1CCn2c(nnc2-c2ncccn2)C1] | *** | |
| 51 | 7-{[2-chloro-3-(trifluoromethyl)phenyl]carbonyl}-3-(5-methyl-2-pyridinyl)-5,6,7,8-tetrahydro[1,2,4]triazolo[4,3-a]pyrazine | 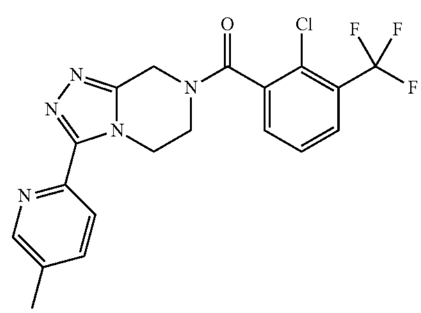 [SMILES: Cc1ccc(-c2nnc3n2CCN(C(=O)c2cccc(C(F)(F)F)c2Cl)C3)nc1] | ** | |
| 52 | 7-{[2-chloro-3-(trifluoromethyl)phenyl]carbonyl}-3-(3-fluoro-2-pyridinyl)-5,6,7,8-tetrahydro[1,2,4]triazolo[4,3-a]pyrazine | 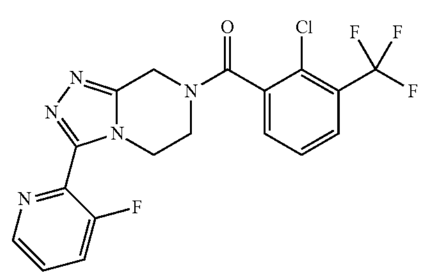 [SMILES: O=C(c1cccc(C(F)(F)F)c1Cl)N1CCn2c(nnc2-c2ncccc2F)C1] | *** | |

-continued

| Ex | Name | Structure | Assay 1 | Assay 2 |
|---|---|---|---|---|
| 53 | 7-{[2-chloro-3-(trifluoromethyl)phenyl]carbonyl}-3-(6-fluoro-2-pyridinyl)-5,6,7,8-tetrahydro[1,2,4]triazolo[4,3-a]pyrazine | 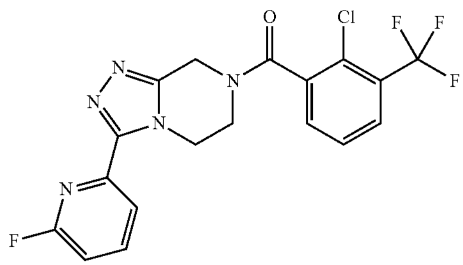 [SMILES: O=C(c1cccc(C(F)(F)F)c1Cl)N1CCn2c(nnc2-c2cccc(F)n2)C1] | *** | |
| 54 | 7-[(2,3-dichlorophenyl)carbonyl]-3-(5-fluoro-2-pyridinyl)-5,6,7,8-tetrahydro[1,2,4]triazolo[4,3-a]pyrazine | 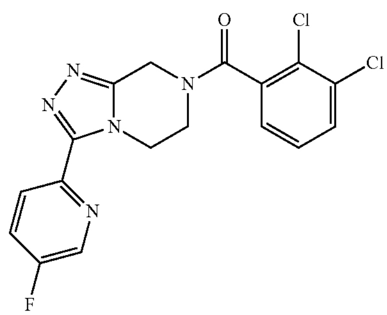 [SMILES: O=C(c1cccc(Cl)c1Cl)N1CCn2c(nnc2-c2ccc(F)cn2)C1] | *** | |
| 55 | 7-[(2,3-dichlorophenyl)carbonyl]-3-(6-fluoro-2-pyridinyl)-5,6,7,8-tetrahydro[1,2,4]triazolo[4,3-a]pyrazine | 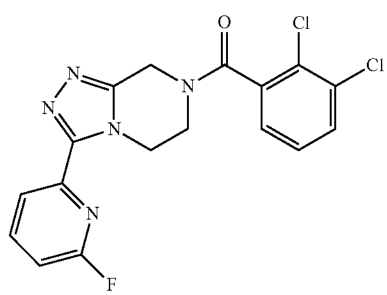 [SMILES: O=C(c1cccc(Cl)c1Cl)N1CCn2c(nnc2-c2cccc(F)n2)C1] | ** | |
| 56 | 7-{[2-chloro-3-(trifluoromethyl)phenyl]carbonyl}-3-(4-methyl-2-pyridinyl)-5,6,7,8-tetrahydro[1,2,4]triazolo[4,3-a]pyrazine | 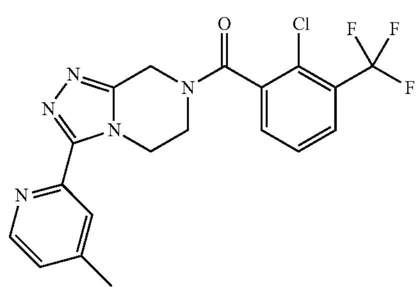 [SMILES: Cc1ccnc(-c2nnc3n2CCN(C(=O)c2cccc(C(F)(F)F)c2Cl)C3)c1] | *** | |
| 57 | 7-[(2,3-dichlorophenyl)carbonyl]-3-(3-pyridazinyl)-5,6,7,8-tetrahydro[1,2,4]triazolo[4,3-a]pyrazine | 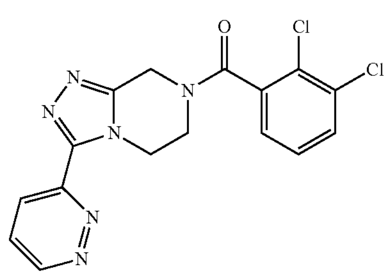 [SMILES: O=C(c1cccc(Cl)c1Cl)N1CCn2c(nnc2-c2cccnn2)C1] | ** | |

| Ex | Name | Structure | Assay 1 | Assay 2 |
|---|---|---|---|---|
| 58 | 7-[(2,3-dichlorophenyl)carbonyl]-3-(2-pyrimidinyl)-5,6,7,8-tetrahydro[1,2,4]triazolo[4,3-a]pyrazine | 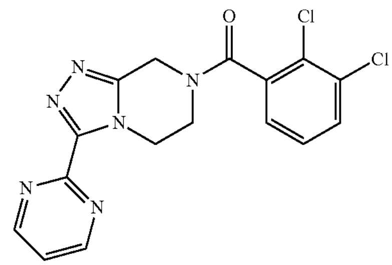 [SMILES: O=C(c1cccc(Cl)c1Cl)N1CCn2c(nnc2-c2ncccn2)C1] | ** | |
| 59 | 7-[(2-chloro-4-fluorophenyl)carbonyl]-3-(3-pyridazinyl)-5,6,7,8-tetrahydro[1,2,]triazolo[4,3-a]pyrazine | 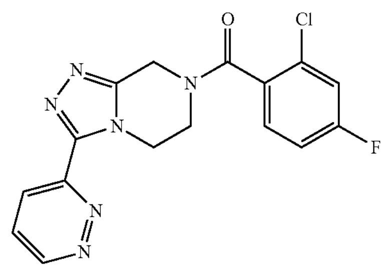 [SMILES: O=C(c1ccc(F)cc1Cl)N1CCn2c(nnc2-c2cccnn2)C1] | * | |
| 60 | 7-[(2,3-dichlorophenyl)carbonyl]-3-(5-methyl-2-pyridinyl)-5,6,7,8-tetrahydro[1,2,4]triazolo[4,3-a]pyrazine | 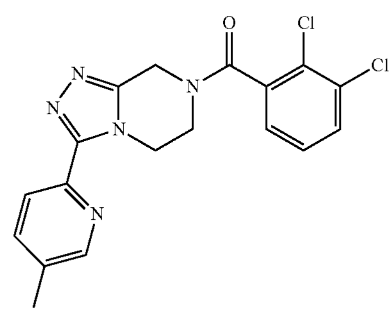 [SMILES: Cc1ccc(-c2nnc3n2CCN(C(=O)c2cccc(Cl)c2Cl)C3)nc1] | ** | |
| 61 | 7-[(2,3-dichlorophenyl)carbonyl]-3-(3-pyridinyl)-5,6,7,8-tetrahydro[1,2,4]triazolo[4,3-a]pyrazine | 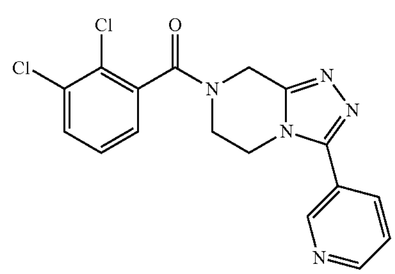 [SMILES: O=C(c1cccc(Cl)c1Cl)N1CCn2c(nnc2-c2cccnc2)C1] | *** | |
| 62 | 7-[(2,3-dichlorophenyl)carbonyl]-3-(4-pyrimdiinyl)-5,6,7,8-tetrahydro[1,2,4]triazolo[4,3-a]pyrazine | 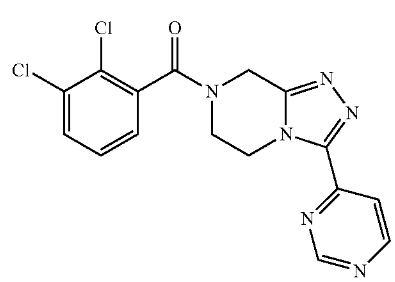 [SMILES: O=C(c1cccc(Cl)c1Cl)N1CCn2c(nnc2-c2ccncn2)C1] | *** | |

| Ex | Name | Structure | Assay 1 | Assay 2 |
|---|---|---|---|---|
| 63 | 7-[(2,3-dichlorophenyl)carbonyl]-3-(1-methyl-1H-pyrazol-3-yl)-5,6,7,8-tetrahydro[1,2,4]triazolo[4,3-a]pyrazine | 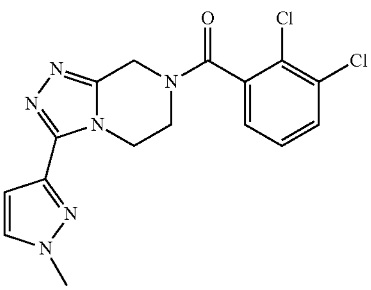 [SMILES: Cn1ccc(-c2nnc3n2CCN(C(=O)c2cccc(Cl)c2Cl)C3)n1] | *** | |
| 64 | 7-[(2,3-dichlorophenyl)carbonyl]-3-(1H-pyrrol-2-yl)-5,6,7,8-tetrahydro[1,2,4]triazolo[4,3-a]pyrazine | 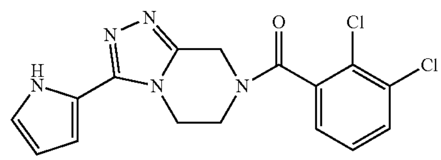 [SMILES: O=C(c1cccc(Cl)c1Cl)N1CCn2c(nnc2-c2ccc[nH]2)C1] | *** | |
| 65 | 7-{[2-chloro-3-(trifluoromethyl)phenyl]carbonyl}-3-(2-methyl-3-pyridinyl)-5,6,7,8-tetrahydro[1,2,4]triazolo[4,3-a]pyrazine | 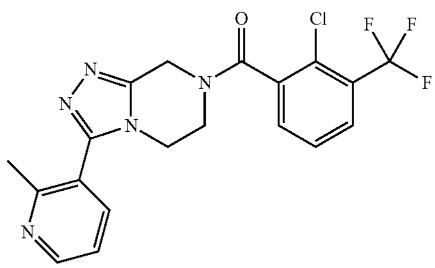 [SMILES: Cc1ncccc1-c1nnc2n1CCN(C(=O)c1cccc(C(F)(F)F)c1Cl)C2] | ** | |
| 66 | 7-[(2,3-dichlorophenyl)carbonyl]-3-(3-methyl-2-pyridinyl)-5,6,7,8-tetrahydro[1,2,4]triazolo[4,3-a]pyrazine | 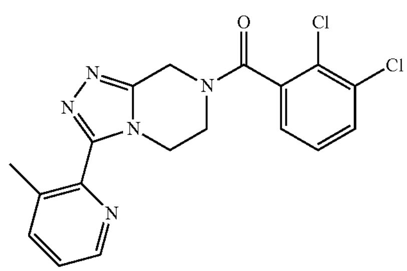 [SMILES: Cc1cccnc1-c1nnc2n1CCN(C(=O)c1cccc(Cl)c1Cl)C2] | ** | |
| 67 | 7-[(2,3-dichlorophenyl)carbonyl]-3-(1,3-thiazol-4-yl)-5,6,7,8-tetrahydro[1,2,4]triazolo[4,3-a]pyrazine | 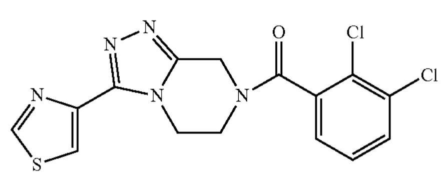 [SMILES: O=C(c1cccc(Cl)c1Cl)N1CCn2c(nnc2-c2cscn2)C1] | *** | |
| 68 | 7-{[2-chloro-3-(trifluoromethyl)phenyl]carbonyl}-3-(1-methyl-1H-pyrazol-5-yl)-5,6,7,8-tetrahydro[1,2,4]triazolo[4,3-a]pyrazine | 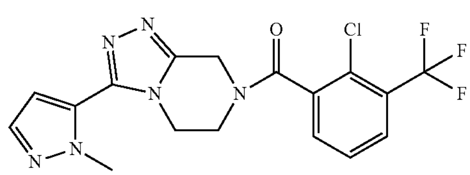 [SMILES: Cn1nccc1-c1nnc2n1CCN(C(=O)c1cccc(C(F)(F)F)c1Cl)C2] | ** | |

| Ex | Name | Structure | Assay 1 | Assay 2 |
|---|---|---|---|---|
| 69 | 7-[(2,3-dichlorophenyl)carbonyl]-3-(6-methyl-2-pyridinyl)-5,6,7,8-tetrahydro[1,2,4]triazolo[4,3-a]pyrazine | 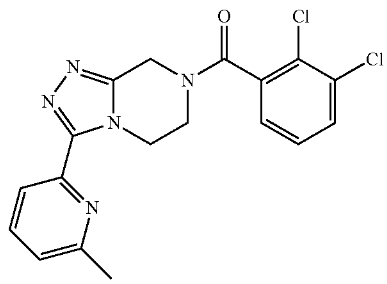 [SMILES: Cc1cccc(-c2nnc3n2CCN(C(=O)c2cccc(Cl)c2Cl)C3)n1] | *** | |
| 70 | 7-[(2,3-dichlorophenyl)carbonyl]-3-phenyl-5,6,7,8-tetrahydro[1,2,4]triazolo[4,3-a]pyrazine | 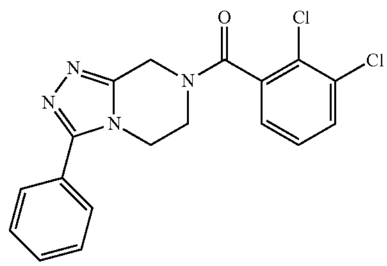 [SMILES: O=C(c1cccc(Cl)c1Cl)N1CCn2c(nnc2-c2ccccc2)C1] | *** | |
| 71 | 7-[(2-chloro-4-fluorophenyl)carbonyl]-3-(5-methyl-3-isoxazolyl)-5,6,7,8-tetrahydro[1,2,4]triazolo[4,3-a]pyrazine | 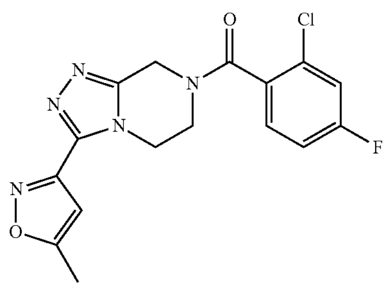 [SMILES: Cc1cc(-c2nnc3n2CCN(C(=O)c2ccc(F)cc2Cl)C3)no1] | * | |
| 72 | 7-[(2-chloro-4-fluorophenyl)carbonyl]-3-(1-methyl-1H-pyrazol-3-yl)-5,6,7,8-tetrahydro[1,2,4]triazolo[4,3-a]pyrazine | 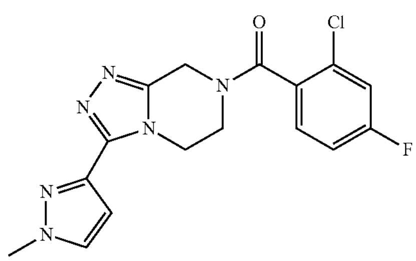 [SMILES: Cn1ccc(-c2nnc3n2CCN(C(=O)c2ccc(F)cc2Cl)C3)n1] | ** | |
| 73 | 7-[(2,3-dichlorophenyl)carbonyl]-3-(2-methyl-3-pyridinyl)-5,6,7,8-tetrahydro[1,2,4]triazolo[4,3-a]pyrazine | 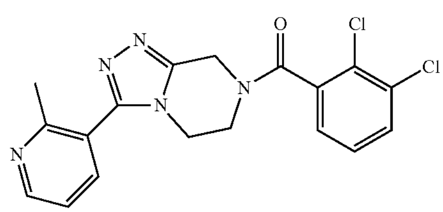 [SMILES: Cc1ncccc1-c1nnc2n1CCN(C(=O)c1cccc(Cl)c1Cl)C2] | ** | |
| 74 | 7-[(2-chloro-4-fluorophenyl)carbonyl]-3-(2-methyl-3-pyridinyl)-5,6,7,8-tetrahydro[1,2,4]triazolo[4,3-a]pyrazine | 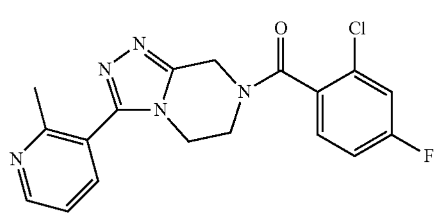 [SMILES: Cc1ncccc1-c1nnc2n1CCN(C(=O)c1ccc(F)cc1Cl)C2] | * | |

| Ex | Name | Structure | Assay 1 | Assay 2 |
|---|---|---|---|---|
| 75 | 7-[(2-chlorophenyl)carbonyl]-3-(2-pyridinyl)-5,6,7,8-tetrahydro[1,2,4]triazolo[4,3-a]pyrazine | 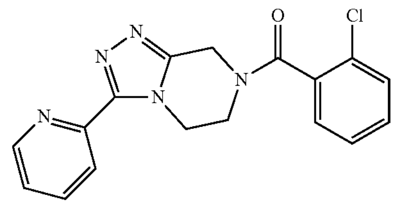 [SMILES: O=C(c1ccccc1Cl)N1CCn2c(nnc2-c2ccccn2)C1] | ** | |
| 76 | 7-[(2,4-dichlorophenyl)carbonyl]-3-(2-pyridinyl)-5,6,7,8-tetrahydro[1,2,4]triazolo[4,3-a]pyrazine | 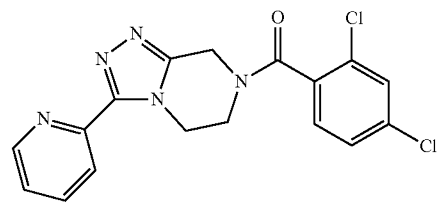 [SMILES: O=C(c1ccc(Cl)cc1Cl)N1CCn2c(nnc2-c2ccccn2)C1] | *** | |
| 77 | 7-{[2-chloro-3-(trifluoromethyl)phenyl]carbonyl}-3-(2-furanyl)-5,6,7,8-tetrahydro[1,2,4]triazolo[4,3-a]pyrazine | 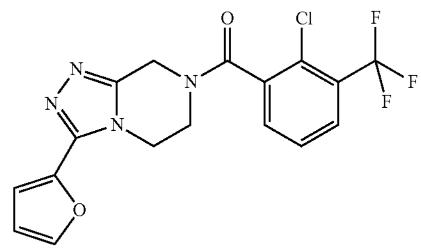 [SMILES: O=C(c1cccc(C(F)(F)F)c1Cl)N1CCn2c(nnc2-c2ccco2)C1] | *** | |
| 78 | 7-[(2,4-difluorophenyl)carbonyl]-3-(2-pyridinyl)-5,6,7,8-tetrahydro[1,2,4]triazolo[4,3-a]pyrazine | 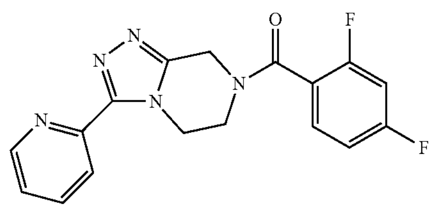 [SMILES: O=C(c1ccc(F)cc1F)N1CCn2c(nnc2-c2ccccn2)C1] | ** | |
| 79 | 7-[(2-chloro-6-fluorophenyl)carbonyl]-3-(2-pyridinyl)-5,6,7,8-tetrahydro[1,2,4]triazolo[4,3-a]pyrazine | 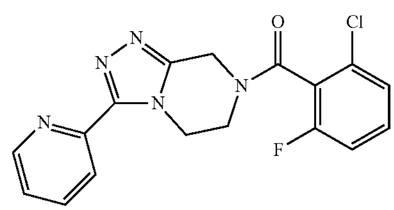 [SMILES: O=C(c1c(F)cccc1Cl)N1CCn2c(nnc2-c2ccccn2)C1] | * | |
| 80 | 7-[(3-chlorophenyl)carbonyl]-3-(2-pyridinyl)-5,6,7,8-tetrahydro[1,2,4]triazolo[4,3-a]pyrazine | 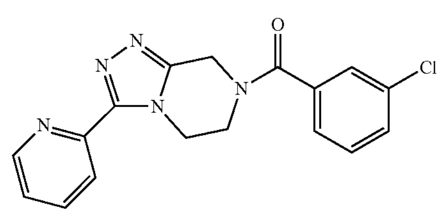 [SMILES: O=C(c1cccc(Cl)c1)N1CCn2c(nnc2-c2ccccn2)C1] | ** | |
| 81 | 7-[(2,3-dichlorophenyl)carbonyl]-3-(1-methyl-1H-pyrazol-5-yl)-5,6,7,8-tetrahydro[1,2,4]triazolo[4,3-]pyrazine | 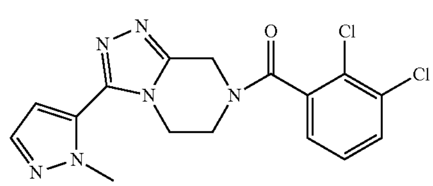 [SMILES: Cn1nccc1-c1nnc2n1CCN(C(=O)c1cccc(Cl)c1Cl)C2] | ** | |

-continued

| Ex | Name | Structure | Assay 1 | Assay 2 |
|---|---|---|---|---|
| 82 | -[(2-chloro-4-fluorophenyl)carbonyl]-3-(1-methyl-1H-pyrrol-2-yl)-5,6,7,8-tetrahydro[1,2,4]triazolo[4,3-a]pyrazine | 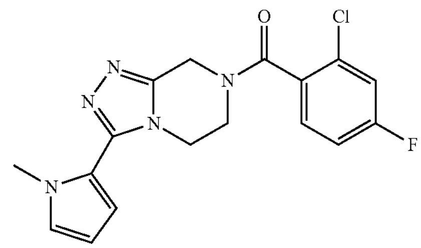 [SMILES: Cn1cccc1-c1nnc2n1CCN(C(=O)c1ccc(F)cc1Cl)C2] | ** | |
| 83 | 7-{[2-chloro-3-(trifluoromethyl)phenyl]carbonyl}-3-(3,5-difluoro-2-pyridinyl)-5,6,7,8-tetrahydro[1,2,4]triazolo[4,3-a]pyrazine | 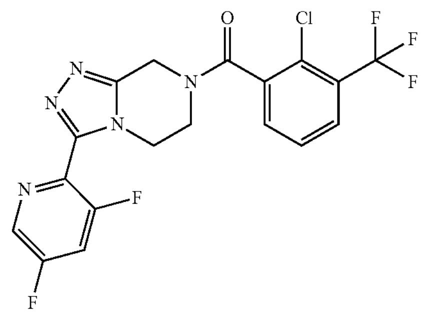 [SMILES: O=C(c1cccc(C(F)(F)F)c1Cl)N1CCn2c(nnc2-c2ncc(F)cc2F)C1] | *** | |
| 84 | 7-[(2-chloro-4-fluorophenyl)carbonyl]-3-(3,5-difluoro-2-pyridinyl)-5,6,7,8-tetrahydro[1,2,4]triazolo[4,3-a]pyrazine | 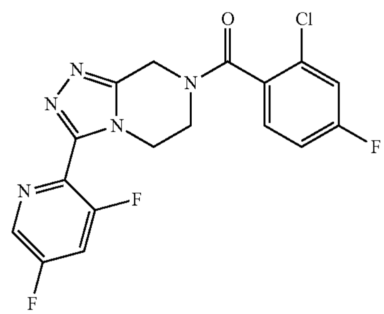 [SMILES: O=C(c1ccc(F)cc1Cl)N1CCn2c(nnc2-c2ncc(F)cc2F)C1] | ** | |
| 85 | 7-[(2-chloro-4-fluorophenyl)carbonyl]-3-(2-pyrazinyl)-5,6,7,8-tetrahydro[1,2,4]triazolo[4,3-a]pyrazine | 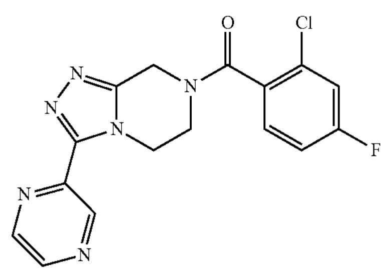 | *** | |
| 86 | 3-(2-pyridinyl)-7-{[3-(trifluoromethyl)phenyl]carbonyl}-5,6,7,8-tetrahydro[1,2,4]triazolo[4,3-a]pyrazine | 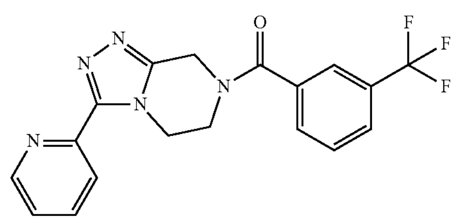 [SMILES: O=C(c1cccc(C(F)(F)F)c1)N1CCn2c(nnc2-c2ccccn2)C1] | ** | |
| 87 | 2-{[3-(2-pyridinyl)-5,6-dihydro[1,2,4]triazolo[4,3-a]pyrazin-7(8H)-yl]carbonyl}benzonitrile | 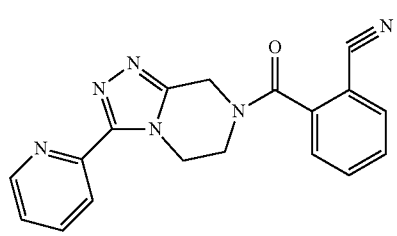 [SMILES: N#Cc1ccccc1C(=O)N1CCn2c(nnc2-c2ccccn2)C1] | ** | |

| Ex | Name | Structure | Assay 1 | Assay 2 |
|---|---|---|---|---|
| 88 | 7-[(2,3-difluorophenyl)carbonyl]-3-(2-pyridinyl)-5,6,7,8-tetrahydro[1,2,4]triazolo[4,3-a]pyrazine | 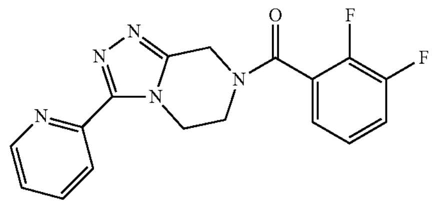 [SMILES: O=C(c1cccc(F)c1F)N1CCn2c(nnc2-c2ccccn2)C1] | ** | |
| 89 | 7-[(2,6-dichlorophenyl)carbonyl]-3-(2-pyridinyl)-5,6,7,8-tetrahydro[1,2,4]triazolo[4,3-a]pyrazine | 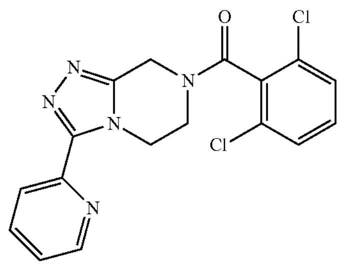 [SMILES: O=C(c1c(Cl)cccc1Cl)N1CCn2c(nnc2-c2ccccn2)C1] | * | |
| 90 | 7-[(2-chloro-4-fluorophenyl)carbonyl]-3-(1,3-thiazol-4-yl)-5,6,7,8-tetrahydro[1,2,4]triazolo[4,3-a]pyrazine | 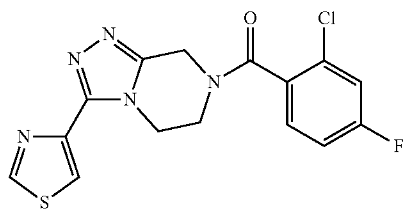 [SMILES: O=C(c1ccc(F)cc1Cl)N1CCn2c(nnc2-c2cscn2)C1] | *** | |
| 91 | 7-{[2-fluoro-3-(trifluoromethyl)phenyl]carbonyl}-3-(2-pyridinyl)-5,6,7,8-tetrahydro[1,2,4]triazolo[4,3-a]pyrazine | 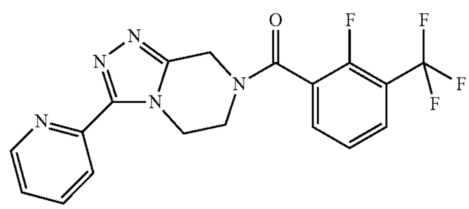 [SMILES: O=C(c1cccc(C(F)(F)F)c1F)N1CCn2c(nnc2-c2ccccn2)C1] | *** | |
| 92 | 7-[(2,4-dichlorophenyl)carbonyl]-3-(2-pyrazinyl)-5,6,7,8-tetrahydro[1,2,4]triazolo[4,3-a]pyrazine | 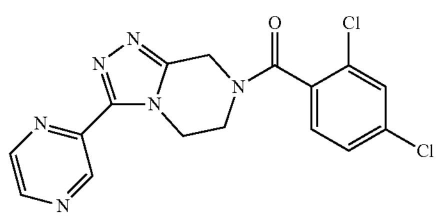 [SMILES: O=C(c1ccc(Cl)cc1Cl)N1CCn2c(nnc2-c2cnccn2)C1] | *** | |
| 93 | 7-[(2,4-dichlorophenyl)carbonyl]-3-(3-fluoro-2-pyridinyl)-5,6,7,8-tetrahydro[1,2,4]triazolo[4,3-a]pyrazine | 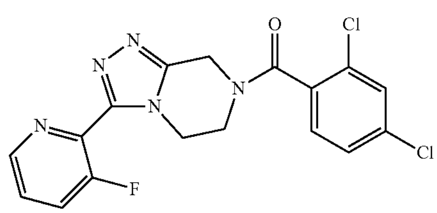 [SMILES: O=C(c1ccc(Cl)cc1Cl)N1CCn2c(nnc2-c2ncccc2F)C1] | ** | |
| 94 | 7-{[4-fluoro-2-(trifluoromethyl)phenyl]carbonyl}-3-(2-pyridinyl)-5,6,7,8-tetrahydro[1,2,4]triazolo[4,3-a]pyrazine | 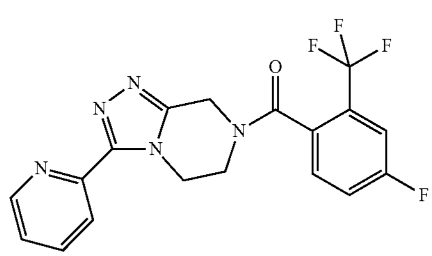 [SMILES: O=C(c1ccc(F)cc1C(F)(F)F)N1CCn2c(nnc2-c2ccccn2)C1] | ** | |

| Ex | Name | Structure | Assay 1 | Assay 2 |
|---|---|---|---|---|
| 95 | 7-[(2,4-dichlorophenyl)carbonyl]-3-(5-fluoro-2-pyridinyl)-5,6,7,8-tetrahydro[1,2,4]triazolo[4,3-a]pyrazine | 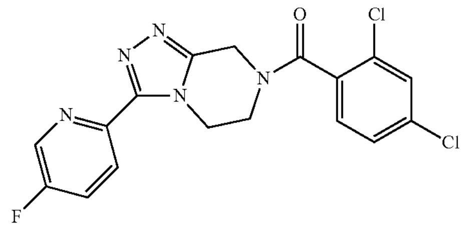 [SMILES: O=C(c1ccc(Cl)cc1Cl)N1CCn2c(nnc2-c2ccc(F)cn2)C1] | ** | |
| 96 | 7-[(4-chloro-2-fluorophenyl)carbonyl]-3-(2-pyridinyl)-5,6,7,8-tetrahydro[1,2,4]triazolo[4,3-a]pyrazine | 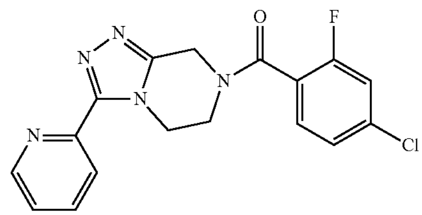 [SMILES: O=C(c1ccc(Cl)cc1F)N1CCn2c(nnc2-c2ccccn2)C1] | ** | |
| 97 | 7-[(2,4-dichlorophenyl)carbonyl]-3-(1,3-thiazol-4-yl)-5,6,7,8-tetrahydro[1,2,4]triazolo[4,3-a]pyrazine | 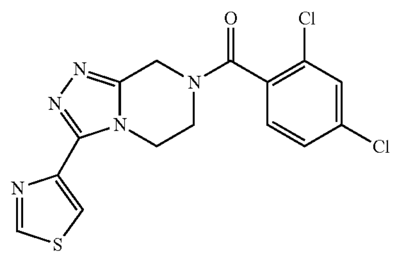 [SMILES: O=C(c1ccc(Cl)cc1Cl)N1CCn2c(nnc2-c2cscn2)C1] | *** | |
| 98 | 7-[(2,3-dichlorophenyl)carbonyl]-3-(2,4-difluorophenyl)-5,6,7,8-tetrahydro[1,2,4]triazolo[4,3-a]pyrazine | 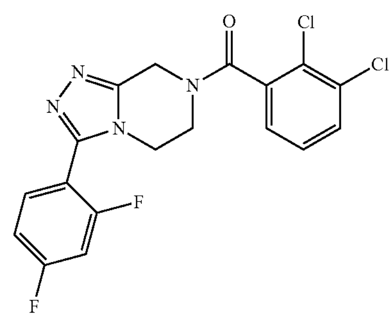 [SMILES: O=C(c1cccc(Cl)c1Cl)N1CCn2c(nnc2-c2ccc(F)cc2F)C1] | ** | |
| 99 | 7-[(2,3-dichlorophenyl)carbonyl]-3-(4-fluorophenyl)-5,6,7,8-tetrahydro[1,2,4]triazolo[4,3-a]pyrazine | 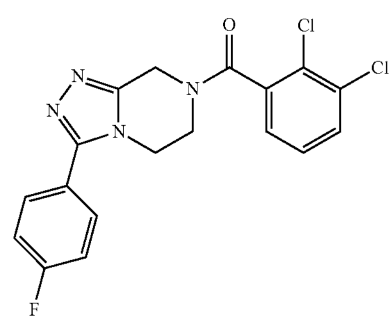 [SMILES: O=C(c1cccc(Cl)c1Cl)N1CCn2c(nnc2-c2ccc(F)cc2)C1] | *** | |

| Ex | Name | Structure | Assay 1 | Assay 2 |
|---|---|---|---|---|
| 100 | 7-[(2,4-dichlorophenyl)carbonyl]-3-(4-fluorophenyl)-5,6,7,8-tetrahydro[1,2,4]triazolo[4,3-a]pyrazine | 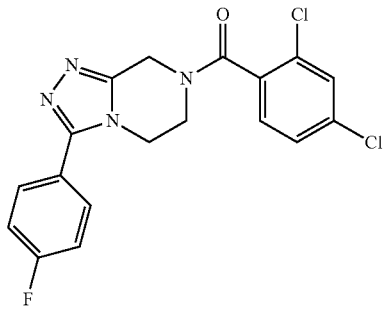 [SMILES: O=C(c1ccc(Cl)cc1Cl)N1CCn2c(nnc2-c2ccc(F)cc2)C1] | * | |
| 101 | 7-[(2,4-dichlorophenyl)carbonyl]-3-(2,4-difluorophenyl)-5,6,7,8-tetrahydro[1,2,4]triazolo[4,3-a]pyrazine | 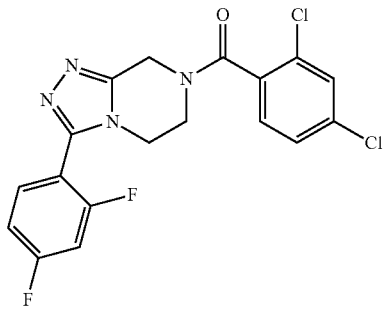 [SMILES: O=C(c1ccc(Cl)cc1Cl)N1CCn2c(nnc2-c2ccc(F)cc2F)C1] | ** | |
| 102 | 7-[(2,4-dichlorophenyl)carbonyl]-3-(4-pyrimidinyl)-5,6,7,8-tetrahydro[1,2,4]triazolo[4,3-a]pyrazine | 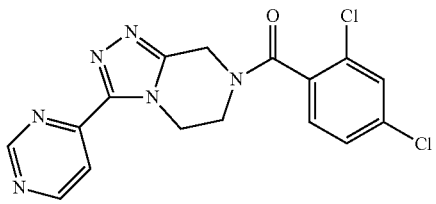 | ** | |
| 103 | 7-[(2-chlorophenyl)carbonyl]-3-(1,3-thiazol-4-yl)-5,6,7,8-tetrahydro[1,2,4]triazolo[4,3-a]pyrazine | 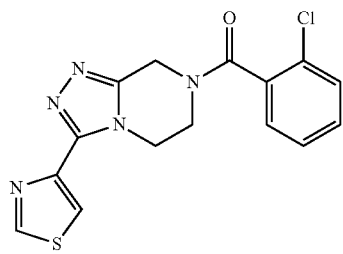 [SMILES: O=C(c1ccccc1Cl)N1CCn2c(nnc2-c2cscn2)C1] | ** | |
| 104 | 7-{[4-chloro-3-(trifluoromethyl)phenyl]carbonyl}-3-(2-pyrazinyl)-5,6,7,8-tetrahydro[1,2,4]triazolo[4,3-a]pyrazine | 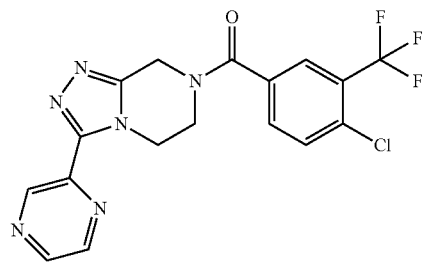 [SMILES: O=C(c1ccc(Cl)c(C(F)(F)F)c1)N1CCn2c(nnc2-c2cnccn2)C1] | ** | |

| Ex | Name | Structure | Assay 1 | Assay 2 |
|---|---|---|---|---|
| 105 | 7-[(3-chloro-4-fluorophenyl)carbonyl]-3-(2-pyrazinyl)-5,6,7,8-tetrahydro[1,2,4]triazolo[4,3-a]pyrazine | 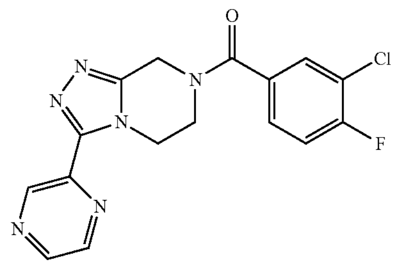 [SMILES: O=C(c1ccc(F)c(Cl)c1)N1CCn2c(nnc2-c2cnccn2)C1] | ** | |
| 106 | 7-[(4-chloro-2-fluorophenyl)carbonyl]-3-(2-pyrazinyl)-5,6,7,8-tetrahydro[1,2,4]triazolo[4,3-a]pyrazine | 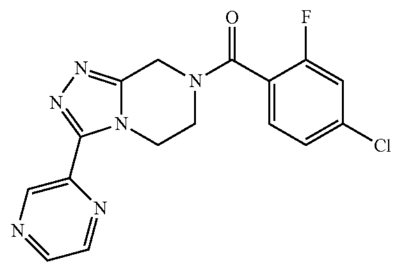 [SMILES: O=C(c1ccc(Cl)cc1F)N1CCn2c(nnc2-c2cnccn2)C1] | *** | |
| 107 | 7-[(4-fluoro-2-methylphenyl)carbonyl]-3-(2-pyrazinyl)-5,6,7,8-tetrahydro[1,2,4]triazolo[4,3-a]pyrazine | 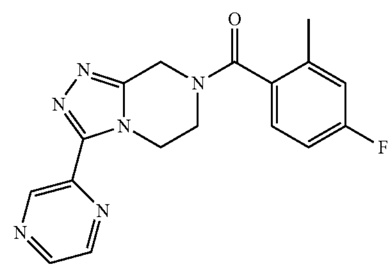 [SMILES: Cc1cc(F)ccc1C(=O)N1CCn2c(nnc2-c2cnccn2)C1] | ** | |
| 108 | 7-{[4-fluoro-3-(trifluoromethyl)phenyl]carbonyl}-3-(2-pyrazinyl)-5,6,7,8-tetrahydro[1,2,4]triazolo[4,3-a]pyrazine | 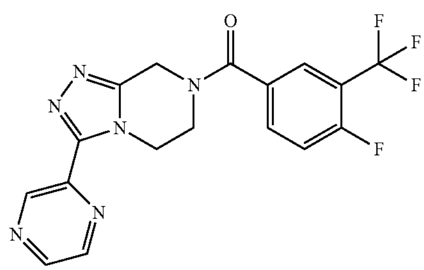 [SMILES: O=C(c1ccc(F)c(C(F)(F)F)c1)N1CCn2c(nnc2-c2cnccn2)C1] | ** | |
| 109 | 3-Bromo-7-[(2-chloro-4-fluorophenyl)carbonyl]-5,6,7,8-tetrahydro[1,2,4]triazolo[4,3-a]pyrazine | 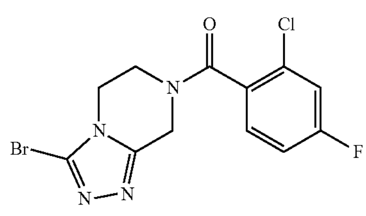 [SMILES: O=C(c1ccc(F)cc1Cl)N1CCn2c(Br)nnc2C1] | * | |
| 110 | 7-[(2,4-Dichloro-3-fluorophenyl)carbonyl]-3-(5-fluoro-2-pyridinyl)-5,6,7,8-tetrahydro[1,2,4]triazolo[4,3-a]pyrazine | 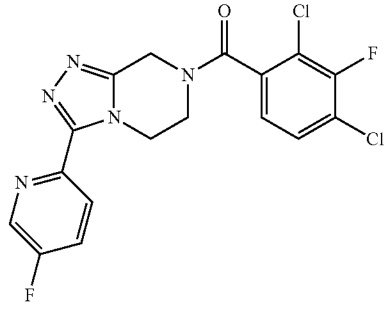 [SMILES: O=C(c1ccc(Cl)c(F)c1Cl)N1CCn2c(nnc2-c2ccc(F)cn2)C1] | *** | |

| Ex | Name | Structure | Assay 1 | Assay 2 |
|---|---|---|---|---|
| 111 | 7-[(2,4-Dichloro-3-fluorophenyl)carbonyl]-3-(2-pyrazinyl)-5,6,7,8-tetrahydro[1,2,4]triazolo[4,3-a]pyrazine | 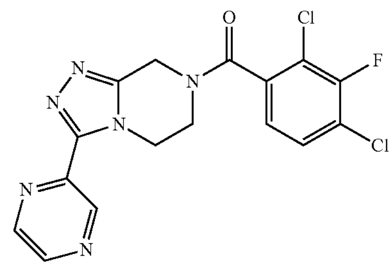 [SMILES: O=C(c1ccc(Cl)c(F)c1Cl)N1CCn2c(nnc2-c2cnccn2)C1] | * | * |
| 112 | 7-[(2,4-Dichloro-3-fluorophenyl)carbonyl]-3-(4-pyrimidinyl)-5,6,7,8-tetrahydro[1,2,4]triazolo[4,3-a]pyrazine | 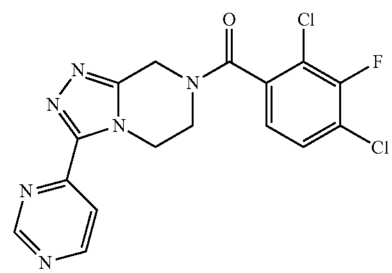 [SMILES: O=C(c1ccc(Cl)c(F)c1Cl)N1CCn2c(nnc2-c2ccncn2)C1] | ** | |
| 113 | 7-[(2,3-Dichloro-4-fluorophenyl)carbonyl]-3-(2-pyrazinyl)-5,6,7,8-tetrahydro[1,2,4]triazolo[4,3-a]pyrazine | 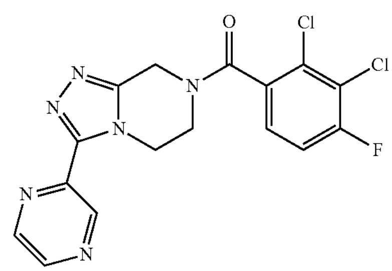 [SMILES: O=C(c1ccc(F)c(Cl)c1Cl)N1CCn2c(nnc2-c2cnccn2)C1] | *** | |
| 114 | 7-[(2,3-Dichloro-4-fluorophenyl)carbonyl]-3-(5-fluoro-2-pyridinyl)-5,6,7,8-tetrahydro[1,2,4]triazolo[4,3-a]pyrazine | 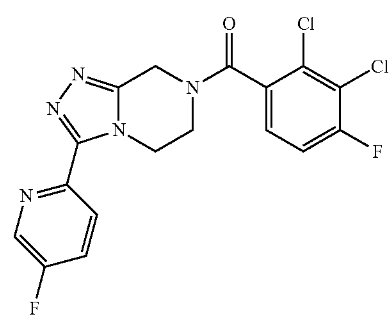 [SMILES: O=C(c1ccc(F)c(Cl)c1Cl)N1CCn2c(nnc2-c2ccc(F)cn2)C1] | * | * |
| 115 | 7-[(3,4-dichlorophenyl)carbonyl]-3-(2-pyrazinyl)-5,6,7,8-tetrahydro[1,2,4]triazolo[4,3-a]pyrazine | 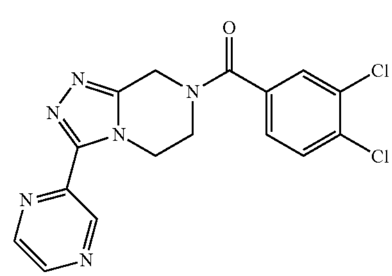 [SMILES: O=C(c1ccc(Cl)c(Cl)c1)N1CCn2c(nnc2-c2cnccn2)C1] | ** | |

| Ex | Name | Structure | Assay 1 | Assay 2 |
|---|---|---|---|---|
| 116 | 7-[(2-chlorophenyl)carbonyl]-3-(4-pyrimidinyl)-5,6,7,8-tetrahydro[1,2,4]triazolo[4,3-a]pyrazine | 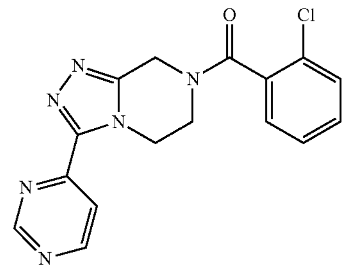 [SMILES: O=C(c1ccccc1Cl)N1CCn2c(nnc2-c2ccncn2)C1] | * | |
| 117 | 7-[(2-chlorophenyl)carbonyl]-3-(2-furanyl)-5,6,7,8-tetrahydro[1,2,4]triazolo[4,3-a]pyrazine | 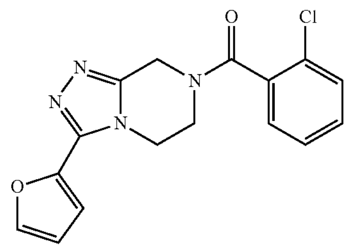 [SMILES: O=C(c1ccccc1Cl)N1CCn2c(nnc2-c2ccco2)C1] | *** | |
| 118 | 7-[(2-chlorophenyl)carbonyl]-3-(5-fluoro-2-pyridinyl)-5,6,7,8-tetrahydro[1,2,4]triazolo[4,3-a]pyrazine | 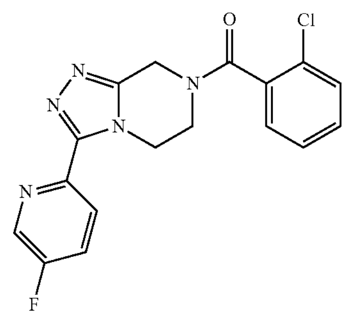 [SMILES: O=C(c1ccccc1Cl)N1CCn2c(nnc2-c2ccc(F)cn2)C1] | ** | |
| 119 | 7-[(2-chlorophenyl)carbonyl]-3-(4-fluorophenyl)-5,6,7,8-tetrahydro[1,2,4]triazolo[4,3-a]pyrazine | 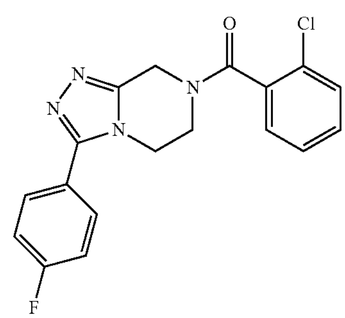 [SMILES: O=C(c1ccccc1Cl)N1CCn2c(nnc2-c2ccc(F)cc2)C1] | ** | |
| 120 | -[(2-chlorophenyl)carbonyl]-3-(2-pyrazinyl)-5,6,7,8-tetrahydro[1,2,4]triazolo[4,3-a]pyrazine | 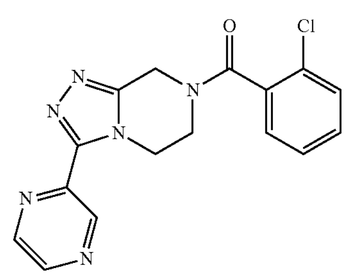 [SMILES: O=C(c1ccccc1Cl)N1CCn2c(nnc2-c2cnccn2)C1] | ** | |

-continued

| Ex | Name | Structure | Assay 1 | Assay 2 |
|---|---|---|---|---|
| 121 | 7-[(2-chlorophenyl)carbonyl]-3-(3-fluoro-2-pyridinyl)-5,6,7,8-tetrahydro[1,2,4]triazolo[4,3-a]pyrazine | 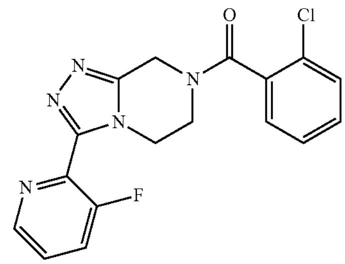 [SMILES: O=C(c1ccccc1Cl)N1CCn2c(nnc2-c2ncccc2F)C1] | ** | |
| 122 | 3-(2-pyridinyl)-7-{[2-(trifluoromethyl)phenyl]carbonyl}-5,6,7,8-tetrahydro[1,2,4]triazolo[4,3-a]pyrazine | 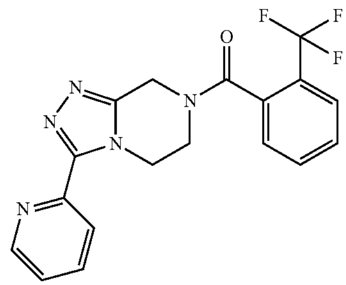 [SMILES: O=C(c1ccccc1C(F)(F)F)N1CCn2c(nnc2-c2ccccn2)C1] | ** | |
| 123 | -[(2-chloro-4-fluorophenyl)carbonyl]-3-(3-fluorophenyl)-5,6,7,8-tetrahydro[1,2,4]triazolo[4,3-a]pyrazine | 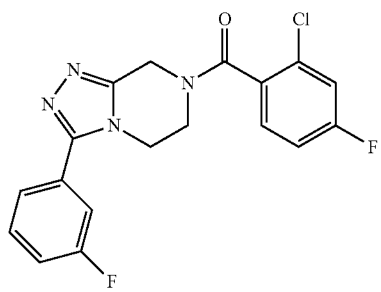 [SMILES: O=C(c1ccc(F)cc1Cl)N1CCn2c(nnc2-c2cccc(F)c2)C1] | ** | |
| 124 | 7-[(2-chloro-4-fluorophenyl)carbonyl]-3-(3,4-difluorophenyl)-5,6,7,8-tetrahydro[1,2,4]triazolo[4,3-a]pyrazine | 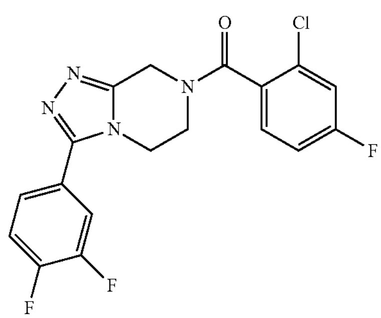 [SMILES: O=C(c1ccc(F)cc1Cl)N1CCn2c(nnc2-c2ccc(F)c(F)c2)C1] | ** | |
| 125 | 7-[(2-chloro-4-fluorophenyl)carbonyl]-3-[3-(methyloxy)phenyl]-5,6,7,8-tetrahydro[1,2,4]triazolo[4,3-a]pyrazine | 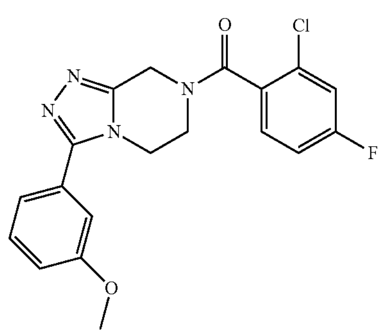 [SMILES: COc1cccc(-c2nnc3n2CCN(C(=O)c2ccc(F)cc2Cl)C3)c1] | ** | |

| Ex | Name | Structure | Assay 1 | Assay 2 |
|---|---|---|---|---|
| 126 | 7-[(2-chloro-4-fluorophenyl)carbonyl]-3-(3-chlorophenyl)-5,6,7,8-tetrahydro[1,2,4]triazolo[4,3-a]pyrazine | 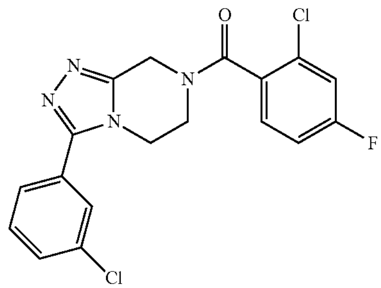 |  |  |
| 127 | 7-[(2-chloro-4-fluorophenyl)carbonyl]-3-[2-(methyloxy)phenyl]-5,6,7,8-tetrahydro[1,2,4]triazolo[4,3-a]pyrazine | 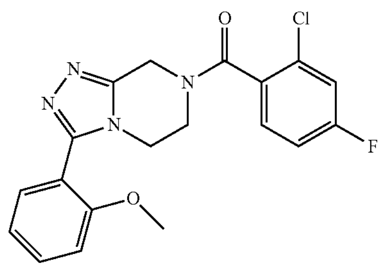 [SMILES: COc1ccccc1-c1nnc2n1CCN(C(=O)c1ccc(F)cc1Cl)C2] | * | |
| 128 | 2-{7-[(2-chloro-4-fluorophenyl)carbonyl]-5,6,7,8-tetrahydro[1,2,4]triazolo[4,3-a]pyrazin-3-yl}phenol | 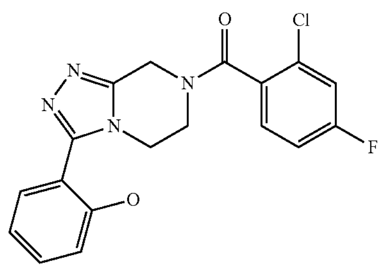 [SMILES: O=C(c1ccc(F)cc1Cl)N1CCn2c(nnc2-c2ccccc2O)C1] | * | |
| 129 | 8-{7-[(2-chloro-4-fluorophenyl)carbonyl]-5,6,7,8-tetrahydro[1,2,4]triazolo[4,3-a]pyrazin-3-yl}quinoline | 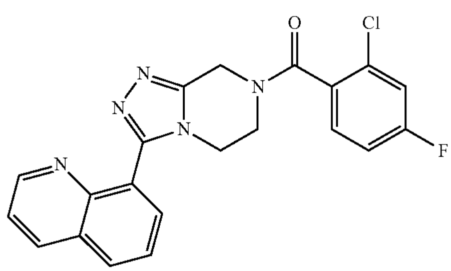 [SMILES: O=C(c1ccc(F)cc1Cl)N1CCn2c(nnc2-c2cccc3cccnc23)C1] | * | |
| 130 | 7-[(2-chloro-4-fluorophenyl)carbonyl]-3-(2,3-dichlorophenyl)-5,6,7,8-tetrahydro[1,2,4]triazolo[4,3-a]pyrazine | 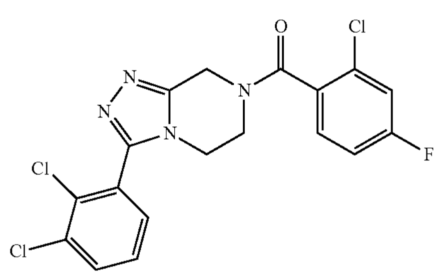 [SMILES: O=C(c1ccc(F)cc1Cl)N1CCn2c(nnc2-c2cccc(Cl)c2Cl)C1] | ** | |

-continued

| Ex | Name | Structure | Assay 1 | Assay 2 |
|---|---|---|---|---|
| 131 | 7-[(2-chloro-4-fluorophenyl)carbonyl]-3-(2,3-difluorophenyl)-5,6,7,8-tetrahydro[1,2,4]triazolo[4,3-a]pyrazine | 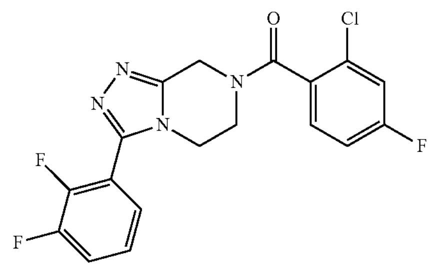 [SMILES: O=C(c1ccc(F)cc1Cl)N1CCn2c(nnc2-c2cccc(F)c2F)C1] | ** | |
| 132 | 7-[(2-chloro-4-fluorophenyl)carbonyl]-3-(1H-indol-7-yl)-5,6,7,8-tetrahydro[1,2,4]triazolo[4,3-a]pyrazine | 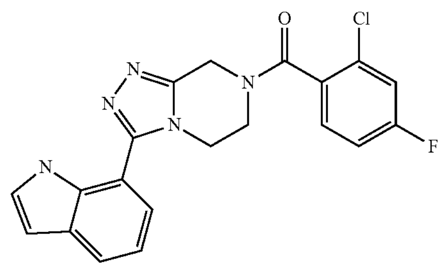 [SMILES: O=C(c1ccc(F)cc1Cl)N1CCn2c(nnc2-c2cccc3cc[nH]c23)C1] | ** | |
| 133 | 7-{[2-chloro-3-(trifluoromethyl)phenyl]carbonyl}-3-cyclopropyl-5,6,7,8-tetrahydro[1,2,4]triazolo[4,3-a]pyrazine | 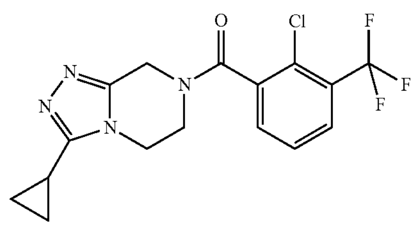 [SMILES: O=C(c1cccc(C(F)(F)F)c1Cl)N1CCn2c(nnc2C2CC2)C1] | ** | |
| 134 | 7-{[2-chloro-3-(trifluoromethyl)phenyl]carbonyl}-3-propyl-5,6,7,8-tetrahydro[1,2,4]triazolo[4,3-a]pyrazine | 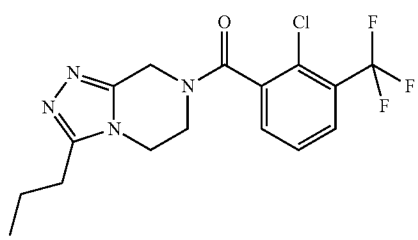 [SMILES: CCCc1nnc2n1CCN(C(=O)c1cccc(C(F)(F)F)c1Cl)C2] | ** | |
| 135 | 7-{[2-chloro-3-(trifluoromethyl)phenyl]carbonyl}-3-cyclohexyl-5,6,7,8-tetrahydro[1,2,4]triazolo[4,3-a]pyrazine | 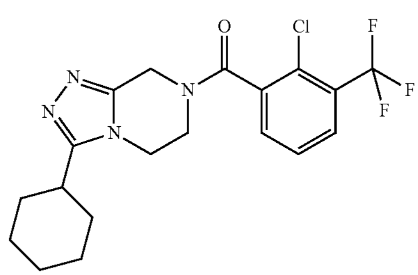 [SMILES: O=C(c1cccc(C(F)(F)F)c1Cl)N1CCn2c(nnc2C2CCCCC2)C1] | ** | |
| 136 | 7-[(2-chloro-4-fluorophenyl)carbonyl]-3-(2-methyl-1,3-thiazol-4-yl)-5,6,7,8-tetrahydro[1,2,4]triazolo[4,3-a]pyrazine | 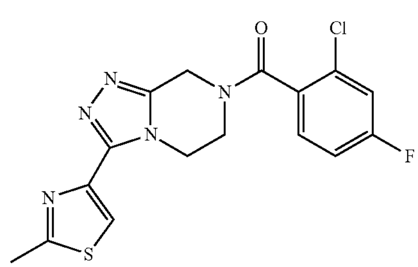 [SMILES: Cc1nc(-c2nnc3n2CCN(C(=O)c2ccc(F)cc2Cl)C3)cs1] | * | |

| Ex | Name | Structure | Assay 1 | Assay 2 |
|---|---|---|---|---|
| 137 | 7-{[2-chloro-3-(trifluoromethyl)phenyl]carbonyl}-3-[2-(methyloxy)ethyl]-5,6,7,8-tetrahydro[1,2,4]triazolo[4,3-a]pyrazine | 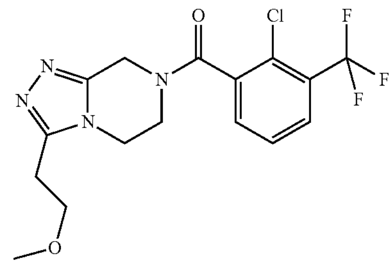 [SMILES: COCCc1nnc2n1CCN(C(=O)c1cccc(C(F)(F)F)c1Cl)C2] | | ** |
| 138 | 2-(7-{[2-chloro-3-(trifluoromethyl)phenyl]carbonyl}-5,6,7,8-tetrahydro[1,2,4]triazolo[4,3-a]pyrazin-3-yl)phenol | 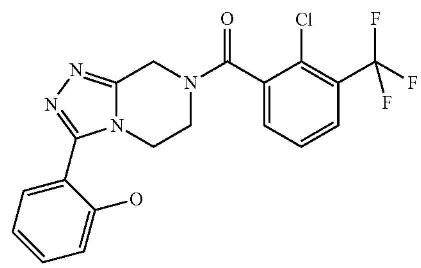 [SMILES: O=C(c1cccc(C(F)(F)F)c1Cl)N1CCn2c(nnc2-c2ccccc2O)C1] | | ** |
| 139 | 7-{[2-chloro-3-(trifluoromethyl)phenyl]carbonyl}-3-cyclopentyl-5,6,7,8-tetrahydro[1,2,4]triazolo[4,3-a]pyrazine | 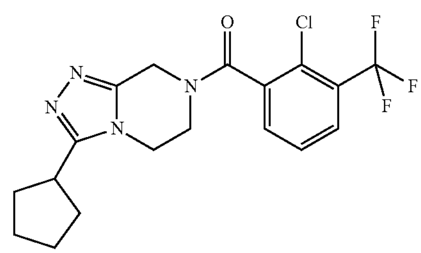 [SMILES: O=C(c1cccc(C(F)(F)F)c1Cl)N1CCn2c(nnc2C2CCCC2)C1] | | ** |
| 140 | 7-[(2-chloro-4-fluorophenyl)carbonyl]-3-(1-methyl-1H-imidazol-2-yl)-5,6,7,8-tetrahydro[1,2,4]triazolo[4,3-a]pyrazine | 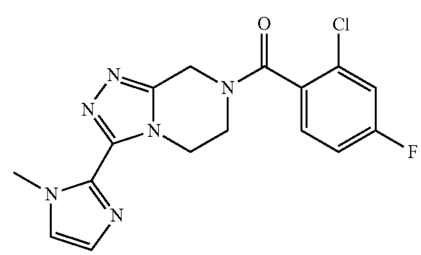 [SMILES: Cn1ccnc1-c1nnc2n1CCN(C(=O)c1ccc(F)cc1Cl)C2] | | * |
| 141 | 7-[(2-chloro-4-fluorophenyl)carbonyl]-3-(5-chloro-2-pyrazinyl)-5,6,7,8-tetrahydro[1,2,4]triazolo[4,3-a]pyrazine | 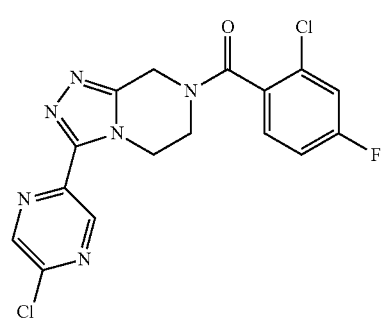 | | * |

-continued

| Ex | Name | Structure | Assay 1 | Assay 2 |
|---|---|---|---|---|
| 142 | 7-{[4-chloro-2-(trifluoromethyl)phenyl]carbonyl}-3-(2-pyrazinyl)-5,6,7,8-tetrahydro[1,2,4]triazolo[4,3-a]pyrazine | 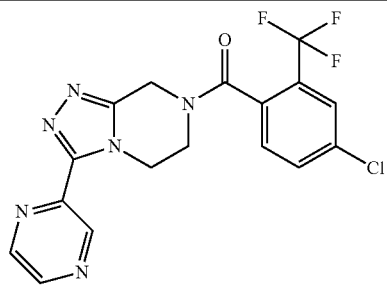 | | ** |
| 143 | 7-[(2,4-dimethylphenyl)carbonyl]-3-(2-pyrazinyl)-5,6,7,8-tetrahydro[1,2,4]triazolo[4,3-a]pyrazine | 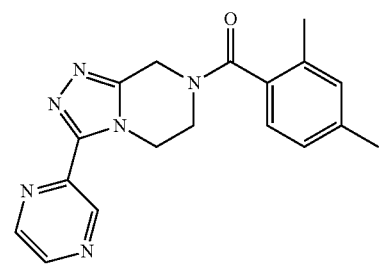 [SMILES: Cc1ccc(C(=O)N2CCn3c(nnc3-c3cnccn3)C2)c(C)c1] | | * |
| 144 | 7-[(2-chloro-4-fluorophenyl)carbonyl]-3-(1,3-thiazol-2-yl)-5,6,7,8-tetrahydro[1,2,4]triazolo[4,3-a]pyrazine | 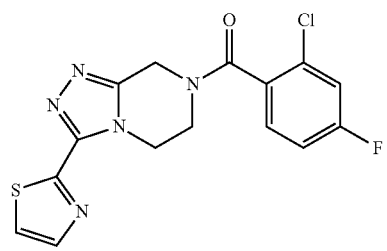 [SMILES: O=C(c1ccc(F)cc1Cl)N1CCn2c(nnc2-c2nccs2)C1] | | ** |
| 145 | 7-[(4-chloro-2-methylphenyl)carbonyl]-3-(2-pyrazinyl)-5,6,7,8-tetrahydro[1,2,4]triazolo[4,3-a]pyrazine | 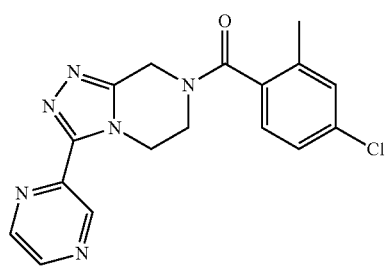 [SMILES: Cc1cc(Cl)ccc1C(=O)N1CCn2c(nnc2-c2cnccn2)C1] | | ** |
| 146 | 7-[(3-chloro-4-fluoro-2-methylphenyl)carbonyl]-3-(2-pyrazinyl)-5,6,7,8-tetrahydro[1,2,4]triazolo[4,3-a]pyrazine | 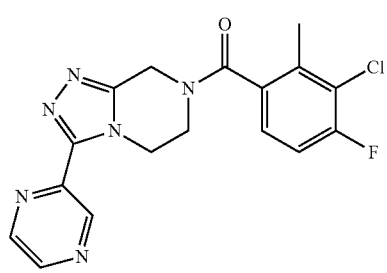 [SMILES: Cc1c(C(=O)N2CCn3c(nnc3-c3cnccn3)C2)ccc(F)c1Cl] | | *** |
| 147 | 7-[(2-bromo-4-fluorophenyl)carobnyl]-3-(2-pyrazinyl)-5,6,7,8-tetrahydro[1,2,4]triazolo[4,3-a]pyrazine | 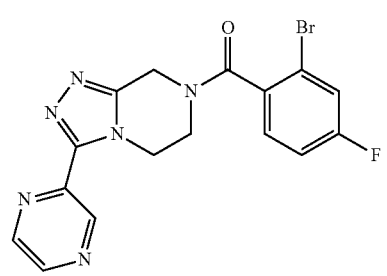 | | *** |

| Ex | Name | Structure | Assay 1 | Assay 2 |
|---|---|---|---|---|
| 148 | 7-{[4-methyl-2-(trifluoromethyl)phenyl]carbonyl}-3-(2-pyrazinyl)-5,6,7,8-tetrahydro[1,2,4]triazolo[4,3-a]pyrazine | 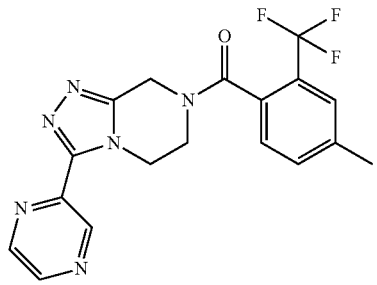 [SMILES: Cc1ccc(C(=O)N2CCn3c(nnc3-c3cnccn3)C2)c(C(F)(F)F)c1] | | * |
| 149 | 7-[(2,4-dichloro-3-fluorophenyl)carbonyl]-3-(1,3-thiazol-4-yl)-5,6,7,8-tetrahydro[1,2,4]triazolo[4,3-a]pyrazine | 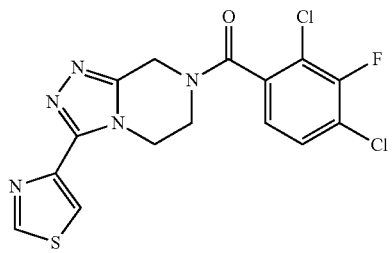 | | ** |
| 150 | 2-{7-[(2,4-dichloro-3-fluorophenyl)carbonyl]-5,6,7,8-tetrahydro[1,2,4]triazolo[4,3-a]pyrazin-3-yl}-5-fluorophenol | 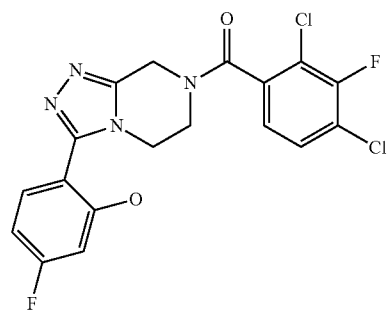 [SMILES: O=C(c1ccc(Cl)c(F)c1Cl)N1CCn2c(nnc2-c2ccc(F)cc2O)C1] | | ** |
| 151 | 7-[(3,4-difluoro-2-methylphenyl)carbonyl}-3-(2-pyrazinyl)-5,6,7,8-tetrahydro[1,2,4]triazolo[4,3-a]pyrazine | 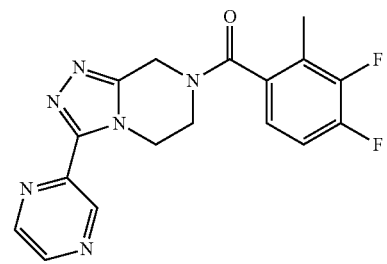 [SMILES: Cc1c(C(=O)N2CCn3c(nnc3-c3cnccn3)C2)ccc(F)c1F] | | *** |
| 152 | 7-[(2,3-dichloro-4-methylphenyl)carbonyl]-3-(2-pyrazinyl)-5,6,7,8-tetrahydro[1,2,4]triazolo[4,3-a]pyrazine | 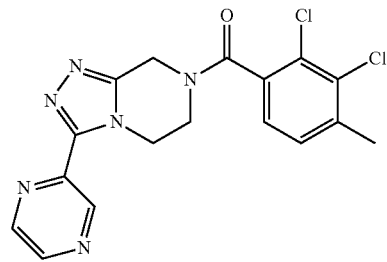 | | *** |

-continued

| Ex | Name | Structure | Assay 1 | Assay 2 |
|---|---|---|---|---|
| 153 | 7-[(2-chloro-4-fluoro-3-methylphenyl)carbonyl]-3-(2-pyrazinyl)-5,6,7,8-tetrahydro[1,2,4]triazolo[4,3-a]pyrazine | 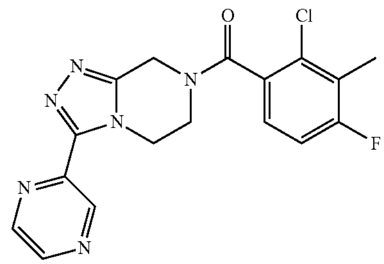 | | *** |
| 154 | 7-[(2,4-dichloro-3-methylphenyl)carbonyl]-3-(2-pyrazinyl)-5,6,7,8-tetrahydro[1,2,4]triazolo[4,3-a]pyrazine | 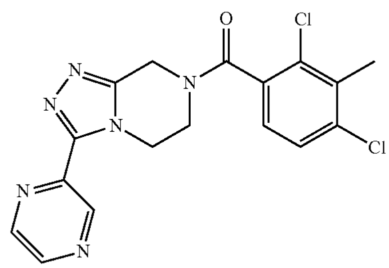 | | *** |
| 155 | 7-[(3,4-difluoro-2-methylphenyl)carobnyl]-3-(5-fluoro-2-pyridinyl)-5,6,7,8-tetrahydro[1,2,4]triazolo[4,3-a]pyrazine | 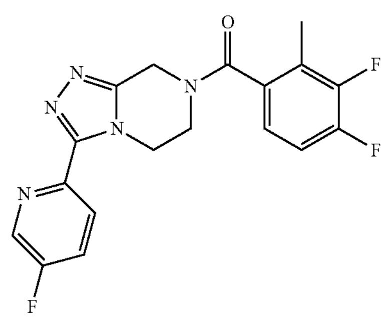 [SMILES: Cc1c(C(=O)N2CCn3c(nnc3-c3ccc(F)cn3)C2)ccc(F)c1F] | | ** |
| 156 | 7-[(3-chloro-4-fluoro-2-methylphenyl)carbonyl]-3-(5-fluoro-2-pyridinyl)-5,6,7,8-tetrahydro[1,2,4]triazolo[4,3-a]pyrazine | 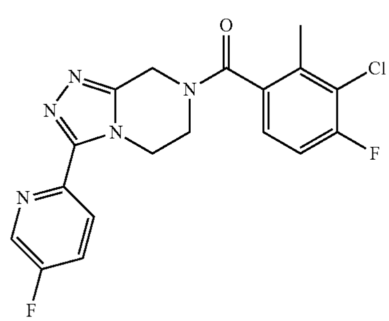 [SMILES: Cc1c(C(=O)N2CCn3c(nnc3-c3ccc(F)cn3)C2)ccc(F)c1Cl] | | *** |
| 157 | 7-[(2,4-dichlorophenyl)carbonyl]-3-(5-isoxazolyl)-5,6,7,8-tetrahydro[1,2,4]triazolo[4,3-a]pyrazine | 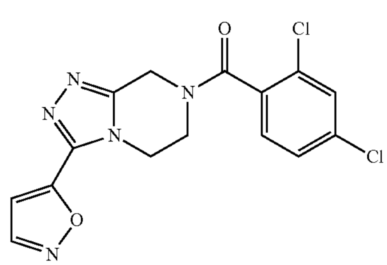 [SMILES: O=C(c1ccc(Cl)cc1Cl)N1CCn2c(nnc2-c2ccno2)C1] | | * |

-continued

| Ex | Name | Structure | Assay 1 | Assay 2 |
|---|---|---|---|---|
| 158 | 7-[(2,4-dichlorophenyl)carbonyl]-3-(5-isothiazolyl)-5,6,7,8-tetrahydro[1,2,4]triazolo[4,3-a]pyrazine | 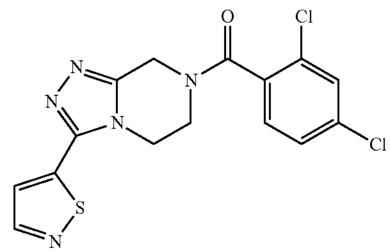 [SMILES: O=C(c1ccc(Cl)cc1Cl)N1CCn2c(nnc2-c2ccns2)C1] | | ** |
| 159 | 7-{[2-chloro-3-(trifluoromethyl)phenyl]carbonyl}-3-(5-methyl-2-furanyl)-5,6,7,8-tetrahydro[1,2,4]triazolo[4,3-a]pyrazine | 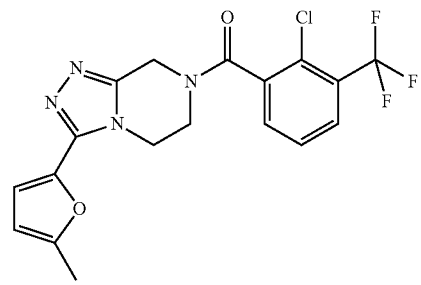 [SMILES: Cc1ccc(-c2nnc3n2CCN(C(=O)c2cccc(C(F)(F)F)c2Cl)C3)o1] | | *** |
| 160 | 7-[(2,4-dichlorophenyl)carbonyl]-3-(1,2,5-thiadiazol-3-yl)-5,6,7,8-tetrahydro[1,2,4]triazolo[4,3-a]pyrazine | 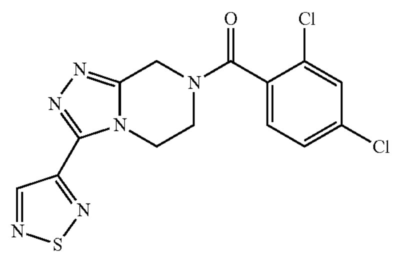 [SMILES: O=C(c1ccc(Cl)cc1Cl)N1CCn2c(nnc2-c2cnsn2)C1] | | ** |
| 161 | 7-[(2,4-dichlorophenyl)carbonyl]-3-(3-isoxazolyl)-5,6,7,8-tetrahydro[1,2,4]triazolo[4,3-a]pyrazine | 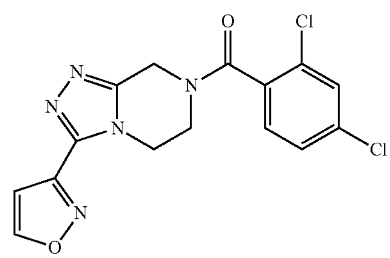 [SMILES: O=C(c1ccc(Cl)cc1Cl)N1CCn2c(nnc2-c2ccon2)C1] | | * |
| 163 | 3-(7-{[2-chloro-3-(trifluoromethyl)phenyl]carbonyl}-5,6,7,8-tetrahydro[1,2,4]triazolo[4,3-a]pyrazin-3-yl)-2-pyridinol | 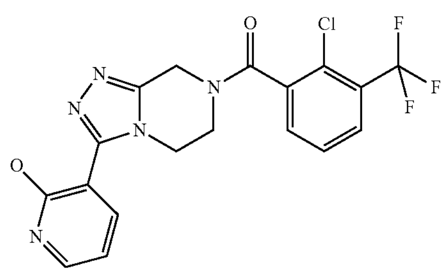 [SMILES: O=C(c1cccc(C(F)(F)F)c1Cl)N1CCn2c(nnc2-c2cccnc2O)C1] | | ** |
| 164 | 7-{[2-chloro-3-(trifluoromethyl)phenyl]carbonyl}-3-(1,2,4-thiadiazol-5-yl)-5,6,7,8-tetrahydro[1,2,4]triazolo[4,3-a]pyrazine | 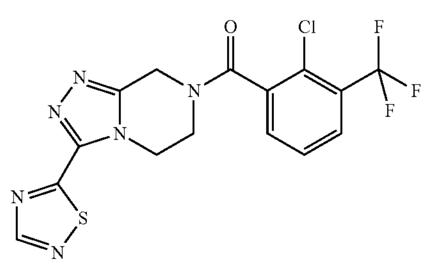 [SMILES: O=C(c1cccc(C(F)(F)F)c1Cl)N1CCn2c(nnc2-c2ncns2)C1] | | *** |

-continued

| Ex | Name | Structure | Assay 1 | Assay 2 |
|---|---|---|---|---|
| 165 | 7-[(2-chloro-4-fluorophenyl)carbonyl]-3-(5-fluoro-2-pyrazinyl)-5,6,7,8-tetrahydro[1,2,4]triazolo[4,3-a]pyrazine | 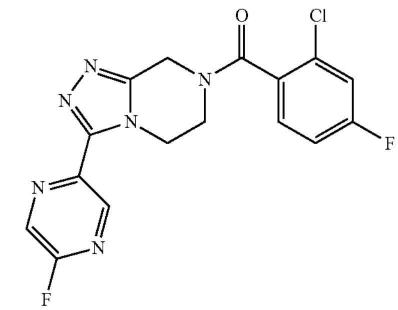 [SMILES: O=C(c1ccc(F)cc1Cl)N1CCn2c(nnc2-c2cnc(F)cn2)C1] | | ** |
| 166 | 2-(7-{[2-chloro-3-(trifluoromethyl)phenyl]carbonyl}-5,6,7,8-tetrahydro[1,2,4]triazolo[4,3-a]pyrazin-3-yl)-3-pyridinol | 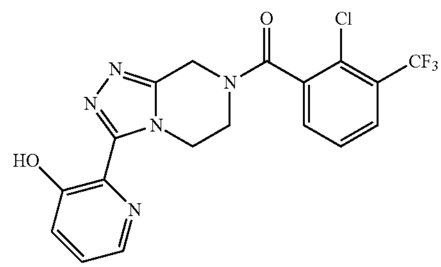 [SMILES: O=C(c1cccc(C(F)(F)F)c1Cl)N1CCn2c(nnc2-c2ncccc2O)C1] | | *** |
| 167 | 7-[(2,3-dichloro-4-fluorophenyl)carbonyl]-3-(5-methyl-2-furanyl)-5,6,7,8-tetrahydro[1,2,4]triazolo[4,3-a]pyrazine | 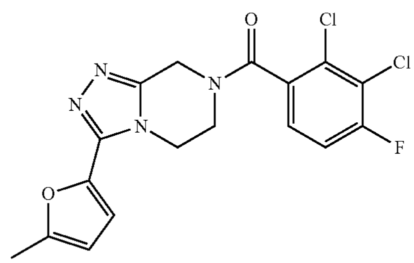 [SMILES: Cc1ccc(-c2nnc3n2CCN(C(=O)c2ccc(F)c(Cl)c2Cl)C3)o1] | | ** |
| 168 | 7-[(2,3-dichloro-4-fluorophenyl)carbonyl]-3-(3-pyridazinyl)-5,6,7,8-tetrahydro[1,2,4]triazolo[4,3-a]pyrazine | 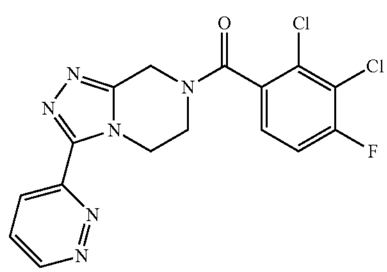 [SMILES: O=C(c1ccc(F)c(Cl)c1Cl)N1CCn2c(nnc2-c2cccnn2)C1] | | * |
| 169 | 7-[(2,3-dichloro-4-fluorophenyl)carbonyl]-3-(1,2,4-thiadiazol-5-yl)-5,6,7,8-tetrahydro[1,2,4]triazolo[4,3-a]pyrazine | 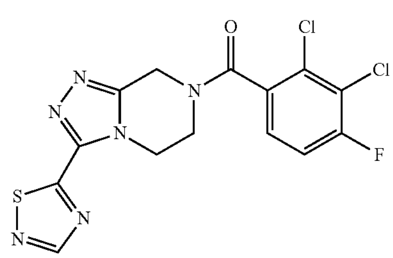 [SMILES: O=C(c1ccc(F)c(Cl)c1Cl)N1CCn2c(nnc2-c2ncns2)C1] | | *** |

-continued

| Ex | Name | Structure | Assay 1 | Assay 2 |
|---|---|---|---|---|
| 170 | 7-[(2,4-dichloro-3-fluorophenyl)carbonyl]-3-(3-fluoro-2-pyridinyl)-5,6,7,8-tetrahydro[1,2,4]triazolo[4,3-a]pyrazine | 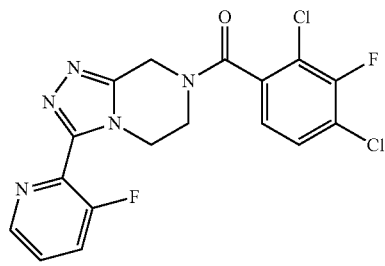 [SMILES: O=C(c1ccc(Cl)c(F)c1Cl)N1CCn2c(nnc2-c2ncccc2F)C1] | | *** |
| 171 | 3-{7-[(2,4-dichloro-3-fluorophenyl)carbonyl]-5,6,7,8-tetrahydro[1,2,4]triazolo[4,3-a]pyrazin-3-yl}-2-pyridinol | 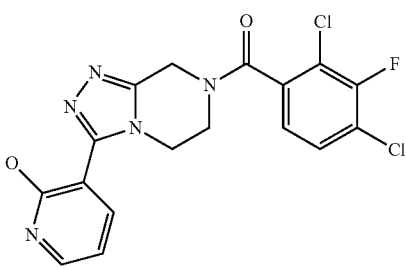 [SMILES: O=C(c1ccc(Cl)c(F)c1Cl)N1CCn2c(nnc2-c2cccnc2O)C1] | | ** |
| 172 | 7-[(2,4-dichloro-3-fluorophenyl)carbonyl]-3-(4-methyl-2-pyridinyl)-5,6,7,8-tetrahydro[1,2,4]triazolo[4,3-a]pyrazine | 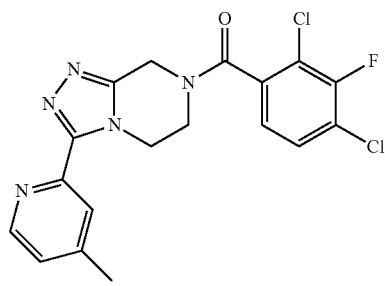 [SMILES: Cc1ccnc(-c2nnc3n2CCN(C(=O)c2ccc(Cl)c(F)c2Cl)C3)c1] | | ** |
| 173 | 7-[(2,4-dichloro-3-fluorophenyl)carbonyl]-3-(2-pyridinyl)-5,6,7,8-tetrahydro[1,2,4]triazolo[4,3-a]pyrazine | 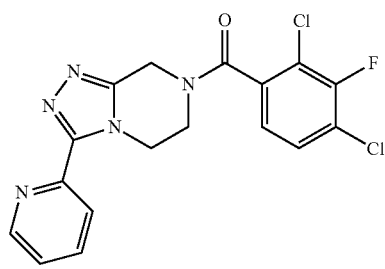 [SMILES: O=C(c1ccc(Cl)c(F)c1Cl)N1CCn2c(nnc2-c2ccccn2)C1] | | *** |
| 174 | 7-[(2,4-dichloro-3-fluorophenyl)carbonyl]-3-[4-(methyloxy)-2-pyridinyl]-5,6,7,8-tetrahydro[1,2,4]triazolo[4,3-a]pyrazine | 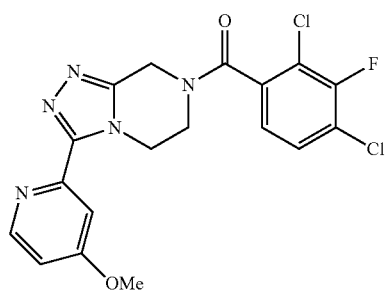 [SMILES: COc1ccnc(-c2nnc3n2CCN(C(=O)c2ccc(Cl)c(F)c2Cl)C3)c1] | | *** |

| Ex | Name | Structure | Assay 1 | Assay 2 |
|---|---|---|---|---|
| 175 | 2-{7-[(2,4-dichloro-3-fluorophenyl)carbonyl]-5,6,7,8-tetrahydro[1,2,4]triazolo[4,3-a]pyrazin-3-yl}-3-pyridinol | 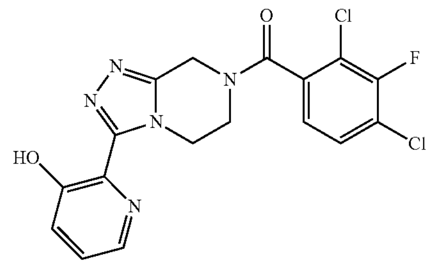 | | ** |
| 176 | 7-[(2,4-dichloro-3-fluorophenyl)carbonyl]-3-[6-(methyloxy)-2-pyridinyl]-5,6,7,8-tetrahydro[1,2,4]triazolo[4,3-a]pyrazine | 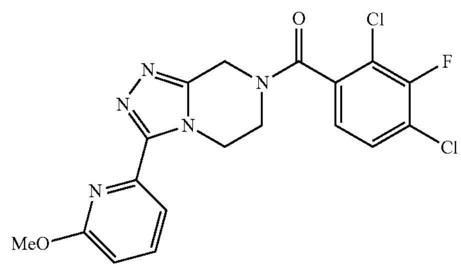 [SMILES: COc1cccc(-c2nnc3n2CCN(C(=O)c2ccc(Cl)c(F)c2Cl)C3)n1] | | ** |
| 177 | 7-[(2,4-dichloro-3-fluorophenyl)carbonyl]-3-(4-methyl-2-pyrimidinyl)-5,6,7,8-tetrahydro[1,2,4]triazolo[4,3-a]pyrazine | 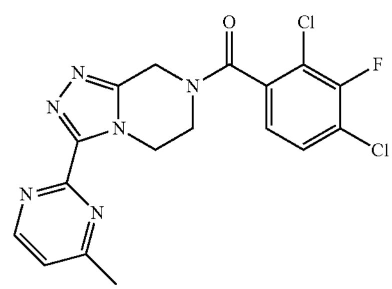 [SMILES: Cc1ccnc(-c2nnc3n2CCN(C(=O)c2ccc(Cl)c(F)c2Cl)C3)n1] | | *** |
| 178 | 7-[(2,4-dichloro-3-fluorophenyl)carbonyl]-3-(5-isothiazolyl)-5,6,7,8-tetrahydro[1,2,4]triazolo[4,3-a]pyrazine | 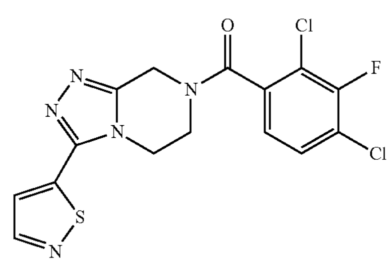 [SMILES: O=C(c1ccc(Cl)c(F)c1Cl)N1CCn2c(nnc2-c2ccns2)C1] | | ** |
| 179 | 7-[(2,4-dichloro-3-fluorophenyl)carbonyl]-3-(4-methyl-1,2,3-thiadiazol-5-yl)-5,6,7,8-tetrahydro[1,2,4]triazolo[4,3-a]pyrazine | 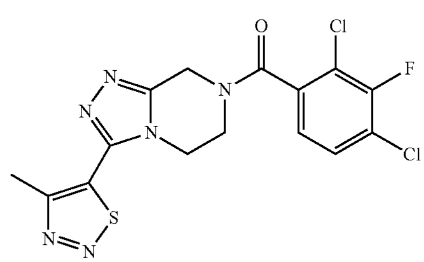 [SMILES: Cc1nnsc1-c1nnc2n1CCN(C(=O)c1ccc(Cl)c(F)c1Cl)C2] | | 6.2 |

-continued

| Ex | Name | Structure | Assay 1 | Assay 2 |
|---|---|---|---|---|
| 180 | 7-{[2-chloro-3-(trifluoromethyl)phenyl]carbonyl}-3-(2-pyridinyl)-5,6,7,8-tetrahydro[1,2,4]triazolo[4,3-a]pyrazine-d$_1$ | 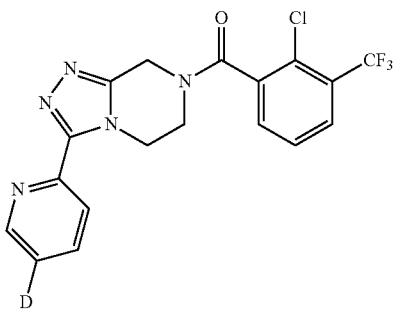 [SMILES: [2H]c1ccc(-c2nnc3n2CCN(C(=O)c2cccc(C(F)(F)F)c2Cl)C3)nc1] | | ** |
| 181 | 7-{[2-chloro-3-(trifluoromethyl)phenyl]carbonyl}-3-(2-pyridinyl)-5,6,7,8-tetrahydro[1,2,4]triazolo[4,3-a]pyrazine-d$_1$ | 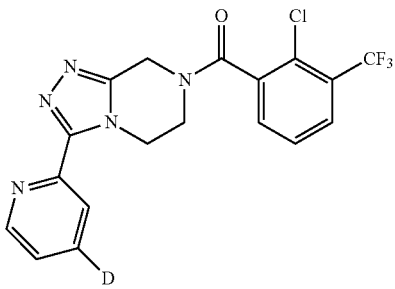 [SMILES: [2H]c1ccnc(-c2nnc3n2CCN(C(=O)c2cccc(C(F)(F)F)c2Cl)C3)c1] | | ** |
| 182 | 7-[(2,4-dichloro-3-fluorophenyl)carbonyl]-3-(2-pyridinyl)-5,6,7,8-tetrahydro[1,2,4]triazolo[4,3-a]pyrazine-d$_1$ | 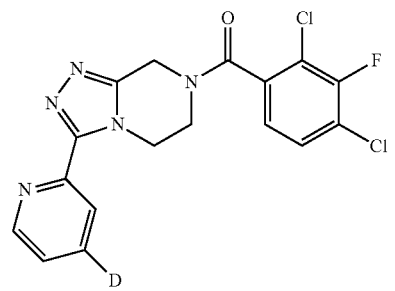 [SMILES: [2H]c1ccnc(-c2nnc3n2CCN(C(=O)c2ccc(Cl)c(F)c2Cl)C3)c1] | | *** |
| 183 | 7-[(2,4-dichloro-3-fluorophenyl)carbonyl]-3-(2-pyridinyl)-5,6,7,8-tetrahydro[1,2,4]triazolo[4,3-a]pyrazine-d$_1$ | 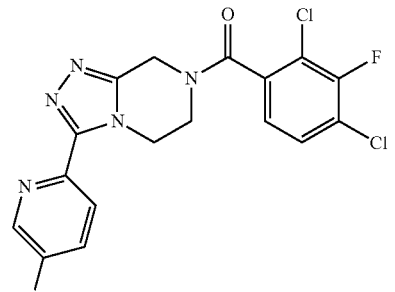 | | *** |
| 184 | 7-[(2,4-dichloro-3-fluorophenyl)carbonyl]-3-(1H-pyrazol-1-yl)-5,6,7,8-tetrahydro[1,2,4]triazolo[4,3-a]pyrazine | 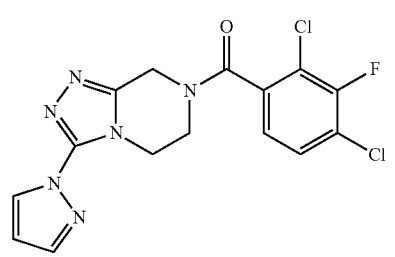 [SMILES: O=C(c1ccc(Cl)c(F)c1Cl)N1CCn2c(nnc2-n2cccn2)C1] | | ** |

| Ex | Name | Structure | Assay 1 | Assay 2 |
|---|---|---|---|---|
| 185 | 7-[(2,4-dichloro-3-fluorophenyl)carbonyl]-3-(1,3-thiazol-5-yl)-5,6,7,8-tetrahydro[1,2,4]triazolo[4,3-a]pyrazine | 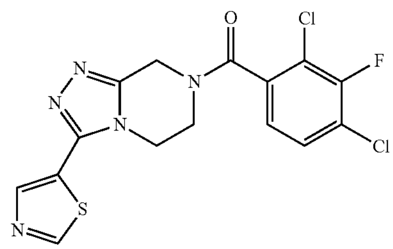 [SMILES: O=C(c1ccc(Cl)c(F)c1Cl)N1CCn2c(nnc2-c2cncs2)C1] | | ** |
| 186 | 7-[(2,4-dichloro-3-fluorophenyl)carbonyl]-3-(1,2,4-thiadiazol-5-yl)-5,6,7,8-tetrahydro[1,2,4]triazolo[4,3-a]pyrazine | 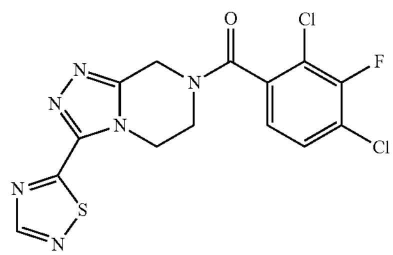 [SMILES: O=C(c1ccc(Cl)c(F)c1Cl)N1CCn2c(nnc2-c2ncns2)C1] | | *** |
| 187 | 7-[(2,4-dichloro-3-fluorophenyl)carbonyl]-3-(1,3-thiazol-2-yl)-5,6,7,8-tetrahydro[1,2,4]triazolo[4,3-a]pyrazine | 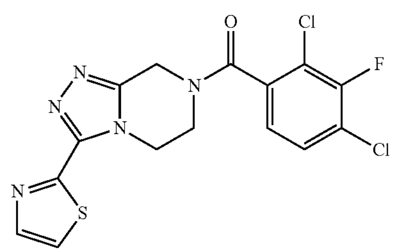 [SMILES: O=C(c1ccc(Cl)c(F)c1Cl)N1CCn2c(nnc2-c2nccs2)C1] | | *** |
| 188 | 7-[(2,4-dichloro-3-fluorophenyl)carbonyl]-3-(5-methyl-1,3-thiazol-2-yl)-5,6,7,8-tetrahydro[1,2,4]triazolo[4,3-a]pyrazine | 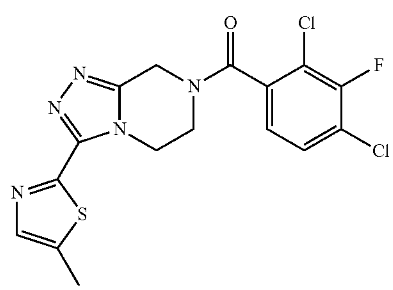 [SMILES: Cc1cnc(-c2nnc3n2CCN(C(=O)c2ccc(Cl)c(F)c2Cl)C3)s1] | | ** |
| 189 | 7-[(2,4-dichloro-3-fluorophenyl)carbonyl]-3-(1,2,3-thiadiazol-4-yl)-5,6,7,8-tetrahydro[1,2,4]triazolo[4,3-a]pyrazine | 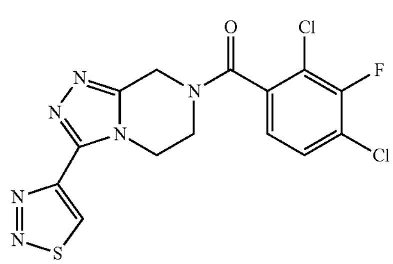 [SMILES: O=C(c1ccc(Cl)c(F)c1Cl)N1CCn2c(nnc2-c2csnn2)C1] | | ** |
| 190 | 7-[(2,4-dichloro-3-fluorophenyl)carbonyl]-3-(1,2,5-thiadiazol-3-yl)-5,6,7,8-tetrahydro[1,2,4]triazolo[4,3-a]pyrazine | 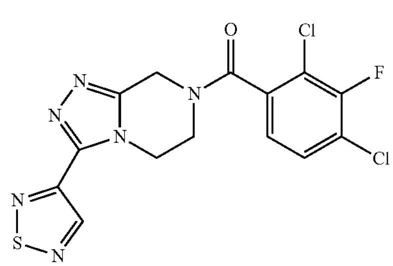 [SMILES: O=C(c1ccc(Cl)c(F)c1Cl)N1CCn2c(nnc2-c2cnsn2)C1] | | *** |

| Ex | Name | Structure | Assay 1 | Assay 2 |
|---|---|---|---|---|
| 191 | 7-[(2,4-dichloro-3-fluorophenyl)carbonyl]-3-(4-methyl-1,3-thiazol-2-yl)-5,6,7,8-tetrahydro[1,2,4]triazolo[4,3-a]pyrazine | 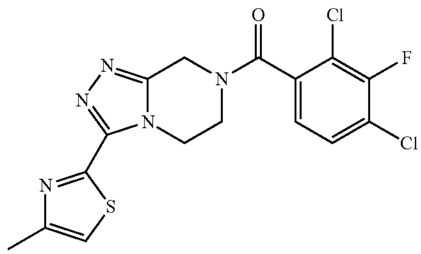 [SMILES: Cc1csc(-c2nnc3n2CCN(C(=O)c2ccc(Cl)c(F)c2Cl)C3)n1] | | ** |
| 192 | 7-[(2,3-dichlorophenyl)carbonyl]-3-(1,2,4-thiadiazol-5-yl)-5,6,7,8-tetrahydro[1,2,4]triazolo[4,3-a]pyrazine | 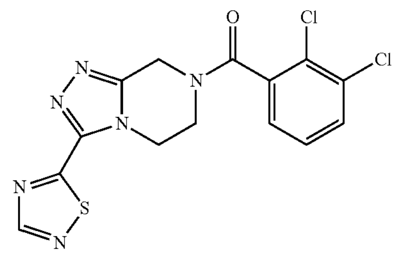 | | *** |
| 193 | 7-[(3-chloro-4-fluoro-2-methylphenyl)carbonyl]-3-(1,2,4-thiadiazol-5-yl)-5,6,7,8-tetrahydro[1,2,4]triazolo[4,3-a]pyrazine | 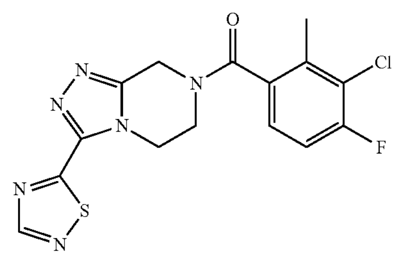 [SMILES: Cc1c(C(=O)N2CCn3c(nnc3-c3ncns3)C2)ccc(F)c1Cl] | | *** |
| 195 | 7-[(3-chloro-2-methylphenyl)carbonyl}-3-(1,2,4-thiadiazol-5-yl)-5,6,7,8-tetrahydro[1,2,4]triazolo[4,3-a]pyrazine | 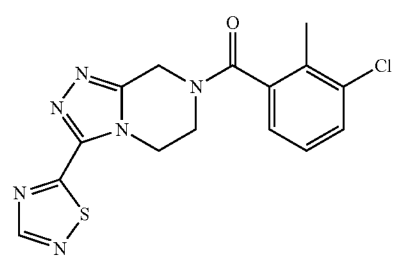 [SMILES: Cc1c(Cl)cccc1C(=O)N1CCn2c(nnc2-c2ncns2)C1] | | *** |
| 197 | 7-[(2,4-dichloro-3-fluorophenyl)carbonyl]-3-(5-methyl-1,3-thiazol-4-yl)-5,6,7,8-tetrahydro[1,2,4]triazolo[4,3-a]pyrazine | 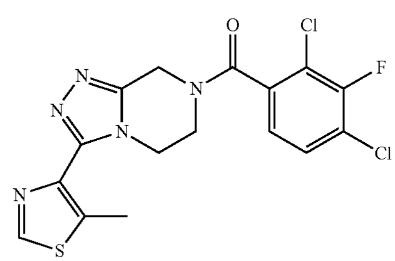 [SMILES: Cc1scnc1-c1nnc2n1CCN(C(=O)c1ccc(Cl)c(F)c1Cl)C2] | | *** |
| 198 | 7-[(2,4-dichloro-3-fluorophenyl)carbonyl]-3-(1,3-thiazol-2-yl)-5,6,7,8-tetrahydro[1,2,4]triazolo[4,3-a]pyrazine | 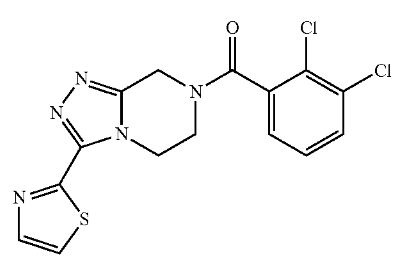 | | *** |

-continued

| Ex | Name | Structure | Assay 1 | Assay 2 |
|---|---|---|---|---|
| 199 | 7-[(2,4-dichlorophenyl)carbonyl]-3-(1,3-thiazol-2-yl)-5,6,7,8-tetrahydro[1,2,4]triazolo[4,3-a]pyrazine | 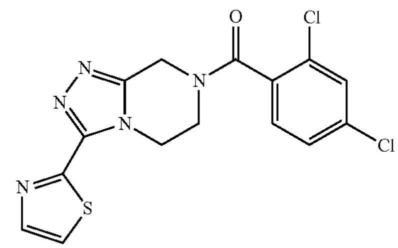 [SMILES: O=C(c1ccc(Cl)cc1Cl)N1CCn2c(nnc2-c2nccs2)C1] | | ** |
| 200 | 7-[(3-chloro-2-methylphenyl)carbonyl]-3-(1,3-thiazol-2-yl)-5,6,7,8-tetrahydro[1,2,4]triazolo[4,3-a]pyrazine | 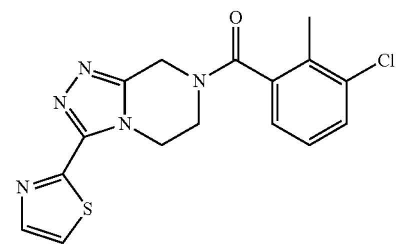 [SMILES: Cc1c(Cl)cccc1C(=O)N1CCn2c(nnc2-c2nccs2)C1] | | ** |
| 201 | 7-[(3-chloro-4-fluoro-2-methylphenyl)carbonyl]-3-(1,3-thiazol-2-yl)-5,6,7,8-tetrahydro[1,2,4]triazolo[4,3-a]pyrazine | 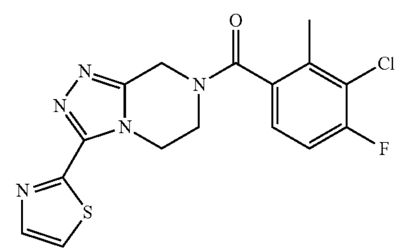 [SMILES: Cc1c(C(=O)N2CCn3c(nnc3-c3nccs3)C2)ccc(F)c1Cl] | | *** |
| 202 | 7-[(3,4-difluoro-2-methylphenyl)carbonyl]-3-(1,2,4-thiadiazol-5-yl)-5,6,7,8-tetrahydro[1,2,4]triazolo[4,3-a]pyrazine | 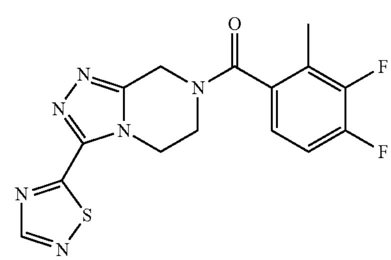 [SMILES: Cc1c(C(=O)N2CCn3c(nnc3-c3ncns3)C2)ccc(F)c1F] | | ** |
| 203 | 7-[(2,4-dichloro-3-fluorophenyl)carbonyl]-3-(4-methyl-3-isothiazolyl)-5,6,7,8-tetrahydro[1,2,4]triazolo[4,3-a]pyrazine | 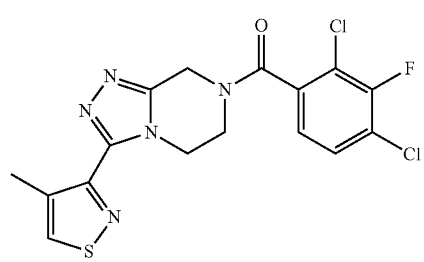 [SMILES: Cc1csnc1-c1nnc2n1CCN(C(=O)c1ccc(Cl)c(F)c1Cl)C2] | | ** |
| 204 | 2-chloro-6-{[3-(2-pyridinyl)-5,6-dihydro[1,2,4]triazolo[4,3-a]pyrazin-7(8H)-yl]carbonyl}benzonitrile | 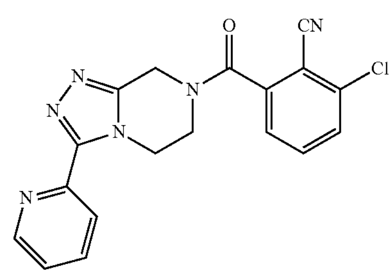 [SMILES: N#Cc1c(Cl)cccc1C(=O)N1CCn2c(nnc2-c2ccccn2)C1] | | *** |

-continued

| Ex | Name | Structure | Assay 1 | Assay 2 |
|---|---|---|---|---|
| 205 | 7-[(2,4-dichlorophenyl)carbonyl]-3-(1,2,4-thiadiazol-5-yl)-5,6,7,8-tetrahydro[1,2,4]triazolo[4,3-a]pyrazine | 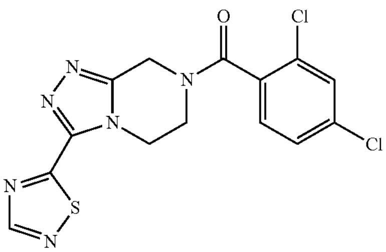 [SMILES: O=C(c1ccc(Cl)cc1Cl)N1CCn2c(nnc2-c2ncns2)C1] | | ** |
| 206 | 7-[(2,4-dichlorophenyl)carbonyl]-3-(5-methyl-1,3-thiazol-4-yl)-5,6,7,8-tetrahydro[1,2,4]triazolo[4,3-a]pyrazine | 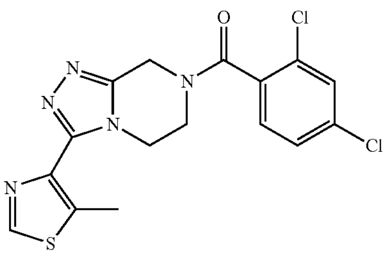 [SMILES: Cc1scnc1-c1nnc2n1CCN(C(=O)c1ccc(Cl)cc1Cl)C2] | | ** |
| 207 | 7-[(3-chloro-2-methylphenyl)carbonyl]-3-(5-methyl-1,3-thiazol-4-yl)-5,6,7,8-tetrahydro[1,2,4]triazolo 4,3-a]pyrazine | 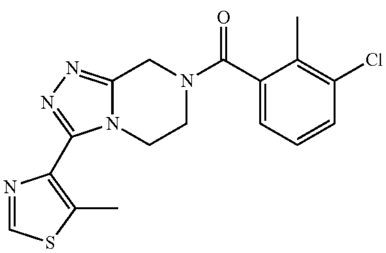 [SMILES: Cc1scnc1-c1nnc2n1CCN(C(=O)c1cccc(Cl)c1C)C2] | | ** |

The invention claimed is:

1. A compound of formula (I) or a pharmaceutically acceptable salt thereof:

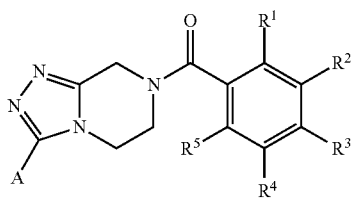

(I)

wherein:

A is hydrogen, $C_{1-4}$alkyl, $C_{3-6}$cycloalkyl, $C_{1-3}$alkoxy, $C_{1-3}$alkoxy $C_{1-2}$fluoroalkyl, halogen, $NR^6R^7$, Het, or phenyl;

wherein said phenyl is optionally substituted by one, two or three substituents independently being fluorine, chlorine, $C_{1-3}$alkyl, OH, methoxy or deuterium;

wherein Het is:

i) a 6-membered heteroaromatic monocyclic ring containing one, two or three ring-nitrogen atoms, or ii) a 5-membered heteroaromatic monocyclic ring containing one, two or three ring heteroatoms independently being N, O or S, wherein no more than one of the 5-membered ring heteroatoms is O or S; or iii) a 9 or 10-membered heteroaromatic bicyclic ring containing one, two or three ring nitrogen atoms;

and wherein Het is optionally substituted with one or two substituents independently being $C_{1-3}$alkyl, fluorine, chlorine, OH, methoxy or deuterium;

and wherein:

$R^1$ is hydrogen, chlorine, fluorine, bromine, $C_1$fluoroalkyl, cyano or $C_{1-3}$alkyl;

$R^2$ is hydrogen, fluorine, chlorine, bromine, $C_1$fluoroalkyl, cyano or $C_{1-3}$alkyl, $R^3$ is hydrogen, fluorine, chlorine or $C_{1-3}$alkyl, $R^4$ is hydrogen;

$R^5$ is hydrogen, fluorine, chlorine or methyl; and $R^6$ and $R^7$ independently are hydrogen or $C_{1-3}$alkyl;

or $R^6$ and $R^7$ are taken together and are —$(CH_2)_2$—O—$(CH_2)_2$—, —$(CH_2)_2$—O—$(CH_2)_3$—, or —$(CH_2)$, 1— wherein $n^1$ is 3, 4, 5 or 6;

wherein, when A is hydrogen, $C_{1-4}$alkyl, $C_{3-6}$cycloalkyl, $C_{1-3}$alkoxy, $C_{1-3}$alkoxy $C_{1-2}$fluoroalkyl, halogen or $NR^6R^7$, then $R^1$ is chlorine, fluorine, bromine, $C_1$fluoroalkyl, cyano or $C_{1-3}$alkyl, and at least one of $R^2$ and $R^3$ is other than hydrogen;

and when A is Het or optionally substituted phenyl, then $R^1$ is hydrogen, chlorine, fluorine, bromine, $C_1$fluoroalkyl, cyano or $C_{1-3}$alkyl, and at least one of $R^1$, $R^2$ and $R^3$ is other than hydrogen;

and wherein, when $R^5$ is fluorine, chlorine or methyl, then $R^1$ is chlorine, fluorine, $C_1$fluoroalkyl or methyl and $R^2$ is hydrogen.

2. A compound which is:

3-bromo-7-{[2-chloro-3-(trifluoromethyl)phenyl]carbonyl}-5,6,7,8-tetrahydro[1,2,4]triazolo[4,3-a]pyrazine, 7-{[2-chloro-3-(trifluoromethyl)phenyl]carbonyl}-3-(trifluoromethyl)-5,6,7,8-tetrahydro[1,2,4]triazolo[4,3-a]pyrazine, 7-{[2-chloro-3-(trifluoromethyl)phenyl]carbonyl}-5,6,7,8-tetrahydro[1,2,4]triazolo[4,3-a]pyrazine, 7-{[2-chloro-3-(trifluoromethyl)phenyl]carbonyl}-3-ethyl-5,6,7,8-tetrahydro[1,2,4]triazolo[4,3-a]pyrazine, 7-[(2,3-dichlorophenyl)carbonyl]-3-ethyl-5,6,7,8-tetrahydro[1,2,4]triazolo[4,3-a]pyrazine, 3-bromo-7-[(2,3-dichlorophenyl)carbonyl]-5,6,7,8-tetrahydro[1,2,4]triazolo[4,3-a]pyrazine, 3-bromo-7-[(2,4-dichlorophenyl)carbonyl]-5,6,7,8-tetrahydro[1,2,4]triazolo[4,3-a]pyrazine, 3-bromo-7-[(2,4,6-trichlorophenyl)carbonyl]-5,6,7,8-tetrahydro[1,2,4]triazolo[4,3-a]pyrazine, 3-bromo-7-{[2-fluoro-3-(trifluoromethyl)phenyl]carbonyl}-5,6,7,8-tetrahydro[1,2,4]triazolo[4,3-a]pyrazine, 7-{[2-chloro-3-(trifluoromethyl)phenyl]carbonyl}-3-(4-pyridinyl)-5,6,7,8-tetrahydro[1,2,4]triazolo[4,3-a]pyrazine, 7-{[2-chloro-3-(trifluoromethyl)phenyl]carbonyl}-3-(2-pyridinyl)-5,6,7,8-tetrahydro[1,2,4]triazolo[4,3-a]pyrazine, 7-{[2-chloro-3-(trifluoromethyl)phenyl]carbonyl}-3-(4-pyrimidinyl)-5,6,7,8-tetrahydro[1,2,4]triazolo[4,3-a]pyrazine, 7-{[2-chloro-3-(trifluoromethyl)phenyl]carbonyl}-3-phenyl-5,6,7,8-tetrahydro[1,2,4]triazolo[4,3-a]pyrazine, 7-{[2-chloro-3-(trifluoromethyl)phenyl]carbonyl}-3-(4-fluorophenyl)-5,6,7,8-tetrahydro[1,2,4]triazolo[4,3-a]pyrazine, 7-{[2-chloro-3-(trifluoromethyl)phenyl]carbonyl}-3-methyl-5,6,7,8-tetrahydro[1,2,4]triazolo[4,3-a]pyrazine, 7-{[2-chloro-3-(trifluoromethyl)phenyl]carbonyl}-3-(3-pyridinyl)-5,6,7,8-tetrahydro[1,2,4]triazolo[4,3-a]pyrazine, 7-{[2-chloro-3-(trifluoromethyl)phenyl]carbonyl}-3-(methyloxy)-5,6,7,8-tetrahydro[1,2,4]triazolo[4,3-a]pyrazine, 7-{[2-chloro-3-(trifluoromethyl)phenyl]carbonyl}-3-(4-morpholinyl)-5,6,7,8-tetrahydro[1,2,4]triazolo[4,3-a]pyrazine, 7-{[2-chloro-3-(trifluoromethyl)phenyl]carbonyl}-3-(1-pyrrolidinyl)-5,6,7,8-tetrahydro[1,2,4]triazolo[4,3-a]pyrazine, 7-{[2-chloro-3-(trifluoromethyl)phenyl]carbonyl}-N,N-dimethyl-5,6,7,8-tetrahydro[1,2,4]triazolo[4,3-a]pyrazin-3-amine, 7-{[2-chloro-3-(trifluoromethyl)phenyl]carbonyl}-N-methyl-5,6,7,8-tetrahydro[1,2,4]triazolo[4,3-a]pyrazin-3-amine, 3-(1-azetidinyl)-7-{[2-chloro-3-(trifluoromethyl)phenyl]carbonyl}-5,6,7,8-tetrahydro[1,2,4]triazolo[4,3-a]pyrazine, 7-{[2-chloro-3-(trifluoromethyl)phenyl]carbonyl}-3-(1-piperidinyl)-5,6,7,8-tetrahydro[1,2,4]triazolo[4,3-a]pyrazine, 7-{[2-chloro-3-(trifluoromethyl)phenyl]carbonyl}-3-(2,4-difluorophenyl)-5,6,7,8-tetrahydro[1,2,4]triazolo[4,3-a]pyrazine, 7-{[2-chloro-3-(trifluoromethyl)phenyl]carbonyl}-3-(1,1-dimethylethyl)-5,6,7,8-tetrahydro[1,2,4]triazolo[4,3-a]pyrazine, 7-{[2-chloro-3-(trifluoromethyl)phenyl]carbonyl}-3-(6-methyl-2-pyridinyl)-5,6,7,8-tetrahydro[1,2,4]triazolo[4,3-a]pyrazine, 7-{[2-chloro-3-(trifluoromethyl)phenyl]carbonyl}-3-(1-methyl-1H-pyrazol-3-yl)-5,6,7,8-tetrahydro[1,2,4]triazolo[4,3-a]pyrazine, 7-{[2-chloro-3-(trifluoromethyl)phenyl]carbonyl}-3-(3-methyl-2-pyridinyl)-5,6,7,8-tetrahydro[1,2,4]triazolo[4,3-a]pyrazine, 7-{[2-chloro-3-(trifluoromethyl)phenyl]carbonyl}-3-(1-methyl-1H-pyrrol-2-yl)-5,6,7,8-tetrahydro[1,2,4]triazolo[4,3-a]pyrazine, 7-[(2-chloro-4-fluorophenyl)carbonyl]-3-phenyl-5,6,7,8-tetrahydro[1,2,4]triazolo[4,3-a]pyrazine, 7-[(2-chloro-4-fluorophenyl)carbonyl]-3-(3-fluoro-2-pyridinyl)-5,6,7,8-tetrahydro[1,2,4]triazolo[4,3-a]pyrazine, 7-[(2-chloro-4-fluorophenyl)carbonyl]-3-(3-methyl-2-pyridinyl)-5,6,7,8-tetrahydro[1,2,4]triazolo[4,3-a]pyrazine, 7-[(2-chloro-4-fluorophenyl)carbonyl]-3-(4-pyrimidinyl)-5,6,7,8-tetrahydro[1,2,4]triazolo[4,3-a]pyrazine, 7-[(2,3-dichlorophenyl)carbonyl]-3-(2-pyrazinyl)-5,6,7,8-tetrahydro[1,2,4]triazolo[4,3-a]pyrazine, 7-{[2-chloro-3-(trifluoromethyl)phenyl]carbonyl}-3-(5-methyl-3-isoxazolyl)-5,6,7,8-tetrahydro[1,2,4]triazolo[4,3-a]pyrazine, 7-[(2-chloro-4-fluorophenyl)carbonyl]-3-(2-pyridinyl)-5,6,7,8-tetrahydro[1,2,4]triazolo[4,3-a]pyrazine, 7-{[2-chloro-3-(trifluoromethyl)phenyl]carbonyl}-3-(1H-pyrrol-2-yl)-5,6,7,8-tetrahydro[1,2,4]triazolo[4,3-a]pyrazine, 7-[(2-chloro-4-fluorophenyl)carbonyl]-3-(3-pyridinyl)-5,6,7,8-tetrahydro[1,2,4]triazolo[4,3-a]pyrazine, 7-[(2-chloro-4-fluorophenyl)carbonyl]-3-(5-fluoro-2-pyridinyl)-5,6,7,8-tetrahydro[1,2,4]triazolo[4,3-a]pyrazine, 7-[(2-chloro-4-fluorophenyl)carbonyl]-3-(6-fluoro-2-pyridinyl)-5,6,7,8-tetrahydro[1,2,4]triazolo[4,3-a]pyrazine, 7-{[2-chloro-3-(trifluoromethyl)phenyl]carbonyl}-3-(1,3-thiazol-4-yl)-5,6,7,8-tetrahydro[1,2,4]triazolo[4,3-a]pyrazine, 7-[(2,3-dichlorophenyl)carbonyl]-3-(2-pyridinyl)-5,6,7,8-tetrahydro[1,2,4]triazolo[4,3-a]pyrazine, 7-{[2-chloro-3-(trifluoromethyl)phenyl]carbonyl}-3-(3-pyridazinyl)-5,6,7,8-tetrahydro[1,2,4]triazolo[4,3-a]pyrazine, 7-{[2-chloro-3-(trifluoromethyl)phenyl]carbonyl}-3-(5-fluoro-2-pyridinyl)-5,6,7,8-tetrahydro[1,2,4]triazolo[4,3-a]pyrazine, 7-{[2-chloro-3-(trifluoromethyl)phenyl]carbonyl}-3-(2-pyrazinyl)-5,6,7,8-tetrahydro[1,2,4]triazolo[4,3-a]pyrazine, 7-[(2-chloro-4-fluorophenyl)carbonyl]-3-(2-pyrimidinyl)-5,6,7,8-tetrahydro[1,2,4]triazolo[4,3-a]pyrazine, 7-[(2,3-dichlorophenyl)carbonyl]-3-(1-methyl-1H-pyrrol-2-yl)-5,6,7,8-tetrahydro[1,2,4]triazolo[4,3-a]pyrazine, 7-[(2,3-dichlorophenyl)carbonyl]-3-(5-methyl-3-isoxazolyl)-5,6,7,8-tetrahydro[1,2,4]triazolo[4,3-a]pyrazine, 7-{[2-chloro-3-(trifluoromethyl)phenyl]carbonyl}-3-(2-pyrimidinyl)-5,6,7,8-tetrahydro[1,2,4]triazolo[4,3-a]pyrazine, 7-{[2-chloro-3-(trifluoromethyl)phenyl]carbonyl}-3-(5-methyl-2-pyridinyl)-5,6,7,8-tetrahydro[1,2,4]triazolo[4,3-a]pyrazine, 7-{[2-chloro-3-(trifluoromethyl)phenyl]carbonyl}-3-(3-fluoro-2-pyridinyl)-5,6,7,8-tetrahydro[1,2,4]triazolo[4,3-a]pyrazine, 7-{[2-chloro-3-(trifluoromethyl)phenyl]carbonyl}-3-(6-fluoro-2-pyridinyl)-5,6,7,8-tetrahydro[1,2,4]triazolo[4,3-a]pyrazine,
7-[(2,3-dichlorophenyl)carbonyl]-3-(5-fluoro-2-pyridinyl)-5,6,7,8-tetrahydro[1,2,4]triazolo[4,3-a]pyrazine,
7-[(2,3-dichlorophenyl)carbonyl]-3-(6-fluoro-2-pyridinyl)-5,6,7,8-tetrahydro[1,2,4]triazolo[4,3-a]pyrazine,
7-{[2-chloro-3-(trifluoromethyl)phenyl]carbonyl}-3-(4-methyl-2-pyridinyl)-5,6,7,8-tetrahydro[1,2,4]triazolo[4,3-a]pyrazine,
7-[(2,3-dichlorophenyl)carbonyl]-3-(3-pyridazinyl)-5,6,7,8-tetrahydro[1,2,4]triazolo[4,3-a]pyrazine,
7-[(2,3-dichlorophenyl)carbonyl]-3-(2-pyrimidinyl)-5,6,7,8-tetrahydro[1,2,4]triazolo[4,3-a]pyrazine,
7-[(2-chloro-4-fluorophenyl)carbonyl]-3-(3-pyridazinyl)-5,6,7,8-tetrahydro[1,2,4]triazolo[4,3-a]pyrazine,
7-[(2,3-dichlorophenyl)carbonyl]-3-(5-methyl-2-pyridinyl)-5,6,7,8-tetrahydro[1,2,4]triazolo[4,3-a]pyrazine,
7-[(2,3-dichlorophenyl)carbonyl]-3-(3-pyridinyl)-5,6,7,8-tetrahydro[1,2,4]triazolo[4,3-a]pyrazine,
7-[(2,3-dichlorophenyl)carbonyl]-3-(4-pyrimidinyl)-5,6,7,8-tetrahydro[1,2,4]triazolo[4,3-a]pyrazine,
7-[(2,3-dichlorophenyl)carbonyl]-3-(1-methyl-1H-pyrazol-3-yl)-5,6,7,8-tetrahydro[1,2,4]triazolo[4,3-a]pyrazine,
7-[(2,3-dichlorophenyl)carbonyl]-3-(1H-pyrrol-2-yl)-5,6,7,8-tetrahydro[1,2,4]triazolo[4,3-a]pyrazine,
7-{[2-chloro-3-(trifluoromethyl)phenyl]carbonyl}-3-(2-methyl-3-pyridinyl)-5,6,7,8-tetrahydro[1,2,4]triazolo[4,3-a]pyrazine,
7-[(2,3-dichlorophenyl)carbonyl]-3-(3-methyl-2-pyridinyl)-5,6,7,8-tetrahydro[1,2,4]triazolo[4,3-a]pyrazine,
7-[(2,3-dichlorophenyl)carbonyl]-3-(1,3-thiazol-4-yl)-5,6,7,8-tetrahydro[1,2,4]triazolo[4,3-a]pyrazine,
7-{[2-chloro-3-(trifluoromethyl)phenyl]carbonyl}-3-(1-methyl-1H-pyrazol-5-yl)-5,6,7,8-tetrahydro[1,2,4]triazolo[4,3-a]pyrazine,
7-[(2,3-dichlorophenyl)carbonyl]-3-(6-methyl-2-pyridinyl)-5,6,7,8-tetrahydro[1,2,4]triazolo[4,3-a]pyrazine,
7-[(2,3-dichlorophenyl)carbonyl]-3-phenyl-5,6,7,8-tetrahydro[1,2,4]triazolo[4,3-a]pyrazine,
7-[(2-chloro-4-fluorophenyl)carbonyl]-3-(5-methyl-3-isoxazolyl)-5,6,7,8-tetrahydro[1,2,4]triazolo[4,3-a]pyrazine,
7-[(2-chloro-4-fluorophenyl)carbonyl]-3-(1-methyl-1H-pyrazol-3-yl)-5,6,7,8-tetrahydro[1,2,4]triazolo[4,3-a]pyrazine,
7-[(2,3-dichlorophenyl)carbonyl]-3-(2-methyl-3-pyridinyl)-5,6,7,8-tetrahydro[1,2,4]triazolo[4,3-a]pyrazine,
7-[(2-chloro-4-fluorophenyl)carbonyl]-3-(2-methyl-3-pyridinyl)-5,6,7,8-tetrahydro[1,2,4]triazolo[4,3-a]pyrazine,
7-[(2-chlorophenyl)carbonyl]-3-(2-pyridinyl)-5,6,7,8-tetrahydro[1,2,4]triazolo[4,3-a]pyrazine,
7-[(2,4-dichlorophenyl)carbonyl]-3-(2-pyridinyl)-5,6,7,8-tetrahydro[1,2,4]triazolo[4,3-a]pyrazine,
3-bromo-7-[(2-chloro-4-fluorophenyl)carbonyl]-5,6,7,8-tetrahydro[1,2,4]triazolo[4,3-a]pyrazine,
7-{[2-chloro-3-(trifluoromethyl)phenyl]carbonyl}-3-(2-furanyl)-5,6,7,8-tetrahydro[1,2,4]triazolo[4,3-a]pyrazine,
7-{[2-(methyloxy)phenyl]carbonyl}-3-(2-pyridinyl)-5,6,7,8-tetrahydro[1,2,4]triazolo[4,3-a]pyrazine,
7-[(2,4-difluorophenyl)carbonyl]-3-(2-pyridinyl)-5,6,7,8-tetrahydro[1,2,4]triazolo[4,3-a]pyrazine,
7-[(2-chloro-6-fluorophenyl)carbonyl]-3-(2-pyridinyl)-5,6,7,8-tetrahydro[1,2,4]triazolo[4,3-a]pyrazine,
7-[(3-chlorophenyl)carbonyl]-3-(2-pyridinyl)-5,6,7,8-tetrahydro[1,2,4]triazolo[4,3-a]pyrazine,
7-[(2,3-dichlorophenyl)carbonyl]-3-(1-methyl-1H-pyrazol-5-yl)-5,6,7,8-tetrahydro[1,2,4]triazolo[4,3-a]pyrazine,
7-[(2-chloro-4-fluorophenyl)carbonyl]-3-(1-methyl-1H-pyrrol-2-yl)-5,6,7,8-tetrahydro[1,2,4]triazolo[4,3-a]pyrazine,
7-{[2-chloro-3-(trifluoromethyl)phenyl]carbonyl}-3-(3,5-difluoro-2-pyridinyl)-5,6,7,8-tetrahydro[1,2,4]triazolo[4,3-a]pyrazine,
7-[(2-chloro-4-fluorophenyl)carbonyl]-3-(3,5-difluoro-2-pyridinyl)-5,6,7,8-tetrahydro[1,2,4]triazolo[4,3-a]pyrazine,
7-[(2-chloro-4-fluorophenyl)carbonyl]-3-(2-pyrazinyl)-5,6,7,8-tetrahydro[1,2,4]triazolo[4,3-a]pyrazine,
3-(2-pyridinyl)-7-{[3-(trifluoromethyl)phenyl]carbonyl}-5,6,7,8-tetrahydro[1,2,4]triazolo[4,3-a]pyrazine,
2-{[3-(2-pyridinyl)-5,6-dihydro[1,2,4]triazolo[4,3-a]pyrazin-7(8H)-yl]carbonyl}benzonitrile,
7-[(2,3-difluorophenyl)carbonyl]-3-(2-pyridinyl)-5,6,7,8-tetrahydro[1,2,4]triazolo[4,3-a]pyrazine,
7-[(2,6-dichlorophenyl)carbonyl]-3-(2-pyridinyl)-5,6,7,8-tetrahydro[1,2,4]triazolo[4,3-a]pyrazine,
7-[(2-chloro-4-fluorophenyl)carbonyl]-3-(1,3-thiazol-4-yl)-5,6,7,8-tetrahydro[1,2,4]triazolo[4,3-a]pyrazine,
7-{[2-fluoro-3-(trifluoromethyl)phenyl]carbonyl}-3-(2-pyridinyl)-5,6,7,8-tetrahydro[1,2,4]triazolo[4,3-a]pyrazine,
7-[(2,4-dichlorophenyl)carbonyl]-3-(2-pyrazinyl)-5,6,7,8-tetrahydro[1,2,4]triazolo[4,3-a]pyrazine,
7-[(2,4-dichlorophenyl)carbonyl]-3-(3-fluoro-2-pyridinyl)-5,6,7,8-tetrahydro[1,2,4]triazolo[4,3-a]pyrazine,
7-{[4-fluoro-2-(trifluoromethyl)phenyl]carbonyl}-3-(2-pyridinyl)-5,6,7,8-tetrahydro[1,2,4]triazolo[4,3-a]pyrazine,
7-[(2,4-dichlorophenyl)carbonyl]-3-(5-fluoro-2-pyridinyl)-5,6,7,8-tetrahydro[1,2,4]triazolo[4,3-a]pyrazine,
7-[(4-chloro-2-fluorophenyl)carbonyl]-3-(2-pyridinyl)-5,6,7,8-tetrahydro[1,2,4]triazolo[4,3-a]pyrazine,
7-[(2,4-dichlorophenyl)carbonyl]-3-(1,3-thiazol-4-yl)-5,6,7,8-tetrahydro[1,2,4]triazolo[4,3-a]pyrazine,
7-[(2,3-dichlorophenyl)carbonyl]-3-(2,4-difluorophenyl)-5,6,7,8-tetrahydro[1,2,4]triazolo[4,3-a]pyrazine,
7-[(2,3-dichlorophenyl)carbonyl]-3-(4-fluorophenyl)-5,6,7,8-tetrahydro[1,2,4]triazolo[4,3-a]pyrazine,
7-[(2,4-dichlorophenyl)carbonyl]-3-(4-fluorophenyl)-5,6,7,8-tetrahydro[1,2,4]triazolo[4,3-a]pyrazine,
7-[(2,4-dichlorophenyl)carbonyl]-3-(2,4-difluorophenyl)-5,6,7,8-tetrahydro[1,2,4]triazolo[4,3-a]pyrazine,
7-[(2,4-dichlorophenyl)carbonyl]-3-(4-pyrimidinyl)-5,6,7,8-tetrahydro[1,2,4]triazolo[4,3-a]pyrazine,
7-[(2-chlorophenyl)carbonyl]-3-(1,3-thiazol-4-yl)-5,6,7,8-tetrahydro[1,2,4]triazolo[4,3-a]pyrazine,
7-{[4-chloro-3-(trifluoromethyl)phenyl]carbonyl}-3-(2-pyrazinyl)-5,6,7,8-tetrahydro[1,2,4]triazolo[4,3-a]pyrazine,
7-[(3-chloro-4-fluorophenyl)carbonyl]-3-(2-pyrazinyl)-5,6,7,8-tetrahydro[1,2,4]triazolo[4,3-a]pyrazine,
7-[(4-chloro-2-fluorophenyl)carbonyl]-3-(2-pyrazinyl)-5,6,7,8-tetrahydro[1,2,4]triazolo[4,3-a]pyrazine,
7-[(4-fluoro-2-methylphenyl)carbonyl]-3-(2-pyrazinyl)-5,6,7,8-tetrahydro[1,2,4]triazolo[4,3-a]pyrazine,
7-{[4-fluoro-3-(trifluoromethyl)phenyl]carbonyl}-3-(2-pyrazinyl)-5,6,7,8-tetrahydro[1,2,4]triazolo[4,3-a]pyrazine, 3-bromo-7-[(2-chloro-4-fluorophenyl)carbonyl]-5,6,7,8-tetrahydro[1,2,4]triazolo[4,3-a]pyrazine, 7-[(2,4-dichloro-3-fluorophenyl)carbonyl]-3-(5-fluoro-2-pyridinyl)-5,6,7,8-tetrahydro[1,2,4]triazolo[4,3-a]pyrazine, 7-[(2,4-dichloro-3-fluorophenyl)carbonyl]-3-(2-pyrazinyl)-5,6,7,8-tetrahydro[1,2,4]triazolo[4,3-a]pyrazine, 7-[(2,4-dichloro-3-fluorophenyl)carbonyl]-3-(4-pyrimidinyl)-5,6,7,8-tetrahydro[1,2,4]triazolo[4,3-a]pyrazine, 7-[(2,3-dichloro-4-fluorophenyl)carbonyl]-3-(2-pyrazinyl)-5,6,7,8-tetrahydro[1,2,4]triazolo[4,3-a]pyrazine, 7-[(2,3-dichloro-4-fluorophenyl)carbonyl]-3-(5-fluoro-2-pyridinyl)-5,6,7,8-tetrahydro[1,2,4]triazolo[4,3-a]pyrazine;

7-[(2-chlorophenyl)carbonyl]-3-(4-pyrimidinyl)-5,6,7,8-tetrahydro[1,2,4]triazolo[4,3-a]pyrazine;

7-[(2-chlorophenyl)carbonyl]-3-(2-furanyl)-5,6,7,8-tetrahydro[1,2,4]triazolo[4,3-a]pyrazine;

7-[(2-chlorophenyl)carbonyl]-3-(5-fluoro-2-pyridinyl)-5,6,7,8-tetrahydro[1,2,4]triazolo[4,3-a]pyrazine;

7-[(2-chlorophenyl)carbonyl]-3-(4-fluorophenyl)-5,6,7,8-tetrahydro[1,2,4]triazolo[4,3-a]pyrazine;

7-[(2-chlorophenyl)carbonyl]-3-(2-pyrazinyl)-5,6,7,8-tetrahydro[1,2,4]triazolo[4,3-a]pyrazine;

7-[(2-chlorophenyl)carbonyl]-3-(3-fluoro-2-pyridinyl)-5,6,7,8-tetrahydro[1,2,4]triazolo[4,3-a]pyrazine;

3-(2-pyridinyl)-7-{[2-(trifluoromethyl)phenyl]carbonyl}-5,6,7,8-tetrahydro[1,2,4]triazolo[4,3-a]pyrazine;

7-[(2-chloro-4-fluorophenyl)carbonyl]-3-(3-fluorophenyl)-5,6,7,8-tetrahydro[1,2,4]triazolo[4,3-a]pyrazine;

7-[(2-chloro-4-fluorophenyl)carbonyl]-3-(3,4-difluorophenyl)-5,6,7,8-tetrahydro[1,2,4]triazolo[4,3-a]pyrazine;

7-[(2-chloro-4-fluorophenyl)carbonyl]-3-[3-(methyloxy)phenyl]-5,6,7,8-tetrahydro[1,2,4]triazolo[4,3-a]pyrazine;

7-[(2-chloro-4-fluorophenyl)carbonyl]-3-(3-chlorophenyl)-5,6,7,8-tetrahydro[1,2,4]triazolo[4,3-a]pyrazine;

7-[(2-chloro-4-fluorophenyl)carbonyl]-3-[2-(methyloxy)phenyl]-5,6,7,8-tetrahydro[1,2,4]triazolo[4,3-a]pyrazine;

2-{7-[(2-chloro-4-fluorophenyl)carbonyl]-5,6,7,8-tetrahydro[1,2,4]triazolo[4,3-a]pyrazin-3-yl}phenol;

8-{7-[(2-chloro-4-fluorophenyl)carbonyl]-5,6,7,8-tetrahydro[1,2,4]triazolo[4,3-a]pyrazin-3-yl}quinoline;

7-[(2-chloro-4-fluorophenyl)carbonyl]-3-(2,3-dichlorophenyl)-5,6,7,8-tetrahydro[1,2,4]triazolo[4,3-a]pyrazine; 7-[(2-chloro-4-fluorophenyl)carbonyl]-3-(2,3-difluorophenyl)-5,6,7,8-tetrahydro[1,2,4]triazolo[4,3-a]pyrazine;

7-[(2-chloro-4-fluorophenyl)carbonyl]-3-(1H-indol-7-yl)-5,6,7,8-tetrahydro[1,2,4]triazolo[4,3-a]pyrazine;

7-{[2-chloro-3-(trifluoromethyl)phenyl]carbonyl}-3-cyclopropyl-5,6,7,8-tetrahydro[1,2,4]triazolo[4,3-a]pyrazine; 7-{[2-chloro-3-(trifluoromethyl)phenyl]carbonyl}-3-propyl-5,6,7,8-tetrahydro[1,2,4]triazolo[4,3-a]pyrazine;

7-{[2-chloro-3-(trifluoromethyl)phenyl]carbonyl}-3-cyclohexyl-5,6,7,8-tetrahydro[1,2,4]triazolo[4,3-a]pyrazine;

7-[(2-chloro-4-fluorophenyl)carbonyl]-3-(2-methyl-1,3-thiazol-4-yl)-5,6,7,8-tetrahydro[1,2,4]triazolo[4,3-a]pyrazine;

7-{[2-chloro-3-(trifluoromethyl)phenyl]carbonyl}-3-[2-(methyloxy)ethyl]-5,6,7,8-tetrahydro[1,2,4]triazolo[4,3-a]pyrazine;

2-(7-{[2-chloro-3-(trifluoromethyl)phenyl]carbonyl}-5,6,7,8-tetrahydro[1,2,4]triazolo[4,3-a]pyrazin-3-yl)phenol;

7-{[2-chloro-3-(trifluoromethyl)phenyl]carbonyl}-3-cyclopentyl-5,6,7,8-tetrahydro[1,2,4]triazolo[4,3-a]pyrazine;

7-[(2-chloro-4-fluorophenyl)carbonyl]-3-(1-methyl-1H-imidazol-2-yl)-5,6,7,8-tetrahydro[1,2,4]triazolo[4,3-a]pyrazine;

7-[(2-chloro-4-fluorophenyl)carbonyl]-3-(5-chloro-2-pyrazinyl)-5,6,7,8-tetrahydro[1,2,4]triazolo[4,3-a]pyrazine;

7-{[4-chloro-2-(trifluoromethyl)phenyl]carbonyl}-3-(2-pyrazinyl)-5,6,7,8-tetrahydro[1,2,4]triazolo[4,3-a]pyrazine;

7-[(2,4-dimethylphenyl)carbonyl]-3-(2-pyrazinyl)-5,6,7,8-tetrahydro[1,2,4]triazolo[4,3-a]pyrazine;

7-[(2-chloro-4-fluorophenyl)carbonyl]-3-(1,3-thiazol-2-yl)-5,6,7,8-tetrahydro[1,2,4]triazolo[4,3-a]pyrazine;

7-[(4-chloro-2-methylphenyl)carbonyl]-3-(2-pyrazinyl)-5,6,7,8-tetrahydro[1,2,4]triazolo[4,3-a]pyrazine;

7-[(3-chloro-4-fluoro-2-methylphenyl)carbonyl]-3-(2-pyrazinyl)-5,6,7,8-tetrahydro[1,2,4]triazolo[4,3-a]pyrazine;

7-[(2-bromo-4-fluorophenyl)carbonyl]-3-(2-pyrazinyl)-5,6,7,8-tetrahydro[1,2,4]triazolo[4,3-a]pyrazine;

7-{[4-methyl-2-(trifluoromethyl)phenyl]carbonyl}-3-(2-pyrazinyl)-5,6,7,8-tetrahydro[1,2,4]triazolo[4,3-a]pyrazine;

7-[(2,4-dichloro-3-fluorophenyl)carbonyl]-3-(1,3-thiazol-4-yl)-5,6,7,8-tetrahydro[1,2,4]triazolo[4,3-a]pyrazine;

2-{7-[(2,4-dichloro-3-fluorophenyl)carbonyl]-5,6,7,8-tetrahydro[1,2,4]triazolo[4,3-a]pyrazin-3-yl}-5-fluorophenol;

7-[(3,4-difluoro-2-methylphenyl)carbonyl]-3-(2-pyrazinyl)-5,6,7,8-tetrahydro[1,2,4]triazolo[4,3-a]pyrazine;

7-[(2,3-dichloro-4-methylphenyl)carbonyl]-3-(2-pyrazinyl)-5,6,7,8-tetrahydro[1,2,4]triazolo[4,3-a]pyrazine;

7-[(2-chloro-4-fluoro-3-methylphenyl)carbonyl]-3-(2-pyrazinyl)-5,6,7,8-tetrahydro[1,2,4]triazolo[4,3-a]pyrazine;

7-[(2,4-dichloro-3-methylphenyl)carbonyl]-3-(2-pyrazinyl)-5,6,7,8-tetrahydro[1,2,4]triazolo[4,3-a]pyrazine;

7-[(3,4-difluoro-2-methylphenyl)carbonyl]-3-(5-fluoro-2-pyridinyl)-5,6,7,8-tetrahydro[1,2,4]triazolo[4,3-a]pyrazine;

7-[(3-chloro-4-fluoro-2-methylphenyl)carbonyl]-3-(5-fluoro-2-pyridinyl)-5,6,7,8-tetrahydro[1,2,4]triazolo[4,3-a]pyrazine;

7-[(2,4-dichlorophenyl)carbonyl]-3-(5-isoxazolyl)-5,6,7,8-tetrahydro[1,2,4]triazolo[4,3-a]pyrazine;

7-[(2,4-dichlorophenyl)carbonyl]-3-(5-isothiazolyl)-5,6,7,8-tetrahydro[1,2,4]triazolo[4,3-a]pyrazine;

7-{[2-chloro-3-(trifluoromethyl)phenyl]carbonyl}-3-(5-methyl-2-furanyl)-5,6,7,8-tetrahydro[1,2,4]triazolo[4,3-a]pyrazine;

7-[(2,4-dichlorophenyl)carbonyl]-3-(1,2,5-thiadiazol-3-yl)-5,6,7,8-tetrahydro[1,2,4]triazolo[4,3-a]pyrazine;

7-[(2,4-dichlorophenyl)carbonyl]-3-(3-isoxazolyl)-5,6,7,8-tetrahydro[1,2,4]triazolo[4,3-a]pyrazine;

3-(7-{[2-chloro-3-(trifluoromethyl)phenyl]carbonyl}-5,6,7,8-tetrahydro[1,2,4]triazolo[4,3-a]pyrazin-3-yl)-2-pyridinol;

7-{[2-chloro-3-(trifluoromethyl)phenyl]carbonyl}-3-(1,2,4-thiadiazol-5-yl)-5,6,7,8-tetrahydro[1,2,4]triazolo[4,3-a]pyrazine;

7-[(2-chloro-4-fluorophenyl)carbonyl]-3-(5-fluoro-2-pyrazinyl)-5,6,7,8-tetrahydro[1,2,4]triazolo[4,3-a]pyrazine;

2-(7-{[2-chloro-3-(trifluoromethyl)phenyl]carbonyl}-5,6,7,8-tetrahydro[1,2,4]triazolo[4,3-a]pyrazin-3-yl)-3-pyridinol; 7-[(2,3-dichloro-4-fluorophenyl)carbonyl]-3-(5-methyl-2-furanyl)-5,6,7,8-tetrahydro[1,2,4]triazolo[4,3-a]pyrazine;

7-[(2,3-dichloro-4-fluorophenyl)carbonyl]-3-(3-pyridazinyl)-5,6,7,8-tetrahydro[1,2,4]triazolo[4,3-a]pyrazine;

7-[(2,3-dichloro-4-fluorophenyl)carbonyl]-3-(1,2,4-thiadiazol-5-yl)-5,6,7,8-tetrahydro[1,2,4]triazolo[4,3-a]pyrazine;

7-[(2,4-dichloro-3-fluorophenyl)carbonyl]-3-(3-fluoro-2-pyridinyl)-5,6,7,8-tetrahydro[1,2,4]triazolo[4,3-a]pyrazine;

3-{7-[(2,4-dichloro-3-fluorophenyl)carbonyl]-5,6,7,8-tetrahydro[1,2,4]triazolo[4,3-a]pyrazin-3-yl}-2-pyridinol; 7-[(2,4-dichloro-3-fluorophenyl)carbonyl]-3-(4-methyl-2-pyridinyl)-5,6,7,8-tetrahydro[1,2,4]triazolo[4,3-a]pyrazine;

7-[(2,4-dichloro-3-fluorophenyl)carbonyl]-3-(2-pyridinyl)-5,6,7,8-tetrahydro[1,2,4]triazolo[4,3-a]pyrazine;

7-[(2,4-dichloro-3-fluorophenyl)carbonyl]-3-[4-(methyloxy)-2-pyridinyl]-5,6,7,8-tetrahydro[1,2,4]triazolo[4,3-a]pyrazine;

2-{7-[(2,4-dichloro-3-fluorophenyl)carbonyl]-5,6,7,8-tetrahydro[1,2,4]triazolo[4,3-a]pyrazin-3-yl}-3-pyridinol;

7-[(2,4-dichloro-3-fluorophenyl)carbonyl]-3-[6-(methyloxy)-2-pyridinyl]-5,6,7,8-tetrahydro[1,2,4]triazolo[4,3-a]pyrazine;

7-[(2,4-dichloro-3-fluorophenyl)carbonyl]-3-(4-methyl-2-pyrimidinyl)-5,6,7,8-tetrahydro[1,2,4]triazolo[4,3-a]pyrazine;

7-[(2,4-dichloro-3-fluorophenyl)carbonyl]-3-(5-isothiazolyl)-5,6,7,8-tetrahydro[1,2,4]triazolo[4,3-a]pyrazine;

7-[(2,4-dichloro-3-fluorophenyl)carbonyl]-3-(4-methyl-1,2,3-thiadiazol-5-yl)-5,6,7,8-tetrahydro[1,2,4]triazolo[4,3-a]pyrazine;

7-{[2-chloro-3-(trifluoromethyl)phenyl]carbonyl}-3-(2-pyridinyl)-5,6,7,8-tetrahydro[1,2,4]triazolo[4,3-a]pyrazine-d1;

7-{[2-chloro-3-(trifluoromethyl)phenyl]carbonyl}-3-(2-pyridinyl)-5,6,7,8-tetrahydro[1,2,4]triazolo[4,3-a]pyrazine-d1;

7-[(2,4-dichloro-3-fluorophenyl)carbonyl]-3-(2-pyridinyl)-5,6,7,8-tetrahydro[1,2,4]triazolo[4,3-a]pyrazine-d1;

7-[(2,4-dichloro-3-fluorophenyl)carbonyl]-3-(2-pyridinyl)-5,6,7,8-tetrahydro[1,2,4]triazolo[4,3-a]pyrazine-d1;

7-[(2,4-dichloro-3-fluorophenyl)carbonyl]-3-(1H-pyrazol-1-yl)-5,6,7,8-tetrahydro[1,2,4]triazolo[4,3-a]pyrazine;

7-[(2,4-dichloro-3-fluorophenyl)carbonyl]-3-(1,3-thiazol-5-yl)-5,6,7,8-tetrahydro[1,2,4]triazolo[4,3-a]pyrazine;

7-[(2,4-dichloro-3-fluorophenyl)carbonyl]-3-(1,2,4-thiadiazol-5-yl)-5,6,7,8-tetrahydro[1,2,4]triazolo[4,3-a]pyrazine;

7-[(2,4-dichloro-3-fluorophenyl)carbonyl]-3-(1,3-thiazol-2-yl)-5,6,7,8-tetrahydro[1,2,4]triazolo[4,3-a]pyrazine;

7-[(2,4-dichloro-3-fluorophenyl)carbonyl]-3-(5-methyl-1,3-thiazol-2-yl)-5,6,7,8-tetrahydro[1,2,4]triazolo[4,3-a]pyrazine;

7-[(2,4-dichloro-3-fluorophenyl)carbonyl]-3-(1,2,3-thiadiazol-4-yl)-5,6,7,8-tetrahydro[1,2,4]triazolo[4,3-a]pyrazine;

7-[(2,4-dichloro-3-fluorophenyl)carbonyl]-3-(1,2,5-thiadiazol-3-yl)-5,6,7,8-tetrahydro[1,2,4]triazolo[4,3-a]pyrazine;

7-[(2,4-dichloro-3-fluorophenyl)carbonyl]-3-(4-methyl-1,3-thiazol-2-yl)-5,6,7,8-tetrahydro[1,2,4]triazolo[4,3-a]pyrazine;

7-[(2,3-dichlorophenyl)carbonyl]-3-(1,2,4-thiadiazol-5-yl)-5,6,7,8-tetrahydro[1,2,4]triazolo[4,3-a]pyrazine;

7-[(3-chloro-4-fluoro-2-methylphenyl)carbonyl]-3-(1,2,4-thiadiazol-5-yl)-5,6,7,8-tetrahydro[1,2,4]triazolo[4,3-a]pyrazine;

7-[(3-chloro-2-methylphenyl)carbonyl]-3-(1,2,4-thiadiazol-5-yl)-5,6,7,8-tetrahydro[1,2,4]triazolo[4,3-a]pyrazine;

7-[(2,4-dichloro-3-fluorophenyl)carbonyl]-3-(5-methyl-1,3-thiazol-4-yl)-5,6,7,8-tetrahydro[1,2,4]triazolo[4,3-a]pyrazine;

7-[(2,4-dichloro-3-fluorophenyl)carbonyl]-3-(1,3-thiazol-2-yl)-5,6,7,8-tetrahydro[1,2,4]triazolo[4,3-a]pyrazine;

7-[(2,4-dichlorophenyl)carbonyl]-3-(1,3-thiazol-2-yl)-5,6,7,8-tetrahydro[1,2,4]triazolo[4,3-a]pyrazine;

7-[(3-chloro-2-methylphenyl)carbonyl]-3-(1,3-thiazol-2-yl)-5,6,7,8-tetrahydro[1,2,4]triazolo[4,3-a]pyrazine;

7-[(3-chloro-4-fluoro-2-methylphenyl)carbonyl]-3-(1,3-thiazol-2-yl)-5,6,7,8-tetrahydro[1,2,4]triazolo[4,3-a]pyrazine;

7-[(3,4-difluoro-2-methylphenyl)carbonyl]-3-(1,2,4-thiadiazol-5-yl)-5,6,7,8-tetrahydro[1,2,4]triazolo[4,3-a]pyrazine;

7-[(2,4-dichloro-3-fluorophenyl)carbonyl]-3-(4-methyl-3-isothiazolyl)-5,6,7,8-tetrahydro[1,2,4]triazolo[4,3-a]pyrazine;

2-chloro-6-{[3-(2-pyridinyl)-5,6-dihydro[1,2,4]triazolo[4,3-a]pyrazin-7(8H)-yl]carbonyl}benzonitrile;

7-[(2,4-dichlorophenyl)carbonyl]-3-(1,2,4-thiadiazol-5-yl)-5,6,7,8-tetrahydro[1,2,4]triazolo[4,3-a]pyrazine; or 7-[(3-chloro-2-methylphenyl)carbonyl]-3-(5-methyl-1,3-thiazol-4-yl)-5,6,7,8-tetrahydro[1,2,4]triazolo[4,3-a]pyrazine;

or a pharmaceutically acceptable salt thereof.

\* \* \* \* \*